(12) United States Patent
Crowley et al.

US011332463B2

(10) Patent No.: US 11,332,463 B2
(45) Date of Patent: May 17, 2022

(54) SPIROPIPERIDINE ALLOSTERIC MODULATORS OF NICOTINIC ACETYLCHOLINE RECEPTORS

(71) Applicant: Merck Sharp & Dohme Corp., Rahway, NJ (US)

(72) Inventors: Brendan M. Crowley, Collegeville, PA (US); Brian T. Campbell, Souderton, PA (US); Harry R. Chobanian, Aberdeen, NJ (US); James I. Fells, Hillsborough, NJ (US); Deodial G. Guiadeen, Chesterfield, NJ (US); Thomas J. Greshock, Belmont, CA (US); Kenneth J. Leavitt, Mount Laurel, NJ (US); Vanessa L. Rada, Hatfield, PA (US); Ian M. Bell, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 25 days.

(21) Appl. No.: 17/049,653

(22) PCT Filed: Apr. 29, 2019

(86) PCT No.: PCT/US2019/029561
§ 371 (c)(1),
(2) Date: Oct. 22, 2020

(87) PCT Pub. No.: WO2019/212927
PCT Pub. Date: Nov. 7, 2019

(65) Prior Publication Data
US 2021/0070745 A1    Mar. 11, 2021

Related U.S. Application Data

(60) Provisional application No. 62/665,091, filed on May 1, 2018.

(51) Int. Cl.
| | | |
|---|---|---|
| *C07D 413/08* | (2006.01) | |
| *C07D 413/14* | (2006.01) | |
| *C07D 417/08* | (2006.01) | |
| *C07D 417/14* | (2006.01) | |
| *C07D 403/08* | (2006.01) | |
| *C07D 513/04* | (2006.01) | |
| *C07D 471/04* | (2006.01) | |
| *C07D 487/04* | (2006.01) | |
| *A61P 25/00* | (2006.01) | |

(52) U.S. Cl.
CPC ............ *C07D 413/14* (2013.01); *A61P 25/00* (2018.01); *C07D 403/08* (2013.01); *C07D 413/08* (2013.01); *C07D 417/08* (2013.01); *C07D 417/14* (2013.01); *C07D 471/04* (2013.01); *C07D 487/04* (2013.01); *C07D 513/04* (2013.01)

(58) Field of Classification Search
CPC .. C07D 413/08; C07D 413/14; C07D 417/08; C07D 417/14; C07D 403/08; C07D 513/04; C07D 471/04; C07D 487/04; A61P 25/00
See application file for complete search history.

(56) References Cited

U.S. PATENT DOCUMENTS

| | | |
|---|---|---|
| 7,723,391 B2 | 5/2010 | Du Bois et al. |
| 8,716,309 B2 | 5/2014 | Maeng et al. |
| 8,765,790 B2 | 7/2014 | Eskildsen et al. |
| 8,815,914 B2 | 8/2014 | Sams et al. |
| 9,790,173 B2 | 10/2017 | Harvey et al. |
| 10,208,081 B2 | 2/2019 | Wang et al. |

FOREIGN PATENT DOCUMENTS

| | | |
|---|---|---|
| EP | 2905279 A1 | 8/2015 |
| JP | 2006522775 A | 10/2006 |
| JP | 2015529651 A | 10/2015 |
| JP | 2017536379 A | 12/2017 |

(Continued)

OTHER PUBLICATIONS

Database Registry [Online] Chemical Abstracts Service, Columbus, Ohio, US; Feb. 14, 2012, XP002792372, Database accession No. 1356558-70-7 compounds with Registry Nos. 1356558-70-7, 1356559-97-1, 1356560-75-2, 1356566-96-5, 1356574-08-7, 1356574-11-2, 1356579-11-7, 1356629-51-0, 1356630-19-7, 1356641-27-4.

(Continued)

*Primary Examiner* — Laura L Stockton
(74) *Attorney, Agent, or Firm* — Patricia A. Shatynski; John C. Todaro

(57) ABSTRACT

The present disclosure relates to compounds of formula I that are useful as modulators of 7 nAChR, compositions comprising such compounds, and the use of such compounds for preventing, treating, or ameliorating disease, particularly disorders of the central nervous system such as cognitive impairments in Alzheimer's disease, Parkinson's disease, and schizophrenia, as well as for L-DOPA induced-dyskinesia and inflammation (I).

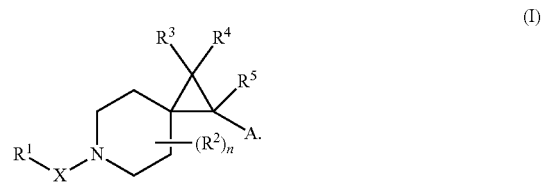

(I)

54 Claims, No Drawings

(56) References Cited

FOREIGN PATENT DOCUMENTS

| WO | 2004089372 | A1 | 10/2004 |
| WO | 2009043784 | A1 | 4/2009 |
| WO | 2012103583 | A1 | 8/2012 |
| WO | 2013007621 | A1 | 1/2013 |
| WO | 2014006117 | A1 | 1/2014 |
| WO | 2014006120 | A1 | 1/2014 |
| WO | 2014019023 | A1 | 2/2014 |
| WO | 2014090731 | A1 | 6/2014 |
| WO | 2017107979 | A1 | 6/2017 |
| WO | 2017165256 | A1 | 9/2017 |

OTHER PUBLICATIONS

Database Registry [Online] Chemical Abstracts Service, Columbus, Ohio, US; Mar. 17, 2013, XP002792373, Database accession No. 1424551-29-0 compounds with Registry Nos. 1424551-29-0.

Database Registry [Online] Chemical Abstracts Service, Columbus, Ohio, US; May 19, 2017, XP002792374, Database accession No. 2095972-46-4 compounds with Registry Nos. 2095972-46-4, 2096051-98-6, 2096104-16-2, 2096112-08-0, 2096158-21-1, 2096158-25-5, 2096165-44-3, 2096235-56-0, 2096235-64-0 and 2096280-74-7.

Database Registry [Online] Chemical Abstracts Service, Columbus, Ohio, US; Sep. 28, 2011, XP002792370, Database accession No. 1333571-90-6 compounds with Registry Nos. 1333571-90-6 and 1333607-68-3.

Database Registry [Online] Chemical Abstracts Service, Columbus, Ohio, US; Sep. 29, 2011, XP002792371, Database accession No. 1333782-86-7 compounds with Registry Nos. 1333782-86-7, 1333802-73-5, 1333809-40-7, 1333812-96-6, 1333844-27-1, 1333903-90-4 and 1334014-80-0.

Database Registry [Online] Chemical Abstracts Service, Columbus, Ohio, US; Mar. 6, 2018, XP002792375, Database accession No. 2185091-40-9 compounds with Registry Nos. 2185091-40-9, 2185107-01-9, 2185107-05-3, 2185147-37-7 and 2185160-46-5.

Database Registry [Online] Chemical Abstracts Service, Columbus, Ohio, US; Jul. 7, 2011, XP002792369, Database accession No. 1311654-00-8 compounds with Registry Nos. 1311654-00-8, 1311670-59-3, 1311732-82-7 and 1311864-00-2.

SPIROPIPERIDINE ALLOSTERIC MODULATORS OF NICOTINIC ACETYLCHOLINE RECEPTORS

CROSS REFERENCE TO RELATED APPLICATIONS

This application is a U.S. National Phase application under 35 U.S.C. § 371 of PCT Application No. PCT/US2019/029561, filed Apr. 29, 2019, which claims priority under 35 U.S.C. § 119(e) from U.S. Provisional Application Ser. No. 62/665,091, filed on May 1, 2018.

FIELD OF THE INVENTION

The present disclosure relates to compounds that are useful as modulators of α7 nAChR, compositions comprising such compounds, and the use of such compounds for preventing, treating, or ameliorating disease, particularly disorders of the central nervous system such as cognitive impairments in Alzheimer's disease, Parkinson's disease, and schizophrenia.

BACKGROUND OF THE INVENTION

The α7 nAChR is a fast desensitizing ligand-gated ion channel that has high permeability to $Ca^{2+}$. In human brain, α7 nAChRs are highly expressed in the cortex and hippocampus, regions associated with cognition, see for example, Breese et al. *J. Comp. Neurol.* (1997) 387:385-398. In neurons, α7 nAChRs are localized in both pre-synaptic and post-synaptic structures, where activation of the receptor can modulate neurotransmitter release, neuronal excitability, and intracellular signalling, see for example, Frazier et al. *J. Neurosci.* (1998) 18:1187-1195.

Cognitive impairments are prevalent in many neurological and psychiatric diseases, including Alzheimer's disease (AD), schizophrenia, and Parkinson's disease, and dysfunction in cholinergic signalling contributes to the cognitive impairments of these diseases, see for example, Francis et al. *J. Neurol. Neurosurg. Psychiatry* (1999) 66:137-147. For example, a principal feature of the pathogenesis in AD is the loss of cholinergic neurons in the basal forebrain nuclei, whereas increasing cholinergic transmission via inhibition of acetylcholine esterase is the standard of care for the cognitive symptoms of AD. More specific to the α7 nAChR, it was recently demonstrated that encenicline, a partial agonist of the α7 nAChR, improves cognition in Alzheimer's disease, see for example, Moebius H et al., $67^{th}$ *Annual Meeting. Am. Acad. Neurol.* (AAN) 2015, Abst P7.100. Evidence implicating α7 nAChRs in the etiology of schizophrenia comes from studies demonstrating reduced expression of neuronal α7 nAChRs in the brain of schizophrenic patients and the observation that schizophrenics frequently smoke, which is believed to be a form of self-medication. In addition, variants in the promotor region of the gene coding for the α7 nAChR, CHRNA7, which impacts expression of the α7 nAChR protein, are associated with symptoms of schizophrenia, see for example, Sinkus et al. *Neuropharmacology* (2015) 96:274-288. Moreover, accumulating evidence from clinical trials has indicated that activating α7 nAChR with agonists may have beneficial effects on cognition, see for example, Keefe et al. *Neuropsychopharmacology* (2015) 40:3053-3060 and Bertrand et al. *Pharmacology Reviews* (2015) 67:1025-1073. Therefore, targeting the α7 nAChR represents a therapeutic strategy for the treatment of cognitive impairments associated with various cognitive disorders.

Parkinson's disease (PD) is a neurodegenerative disease characterized by progressive deficits in motor function, such as tremor, bradykinesia, rigidity and impaired postural reflex. The main pathological finding associated with the disease is degeneration of dopaminergic neurons in the substantia nigra, resulting in loss of dopaminergic tone in the striatum. L-DOPA is the current standard treatment for the motor symptoms in PD. However, chronic treatment with L-DOPA in PD patients also induces dyskinesia, a side effect of L-DOPA therapy. New lines of evidence indicate that activating α7 nAChRs acutely alleviates dyskinesia in several animal models, see for example, Zhang et al. *J. Pharmacol. Exp. Ther.* (2014) 351:25-32. In addition, accumulating evidence shows that pretreatment with α7 nAChR agonists may protect against neurodegeneration in nigrostriatal neurons, suggesting α7 activation may have disease modifying properties too, see for example, Suzuki et al. *J. Neurosci. Res.* (2013) 91:462-471. Overall, α7 nAChR is an attractive target for both ameliorating disease progression and managing dyskinesia.

In addition to its expression in the central nervous system, the α7 nAChR is widely expressed in peripheral immune cells including macrophage, monocytes, dendritic cells, and B and T cells, see for example, Rosas-Ballina et al. *Science* (2011) 334:98-101. Activation of peripheral α7 nAChRs is critical for inhibiting the release of proinflammatory cytokines via the cholinergic anti-inflammatory pathway, see for example, Wang et al. *Nature* (2003) 421:384-388. Therefore, α7 nAChR is a potential target for several inflammatory diseases such as rheumatoid arthritis, and atherosclerosis, see for example, W J de Jonge et al. *British J. Pharmacol.* (2007) 151:915-929.

In recent years, α7-selective positive allosteric modulators (PAMs) have been proposed as a therapeutic approach to treating cognitive impairments in AD, PD, and schizophrenia, as well as L-DOPA induced-dyskinesia and inflammation. In contrast to α7 agonists that activate the channel irrespective of endogenous agonist, PAMs increase the potency of the endogenous agonist without perturbing the temporal and spatial integrity of neurotransmission. There are two classes of α7 PAMs, type I and type II, which differ based on the functional properties of modulation. The type I PAMs (e.g. NS1738, see for example, Timmermann et al. *J. Pharmacol. Exp. Ther.* (2007) 323:294-307) predominantly affect the peak current with little or no effect on receptor desensitization, while the type II PAMs (e.g. PNU120596, see for example, Hurst et al. *J. Neurosci.* (2005) 25:4396-4405) markedly delay desensitization of the receptor. Additionally, α7 nAChR PAMs may have improved selectivity over related channel targets, presumably through binding to non-conserved regions of the receptor.

The present invention is directed to a new class of compounds that exhibit positive allosteric modulation of the α7 nAChR.

SUMMARY OF THE INVENTION

The present disclosure relates to novel compounds of formula I and II and pharmaceutically acceptable salts thereof. These compounds may be useful, either as compounds or their pharmaceutically acceptable salts (when appropriate), in the modulation of the α7 nAChR, the prevention, treatment, or amelioration of disease, particularly disorders of the central nervous system such as cognitive impairments in Alzheimer's disease, Parkinson's disease, and schizophrenia and/or as pharmaceutical composition ingredients. As pharmaceutical composition ingredients, these compounds and their salts may be the primary active therapeutic agent, and, when appropriate, may be combined with other therapeutic agents including but not limited to acetylcholinesterase inhibitors, NMDA receptor antagonists, beta-secretase inhibitors, M4 mAChR agonists or PAMs, mGluR2 antagonists or NAMs or PAMs, 5-HT6 antagonists, histamine H3 receptor antagonists, PDE4 inhibitors, PDE9 inhibitors, HDAC6 inhibitors, antipsychotics, MAO-B inhibitors, and levodopa.

In one aspect, the present invention relates to a compound of formula I:

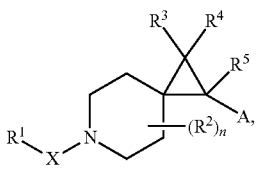

(I)

or a pharmaceutically acceptable salt thereof, wherein:

n is 0, 1 or 2;

X is $S(O)_2$ or $C(O)$;

$R^1$ is selected from $NR^aR^b$ and $R^c$;

$R^a$ is selected from H, $(C_1-C_4)$alkyl, $(C_3-C_6)$cycloalkyl, aryl, heteroaryl, and heterocyclyl said alkyl, cycloalkyl, aryl, heteroaryl and heterocyclyl are optionally substituted with one or more substituents independently selected from $R^8$;

$R^b$ is H or $(C_1-C_4)$alkyl;

$R^c$ is $(C_1-C_4)$alkyl, wherein said alkyl is optionally substituted with $R^9$; or $R^c$ is heteroaryl, wherein said heteroaryl is optionally substituted with one or more $R^{10}$;

A is a 5-membered heteroaryl ring which is substituted with 1 to 3 R groups each independently selected from OH, oxo, $NR^6R^7$, CN, alkoxy, halogen, aminoalkyl, hydroxyalkyl, alkyl, alkenyl, alkynyl, cycloalkyl, aryl, heteroaryl, and heterocyclyl, wherein said R groups selected from alkyl, alkenyl, alkynyl, cycloalkyl, aryl, heteroaryl, and heterocyclyl, are optionally substituted with one or more substituents independently selected from $R^{11}$;

$R^2$ is independently halogen, $(C_1-C_4)$alkyl, or $O(C_1-C_4)$alkyl, wherein said alkyl is optionally substituted with one or more halogen;

or, two $R^2$ when both are $(C_1-C_4)$alkyl and are attached to the same carbon atom, optionally can come together to form a cyclopropyl, cyclobutyl, or cyclopentyl ring or, two $R^2$ when both are $(C_1-C_4)$alkyl and are not attached to the same carbon atom, optionally can come together and form a bridged ring, wherein said cyclopropyl, cyclobutyl, cyclopentyl or bridged ring may be optionally substituted with one or more substituents independently selected from OH, halogen, or $(C_1-C_4)$alkyl;

$R^3$ is H, halogen or $(C_1-C_4)$alkyl, wherein said alkyl is optionally substituted with one or more halogen;

$R^4$ is H, halogen or $(C_1-C_4)$alkyl, wherein said alkyl is optionally substituted with one or more halogen;

or, $R^3$ and $R^4$ optionally can come together to form a cyclopropyl, cyclobutyl, cyclopentyl or cyclohexyl ring wherein said ring may be optionally substituted with one or more substituents independently selected from OH, halogen, or $(C_1-C_4)$alkyl;

$R^5$ is H or $(C_1-C_4)$alkyl;

$R^6$ is H or $(C_1-C_4)$alkyl;

$R^7$ is H or $(C_1-C_4)$alkyl;

$R^8$ is OH, $(C_1-C_4)$alkyl, aryl, heteroaryl, or heterocyclyl;

$R^9$ is aryl, heteroaryl, or heterocyclyl;

$R^{10}$ is methyl or hydroxyl;

$R^{11}$ is halogen, OH, oxo, $CF_3$, $OCF_3$, CN, $(C_1-C_6)$alkyl, $O(C_1-C_6)$alkyl, $S(C_1-C_4)$alkyl, $C=O(C_1-C_4)$alkyl, $NR^{12}R^{13}$, $(C=O)NR^6R^7$, $(C=O)OR^6$, $(C_2-C_4)$alkenyl, $(C_2-C_4)$alkynyl, $(C_3-C_6)$cycloalkyl, $O(C_3-C_6)$cycloalkyl, $C=O$ $(C_3-C_6)$cycloalkyl, aryl, O-aryl, heteroaryl, or heterocyclyl, wherein said alkyl, cycloalkyl, aryl, heteroaryl, and heterocyclyl are optionally substituted with one or more halogen, $(C_1-C_4)$alkyl, $(C_3-C_6)$cycloalkyl, $CF_3$, $OCF_3$, $OCH_3$, CN, OH and oxo;

$R^{12}$ is $(C_1-C_4)$alkyl, heterocyclyl, cycloalkyl, heteroaryl, aryl, or $(C=O)R^6$, each optionally substituted with one or more substituents independently selected from halogen, $(C_1-C_4)$alkyl, and OH; and $R^{13}$ is $(C_1-C_4)$alkyl, heterocyclyl, cycloalkyl, heteroaryl, aryl, or $(C=O)R^6$, each optionally substituted with one or more substituents independently selected from halogen, $(C_1-C_4)$alkyl, and OH.

The present invention also includes pharmaceutical compositions containing a compound of the present invention and methods of preparing such pharmaceutical compositions. The present invention further includes methods of preventing, treating, or ameliorating the cognitive impairments associated with Alzheimer's disease, Parkinson's disease, and schizophrenia.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts thereof. The compounds of formula I and II are positive allosteric modulators of α7 nAChR.

In a first embodiment of the invention, —X—$R^1$ is

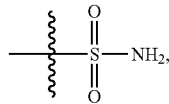 [SMILES: *S(N)(=O)=O]

and the other groups are as provided in the general formula above.

In a second embodiment of the invention, $R^2$ is independently methyl, ethyl or F, and the other groups are as provided in the general formula above, or as in the first embodiment.

In a third embodiment of the invention, A is a 5-membered heteroaryl ring which is substituted with 1 R group independently selected from OH, oxo, $NR^6R^7$, CN, alkoxy, halogen, aminoalkyl, hydroxyalkyl, alkyl, alkenyl, alkynyl, cycloalkyl, aryl, heteroaryl, and heterocyclyl, wherein said R group selected from alkyl, alkenyl, alkynyl, cycloalkyl, aryl, heteroaryl, and heterocyclyl, are further optionally substituted with one or more substituents independently selected from R¹¹, and the other groups are as provided in the general formula above, or as in the first and second embodiments.

In a fourth embodiment of the invention, R is alkyl, cycloalkyl, aryl, heteroaryl, or heterocyclyl, each optionally substituted with one or more substituents independently selected from R¹¹, and the other groups are as provided in the general formula above, or as in the first, second and third embodiments.

In a fifth embodiment of the invention, R is cyclohexyl, phenyl, pyrazolyl, pyridinyl or isoxazolyl, each optionally substituted with one or more substituents independently selected from R¹¹, and the other groups are as provided in the general formula above, or as in the first through fourth embodiments.

In a sixth embodiment of the invention, $R^3$ and $R^4$ are independently selected from H, F, and methyl, and the other groups are as provided in the general formula above, or as in the first through fifth embodiments.

In a seventh embodiment of the invention, the compound of the invention has the formula (II):

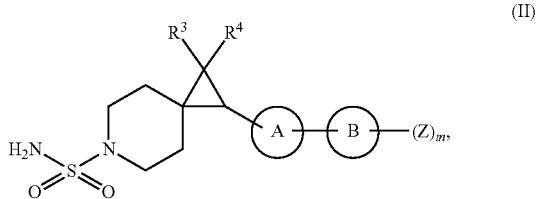

(II)

or a pharmaceutically acceptable salt thereof, wherein;
m is 0, 1, 2 or 3;
Z is independently selected from F, Cl, Br, methyl, methoxy, ethyl, ethoxy, propyl, —CH₂OH, —CH₂CH₂OH, —CF₃, —CH₂CF₃, —OCF₃, —OCHF₂, —OCH₂CF₃, and cyclopropyl;
Ring A is oxadiazolyl, oxazolyl, isoxazolyl, thiadiazolyl, isothiazolyl, thiazolyl, pyrazolyl or imidazolyl;
Ring B is cyclohexyl, phenyl, pyrazolyl, pyridinyl or isoxazolyl;
$R^3$ is H, F or (C₁-C₄)alkyl, wherein said alkyl is optionally substituted with one or more halogen; and
$R^4$ is H, F or (C₁-C₄)alkyl, wherein said alkyl is optionally substituted with one or more halogen.

In an eighth embodiment of the invention, the compound of the invention has the formula (II) or a pharmaceutically acceptable salt thereof, wherein;
m is 0, 1 or 2;
Z is independently selected from F, Cl, Br, methyl, methoxy, ethyl, ethoxy, propyl, —CH₂OH, —CH₂CH₂OH, —CF₃, —CH₂CF₃, —OCF₃, —OCHF₂, —OCH₂CF₃, and cyclopropyl;
Ring A is oxadiazolyl, oxazolyl, isoxazolyl, or thiazolyl;
Ring B is phenyl, pyrazolyl, pyridinyl or isoxazolyl; and
$R^3$ and $R^4$ are both H, or $R^3$ and $R^4$ are both F.

The invention is also directed to a compound, or a pharmaceutically acceptable salt thereof, selected from the following exemplified compounds:
(1R)-1-{5-[2-Methyl-5-(trifluoromethyl)phenyl]-1,2,4-oxadiazol-3-yl}-6-azaspiro[2.5]octane-6-sulfonamide;
(1R)-1-[5-(2,5-Dimethylphenyl)-1,2,4-oxadiazol-3-yl]-6-azaspiro[2.5]octane-6-sulfonamide;
4,4-Difluoro-1-{3-[3-(2,2,2-trifluoroethoxy)phenyl]-1,2,4-oxadiazol-5-yl}-6-azaspiro[2.5]octane-6-sulfonamide, diastereomer C;
1-{3-[3-(Difluoromethoxy)phenyl]-1,2,4-oxadiazol-5-yl}-4-fluoro-6-azaspiro[2.5]octane-6-sulfonamide, diastereomer E;
(1R)-1-{3-[4-Fluoro-2-(trifluoromethyl)phenyl]-1,2,4-oxadiazol-5-yl}-6-azaspiro[2.5]octane-6-sulfonamide;
1-{3-[4-Fluoro-2-(trifluoromethyl)phenyl]-1,2,4-oxadiazol-5-yl}-4-methyl-6-azaspiro[2.5]octane-6-sulfonamide, diastereomer D;
(1R)-1-{2-[3-(Trifluoromethoxy)phenyl]-1,3-thiazol-4-yl}-6-azaspiro[2.5]octane-6-sulfonamide;
(1R)-1-{5-[4-Methyl-1-(2,2,2-trifluoroethyl)-1H-pyrazol-5-yl]-1,2,4-oxadiazol-3-yl}-6-azaspiro[2.5]octane-6-sulfonamide;
(2R)-2-[5-(1,4-Dimethyl-1H-pyrazol-5-yl)-1,2,4-oxadiazol-3-yl]-1,1-difluoro-6-azaspiro[2.5]octane-6-sulfonamide;
(2R)-2-{5-[2-(Difluoromethoxy)pyridin-4-yl]-1,2,4-oxadiazol-3-yl}-1,1-difluoro-6-azaspiro[2.5]octane-6-sulfonamide;
(2R)-2-[3-(3-Cyclopropylisoxazol-4-yl)-1,2,4-oxadiazol-5-yl]-1,1-difluoro-6-azaspiro[2.5]octane-6-sulfonamide;
(2R)-1,1-Difluoro-2-{3-[1-(2,2,2-trifluoroethyl)-1H-pyrazol-5-yl]-1,2,4-oxadiazol-5-yl}-6-azaspiro[2.5]octane-6-sulfonamide;
(2R)-2-{5-[2-(Difluoromethoxy)-5-methylpyridin-4-yl]-1,2,4-oxadiazol-3-yl}-1,1-difluoro-6-azaspiro[2.5]octane-6-sulfonamide;
(2R)-1,1-Difluoro-2-{5-[1-methyl-4-(trifluoromethyl)-1H-pyrazol-5-yl]-1,2,4-oxadiazol-3-yl}-6-azaspiro[2.5]octane-6-sulfonamide;
(1R)-1-{1-[3-(Trifluoromethoxy)phenyl]-1H-pyrazol-4-yl}-6-azaspiro[2.5]octane-6-sulfonamide;
(2R)-2-[5-(1-Cyclopropyl-1H-pyrazol-5-yl)-1,3,4-oxadiazol-2-yl]-1,1-difluoro-6-azaspiro[2.5]octane-6-sulfonamide;
(2S)-2-[5-(1-Cyclopropyl-1H-pyrazol-5-yl)-1,3,4-thiadiazol-2-yl]-1,1-difluoro-6-azaspiro[2.5]octane-6-sulfonamide;
(2R)-2-[5-(6,7-Dihydro-4H-pyrazolo[5,1-c][1,4]thiazin-3-yl)-1,2,4-oxadiazol-3-yl]-1,1-difluoro-6-azaspiro[2.5]octane-6-sulfonamide;
(2R)-1,1-Difluoro-2-{5-[1-methyl-3-(trifluoromethyl)-1H-pyrazol-4-yl]-1,2,4-oxadiazol-3-yl}-6-azaspiro[2.5]octane-6-sulfonamide;
(2R)-1,1-Difluoro-2-[5-(2-methyl-2,4,5,6-tetrahydrocyclopenta[c]pyrazol-3-yl)-1,2,4-oxadiazol-3-yl]-6-azaspiro[2.5]octane-6-sulfonamide;
1,1-Difluoro-2-{3-[4-fluoro-2-(trifluoromethyl)phenyl]-1,2,4-oxadiazol-5-yl}-6-(methylsulfonyl)-6-azaspiro[2.5]octane;
(2R)-1,1-Difluoro-2-[5-(1,3,4-trimethyl-1H-pyrazol-5-yl)-1,2,4-oxadiazol-3-yl]-6-azaspiro[2.5]octane-6-sulfonamide;
(1R)-1-[4-(3-Cyclopropylisoxazol-4-yl)-1,3-oxazol-2-yl]-6-azaspiro[2.5]octane-6-sulfonamide;
(2R)-1,1-Difluoro-2-{2-[4-fluoro-2-(trifluoromethyl)phenyl]-1,3-oxazol-4-yl}-6-azaspiro[2.5]octane-6-sulfonamide;
(2R)-2-[5-(1-Cyclopropyl-4-methyl-1H-pyrazol-3-yl)-1,2,4-oxadiazol-3-yl]-1,1-difluoro-6-azaspiro[2.5]octane-6-sulfonamide;
1-[5-(5-Chloro-2-methoxyphenyl)-1,2,4-oxadiazol-3-yl]-6-(methylsulfonyl)-6-azaspiro[2.5]octane, enantiomer A;
(1R)-1-[5-(1-Ethyl-5-methyl-1H-pyrazol-3-yl)-1,2,4-oxadiazol-3-yl]-6-azaspiro[2.5]octane-6-sulfonamide;
(1R)-1-[5-(3-Cyclopropyl-5-methylisoxazol-4-yl)-1,3-oxazol-2-yl]-6-azaspiro[2.5]octane-6-sulfonamide;

(2R)-2-{5-[1-Cyclopropyl-3-(trifluoromethyl)-1H-pyrazol-5-yl]-1,2,4-oxadiazol-3-yl}-1,1-difluoro-6-azaspiro[2.5]octane-6-sulfonamide;

(2R)-2-[5-(2-Cyclopropyl-5-methylphenyl)-1,2,4-oxadiazol-3-yl]-1,1-difluoro-6-azaspiro[2.5]octane-6-sulfonamide;

(2R)-2-[2-(3-Cyclopropylisoxazol-4-yl)-1,3-oxazol-4-yl]-1,1-difluoro-6-azaspiro[2.5]octane-6-sulfonamide;

2-[3-(2,5-Dimethylphenyl)-1,2,4-oxadiazol-5-yl]-1,1-difluoro-6-(methylsulfonyl)-6-azaspiro[2.5]octane;

(1R)-1-[5-(2-Methylphenyl)-1,2,4-oxadiazol-3-yl]-6-azaspiro[2.5]octane-6-sulfonamide;

(2R)-2-[5-(2,5-Dimethylphenyl)-1,2,4-oxadiazol-3-yl]-1,1-difluoro-6-azaspiro[2.5]octane-6-sulfonamide;

(2R)-2-{2-[2-(Difluoromethoxy)pyridin-4-yl]-1,3-oxazol-4-yl}-1,1-difluoro-6-azaspiro[2.5]octane-6-sulfonamide;

1,1-Difluoro-2-{1-[4-fluoro-2-(trifluoromethyl)phenyl]-1H-pyrazol-3-yl}-6-azaspiro[2.5]octane-6-sulfonamide;

1,1-Difluoro-2-{5-[4-fluoro-2-(trifluoromethyl)phenyl]-1,2,4-thiadiazol-3-yl}-6-azaspiro[2.5]octane-6-sulfonamide;

(1R)-1-[3-(5-Chloro-2-methoxyphenyl)-1,2,4-oxadiazol-5-yl]-6-azaspiro[2.5]octane-6-sulfonamide;

(2R)-1,1-Difluoro-2-(3-phenyl-1,2,4-oxadiazol-5-yl)-6-azaspiro[2.5]octane-6-sulfonamide;

(2R)-1,1-Difluoro-2-{3-[4-fluoro-2-(trifluoromethyl)phenyl]-1,2,4-oxadiazol-5-yl}-6-azaspiro[2.5]octane-6-sulfonamide;

(1R)-1-{3-[5-Fluoro-2-(trifluoromethyl)phenyl]-1,2,4-oxadiazol-5-yl}-6-azaspiro[2.5]octane-6-sulfonamide;

(1R)-1-{3-[3-(Difluoromethoxy)phenyl]-1,2,4-oxadiazol-5-yl}-6-azaspiro[2.5]octane-6-sulfonamide;

(2R)-1,1-Difluoro-2-[3-(3-fluorophenyl)-1,2,4-oxadiazol-5-yl]-6-azaspiro[2.5]octane-6-sulfonamide;

(2R)-2-[3-(2,4-Difluorophenyl)-1,2,4-oxadiazol-5-yl]-1,1-difluoro-6-azaspiro[2.5]octane-6-sulfonamide;

(2R)-1,1-Difluoro-2-{3-[4-(2-hydroxypropan-2-yl)phenyl]-1,2,4-oxadiazol-5-yl}-6-azaspiro[2.5]octane-6-sulfonamide;

1-[3-(5-Chloro-2-methoxyphenyl)-1,2,4-oxadiazol-5-yl]-6-[(pyridin-2-ylmethyl)sulfonyl]-6-azaspiro[2.5]octane;

1-[3-(5-Chloro-2-methoxyphenyl)-1,2,4-oxadiazol-5-yl]-6-(thiophen-3-ylsulfonyl)-6-azaspiro[2.5]octane;

1-[3-(5-Chloro-2-methoxyphenyl)-1,2,4-oxadiazol-5-yl]-6-[(tetrahydro-2H-pyran-2-ylmethyl)sulfonyl]-6-azaspiro[2.5]octane;

1-[3-(5-Chloro-2-methoxyphenyl)-1,2,4-oxadiazol-5-yl]-6-[(1-methyl-1H-pyrazol-3-yl)sulfonyl]-6-azaspiro[2.5]octane;

1-[3-(5-Chloro-2-methoxyphenyl)-1,2,4-oxadiazol-5-yl]-6-[(2-phenylethyl)sulfonyl]-6-azaspiro[2.5]octane;

4-({1-[3-(5-Chloro-2-methoxyphenyl)-1,2,4-oxadiazol-5-yl]-6-azaspiro[2.5]oct-6-yl}sulfonyl)-2,1,3-benzoxadiazole;

6-({1-[3-(5-Chloro-2-methoxyphenyl)-1,2,4-oxadiazol-5-yl]-6-azaspiro[2.5]oct-6-yl}sulfonyl)-1,3-benzothiazole;

4-({1-[3-(5-Chloro-2-methoxyphenyl)-1,2,4-oxadiazol-5-yl]-6-azaspiro[2.5]oct-6-yl}sulfonyl)-5-hydroxy-3-methyl-1,2,3-oxadiazol-3-ium trifluoroacetate;

N-tert-Butyl-1-[3-(5-chloro-2-methoxyphenyl)-1,2,4-oxadiazol-5-yl]-6-azaspiro[2.5]octane-6-carboxamide;

1-[3-(5-Chloro-2-methoxyphenyl)-1,2,4-oxadiazol-5-yl]-N-cyclohexyl-6-azaspiro[2.5]octane-6-carboxamide;

1-[3-(5-Chloro-2-methoxyphenyl)-1,2,4-oxadiazol-5-yl]-N-(pyridin-2-ylmethyl)-6-azaspiro[2.5]octane-6-sulfonamide;

1-[3-(5-Chloro-2-methoxyphenyl)-1,2,4-oxadiazol-5-yl]-N-(isothiazol-5-ylmethyl)-6-azaspiro[2.5]octane-6-carboxamide;

N-Benzyl-1-[3-(5-chloro-2-methoxyphenyl)-1,2,4-oxadiazol-5-yl]-6-azaspiro[2.5]octane-6-carboxamide;

1-[3-(5-Chloro-2-methoxyphenyl)-1,2,4-oxadiazol-5-yl]-6-(methylsulfonyl)-6-azaspiro[2.5]octane;

1-{3-[2-(Methylamino)pyridin-3-yl]-1,2,4-oxadiazol-5-yl}-6-azaspiro[2.5]octane-6-sulfonamide;

1-{3-[2-(Pyrrolidin-1-yl)pyridin-4-yl]-1,2,4-oxadiazol-5-yl}-6-azaspiro[2.5]octane-6-sulfonamide;

2-[3-(3,5-Dimethylisoxazol-4-yl)-1,2,4-oxadiazol-5-yl]-1,1-difluoro-6-azaspiro[2.5]octane-6-sulfonamide;

(1R)-1-[3-(3-Cyclopropylisoxazol-4-yl)-1,2,4-oxadiazol-5-yl]-6-azaspiro[2.5]octane-6-sulfonamide;

(2R)-2-[3-(3-Cyclopropyl-5-methylisoxazol-4-yl)-1,2,4-oxadiazol-5-yl]-1,1-difluoro-6-azaspiro[2.5]octane-6-sulfonamide;

(2R)-2-(3-Cyclohexyl-1,2,4-oxadiazol-5-yl)-1,1-difluoro-6-azaspiro[2.5]octane-6-sulfonamide;

(2R)-1,1-Difluoro-2-[3-(2-methylpyridin-3-yl)-1,2,4-oxadiazol-5-yl]-6-azaspiro[2.5]octane-6-sulfonamide;

(2R)-1,1-Difluoro-2-{3-[2-(trifluoromethyl)pyridin-4-yl]-1,2,4-oxadiazol-5-yl}-6-azaspiro[2.5]octane-6-sulfonamide;

(2R)-2-{3-[2-(Difluoromethoxy)pyridin-4-yl]-1,2,4-oxadiazol-5-yl}-1,1-difluoro-6-azaspiro[2.5]octane-6-sulfonamide;

(2R)-2-[3-(1-Cyclopropyl-4-methyl-1H-pyrazol-5-yl)-1,2,4-oxadiazol-5-yl]-1,1-difluoro-6-azaspiro[2.5]octane-6-sulfonamide;

(2R)-1,1-Difluoro-2-[3-(imidazo[1,2-a]pyridin-7-yl)-1,2,4-oxadiazol-5-yl]-6-azaspiro[2.5]octane-6-sulfonamide;

(1R)-1-{3-[5-Cyclopropyl-3-(trifluoromethyl)isoxazol-4-yl]-1,2,4-oxadiazol-5-yl}-6-azaspiro[2.5]octane-6-sulfonamide;

1-[3-(5-Chloro-2-methoxyphenyl)-1,2,4-oxadiazol-5-yl]-6-azaspiro[2.5]octane-6-sulfonamide;

(2R)-2-[3-(1-Cyclopropyl-1H-pyrazol-5-yl)-1,2,4-oxadiazol-5-yl]-1,1-difluoro-6-azaspiro[2.5]octane-6-sulfonamide;

(2R)-2-{3-[3-Cyclopropyl-5-(trifluoromethyl)isoxazol-4-yl]-1,2,4-oxadiazol-5-yl}-1,1-difluoro-6-azaspiro[2.5]octane-6-sulfonamide;

(2R)-2-{3-[5-Cyclopropyl-3-(trifluoromethyl)isoxazol-4-yl]-1,2,4-oxadiazol-5-yl}-1,1-difluoro-6-azaspiro[2.5]octane-6-sulfonamide;

1,1-Dichloro-2-{3-[4-fluoro-2-(trifluoromethyl)phenyl]-1,2,4-oxadiazol-5-yl}-6-azaspiro[2.5]octane-6-sulfonamide;

(1R)-1-{5-[3-(Trifluoromethyl)phenyl]-1,2,4-oxadiazol-3-yl}-6-azaspiro[2.5]octane-6-sulfonamide;

(1R)-1-[5-(5-Chloro-2-methoxyphenyl)-1,2,4-oxadiazol-3-yl]-6-azaspiro[2.5]octane-6-sulfonamide;

(1R)-1-[5-(2-Cyanophenyl)-1,2,4-oxadiazol-3-yl]-6-azaspiro[2.5]octane-6-sulfonamide;

(1R)-1-{5-[2-(Difluoromethoxy)phenyl]-1,2,4-oxadiazol-3-yl}-6-azaspiro[2.5]octane-6-sulfonamide;

(1R)-1-{5-[4-(Trifluoromethyl)phenyl]-1,2,4-oxadiazol-3-yl}-6-azaspiro[2.5]octane-6-sulfonamide;

(1R)-1-{5-[5-Bromo-2-(trifluoromethyl)phenyl]-1,2,4-oxadiazol-3-yl}-6-azaspiro[2.5]octane-6-sulfonamide;

(1R)-1-{5-[4-Chloro-2-(trifluoromethyl)phenyl]-1,2,4-oxadiazol-3-yl}-6-azaspiro[2.5]octane-6-sulfonamide;

(1R)-1-(5-Phenyl-1,2,4-oxadiazol-3-yl)-6-azaspiro[2.5]octane-6-sulfonamide;

(1R)-1-{5-[2-(Difluoromethoxy)-4-(trifluoromethyl)phenyl]-1,2,4-oxadiazol-3-yl}-6-azaspiro[2.5]octane-6-sulfonamide;
(1R)-1-{5-[4-Chloro-2-(difluoromethoxy)phenyl]-1,2,4-oxadiazol-3-yl}-6-azaspiro[2.5]octane-6-sulfonamide;
(1R)-1-{5-[3-(Difluoromethoxy)phenyl]-1,2,4-oxadiazol-3-yl}-6-azaspiro[2.5]octane-6-sulfonamide;
(1R)-1-{5-[2-Fluoro-6-(trifluoromethyl)phenyl]-1,2,4-oxadiazol-3-yl}-6-azaspiro[2.5]octane-6-sulfonamide;
(1R)-1-[5-(4-Methoxyphenyl)-1,2,4-oxadiazol-3-yl]-6-azaspiro[2.5]octane-6-sulfonamide;
(1R)-1-{5-[4-(Difluoromethoxy)phenyl]-1,2,4-oxadiazol-3-yl}-6-azaspiro[2.5]octane-6-sulfonamide;
(1R)-1-[5-(2,4-Difluorophenyl)-1,2,4-oxadiazol-3-yl]-6-azaspiro[2.5]octane-6-sulfonamide;
(1R)-1-{5-[4-Fluoro-2-(trifluoromethyl)phenyl]-1,2,4-oxadiazol-3-yl}-6-azaspiro[2.5]octane-6-sulfonamide;
(1R)-1-{5-[2-(Trifluoromethyl)phenyl]-1,2,4-oxadiazol-3-yl}-6-azaspiro[2.5]octane-6-sulfonamide;
(1R)-1-{5-[2-(2,2,2-Trifluoroethoxy)phenyl]-1,2,4-oxadiazol-3-yl}-6-azaspiro[2.5]octane-6-sulfonamide;
(1R)-1-[5-(2,4-Dimethylphenyl)-1,2,4-oxadiazol-3-yl]-6-azaspiro[2.5]octane-6-sulfonamide;
(1R)-1-{5-[2-(Trifluoromethoxy)phenyl]-1,2,4-oxadiazol-3-yl}-6-azaspiro[2.5]octane-6-sulfonamide;
(1R)-1-{5-[5-Fluoro-2-(trifluoromethoxy)phenyl]-1,2,4-oxadiazol-3-yl}-6-azaspiro[2.5]octane-6-sulfonamide;
(1R)-1-{5-[5-Chloro-2-(trifluoromethoxy)phenyl]-1,2,4-oxadiazol-3-yl}-6-azaspiro[2.5]octane-6-sulfonamide;
(1R)-1-{5-[4-(2-Hydroxypropan-2-yl)phenyl]-1,2,4-oxadiazol-3-yl}-6-azaspiro[2.5]octane-6-sulfonamide;
(1R)-1-{5-[2-(Difluoromethoxy)-4-fluorophenyl]-1,2,4-oxadiazol-3-yl}-6-azaspiro[2.5]octane-6-sulfonamide;
(1R)-1-[5-(2,4,5-Trimethylphenyl)-1,2,4-oxadiazol-3-yl]-6-azaspiro[2.5]octane-6-sulfonamide;
(2R)-2-[5-(2-Cyclopropylphenyl)-1,2,4-oxadiazol-3-yl]-1,1-difluoro-6-azaspiro[2.5]octane-6-sulfonamide;
(1R)-1-[5-(5-Fluoro-2-methoxyphenyl)-1,2,4-oxadiazol-3-yl]-6-azaspiro[2.5]octane-6-sulfonamide;
(1R)-1-[5-(1-Cyclopropyl-3-methyl-1H-indol-5-yl)-1,2,4-oxadiazol-3-yl]-6-azaspiro[2.5]octane-6-sulfonamide;
(1R)-1-[5-(2-Methylpyridin-3-yl)-1,2,4-oxadiazol-3-yl]-6-azaspiro[2.5]octane-6-sulfonamide;
(1R)-1-{5-[3-(Propan-2-yl)cyclobutyl]-1,2,4-oxadiazol-3-yl}-6-azaspiro[2.5]octane-6-sulfonamide;
(1R)-1-{5-[2-Fluoro-6-(trifluoromethyl)benzyl]-1,2,4-oxadiazol-3-yl}-6-azaspiro[2.5]octane-6-sulfonamide;
(1R)-1-{5-[2-Fluoro-5-(trifluoromethyl)benzyl]-1,2,4-oxadiazol-3-yl}-6-azaspiro[2.5]octane-6-sulfonamide;
(1R)-1-[5-(2,6-Dimethylbenzyl)-1,2,4-oxadiazol-3-yl]-6-azaspiro[2.5]octane-6-sulfonamide;
(1R)-1-[5-(3-Methylcyclohexyl)-1,2,4-oxadiazol-3-yl]-6-azaspiro[2.5]octane-6-sulfonamide;
(1R)-1-{5-[1-(2-Chlorophenyl)ethyl]-1,2,4-oxadiazol-3-yl}-6-azaspiro[2.5]octane-6-sulfonamide;
(1R)-1-{5-[5-Fluoro-2-(trifluoromethyl)benzyl]-1,2,4-oxadiazol-3-yl}-6-azaspiro[2.5]octane-6-sulfonamide;
(1R)-1-{5-[1-(2,5-Difluorophenyl)cyclobutyl]-1,2,4-oxadiazol-3-yl}-6-azaspiro[2.5]octane-6-sulfonamide;
(1R)-1-[5-(Spiro[2.5]oct-4-yl)-1,2,4-oxadiazol-3-yl]-6-azaspiro[2.5]octane-6-sulfonamide;
(1R)-1-{5-[4-Fluoro-2-(trifluoromethyl)benzyl]-1,2,4-oxadiazol-3-yl}-6-azaspiro[2.5]octane-6-sulfonamide;
(1R)-1-[5-(4-Fluoro-2,3-dihydro-1H-inden-1-yl)-1,2,4-oxadiazol-3-yl]-6-azaspiro[2.5]octane-6-sulfonamide;
(1R)-1-(5-{1-[3-(Trifluoromethyl)phenyl]cyclopropyl}-1,2,4-oxadiazol-3-yl)-6-azaspiro[2.5]octane-6-sulfonamide;
(1R)-1-[5-(3-Phenylcyclobutyl)-1,2,4-oxadiazol-3-yl]-6-azaspiro[2.5]octane-6-sulfonamide;
(1R)-1-[5-(3,6-Dimethylpyridin-2-yl)-1,2,4-oxadiazol-3-yl]-6-azaspiro[2.5]octane-6-sulfonamide;
(1R)-1-{5-[6-(Trifluoromethyl)pyridin-2-yl]-1,2,4-oxadiazol-3-yl}-6-azaspiro[2.5]octane-6-sulfonamide;
(1R)-1-{5-[2-(2,2,2-Trifluoroethoxy)pyridin-4-yl]-1,2,4-oxadiazol-3-yl}-6-azaspiro[2.5]octane-6-sulfonamide;
(1R)-1-{5-[3-Methyl-6-(trifluoromethyl)pyridin-2-yl]-1,2,4-oxadiazol-3-yl}-6-azaspiro[2.5]octane-6-sulfonamide;
(1R)-1-[5-(Spiro[3.3]hept-2-yl)-1,2,4-oxadiazol-3-yl]-6-azaspiro[2.5]octane-6-sulfonamide;
(1R)-1-[5-(1-Ethyl-3-methyl-1H-pyrazol-5-yl)-1,2,4-oxadiazol-3-yl]-6-azaspiro[2.5]octane-6-sulfonamide;
(1R)-1-{5-[1-(2,2,2-Trifluoroethyl)-1H-pyrazol-4-yl]-1,2,4-oxadiazol-3-yl}-6-azaspiro[2.5]octane-6-sulfonamide;
(1R)-1-{5-[4-(Trifluoromethyl)-1,3-oxazol-5-yl]-1,2,4-oxadiazol-3-yl}-6-azaspiro[2.5]octane-6-sulfonamide;
(1R)-1-[5-(4-Ethyl-1,3-oxazol-5-yl)-1,2,4-oxadiazol-3-yl]-6-azaspiro[2.5]octane-6-sulfonamide;
(1R)-1-{5-[1-(2,2,2-Trifluoroethyl)-1H-pyrazol-3-yl]-1,2,4-oxadiazol-3-yl}-6-azaspiro[2.5]octane-6-sulfonamide;
(1R)-1-[5-(3-Cyclopropylisoxazol-4-yl)-1,2,4-oxadiazol-3-yl]-6-azaspiro[2.5]octane-6-sulfonamide;
(1R)-1-[5-(4,5-Dimethylisoxazol-3-yl)-1,2,4-oxadiazol-3-yl]-6-azaspiro[2.5]octane-6-sulfonamide;
(1R)-1-{5-[(3,5-Dimethylisoxazol-4-yl)methyl]-1,2,4-oxadiazol-3-yl}-6-azaspiro[2.5]octane-6-sulfonamide;
(1R)-1-{5-[3-(Trifluoromethyl)isoxazol-4-yl]-1,2,4-oxadiazol-3-yl}-6-azaspiro[2.5]octane-6-sulfonamide;
(1R)-1-{5-(1-Cyclopropyl-1H-pyrazol-5-yl)-1,2,4-oxadiazol-3-yl]-6-azaspiro[2.5]octane-6-sulfonamide;
(1R)-1-{5-[2-(1H-Imidazol-1-yl)-5-(trifluoromethyl)pyridin-4-yl]-1,2,4-oxadiazol-3-yl}-6-azaspiro[2.5]octane-6-sulfonamide;
(1R)-1-{5-[1-Methyl-4-(trifluoromethyl)-1H-pyrazol-5-yl]-1,2,4-oxadiazol-3-yl}-6-azaspiro[2.5]octane-6-sulfonamide;
(2R)-2-{5-[2-(Cyclopropyloxy)pyridin-4-yl]-1,2,4-oxadiazol-3-yl}-1,1-difluoro-6-azaspiro[2.5]octane-6-sulfonamide;
(2R)-2-[5-(1-Cyclopropyl-1H-pyrazol-5-yl)-1,2,4-oxadiazol-3-yl]-1,1-difluoro-6-azaspiro[2.5]octane-6-sulfonamide;
(2R)-2-[5-(1-tert-Butyl-1H-pyrazol-5-yl)-1,2,4-oxadiazol-3-yl]-1,1-difluoro-6-azaspiro[2.5]octane-6-sulfonamide;
(2R)-1,1-Difluoro-2-[5-(3-methylimidazo[1,2-a]pyridin-7-yl)-1,2,4-oxadiazol-3-yl]-6-azaspiro[2.5]octane-6-sulfonamide;
(2R)-2-[5-(3-Cyclopropyl-1-ethyl-1H-pyrazol-4-yl)-1,2,4-oxadiazol-3-yl]-1,1-difluoro-6-azaspiro[2.5]octane-6-sulfonamide;
(2R)-1,1-Difluoro-2-{5-[1-methyl-5-(trifluoromethyl)-1H-pyrazol-4-yl]-1,2,4-oxadiazol-3-yl}-6-azaspiro[2.5]octane-6-sulfonamide;
(2R)-2-{5-[1-tert-Butyl-5-(trifluoromethyl)-1H-pyrazol-4-yl]-1,2,4-oxadiazol-3-yl}-1,1-difluoro-6-azaspiro[2.5]octane-6-sulfonamide;
(2R)-1,1-Difluoro-2-[5-(4,5,6,7-tetrahydropyrazolo[1,5-a]pyridin-3-yl)-1,2,4-oxadiazol-3-yl]-6-azaspiro[2.5]octane-6-sulfonamide;
(2R)-2-[5-(1-Cyclopropyl-4-methyl-1H-pyrazol-5-yl)-1,2,4-oxadiazol-3-yl]-1,1-difluoro-6-azaspiro[2.5]octane-6-sulfonamide;
(2R)-2-[5-(5,6-Dihydro-4H-pyrrolo[1,2-b]pyrazol-3-yl)-1,2,4-oxadiazol-3-yl]-1,1-difluoro-6-azaspiro[2.5]octane-6-sulfonamide;

(2R)-1,1-Difluoro-2-[5-(1-methyl-1H-pyrazol-5-yl)-1,2,4-oxadiazol-3-yl]-6-azaspiro[2.5]octane-6-sulfonamide;
(2R)-1,1-Difluoro-2-[5-(1-methyl-1,4,5,6-tetrahydrocyclopenta[c]pyrazol-3-yl)-1,2,4-oxadiazol-3-yl]-6-azaspiro[2.5]octane-6-sulfonamide;
(2R)-1,1-Difluoro-2-{5-[1-methyl-3-(trifluoromethyl)-1H-pyrazol-5-yl]-1,2,4-oxadiazol-3-yl}-6-azaspiro[2.5]octane-6-sulfonamide;
(2R)-2-{5-[1-Cyclopropyl-5-(trifluoromethyl)-1H-pyrazol-3-yl]-1,2,4-oxadiazol-3-yl}-1,1-difluoro-6-azaspiro[2.5]octane-6-sulfonamide;
(2R)-2-[5-(2-Cyclopropyl-4,5,6,7-tetrahydro-2H-indazol-3-yl)-1,2,4-oxadiazol-3-yl]-1,1-difluoro-6-azaspiro[2.5]octane-6-sulfonamide;
(2R)-2-{5-[1-Cyclopropyl-4-(trifluoromethyl)-1H-pyrazol-5-yl]-1,2,4-oxadiazol-3-yl}-1,1-difluoro-6-azaspiro[2.5]octane-6-sulfonamide;
(2R)-2-[5-(3-Cyclopropylpyridazin-4-yl)-1,2,4-oxadiazol-3-yl]-1,1-difluoro-6-azaspiro[2.5]octane-6-sulfonamide;
(1R)-1-[5-(3-Cyclopropylpyridazin-4-yl)-1,2,4-oxadiazol-3-yl]-6-azaspiro[2.5]octane-6-sulfonamide;
(2R)-1,1-Difluoro-2-{5-[2-(propan-2-yloxy)pyridin-4-yl]-1,2,4-oxadiazol-3-yl}-6-azaspiro[2.5]octane-6-sulfonamide;
(1R)-1-[5-(1,4-Dimethyl-1H-pyrazol-5-yl)-1,2,4-oxadiazol-3-yl]-6-azaspiro[2.5]octane-6-sulfonamide;
(2R)-1,1-Difluoro-2-[5-(4H-pyrazolo[1,5-c][1,3]thiazol-3-yl)-1,2,4-oxadiazol-3-yl]-6-azaspiro[2.5]octane-6-sulfonamide;
(2R)-2-{5-[1-Cyclopropyl-5-methyl-3-(trifluoromethyl)-1H-pyrazol-4-yl]-1,2,4-oxadiazol-3-yl}-1,1-difluoro-6-azaspiro[2.5]octane-6-sulfonamide;
(2R)-2-{5-[3-Cyclopropyl-5-(trifluoromethyl)isoxazol-4-yl]-1,2,4-oxadiazol-3-yl}-1,1-difluoro-6-azaspiro[2.5]octane-6-sulfonamide;
(2R)-1,1-Difluoro-2-[5-(pyridin-3-yl)-1,2,4-oxadiazol-3-yl]-6-azaspiro[2.5]octane-6-sulfonamide;
(1R)-1-{5-[4-(Trifluoromethyl)pyridin-3-yl]-1,2,4-oxadiazol-3-yl}-6-azaspiro[2.5]octane-6-sulfonamide;
(1R)-1-{5-[2-(Trifluoromethyl)pyridin-3-yl]-1,2,4-oxadiazol-3-yl}-6-azaspiro[2.5]octane-6-sulfonamide;
(1R)-1-{5-[2-(2,2,2-Trifluoroethoxy)pyridin-3-yl]-1,2,4-oxadiazol-3-yl}-6-azaspiro[2.5]octane-6-sulfonamide;
(1R)-1-{5-[5-(2,2,2-Trifluoroethoxy)pyridin-3-yl]-1,2,4-oxadiazol-3-yl}-6-azaspiro[2.5]octane-6-sulfonamide;
(1R)-1-{5-[2-Methyl-5-(trifluoromethyl)pyridin-3-yl]-1,2,4-oxadiazol-3-yl}-6-azaspiro[2.5]octane-6-sulfonamide;
(1R)-1-{5-[1-(Propan-2-yl)-1H-pyrazol-5-yl]-1,2,4-oxadiazol-3-yl}-6-azaspiro[2.5]octane-6-sulfonamide;
(1R)-1-{5-[6-(2,2,2-Trifluoroethoxy)pyridin-3-yl]-1,2,4-oxadiazol-3-yl}-6-azaspiro[2.5]octane-6-sulfonamide;
(1R)-1-[5-(1-Cyclopropyl-4-methyl-1H-pyrazol-5-yl)-1,2,4-oxadiazol-3-yl]-6-azaspiro[2.5]octane-6-sulfonamide;
(1R)-1-[5-(2-Methyl-4,5,6,7-tetrahydro-2H-indazol-3-yl)-1,2,4-oxadiazol-3-yl]-6-azaspiro[2.5]octane-6-sulfonamide;
(2R)-1,1-Difluoro-2-[5-(2-methyl-4,5,6,7-tetrahydro-2H-indazol-3-yl)-1,2,4-oxadiazol-3-yl]-6-azaspiro[2.5]octane-6-sulfonamide;
(2R)-1,1-Difluoro-2-[5-(pyridin-2-yl)-1,2,4-oxadiazol-3-yl]-6-azaspiro[2.5]octane-6-sulfonamide;
(2R)-1,1-Difluoro-2-{5-[3-(trifluoromethyl)isoxazol-4-yl]-1,2,4-oxadiazol-3-yl}-6-azaspiro[2.5]octane-6-sulfonamide;
(1R)-1-[5-(2,3-Dihydro-1H-inden-4-yl)-1,2,4-oxadiazol-3-yl]-6-azaspiro[2.5]octane-6-sulfonamide;
(1R)-1-(5-{3-[5-(Trifluoromethyl)-1H-pyrazol-1-yl]phenyl}-1,2,4-oxadiazol-3-yl)-6-azaspiro[2.5]octane-6-sulfonamide;
(1R)-1-[5-(2-Phenoxyphenyl)-1,2,4-oxadiazol-3-yl]-6-azaspiro[2.5]octane-6-sulfonamide;
(1R)-1-[5-(5,6,7,8-Tetrahydronaphthalen-2-yl)-1,2,4-oxadiazol-3-yl]-6-azaspiro[2.5]octane-6-sulfonamide;
(1R)-1-{5-[2-(1H-Pyrrol-1-yl)phenyl]-1,2,4-oxadiazol-3-yl}-6-azaspiro[2.5]octane-6-sulfonamide;
(1R)-1-[5-(4'-Fluorobiphenyl-3-yl)-1,2,4-oxadiazol-3-yl]-6-azaspiro[2.5]octane-6-sulfonamide;
(1R)-1-{5-[2-(1-Cyanocyclopropyl)phenyl]-1,2,4-oxadiazol-3-yl}-6-azaspiro[2.5]octane-6-sulfonamide;
(1R)-1-{5-[2-(Pyrimidin-2-yl)phenyl]-1,2,4-oxadiazol-3-yl}-6-azaspiro[2.5]octane-6-sulfonamide;
(1R)-1-{5-[2-(1H-Pyrazol-1-yl)phenyl]-1,2,4-oxadiazol-3-yl}-6-azaspiro[2.5]octane-6-sulfonamide;
(1R)-1-{5-[3-(2,2,2-Trifluoroethoxy)pyridin-2-yl]-1,2,4-oxadiazol-3-yl}-6-azaspiro[2.5]octane-6-sulfonamide;
(1R)-1-{5-[4-Fluoro-2-(trifluoromethyl)phenyl]-1,3,4-oxadiazol-2-yl}-6-azaspiro[2.5]octane-6-sulfonamide;
(1R)-1-{5-[3-(Trifluoromethyl)phenyl]-1,3,4-oxadiazol-2-yl}-6-azaspiro[2.5]octane-6-sulfonamide;
(1R)-1-{5-[3-(Trifluoromethoxy)phenyl]-1,3,4-oxadiazol-2-yl}-6-azaspiro[2.5]octane-6-sulfonamide;
(1R)-1-[5-(2,5-Difluorophenyl)-1,3,4-thiadiazol-2-yl]-6-azaspiro[2.5]octane-6-sulfonamide;
(1R)-1-[5-(5-Fluoro-2-methylphenyl)-1,3,4-oxadiazol-2-yl]-6-azaspiro[2.5]octane-6-sulfonamide;
(1R)-1-{5-[2-(2,2,2-Trifluoroethoxy)phenyl]-1,3,4-oxadiazol-2-yl}-6-azaspiro[2.5]octane-6-sulfonamide;
(1R)-1-{5-[2-(2,2,2-Trifluoroethoxy)phenyl]-1,3,4-thiadiazol-2-yl}-6-azaspiro[2.5]octane-6-sulfonamide;
(1R)-1-[5-(2-Methylphenyl)-1,3,4-thiadiazol-2-yl]-6-azaspiro[2.5]octane-6-sulfonamide;
(1R)-1-{5-[4-Fluoro-2-(trifluoromethyl)phenyl]-1,3,4-thiadiazol-2-yl}-6-azaspiro[2.5]octane-6-sulfonamide;
(1R)-1-{5-[3-(Difluoromethoxy)phenyl]-1,3,4-thiadiazol-2-yl}-6-azaspiro[2.5]octane-6-sulfonamide;
(1R)-1-[5-(3-Cyclopropyl-5-methylisoxazol-4-yl)-1,3,4-oxadiazol-2-yl]-6-azaspiro[2.5]octane-6-sulfonamide;
(1R)-1-[5-(3-Cyclopropyl-5-methylisoxazol-4-yl)-1,3,4-thiadiazol-2-yl]-6-azaspiro[2.5]octane-6-sulfonamide;
(2R)-1,1-Difluoro-2-[5-(2-methylphenyl)-1,3,4-oxadiazol-2-yl]-6-azaspiro[2.5]octane-6-sulfonamide;
(2R)-1,1-Difluoro-2-[5-(2-methylphenyl)-1,3,4-thiadiazol-2-yl]-6-azaspiro[2.5]octane-6-sulfonamide;
(1R)-1-(4-Phenyl-1,3-oxazol-2-yl)-6-azaspiro[2.5]octane-6-sulfonamide;
(1R)-1-[2-(3-Cyclopropylisoxazol-4-yl)-1,3-thiazol-4-yl]-6-azaspiro[2.5]octane-6-sulfonamide;
(1R)-1-[1-(3,5-Dimethylisoxazol-4-yl)-1H-pyrazol-4-yl]-6-azaspiro[2.5]octane-6-sulfonamide;
(2R)-2-[2-(3-Cyclopropylisoxazol-4-yl)-1,3-thiazol-4-yl]-1,1-difluoro-6-azaspiro[2.5]octane-6-sulfonamide;
(2R)-2-{3-[2-(Difluoromethoxy)pyridin-4-yl]isoxazol-5-yl}-1,1-difluoro-6-azaspiro[2.5]octane-6-sulfonamide;
(2R)-2-[4-(3-Cyclopropylisoxazol-4-yl)-1-methyl-1H-imidazol-2-yl]-1,1-difluoro-6-azaspiro[2.5]octane-6-sulfonamide;
(2R)-2-(3'-Cyclopropyl-3,4'-biisoxazol-5-yl)-1,1-difluoro-6-azaspiro[2.5]octane-6-sulfonamide;
(2R)-1,1-Difluoro-2-{4-[4-fluoro-2-(trifluoromethyl)phenyl]-1,3-oxazol-2-yl}-6-azaspiro[2.5]octane-6-sulfonamide;
(1S)-1-[3-(5-Chloro-2-methoxyphenyl)-1,2,4-oxadiazol-5-yl]-6-azaspiro[2.5]octane-6-sulfonamide;

(2S)-1,1-Difluoro-2-{3-[4-fluoro-2-(trifluoromethyl)phenyl]-1,2,4-oxadiazol-5-yl}-6-azaspiro[2.5]octane-6-sulfonamide;
(2S)-2-(3-Cyclohexyl-1,2,4-oxadiazol-5-yl)-1,1-difluoro-6-azaspiro[2.5]octane-6-sulfonamide;
(2S)-1,1-Difluoro-2-[3-(3-fluorophenyl)-1,2,4-oxadiazol-5-yl]-6-azaspiro[2.5]octane-6-sulfonamide;
(2S)-1,1-Difluoro-2-[5-(2-methylphenyl)-1,3,4-oxadiazol-2-yl]-6-azaspiro[2.5]octane-6-sulfonamide;
(2R)-1,1-Difluoro-2-[5-(2-methylphenyl)-1,3,4-thiadiazol-2-yl]-6-azaspiro[2.5]octane-6-sulfonamide;
1-{3-[3-(Difluoromethoxy)phenyl]-1,2,4-oxadiazol-5-yl}-4-fluoro-6-azaspiro[2.5]octane-6-sulfonamide;
1-{3-[3-(Difluoromethoxy)phenyl]-1,2,4-oxadiazol-5-yl}-4-fluoro-6-azaspiro[2.5]octane-6-sulfonamide;
4,4-Difluoro-1-(3-phenyl-1,2,4-oxadiazol-5-yl)-6-azaspiro[2.5]octane-6-sulfonamide;
1-[3-(2,5-Dimethylphenyl)-1,2,4-oxadiazol-5-yl]-4,4-difluoro-6-azaspiro[2.5]octane-6-sulfonamide;
4-Methyl-1-{3-[2-(2,2,2-trifluoroethoxy)pyridin-4-yl]-1,2,4-oxadiazol-5-yl}-6-azaspiro[2.5]octane-6-sulfonamide;
1-[3-(3-Cyclopropylisoxazol-4-yl)-1,2,4-oxadiazol-5-yl]-4-fluoro-6-azaspiro[2.5]octane-6-sulfonamide;
1-[3-(3-Cyclopropylisoxazol-4-yl)-1,2,4-oxadiazol-5-yl]-4-fluoro-6-azaspiro[2.5]octane-6-sulfonamide;
1-[3-(3-Cyclopropylisoxazol-4-yl)-1,2,4-oxadiazol-5-yl]-4-fluoro-6-azaspiro[2.5]octane-6-sulfonamide;
1-[3-(3-Cyclopropylisoxazol-4-yl)-1,2,4-oxadiazol-5-yl]-4-fluoro-6-azaspiro[2.5]octane-6-sulfonamide;
1-[3-(3-Cyclopropylisoxazol-4-yl)-1,2,4-oxadiazol-5-yl]-4-fluoro-6-azaspiro[2.5]octane-6-sulfonamide;
2-[3-(3-Cyclopropylisoxazol-4-yl)-1,2,4-oxadiazol-5-yl]-1,1,4-trifluoro-6-azaspiro[2.5]octane-6-sulfonamide;
2-[3-(3-Cyclopropylisoxazol-4-yl)-1,2,4-oxadiazol-5-yl]-1,1,4-trifluoro-6-azaspiro[2.5]octane-6-sulfonamide;
2-[3-(3-Cyclopropylisoxazol-4-yl)-1,2,4-oxadiazol-5-yl]-1,1,4-trifluoro-6-azaspiro[2.5]octane-6-sulfonamide;
2-[3-(3-Cyclopropylisoxazol-4-yl)-1,2,4-oxadiazol-5-yl]-1,1,4-trifluoro-6-azaspiro[2.5]octane-6-sulfonamide;
1,1,4-Trifluoro-2-{3-[4-fluoro-2-(trifluoromethyl)phenyl]-1,2,4-oxadiazol-5-yl}-6-azaspiro[2.5]octane-6-sulfonamide;
1,1,4-Trifluoro-2-{3-[4-fluoro-2-(trifluoromethyl)phenyl]-1,2,4-oxadiazol-5-yl}-6-azaspiro[2.5]octane-6-sulfonamide;
1,1,4-Trifluoro-2-{3-[4-fluoro-2-(trifluoromethyl)phenyl]-1,2,4-oxadiazol-5-yl}-6-azaspiro[2.5]octane-6-sulfonamide;
1,1-Difluoro-2-{3-[4-fluoro-2-(trifluoromethyl)phenyl]-1,2,4-thiadiazol-5-yl}-6-azaspiro[2.5]octane-6-sulfonamide;
1-Fluoro-2-{3-[4-fluoro-2-(trifluoromethyl)phenyl]-1,2,4-oxadiazol-5-yl}-6-azaspiro[2.5]octane-6-sulfonamide;
1-{3-[4-Fluoro-2-(trifluoromethyl)phenyl]-1,2,4-oxadiazol-5-yl}-2-methyl-6-azaspiro[2.5]octane-6-sulfonamide;
2-{3-[4-Fluoro-2-(trifluoromethyl)phenyl]-1,2,4-oxadiazol-5-yl}-1,1-dimethyl-6-azaspiro[2.5]octane-6-sulfonamide;
1,1-Difluoro-2-{5-[4-fluoro-2-(trifluoromethyl)phenyl]isothiazol-3-yl}-6-azaspiro[2.5]octane-6-sulfonamide;
1-[5-(5-Chloro-2-methoxyphenyl)-1,2,4-oxadiazol-3-yl]-6-(methylsulfonyl)-6-azaspiro[2.5]octane;
1,1-Difluoro-2-[5-(piperidin-1-yl)-1,2,4-thiadiazol-3-yl]-6-azaspiro[2.5]octane-6-sulfonamide;
1,1-Difluoro-2-[5-(piperidin-1-yl)-1,2,4-thiadiazol-3-yl]-6-azaspiro[2.5]octane-6-sulfonamide;
3'-[5-(2,5-Dimethylphenyl)-1,2,4-oxadiazol-3-yl]-2',2'-difluoro-3-azaspiro[bicyclo[3.2.1]octane-8,1'-cyclopropane]-3-sulfonamide; and 2-[5-(2,5-Dimethylphenyl)-1,2,4-oxadiazol-3-yl]-1,1-difluoro-5-methyl-6-azaspiro[2.5]octane-6-sulfonamide.

Other embodiments of the present invention include the following:

(a) A pharmaceutical composition comprising a compound of formula I or II and a pharmaceutically acceptable carrier.

(b) The pharmaceutical composition of (a), further comprising a second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

(c) The pharmaceutical composition of (b), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(d) A pharmaceutical combination that is (i) a compound of formula I or II and (ii) a second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa wherein the compound of formula I or II and the second therapeutic agent are each employed in an amount that renders the combination effective for treating cognitive impairments associated with Alzheimer's disease, Parkinson's disease, or schizophrenia.

(e) The combination of (d), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(f) A use of a compound of formula I or II in the preparation of a medicament for modulating α7 nAChR activity in a subject in need thereof.

(g) A use of a compound of formula I or II in the preparation of a medicament for treating cognitive impairments associated with Alzheimer's disease, Parkinson's disease, and schizophrenia in a subject in need thereof.

(h) A method of treating cognitive impairments associated with Alzheimer's disease, Parkinson's disease, and schizophrenia and/or reducing the likelihood or severity of symptoms of cognitive impairments associated with Alzheimer's disease, Parkinson's disease, and schizophrenia in a subject in need thereof, which comprises administering to the subject an effective amount of a compound of formula I or II.

(i) The method of (h), wherein the compound of formula I or II is administered in combination with an effective amount of at least one second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGuR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

(j) The method of (i), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(k) A method of modulating α7 nAChR activity in a subject in need thereof, which comprises administering to the subject the pharmaceutical composition of (a), (b), or (c) or the combination of (d) or (e).

(l) A method of treating cognitive impairments associated with Alzheimer's disease, Parkinson's disease, and schizophrenia and/or reducing the likelihood or severity of symptoms of cognitive impairments associated with Alzheimer's disease, Parkinson's disease, and schizophrenia in a subject in need thereof, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (l) above are understood to include all embodiments of the compounds and/or salts, including such embodiments as result from combinations of embodiments.

Additional embodiments of the invention include the pharmaceutical compositions, combinations, uses and methods set forth in (a) through (l) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

The present invention also includes a compound of the present invention for use (i) in, (ii) as a medicament for, or (iii) in the preparation of a medicament for: (a) preventing or treating cognitive impairments associated with Alzheimer's disease, Parkinson's disease, schizophrenia, and L-DOPA induced-dyskinesia, or (b) treating cognitive impairments associated with Alzheimer's disease, Parkinson's disease, schizophrenia, and L-DOPA induced-dyskinesia and/or reducing the likelihood or severity of symptoms of cognitive impairments associated with Alzheimer's disease, Parkinson's disease, schizophrenia, and L-DOPA induced-dyskinesia, or (c) use in medicine. In these uses, the compounds of the present invention can optionally be employed in combination with one or more second therapeutic agents selected from acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

Chemical names, common names, and chemical structures may be used interchangeably to describe the same structure. If a chemical compound is referred to using both a chemical structure and a chemical name and an ambiguity exists between the structure and the name, the structure is understood to predominate.

As used herein, the term "5-membered heteroaryl ring" refers to a stable unsaturated 5-membered ring that contains from 1 to 4 heteroatoms selected from the group consisting of O, N, and S. A 5-membered heteroaryl ring within the scope of this definition includes but is not limited to: furanyl, imidazolyl, isothiazolyl, isoxazolyl, oxadiazolyl, oxazolyl, pyrazolyl, pyrrolyl, tetrazolyl, thiadiazolyl, thiazolyl, thienyl, and triazolyl.

In another embodiment, "5-membered heteroaryl ring" is furanyl, imidazolyl, isothiazolyl, isoxazolyl, oxadiazolyl, oxazolyl, pyrazolyl, pyrrolyl, tetrazolyl, thiadiazolyl, thiazolyl, thienyl, and triazolyl.

As used herein, the term "administration" and variants thereof (e.g., "administering" a compound) in reference to a compound of the invention means providing the compound to the individual in need of treatment. When a compound of the invention is provided in combination with one or more other active agents (e.g., cholinesterase inhibitors such as donepezil, rivastigmine, and galantamine), "administration" and its variants are each understood to include concurrent and sequential administration of the compound or salt and other agents.

The term "alkenyl" refers to a hydrocarbon radical straight or branched containing from 2 to 12 carbon atoms and at least one carbon to carbon double bond. Up to four carbon-carbon double bonds may be present. Thus, "$C_2$-$C_6$ alkenyl" means an alkenyl radical having from 2 to 6 carbon atoms. Thus, "$C_2$-$C_4$ alkenyl" means an alkenyl radical having from 2 to 4 carbon atoms. Alkenyl groups include ethenyl, propenyl, butenyl, 3-methylbutenyl and so on. In one embodiment, an alkenyl group is linear. In another embodiment, an alkenyl group is branched.

The term "alkyl" refers to an aliphatic hydrocarbon group having one of its hydrogen atoms replaced with a bond. An alkyl group may be straight or branched. An alkyl group contains from 1 to 8 carbon atoms [($C_1$-$C_8$)alkyl] or from 1 to 6 carbon atoms [($C_1$-$C_6$)alkyl] or from 1 to 4 carbon atoms [($C_1$-$C_4$)alkyl]. Non-limiting examples of alkyl groups include methyl (Me), ethyl, n-propyl, isopropyl, n-butyl, sec-butyl, isobutyl, and tert-butyl. In one embodiment, an alkyl group is linear. In another embodiment, an alkyl group is branched.

When "alkyl" is substituted, said "alkyl" includes alkyl, O-alkyl, S-alkyl and (C=O)-alkyl.

The term "alkynyl" refers to a hydrocarbon radical straight or branched containing from 2 to 12 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Thus, "$C_2$-$C_4$ alkynyl" means an alkynyl radical having from 2 to 4 carbon atoms. Alkynyl groups include ethynyl, propynyl, butynyl, 3-methylbutynyl and so on. In one embodiment, an alkynyl group is linear. In another embodiment, an alkynyl group is branched.

The term "aryl" refers to any mono- and poly-carbocyclic ring systems wherein the individual carbocyclic rings in the polyring systems are fused or attached to each other via a single bond and wherein at least one ring is aromatic. Suitable aryl groups include phenyl, indanyl, naphthyl, tetrahydronaphthyl, and biphenyl. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

In an embodiment, "aryl" is phenyl.

When "aryl" is substituted, said "aryl" includes aryl and O-aryl.

The term "composition" is intended to encompass a product comprising the specified ingredients, as well as any product which results from combining the specified ingredients.

The term "compound" is intended to encompass chemical agents described by generic formula I or II in all forms. Such chemical agents can be present in different forms such as hydrates, solvates, and polymorphs.

The term "cycloalkyl" as used herein, refers to any non-aromatic mono- and poly-carbocyclic ring systems comprising from 3 to 10 ring carbon atoms [($C_3$-$C_{10}$) cycloalkyl], or from 3 to 6 ring carbon atoms [($C_3$-$C_6$) cycloalkyl] wherein the individual carbocyclic rings in the polyring systems are fused, including spiro ring fusions, or attached to each other via a single bond. Non-limiting examples of monocyclic cycloalkyls include cyclopropyl, cyclobutyl, cyclopentyl, cyclohexyl, bicyclo[4.1.0]heptyl, spiro[2.4]heptyl, spiro[3.3]heptyl, spiro[2.5]octyl, and cycloheptyl. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

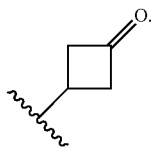 [SMILES: *C1CC(=O)C1]

When "cycloalkyl" is substituted, said "cycloalkyl" includes cycloalkyl, O-cycloalkyl and (C=O)-cycloalkyl.

In an embodiment, "cycloalkyl" is cyclopropyl, cyclobutyl, cyclopentyl or cyclohexyl.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to modulate α7 nAChR activity and thereby elicit the response being sought (i.e., a "therapeutically effective amount"). When the active compound (i.e., active ingredient) is administered as the salt, references to the amount of active ingredient are to the free acid or free base form of the compound.

The term "halogen" (or "halo") refers to atoms of fluorine, chlorine, bromine and iodine (alternatively referred to as fluoro (F), chloro (Cl), bromo (Br), and iodo (I)).

The term "heteroaryl" as used herein, refers to any monocyclic or multicyclic ring system comprising 5 to 14 ring atoms, wherein from 1 to 4 of the ring atoms is independently O, N, or S and the remaining ring atoms are carbon atoms, and wherein at least one ring is aromatic. In one embodiment, a heteroaryl group has 5 to 10 ring atoms. In another embodiment, a heteroaryl group is monocyclic and has 5 or 6 ring atoms. In another embodiment, a heteroaryl group is bicyclic and has 9 or 10 ring atoms. A heteroaryl group is usually joined via a ring carbon atom but may be joined via a non-carbon atom provided that this results in a stable compound, and any nitrogen atom of a heteroaryl can be optionally oxidized to the corresponding N-oxide. The term "heteroaryl" also encompasses a heteroaryl group, as defined above, which is fused to a benzene ring. The term "heteroaryl" also encompasses any fused polycyclic ring system containing at least one ring heteroatom selected from N, O, and S, wherein at least one ring of the fused polycyclic ring system is aromatic. For example, the term "9 to 10-membered bicyclic heteroaryl" encompasses a non-aromatic 5 membered heterocyclic ring that is fused to a benzene or pyridyl ring. Non-limiting examples of heteroaryls include benzimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzoyl and the like, and all isomeric forms thereof. The term "heteroaryl" also refers to partially saturated heteroaryl moieties such as, for example, tetrahydroisoquinolyl, tetrahydroquinolyl and the like, provided that they contain at least one aromatic ring. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring.

In an embodiment, "heteroaryl" is benzimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, or triazolyl.

In another embodiment, "heteroaryl" is carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, or triazolyl.

In another embodiment, "heteroaryl" is furanyl, imidazolyl, indolinyl, indolyl, indolazinyl, indazolyl, isoindolyl, isoquinolyl, isothiazolyl, isoxazolyl, oxadiazolyl, oxazolyl, pyrazinyl, pyrazolyl, pyridazinyl, pyridazinyl, pyridyl, pyrimidyl, pyrrolyl, thiadiazolyl, thiazolyl, thienyl, or triazolyl.

The term "heterocycle" or "heterocyclyl" as used herein is intended to mean a 3- to 10-membered non-aromatic heterocycle containing from 1 to 4 heteroatoms selected from the group consisting of O, N, and S, and includes monocyclic or bicyclic groups (fused, bridged or spirocyclic). Further examples of "heterocyclyl" include, but are not limited to the following: oxazoline, isoxazoline, oxetanyl, tetrahydropyranyl, azetidinyl, 1,4-dioxanyl, hexahydroazepinyl, piperazinyl, piperidinyl, pyrrolidinyl, morpholinyl, thiomorpholinyl, dihydrofuranyl, dihydroimidazolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, tetrahydrofuranyl, and tetrahydrothienyl, and N-oxides thereof. Attachment of a heterocyclyl substituent can occur via a carbon atom or via a heteroatom.

In an embodiment, "heterocycle" or "heterocyclyl" is oxazoline, isoxazoline, oxetanyl, tetrahydropyranyl, azetidinyl, 1,4-dioxanyl, hexahydroazepinyl, piperazinyl, piperidinyl, pyrrolidinyl, morpholinyl, or thiomorpholinyl.

In an embodiment, "heterocycle" or "heterocyclyl" is dihydrofuranyl, dihydroimidazolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, tetrahydrofuranyl, or tetrahydrothienyl.

By "pharmaceutically acceptable" is meant that the ingredients of the pharmaceutical composition must be compatible with each other and not deleterious to the recipient thereof.

The term "preventing" as used herein with respect to Alzheimer's disease or other neurological diseases, refers to reducing the likelihood of disease progression.

The term "subject" (alternatively referred to herein as "patient"), as used herein, refers to an animal, preferably a mammal, most preferably a human.

The term "substituted" means that one or more hydrogens on the designated atom is replaced with a selection from the indicated group, provided that the designated atom's normal valency under the existing circumstances is not exceeded, and that the substitution results in a stable compound. Unless expressly stated to the contrary, substitution by a named substituent is permitted on any atom provided such substitution is chemically allowed and results in a stable compound. Combinations of substituents and/or variables are permissible only if such combinations result in stable compounds. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

In another embodiment of formula I, X is $S(O)_2$.
In another embodiment of formula I, X is C(O).
In another embodiment of formula I, $R^1$ is $NR^aR^b$.
In another embodiment of formula I, R is $R^c$.

In another embodiment of formula I, $R^a$ is H, $(C_1-C_4)$ alkyl, or $(C_3-C_6)$cycloalkyl, wherein said alkyl is optionally substituted with phenyl, pyridinyl, or isothiazolyl.

In another embodiment of formula I, $R^a$ is H or $(C_1-C_4)$ alkyl.
In another embodiment of formula I, $R^a$ is H or methyl.
In another embodiment of formula I, $R^a$ is H.
In another embodiment of formula I, $R^b$ is H or methyl.
In another embodiment of formula I, $R^b$ is H.
In another embodiment of formula I, $R^c$ is $(C_1-C_4)$alkyl, thienyl, pyrazolyl, benzoxadiazolyl, benzothiazolyl, or oxadiazolyl, wherein said thienyl, pyrozolyl, benzoxadiazolyl, and oxadiazolyl are optionally substituted with one or more methyl or hydroxyl, and wherein said alkyl is optionally substituted with pyridinyl, tetrahydropyranyl, isothiazolyl, or phenyl.

In another embodiment of formula I, $R^c$ is methyl.
In another embodiment of formula I, —X—$R^1$ is —(C=O)—$R^1$.
In another embodiment of formula I, —X—$R^1$ is

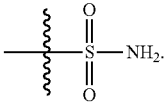 [SMILES: *S(N)(=O)=O]

In another embodiment of formula I or II, A (or Ring A) is oxadiazolyl, thiazolyl, pyrazolyl, thiadiazolyl, oxazolyl, imidazolyl, isothiazolyl, isoxazolyl, furanyl, thienyl, triazolyl, or pyrrolyl.

In another embodiment of formula I or II, A (or Ring A) is oxadiazolyl, thiazolyl, pyrazolyl, thiadiazolyl, oxazolyl, isoxazolyl, or imidazolyl.

In another embodiment of formula I or II, A (or Ring A) is oxadiazolyl, thiazolyl, oxazolyl, pyrazolyl, isoxazolyl, or thiadiazolyl.

In another embodiment of formula I or II, A (or Ring A) is oxadiazolyl, oxazolyl, isoxazolyl, or thiazolyl.

In another embodiment of formula I, R groups are selected from OH, oxo, $NR^6R^7$, CN, alkoxy, halogen, aminoalkyl, hydroxyalkyl, alkyl, alkenyl, alkynyl, cycloalkyl, aryl, heteroaryl, and heterocyclyl, wherein said R groups selected from alkyl, alkenyl, alkynyl, cycloalkyl, aryl, heteroaryl, and heterocyclyl, are further optionally substituted with one or more substituents independently selected from $R^{11}$.

In another embodiment of formula I, R groups are independently selected from $NR^6R^7$, CN, $(C_1-C_4)$alkoxy, halogen, $(C_1-C_4)$alkyl, $(C_3-C_5)$cycloalkyl, phenyl, indanyl, tetrahydronaphthalenyl, pyrazolyl, pyridinyl, oxazolyl, isoxazolyl, tetrahydrocyclopentapyrazolyl, imidazopyridinyl, indolyl, tetrahydropyrazolopyridinyl, dihydropyrrolopyrazolyl, pyridazinyl, pyrazolothiazolyl, and piperidinyl, wherein said alkoxy, alkyl, cycloalkyl, indanyl, tetrahydronaphthalenyl, pyrazolyl, pyridinyl, oxazolyl, isoxazolyl, tetrahydrocyclopentapyrazolyl, imidazopyridinyl, indolyl, tetrahydropyrazolopyridinyl, dihydropyrrolopyrazolyl, pyridazinyl, pyrazolothiazolyl, and piperidinyl are optionally substituted with one or more substituents independently selected from R.

In another embodiment of formula I, R is selected from $(C_3-C_8)$cycloalkyl, phenyl, indanyl, tetrahydronaphthalenyl, pyrazolyl, pyridinyl, oxazolyl, isoxazolyl, tetrahydrocyclopentapyrazolyl, imidazopyridinyl, indolyl, tetrahydropyrazolopyridinyl, dihydropyrrolopyrazolyl, pyridazinyl, pyrazolothiazolyl, and piperidinyl, each optionally substituted with one or more substituents independently selected from R.

In another embodiment of formula I, R is cyclobutyl, cyclopentyl, cyclohexyl, phenyl, pyrazolyl, pyridinyl or isoxazolyl, each optionally substituted with one or more substituents independently selected from F, Cl, Br, methyl, methoxy, ethyl, ethoxy, propyl, $CF_3$, $CH_2CF_3$, $OCH_3$, $OCHF_2$, $OCH_2CF_3$, cyclopropyl, $NR^6R^7$ and CN.

In another embodiment of formula I, R is selected from phenyl, pyrazolyl, pyridinyl and isoxazolyl, wherein said phenyl, pyrazolyl, pyridinyl and isoxazolyl are optionally substituted with one or more substituents independently selected from F, Cl, Br, methyl, methoxy, ethyl, ethoxy, propyl, $CF_3$, $CH_2CF_3$, $OCH_3$, $OCHF_2$, $OCH_2CF_3$, cyclopropyl, $NR^6R^7$ and CN.

In another embodiment of formula I, n is 0, 1, or 2.
In another embodiment of formula I, n is 0 or 1.
In another embodiment of formula I, n is 0.

In another embodiment of formula I, $R^2$ is independently halogen or $(C_1-C_4)$alkyl, wherein said alkyl is optionally substituted with one or more halogen;

or, two $R^2$ when both are $(C_1-C_4)$alkyl and attached to the same carbon atom, optionally can come together to form a cyclopropyl, cyclobutyl, or cyclopentyl ring or, when both are $(C_1-C_4)$alkyl and not attached to the same carbon atom, optionally can come together and form a bridged ring, wherein said cyclopropyl, cyclobutyl, cyclopentyl or bridged ring may be optionally substituted with one or more substituents independently selected from OH, halogen, or $(C_1-C_4)$alkyl.

In another embodiment of formula I, $R^2$ is independently halogen, methyl or ethyl, wherein said methyl or ethyl is optionally substituted with one or more halogen;

or, two $R^2$ when both are methyl or ethyl and attached to the same carbon atom, optionally can come together to form a cyclopropyl, cyclobutyl, or cyclopentyl ring or, when both are methyl or ethyl and not attached to the same carbon atom, optionally can come together and form a bridged ring.

In another embodiment of formula I, $R^2$ is F, or methyl.
In another embodiment of formula I or II, $R^3$ is H, F or methyl.
In another embodiment of formula I or II, $R^4$ is H, F or methyl.
In another embodiment of formula I or II, $R^3$ and $R^4$ optionally can come together to form a cyclopropyl, cyclobutyl, cyclopentyl or cyclohexyl ring wherein said ring may be optionally substituted with one or more substituents independently selected from OH, halogen, or $(C_1-C_4)$alkyl.
In another embodiment of formula I or II, $R^3$ and $R^4$ optionally can come together to form a cyclopropyl, cyclobutyl, cyclopentyl or cyclohexyl ring.
In another embodiment of formula I, $R^5$ is H or methyl.
In another embodiment of formula I, $R^5$ is H.
In another embodiment of formula I, $R^6$ is H or Me.
In another embodiment of formula I, $R^7$ is H or Me.
In another embodiment of formula I, R is OH, $(C_1-C_4)$alkyl, phenyl, pyridinyl, or isothiazolyl.
In another embodiment of formula I, $R^8$ is phenyl, pyridinyl, or isothiazolyl.
In another embodiment of formula I, $R^9$ is pyridinyl, tetrahydropyranyl, or phenyl.
In another embodiment of formula I, $R^{10}$ is methyl or hydroxyl.
In another embodiment of formula I, $R^{11}$ is halogen, OH, oxo, $CF_3$, $OCF_3$, CN, $(C_1-C_4)$alkyl, $O(C_1-C_4)$alkyl, $S(C_1-C_4)$alkyl, $C=O(C_1-C_4)$alkyl, $NR^{12}R^{13}$, $(C=O)NR^6R^7$, $(C=O)OR^6$, $(C_2-C_4)$alkynyl, $(C_3-C_6)$cycloalkyl, $O(C_3-C_6)$cycloalkyl, $C=O(C_3-C_6)$cycloalkyl, aryl, O-aryl, heteroaryl, or heterocyclyl, wherein said alkyl, cycloalkyl, aryl, heteroaryl, and heterocyclyl are optionally independently substituted with one or more halogen, $(C_1-C_4)$alkyl, $(C_3-C_6)$cycloalkyl, $CF_3$, $OCF_3$, $OCH_3$, CN, OH and oxo.

In another embodiment of formula I, $R^{11}$ is F, Cl, Br, OH, $NR^{12}R^{13}$, $CF_3$, $OCF_3$, CN, $(C_1-C_4)$alkyl, $O(C_1-C_4)$alkyl, $(C_3-C_6)$cycloalkyl, $O(C_3-C_6)$cycloalkyl, phenoxy, phenyl, pyridinyl, pyrimidinyl, pyrazolyl, pyrrolyl, or imidazolyl, wherein said alkyl, cycloalkyl, phenoxy, phenyl, pyridinyl, pyrimidinyl, pyrazolyl, pyrrolyl, and imidazolyl are optionally substituted with one or more substituents independently selected from halogen, $(C_1-C_4)$alkyl, CN, and OH, wherein said alkyl is optionally substituted with one or more fluoro.

In another embodiment of formula I, $R^{11}$ is F, Cl, Br, OH, $NR^{12}R^{13}$, $CF_3$, $OCF_3$, CN, $(C_1-C_4)$alkyl, $O(C_1-C_4)$alkyl, $(C_3-C_6)$cycloalkyl, $O(C_3-C_6)$cycloalkyl, phenoxy, phenyl, pyridinyl, pyrimidinyl, pyrazolyl, pyrrolyl, or imidazolyl, wherein said alkyl, cycloalkyl, phenoxy, phenyl, pyridinyl, pyrimidinyl, pyrazolyl, pyrrolyl, and imidazolyl are optionally substituted with one or more substituents independently selected from halogen, $(C_1-C_4)$alkyl, CN, and OH, wherein said alkyl is optionally substituted with one or more fluoro.

In another embodiment of formula I, $R^{11}$ is F, Cl, Br, methyl, methoxy, ethyl, ethoxy, propyl, $CF_3$, $CH_2CF_3$, $OCH_3$, $OCHF_2$, $OCH_2CF_3$, cyclopropyl, $NR^{12}R^{13}$, or CN.

In another embodiment of formula I, $R^{11}$ is F, Cl, Br, methyl, methoxy, ethyl, ethoxy, propyl, —$CH_2OH$, —$CH_2CH_2OH$, —$CF_3$, —$CH_2CF_3$, —$OCF_3$, —$OCHF_2$, —$OCH_2CF_3$, or cyclopropyl.

In another embodiment of formula I, $R^{12}$ is H or $(C_1-C_4)$alkyl.

In another embodiment of formula I, $R^{13}$ is H or $(C_1-C_4)$alkyl.

In another embodiment of formula II, m is 0, 1, 2, or 3.
In another embodiment of formula II, m is 0, 1, or 2.
In another embodiment of formula II, m is 0 or 1.

In the compounds of formula I or II, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I or II. For example, different isotopic forms of hydrogen (H) include protium (H) and deuterium ($^2H$ or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I or II can be prepared without undue experimentation by conventional techniques well known to those skilled in the art or by processes analogous to those described in the Schemes and Examples herein using appropriate isotopically-enriched reagents and/or intermediates.

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

It is understood by one skilled in the art that carbon atoms in organic molecules may often be replaced by silicon atoms to give analogous stable compounds. For example, carbon atoms in alkyl, cycloalkyl, aryl, heteroaryl, and heterocyclyl, groups may often be replaced by silicon atoms to provide stable compounds. All such compounds are within the scope of the present invention.

When any variable (for example, R) occurs more than one time in any constituent or in formula I or in any other formula depicting and describing compounds of the invention, its definition on each occurrence is independent of its definition at every other occurrence. Also, combinations of substituents and/or variables are permissible only if such combinations result in stable compounds.

Certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

Certain of the compounds of the present invention can exist as tautomers. For the purposes of the present invention a reference to a compound of formula I or II is a reference to the compound per se, or to any one of its tautomers per se, or to mixtures of two or more tautomers.

The compounds of the present invention may have utility in preventing, treating, or ameliorating Alzheimer's disease. The compounds may also be useful in preventing, treating, or ameliorating other diseases mediated by the α7 nAChR, such as schizophrenia, sleep disorders, Parkinson's disease, autism, microdeletion syndrome, inflammatory diseases, pain disorders (including acute pain, inflammatory pain and neuropathic pain) and cognitive disorders (including mild cognitive impairment). Other conditions that may be prevented, treated, or ameliorated by the compounds of the invention include pulmonary hypertension, chronic obstructive pulmonary disease (COPD), asthma, urinary incontinence, glaucoma, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, kidney diseases, cancer, and atherosclerosis.

In preferred embodiments, the compounds of the invention may be useful in preventing, treating, or ameliorating Alzheimer's disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

Thus, in another specific embodiment, the present invention provides a method for preventing, treating, or ameliorating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression; emotional/mood disorders; as well as sleep walking and enuresis; and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis); repetitive motion pain; dental pain; cancer pain; myofascial pain (muscular injury, fibromyalgia); perioperative pain (general surgery, gynecological); chronic pain; dysmennorhea, as well as pain associated with angina, and inflammatory pain of varied origins (e.g. osteoarthritis, rheumatoid arthritis, rheumatic disease, teno-synovitis and gout); headache; migraine and cluster headache; primary hyperalgesia; secondary hyperalgesia; primary allodynia; secondary allodynia; or other pain caused by central sensitization.

Potential conditions or disorders that have a strong inflammatory component for which the compounds of the invention may be useful include one or more of the following conditions or diseases: diabetes (systemic inflammation in diabetes marked by increases in blood cytokines e.g. IL-6 and TNFα which may lead to insulin resistance); asthma; arthritis; cystic fibrosis; sepsis; ulcerative colitis; inflammatory bowel disease; atherosclerosis; neuroinflammation associated with neurodegenerative diseases (e.g. Alzheimer's disease, Parkinson's disease, Creutzfeldt-Jacob disease, frontotemporal dementia, corticobasal degeneration, Pick's disease, progressive supranuclear palsy, traumatic brain injury, Huntington's disease, amyotrophic lateral sclerosis).

Compounds of the invention may also be used to treat or prevent or ameliorate dyskinesia and protect against neurodegeneration in nigrostriatal neurons in Parkinson's disease. Furthermore, compounds of the invention may be used to decrease tolerance and/or dependence to opioid treatment of pain, and for treatment of withdrawal syndrome of e.g., alcohol, opioids, and cocaine.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1):1-19; P. Gould, *International J. of Pharmaceutics* (1986) 33:201-217; Anderson et al, *The Practice of Medicinal Chemistry* (1996), Academic Press, New York; and in *The Orange Book* (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For the purposes of preventing, treating, or ameliorating the cognitive impairments in Alzheimer's disease, Parkinson's disease, schizophrenia, L-DOPA induced-dyskinesia, and inflammation, the compounds of the present invention, optionally in the form of a salt, can be administered by any means that produces contact of the active agent with the agent's site of action. They can be administered by one or more conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in Remington's Pharmaceutical Sciences, 18$^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, and the severity of the particular condition.

As noted above, the present invention also relates to a method of preventing, treating, or ameliorating the cognitive impairments in Alzheimer's disease, Parkinson's disease, schizophrenia, L-DOPA induced-dyskinesia, and inflammation with a compound of the present invention in combination with one or more therapeutic agents and a pharmaceutical composition comprising a compound of the present invention and one or more therapeutic agents selected from the group consisting of anti-Alzheimer's Disease agents, for example beta-secretase inhibitors; M1 mAChR agonist or PAMs; M4 mAChR agonists or PAMs; mGluR2 antagonists or NAMs or PAMs; ADAM 10 ligands or activators; gamma-secretase inhibitors, such as LY450139 and TAK 070; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; LRRK2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; PDE IV inhibitors, including MEM1414, HT0712 and AVE8112; GABA$_A$ inverse agonists; GSK3β inhibitors, including AZD1080, SAR502250 and CEP16805; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds of the instant invention include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the compounds of the instant invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride; COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the compound of the instant invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the compounds of the instant invention may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the compounds of the instant invention may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds of the instant invention include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGN XX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

Compounds of the instant invention are useful for the treatment of moderate to severe dementia of the Alzheimer's type alone or in combination with an NMDA receptor antagonist, such as memantine, or in combination with an acetylcholinesterase inhibitor (AChEI) such as donepezil.

Compounds of the instant invention are useful for the treatment of mild to moderate dementia of the Alzheimer's type alone or in combination with either galantamine, rivastigmine, or donepezil.

Compounds of the instant invention are useful for the treatment of dementia associated with Parkinson's disease alone or in combination with rivastigmine.

Compounds of the instant invention are useful for the treatment of motor fluctuations in patients with advanced Parkinson's disease alone or in combination with carbidopa and levodopa.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). A compound of the invention and an additional therapeutic agent may be present in fixed amounts (dosage amounts) in a single dosage unit (e.g., a capsule, a tablet and the like).

The α7 nAChR positive allosteric modulator (PAM) activity of the present compounds may be tested using assays known in the art. The α7 nAChR PAMs described herein have activities in an automated patch-clamp electrophysiology functional assay as described in the examples. The assay was performed using the IonFlux HT in a whole-cell, population patch configuration. See Golden et al. *Assay Drug Dev. Technol.* (2011) 9:608-619. The compounds were assessed for their ability to modulate the function of the human 7 nAChR stably expressed in a HEK cell line both in the presence, and in the absence of the natural 7 agonist acetylcholine. By performing a series of such measurements at different concentrations, the effective concentration of the 7 nAChR PAMs ($EC_{50}$) was determined. See Spencer et al. *Assay Drug Dev. Technol.* (2012) 10:313-324.

The present invention also includes processes for making compounds of formula I or II. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

Many compounds of the present invention may be prepared according to Scheme 1, in which alkyne 1.1 participates in a [3+2] cycloaddition with the nitrile oxide (formed in situ by treatment of oxime 1.2 with PIFA) to afford isoxazole 1.3. Other nitrile oxide precursors, such as nitroalkanes or chlorooximes, can be employed to effect this transformation.

SCHEME 1

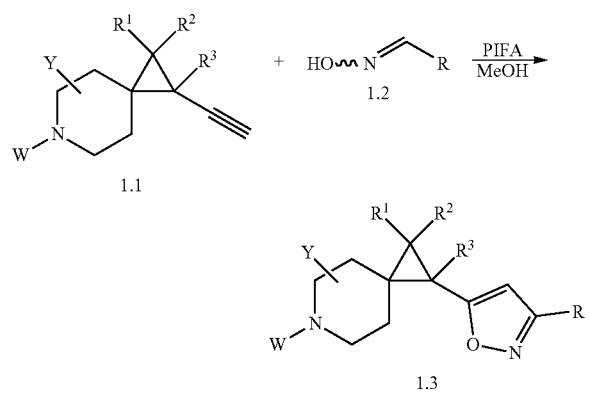

In addition, further compounds of the present invention may be prepared according to Scheme 2, in which acid 2.1 is reacted with CDI in dioxane and then treated with amide oxime 2.2 in dioxane at elevated temperature to afford product 2.3. Other coupling reagents, such as EDC and HOAt, and solvents, such as toluene, dichloroethane, or DMSO, can be employed in this transformation. If 2.3 is a mixture of enantiomers or diastereomers, the mixture may be separated by chiral chromatography. Alternatively, 2.1 and 2.2 may be employed as single enantiomers or diastereomers to obtain 2.3 enriched in a single enantiomer or diastereomer. Other methods of forming the oxadiazole may also be employed, such as reacting the corresponding ester of acid 2.1 with amide oxime 2.2 in the presence of potassium carbonate (or other bases) in ethanol (or other solvents) at elevated temperature or by reacting acid 2.1 with amide oxime 2.2 in the presence of EDC and HOAt followed either by adding T3P to the reaction mixture or by treating the isolated intermediate with TBAF in THF.

SCHEME 2

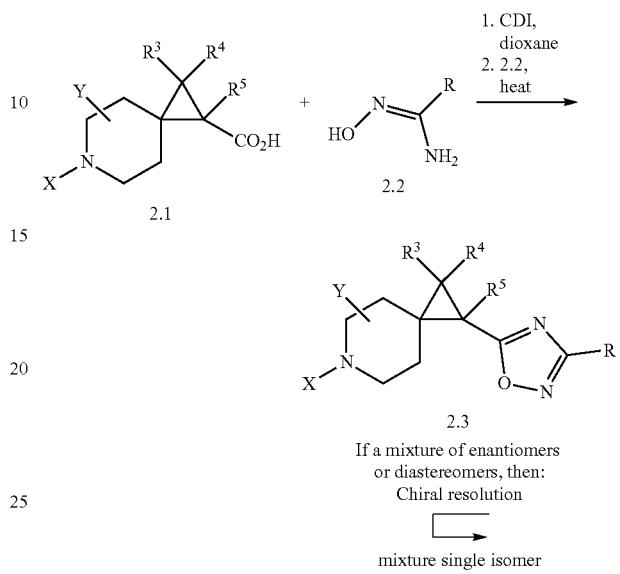

In a similar manner, some compounds of the present invention may be prepared according to Scheme 3, in which the cyclopropane intermediate 3.1 now bears the amide oxime. Acid 3.2 is reacted with CDI in dioxane and then treated with amide oxime 3.1 and warmed to elevated temperature to afford product 3.3.

SCHEME 3

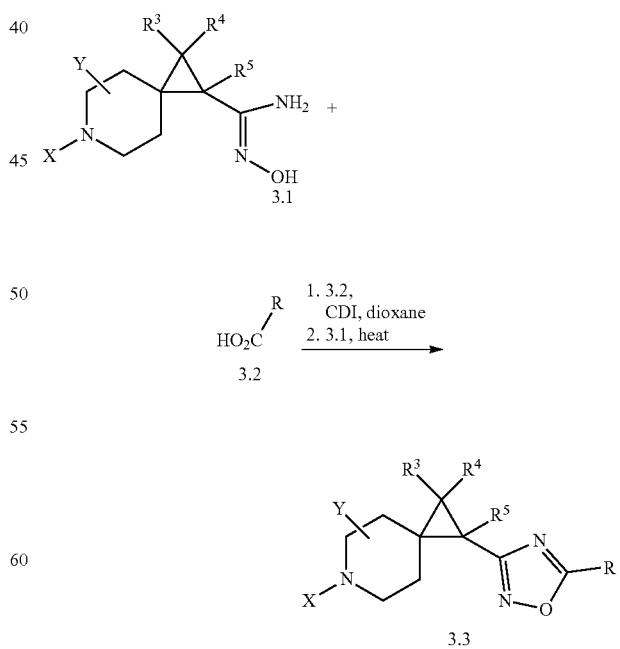

In addition, compounds in the present invention may be prepared according to Scheme 4, in which boronic ester (or boronate acid or boronic acid derivative) 4.1 is reacted with heteroaryl bromide (or chloride, iodide, triflate, or tosylate) 4.2 under palladium-catalyzed conditions to afford product 4.3. A variety of different catalysts (including other metals such as nickel), ligands, bases, and solvents can be employed in this reaction. Other six and five membered heteroaryl halides (such as a 5-chloro-1,2,4-thiadiazole) may be used in place of 4.2. Carbamate 4.3 is then treated with HCl to remove the Boc protecting group and the resulting piperidine reacted with sulfamide to afford product 4.4. Other sulfamylating reagents may be used in this transformation (e.g. tert-butyl (chlorosulfonyl)carbamate). If 4.4 is a mixture of enantiomers or diastereomers, the mixture may be separated by chiral chromatography. Alternatively, 4.1 and 4.2 may be employed as single enantiomers or diastereomers to obtain 4.4 enriched in a single enantiomer or diastereomer.

SCHEME 5

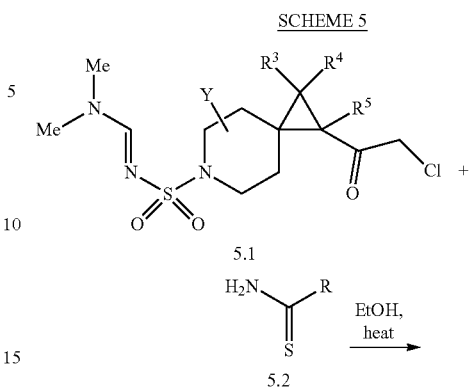

SCHEME 4

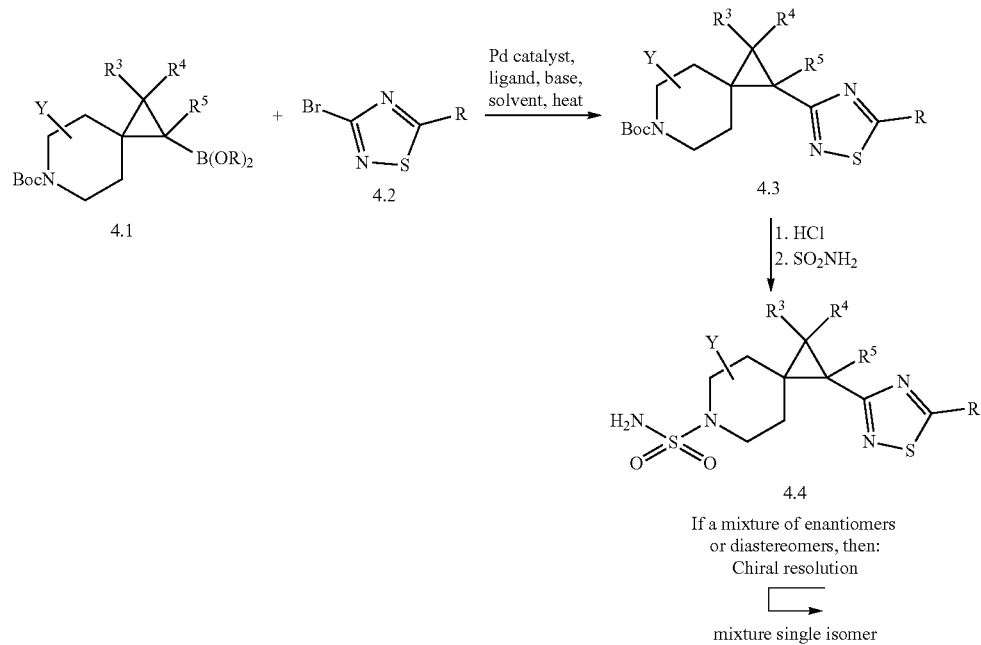

Further compounds of the present invention may be prepared according to Scheme 5, in which haloketone 5.1 is reacted with thioamide 5.2 in ethanol at elevated temperature to afford thiazole 5.3. Soft Lewis acids and other halides and solvents can be employed to effect this transformation as well. Additionally, dehydrating reagents can be employed to complete the formation of the heterocycle after coupling of 5.1 and 5.2 and an amine base can be included to sequester acid formed during the reaction. A variant of 5.2 in which the thioamide is replaced by an amidine could be employed to furnish the corresponding imidazole, which could then be N-alkylated by treatment with an alkyl halide in the presence of a base. The dimethylformamidine protecting group can then be removed by treatment with hydrazine to afford product 5.4.

-continued

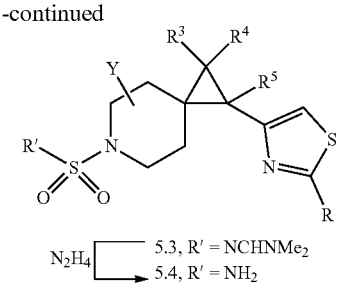

In addition, compounds of the present invention may be prepared according to Scheme 6, in which the iminium salt 6.1 is reacted with hydrazine 6.2 in the presence of HCl in methanol at elevated temperature, to afford pyrazole 6.3. Pyrazole 6.3 is then treated with hydrogen in the presence of palladium hydroxide on carbon to remove the carboxybenzyl protecting group followed by reaction of the resulting piperidine with sulfamide to afford product 6.4.

SCHEME 6

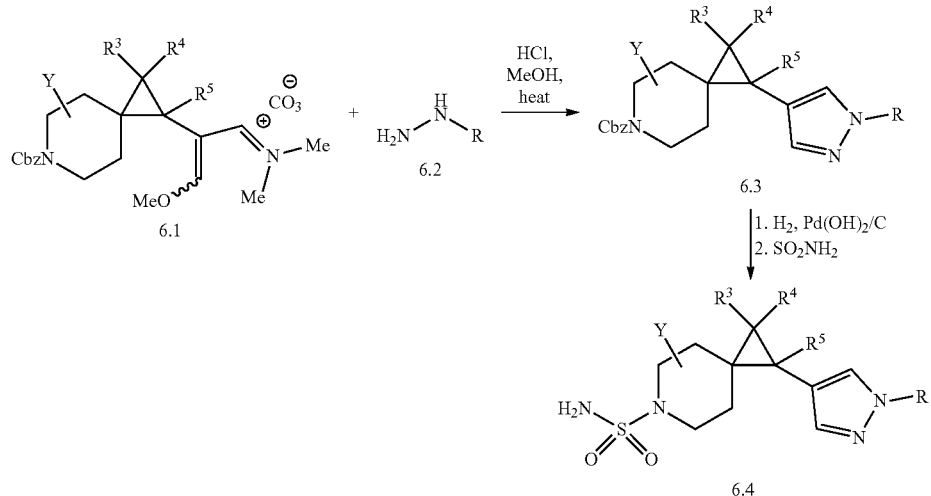

In addition, compounds of the present invention may be prepared according to Scheme 7, in which acid 7.1 is reacted with CDI in 1,4-dioxane and then treated with acyl hydrazide 7.2 at elevated temperature, followed by dehydration of the resultant amide by treatment with phosphorous (V) oxychloride at elevated temperature to afford product 7.3. Other coupling reagents and conditions can be employed to effect this transformation. Additionally, other dehydrating reagents, such as Burgess reagent or triflic anhydride, can be used for this transformation.

SCHEME 7

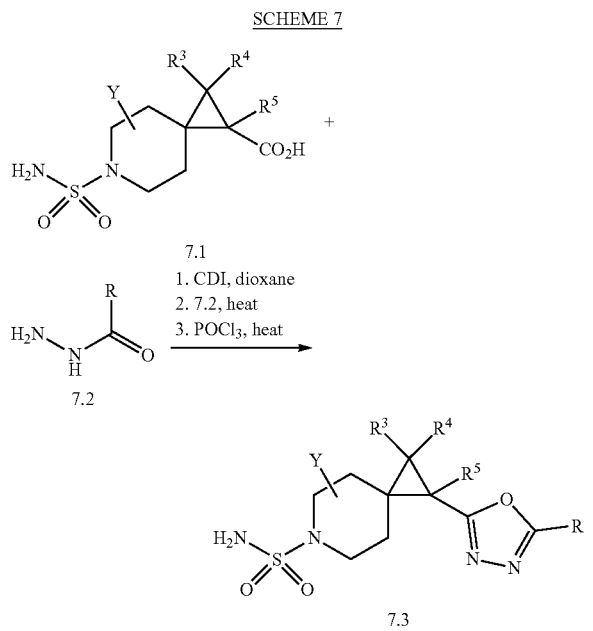

In addition, compounds of the present invention may be prepared according to Scheme 8, in which acid 7.1 is reacted with acyl hydrazide 7.2 in the presence of HATU and NMM. Other coupling reagents and conditions can be employed to effect this transformation. The resulting amide is then treated with Lawesson's reagent and warmed to elevated temperature to afford thiadiazole product 8.1. Other thionating reagents, such $P_4S_{10}$ and hexamethyldisiloxane or hexamethyldisilathiane, and solvents, such as 1,4-dioxane, can be used for this transformation. Additionally, dehydrating reagents, such as PTSA, can be employed to complete the formation of the heterocycle after thionation.

SCHEME 8

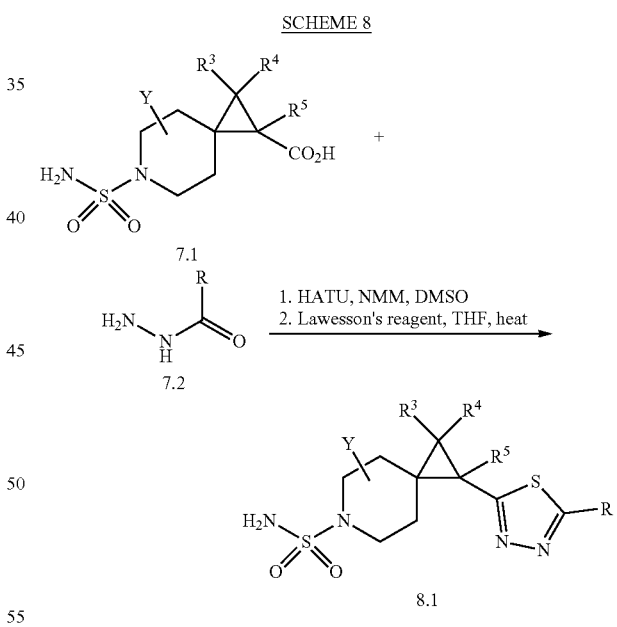

In addition, compounds of the present invention may be prepared according to Scheme 9, in which amide 9.1 is reacted with haloketone 9.2 in the presence of silver trifluoromethanesulfonate at elevated temperature to afford oxazole 9.3. Other soft Lewis acids, such as boron trifluoride diethyl etherate, and halides, such as chloride or iodide, can be employed to effect this transformation. Additionally, dehydrating reagents can be employed to complete the formation of the oxazole after coupling of 9.1 and 9.2. As in Scheme 6, a two-step sequence can then be employed to afford sulfamide 9.4.

SCHEME 9

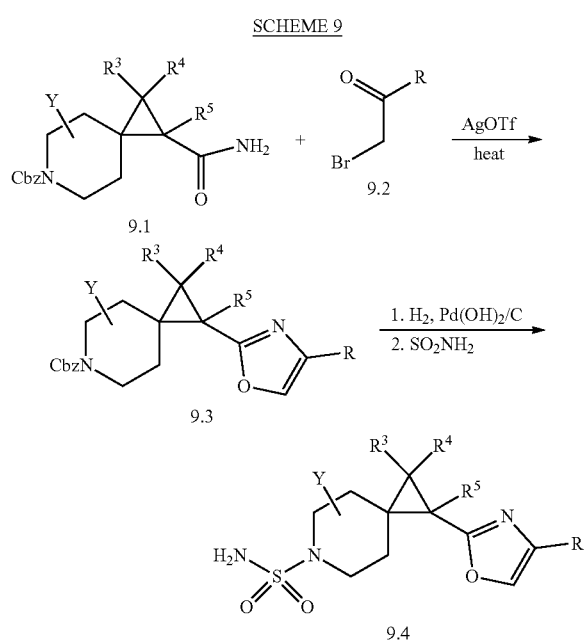

Further regioisomeric oxazole compounds of the present invention may be similarly prepared according to Scheme 10, in which haloketone 10.1 is reacted with amide 10.2 in the presence of silver trifluoromethanesulfonate at elevated temperature to afford oxazole 10.3. Soft Lewis acids and other halides and solvents can be employed to effect this transformation as well. Additionally, dehydrating reagents can be employed to complete the formation of the heterocycle after coupling of 10.1 and 10.2 and an amine base can be included to sequester acid formed during the reaction. The dimethylformamidine protecting group can then be removed by treatment with hydrazine to afford product 10.4.

SCHEME 10

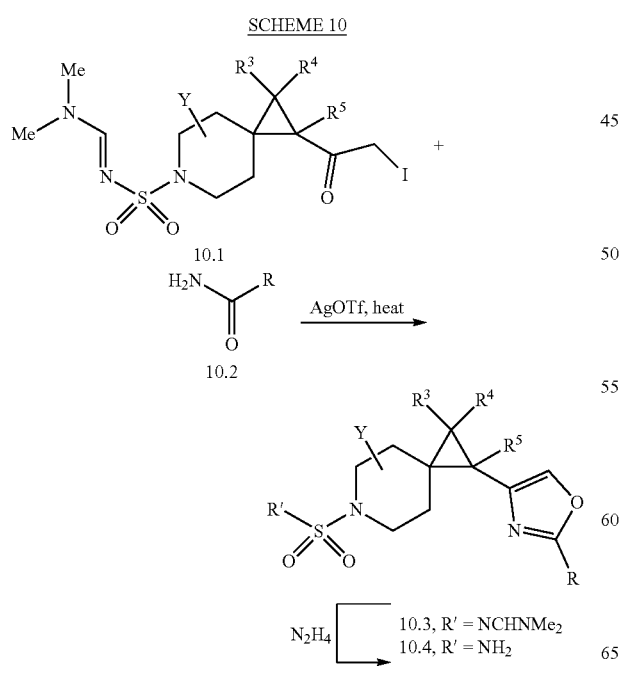

Further compounds of the present invention may be prepared according to Scheme 11, in which acid 7.1 is reacted with HATU in tetrahydrofuran and then treated with amino ketone 11.1 followed by cyclodehydration of the resultant amide by treatment with phosphorous (V) oxychloride to afford product 11.2. Other coupling and dehydrating reagents and conditions can be employed to effect this transformation.

SCHEME 11

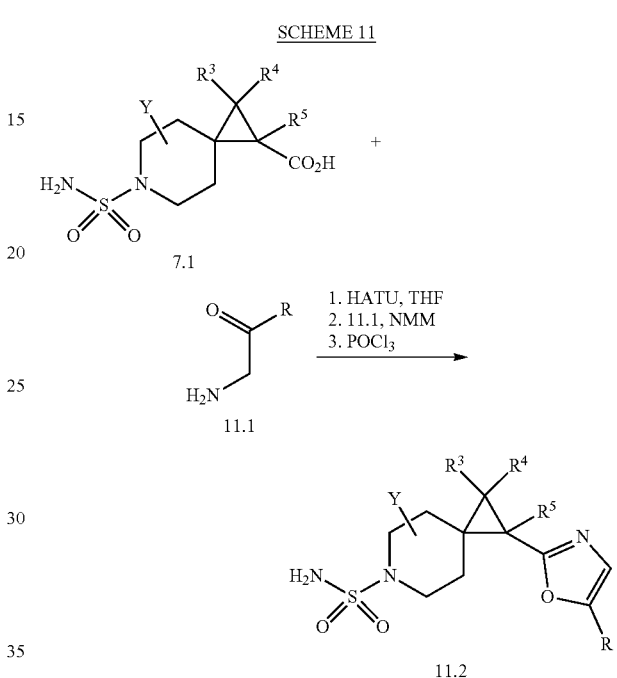

In addition, compounds of the present invention may be prepared according to Scheme 12, in which isoxazole 1.3 is treated with Raney nickel to give vinylogous amide 12.1. Vinylogous amide 12.1 can then be reacted with P4S10 in the presence of choranil and sodium bicarbonate to afford isothiazole 12.1. Other thionating reagents, such as Lawesson's reagent, may be used in this transformation.

SCHEME 12

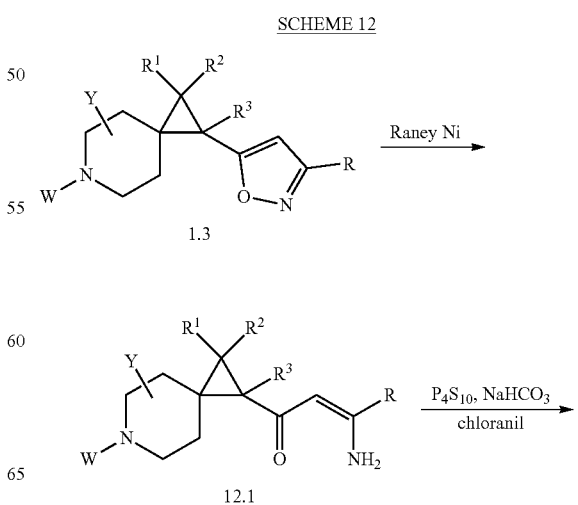

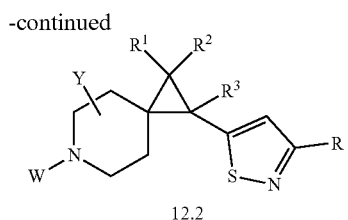

12.2

In addition, compounds of the present invention may be prepared according to Scheme 13, in which pyrazole 13.1 is reacted with aryl boronic acid 13.2 under copper-catalyzed conditions in the presence of oxygen to afford product 13.3. Alternatively, an aryl or heteroaryl halide may be used in place of 13.2 with either a palladium or copper catalyst in the presence of a base and suitable ligand, under inert atmosphere, to form products similar to 13.3. Carbamate 13.3 is then treated with HCl to remove the Boc protecting group and the resulting piperidine reacted with sulfamide to afford product 13.4. Other sulfamylating reagents may be used in this transformation (e.g. tert-butyl (chlorosulfonyl)carbamate, followed by removal of the Boc group with HCl).

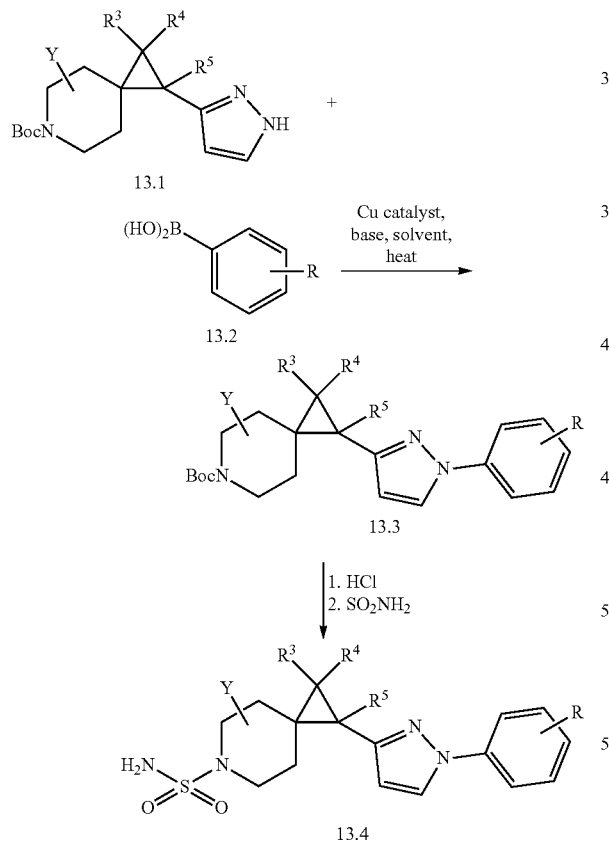

SCHEME 13

Intermediates like 14.6 of the present invention may be prepared according to Scheme 14, which starts with Wittig olefination of ketone 14.1 by reaction with phosphorane 14.2 at elevated temperature to afford product 14.3. α,β-Unsaturated ester 14.3 is then reacted with the ylide formed by treating precursor 14.4 with sodium hydride to afford cyclopropane 14.5. Other bases, such as potassium tert-butoxide, may be employed in this transformation. Alternatively, 14.1 can be converted to the corresponding terminal olefin by treatment with methylenetriphenylphosphorane and then reacted with ethyl diazoacetate in the presence of a rhodium, copper, or palladium catalyst to form the ethyl ester analogue of compound 14.5. Tri- and tetrasubstituted olefins can be employed in this latter transformation to afford cyclopropanes with a higher degree of substitution. Chiral ligands may be employed in these carbene insertion reactions (such as (R,R)-(−)-2,2'-isopropylidenebis(4-tert-butyl-2-oxazoline), used in the presence of copper(I) triflate) to afford enantio- or diastereoenriched products. Cyclopropane 14.5 is then saponified by treatment with sodium hydroxide to afford acid 14.6.

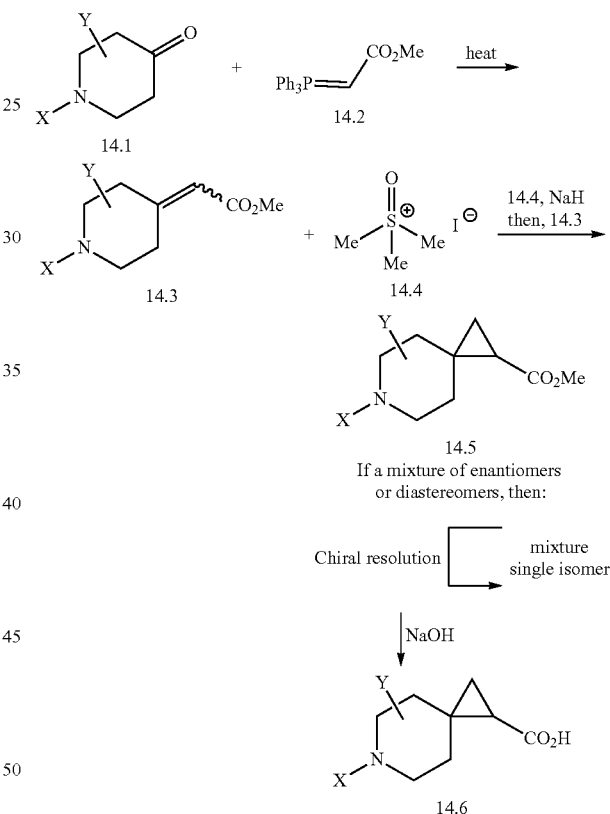

SCHEME 14

Intermediates like 15.5 of the present invention may be prepared according to Scheme 15, which starts with reduction of α,β-unsaturated ester 14.3 by treatment with DIBAL followed by conversion of the resulting allylic alcohol to the corresponding acetate 15.1 by reaction with acetic anhydride in the presence of DMAP and triethylamine. Other reducing reagents, acetylating reagents, and bases may be used in this transformation. Allylic acetate 15.1 can then be difluorocyclopropanated by treatment with (trimethylsilyl)trifluoromethane in the presence of sodium iodide to afford difluorocyclopropane 15.2. Other difluorocarbene sources (such as (bromodifluoromethyl)trimethylsilane or sodium chlorodifluoroacetate) and initiators (such as tetralkylam monium salts) may be employed in this transformation. Removal of the acetate group of 15.2 can be accomplished by treatment with potassium carbonate and the resulting alcohol oxidized to the corresponding acid by reaction with TEMPO. This acid can then be converted to benzyl ester 15.3 by treatment with benzyl bromide. Ester 15.3 can then be treated with HCl to remove the Boc group and the resulting piperidine reaction with sulfamide to afford product 15.4. Removal of the benzyl ester can be accomplished by treatment with palladium on carbon in the presence of hydrogen to give acid 15.5.

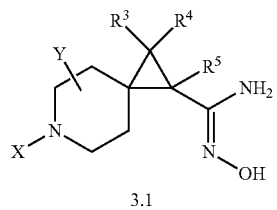

3.1

SCHEME 15

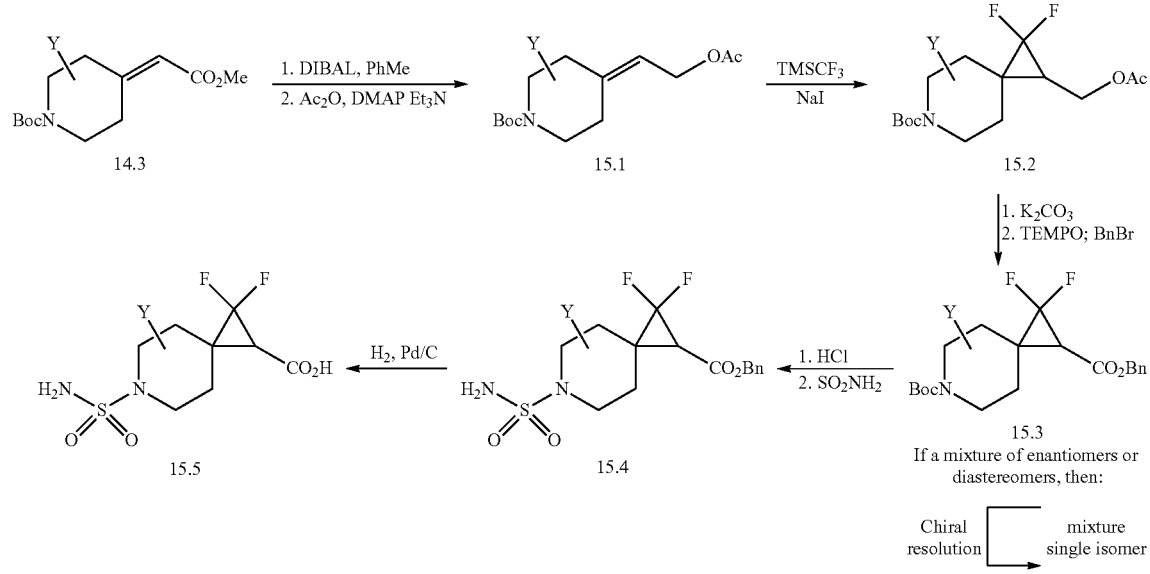

Intermediates like 3.1 of the present invention may be prepared according to Scheme 16. This sequence starts with acid 2.1, which is converted to amide 16.1 by coupling with ammonium chloride in the presence of HATU and NMM (other coupling reagents and bases can be used for this reaction as well). Amide 16.1 is then dehydrated with POCl₃ (other dehydrating reagents can also be employed) followed by treatment of the resulting nitrile with hydroxylamine to afford amide oxime 3.1.

SCHEME 16

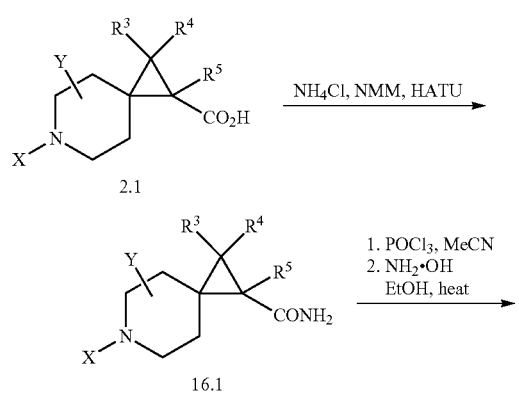

Intermediates like 17.6 of the present invention may be prepared according to Scheme 17, which begins with Wittig olefination of ketone 17.1 by reaction with phosphorane 17.2 at elevated temperature to afford terminal olefin 17.3. Alkene 17.3 is then reacted with vinyl boronate 17.4 in the presence of Grubbs' Catalyst™, 2$^{nd}$ generation, to give vinyl boronate 17.5. Other cross-methathesis catalysts (such as Zhan's catalyst or Hoveyda-Grubbs catalyst) can be employed in this transformation. Vinyl boronate 17.5 can then be difluorocyclopropanated by treatment with (trimethylsilyl)trifluoromethane in the presence of sodium iodide to afford difluorocyclopropane 17.6. Other difluorocarbene sources (such as (bromodifluoromethyl)trimethylsilane or sodium chlorodifluoroacetate) and initiators (such as tetraalkylammonium salts) may be employed in this transformation.

SCHEME 17

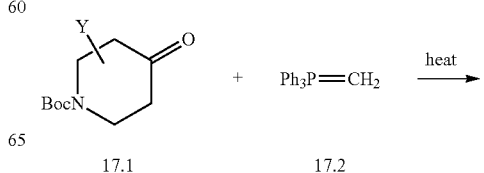

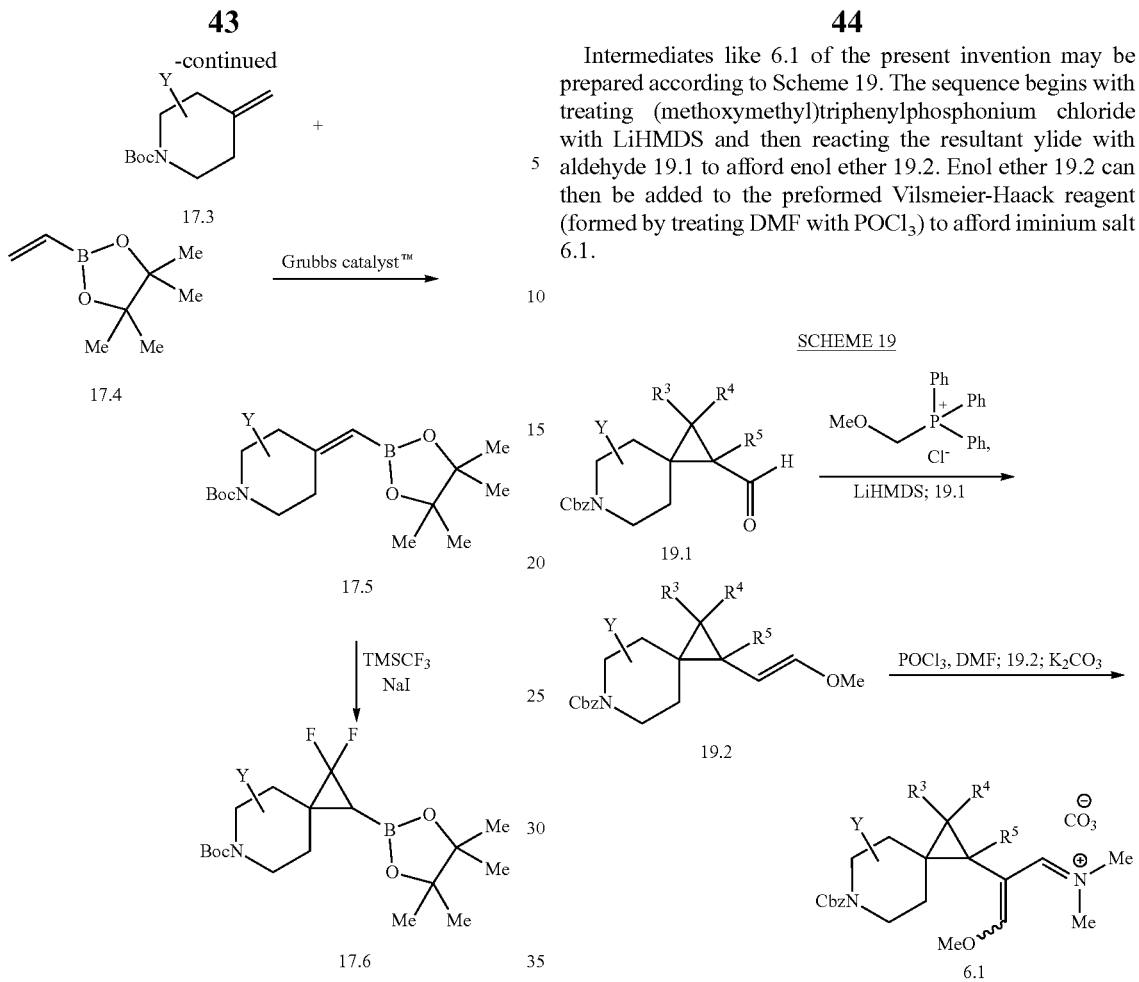

Intermediates like 6.1 of the present invention may be prepared according to Scheme 19. The sequence begins with treating (methoxymethyl)triphenylphosphonium chloride with LiHMDS and then reacting the resultant ylide with aldehyde 19.1 to afford enol ether 19.2. Enol ether 19.2 can then be added to the preformed Vilsmeier-Haack reagent (formed by treating DMF with $POCl_3$) to afford iminium salt 6.1.

Intermediates like 5.1 of the present invention may be prepared according to Scheme 18, in which a solution of acid 7.1 in dichloromethane and N,N-dimethylformamide is treated with oxalyl chloride to form the corresponding acyl chloride. This acyl chloride is then reacted with (trimethylsilyl)diazomethane followed by HCl to afford chloroketone 5.1. This chloroketone can be converted to the corresponding iodide by treatment with sodium iodide in acetone.

SCHEME 18

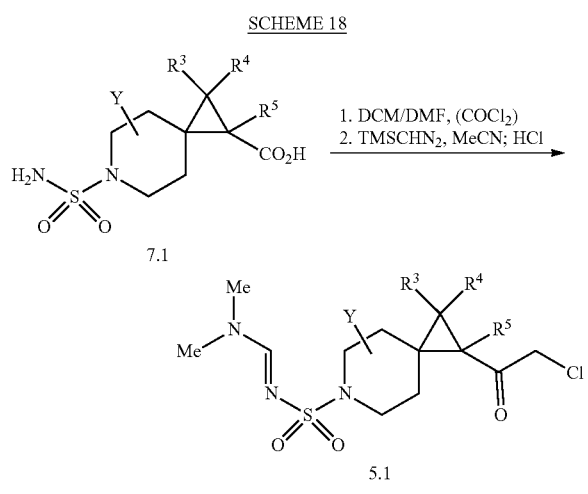

Intermediates like 20.4 in the present invention may be prepared according to Scheme 20, which starts with reduction of α,β-unsaturated ester 14.3 by treatment with DIBAL followed by conversion of the resulting allylic alcohol to the corresponding silyl ether 20.1 by reaction with TBSCl in the presence of imidazole. Other reducing reagents, silating reagents, and bases may be used in this transformation. Allylic silyl ether 20.1 can then be bromofluorocyclopropanated by treatment with dibromo(fluoro)methane in the presence of TBAI and sodium hydroxide to afford bromofluorocyclopropane 20.2. Reduction of bromofluorocyclopropane 20.2 by treatment with Zn in the presence of ammonium chloride can then followed by silyl ether deprotection by reaction with TBAF to afford the fluorocyclopropane alcohol 20.3. Two step oxidation of alcohol 20.3 can be accomplished by first treating with DMP followed by reaction of the resulting aldehyde with sodium chlorite to give acid 20.4.

SCHEME 20

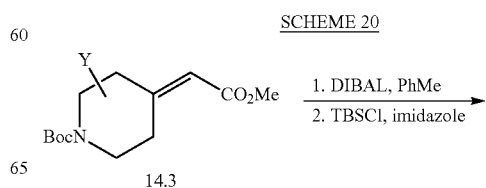

-continued

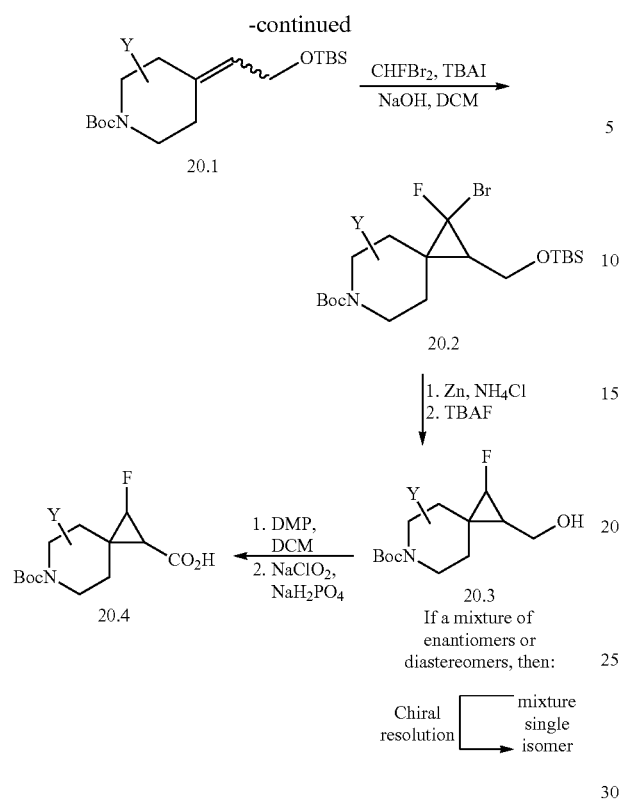

20.3
If a mixture of enantiomers or diastereomers, then:
Chiral resolution: mixture → single isomer Intermediates like 13.1 of the present invention may be prepared according to Scheme 21. The sequence begins with treating acid 21.1 with CDI and reacting the resulting acyl imidazole with N,O-dimethylhydroxylamine hydrochloride to afford the corresponding Weinreb amide. The Weinreb amide can then be treated with ethynylmagnesium bromide to afford alkynyl ketone 21.2. Alkynyl ketone 21.2 can then be treated with hydrazine to afford pyrazole 13.1.

SCHEME 21

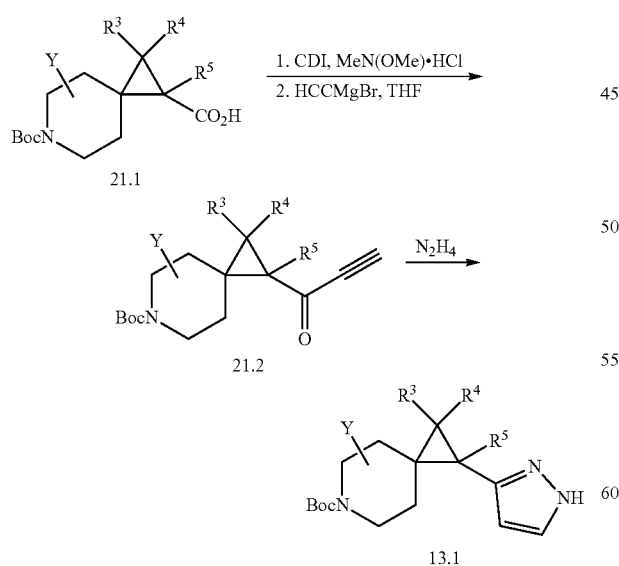

Intermediates like 22.4 in the present invention may be prepared according to Scheme 22, which begins with treatment of triphenylphosphonium bromide 22.1 with n-butyl-lithium and reaction of the resultant ylide with piperidinone 14.1 to afford alkene 22.2. Alkene 22.2 can then be reacted with ethyl diazoacetate in the presence of rhodium acetate to afford cyclopropane 22.3. Other metals, such as copper or palladium, may be used in this transformation. Chiral ligands may be employed in these carbene insertion reactions (such as (R,R)-(−)-2,2'-isopropylidenebis(4-tert-butyl-2-oxazoline), used in the presence of copper(I) triflate) to afford enantio- or diastereoenriched products. Cyclopropane 22.3 is then saponified by treatment with sodium hydroxide to afford acid 22.4.

SCHEME 22

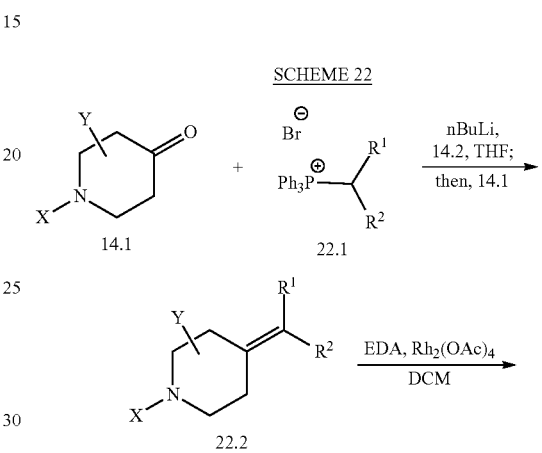

22.3
If a mixture of enantiomers or diastereomers, then:
Chiral resolution: mixture → single isomer Intermediates like alkyne 1.1 may be prepared according to Scheme 23. Alcohol 23.1 can be oxidized by treatment with Dess-Martin periodinane to afford aldehyde 23.2. Other oxidizing reagents (such as Collin's reagent, PCC, or PDC) may be used in these transformations. Aldehyde 23.2 can then be reacted with dimethyl (1-diazo-2-oxopropyl)phosphonate in the presence of potassium carbonate to afford alkyne 9.1. Other bases can be employed in this transformation.

SCHEME 23

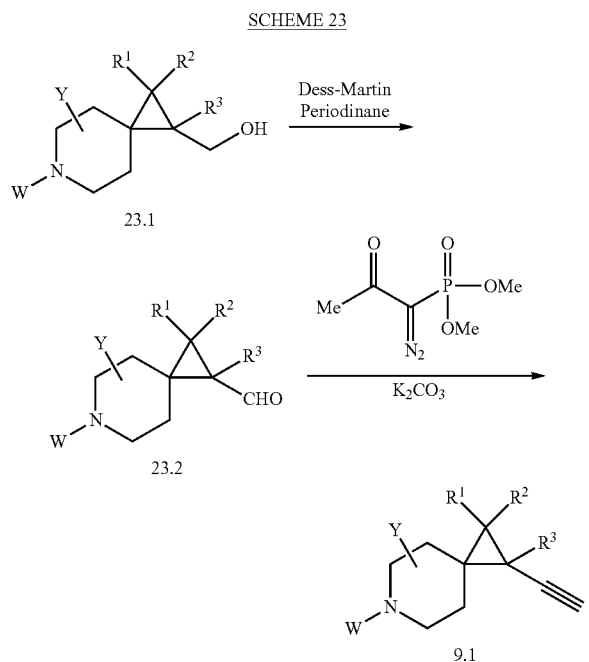

It is understood that the compounds and intermediates of the foregoing reaction schemes may be employed as synthetic intermediates in other schemes that involve similar intermediates to produce alternative compounds of the present invention.

In some cases the order of carrying out the foregoing reaction schemes may be varied to facilitate the reaction or to avoid unwanted reaction products. Additionally, various protecting group strategies familiar to one skilled in the art of organic synthesis may be employed to facilitate the reaction or to avoid unwanted reaction products.

In some cases the final product may be further modified, for example, by manipulation of substituents. These manipulations may include, but are not limited to, reduction, oxidation, alkylation, acylation, and hydrolysis reactions which are commonly known to those skilled in the art.

The following examples are provided so that the invention might be more fully understood. These examples are illustrative only and should not be construed as limiting the invention in any way. Wherein a racemic mixture is produced, the enantiomers may be separated using SFC reverse or normal phase chiral resolution conditions either after isolation of the final product or at a suitable intermediate, followed by processing of the single isomers individually. It is understood that alternative methodologies may also be employed in the synthesis of these key intermediates and examples. Asymmetric methodologies (e.g. chiral catalysis, auxiliaries) may be used where possible and appropriate. The exact choice of reagents, solvents, temperatures, and other reaction conditions, depends upon the nature of the intended product.

The following abbreviations are used throughout the text:

| | |
|---|---|
| Ac | Acetyl |
| AIBN | 2,2'-azobisisobutyronitrile |
| Aq | Aqueous |
| Ar | Aryl |
| $B_2(Pin)_2$ | bis(pinacolato)diboron |
| BINAP | 2,2'-bis(diphenylphosphino)-1,1'-binaphthalene |
| Bn | Benzyl |
| Boc | tert-butoxy carbonyl |
| BOP | (benzotriazol-1-yloxy)tris(dimethylamino)phosphonium hexafluorophosphate |
| Br | Broad |
| BSA | bovine serum albumin |
| Bu | Butyl |
| Ca | circa (approximately) |
| CAN | ammonium cerium(IV) nitrate |
| Cbz | Carboxybenzyl |
| CDI | 1,1'-carbonyldiimidazole |
| D | Doublet |
| DABCO | diazabicyclo[2.2.2]octane |
| DAST | (diethylamino)sulfur trifluoride |
| Dba | Dibenzylideneacetone |
| DBU | 1,8-diazabicyclo[5.4.0]undec-7-ene |
| DCE | 1,2-dichloroethane |
| DCM | Dichloromethane |
| Dd | doublet of doublets |
| DIBAL | diisobutylaluminum hydride |
| DIEA | N,N-diisopropylethylamine |
| DMA | N,N-dimethylacetamide |
| DMAP | 4-(dimethylamino)pyridine |
| DMEM | Dulbecco's Modified Eagle Medium (High Glucose) |
| DMF | N,N-dimethylformamide |
| DMF-DMA | N,N-dimethylformamide dimethylacetal |
| DMP | Dess-Martin periodinane |
| DMPU | N,N'-dimethylpropyleneurea |
| DMSO | Dimethylsulfoxide |
| DPBF | 1,3-diphenylisobenzofuran |
| Dppf | 1,1'-bis(diphenylphosphino)ferrocene |
| EDC | N-(3-dimethylaminopropyl)-N'-ethylcarbodiimide hydrochloride |
| EDTA | ethylenediaminetetraacetic acid |
| Eq | Equivalents |
| ESI | electrospray ionization |
| Et | Ethyl |
| FBS | fetal bovine serum |
| H | Hours |
| HATU | O-(7-azabenzotriazol-1-yl)-N,N,N'N'-tetramethyluronium hexafluorophosphate |
| HEPES | N-(2-hydroxyethyl)piperazine-N'-(2-ethanesulfonic acid) |
| HMDS | Hexamethyldisilazane |
| HMTA | Hexamethylenetetramine |
| HOAt | 1-hydroxy-7-azabenzotriazole |
| HOBt | 1-hydroxybenzotriazole |
| HPLC | high performance liquid chromatography |
| Hz | Hertz |
| Imid | Imidazole |
| i-Pr | Isopropyl |
| J | coupling constant |
| LAH | lithium aluminum hydride |
| LCMS | liquid chromatography-mass spectrometry |
| LDA | lithium diisopropylamide |
| m/z | mass to charge ratio |
| M | Multiplet |
| mCPBA | 3-chloroperbenzoic acid |
| Me | Methyl |
| Min | Minutes |
| MP | macroporous polystyrene |
| Ms | Methanesulfonyl |
| MTBE | methyl tert-butyl ether |
| MW | molecular weight |
| NBS | N-bromosuccinimide |
| NHS | N-hydroxysuccinimide |
| n-BuLi | n-butyllithium |
| n-HexLi | n-hexyllithium |
| NMM | N-rnethyl morpholine |
| NMP | 1-methyl-2-pyrrolidinone |
| NMR | nuclear magnetic resonance |
| Oac | Acetate |
| P | Pentet |
| PBPB | pyridinium bromide perbromide |
| PBS | phosphate-buffered saline |
| PCC | pyridinium thlorochromate |
| PDC | pyridinium di chromate |
| Pd/C | palladium on carbon |
| Ph | Phenyl |

-continued

| | |
|---|---|
| PIFA | [bis(trifluoroacetoxy)iodo]benzene |
| PMBCl | 4-methoxybenzyl chloride |
| Psi | pounds per square inch |
| p-Ts | 4-toluenesulfonyl |
| PTSA | para-toluensulfonic acid |
| Py | Pyridyl |
| Q | Quartet |
| Rt | room temperature |
| S | Singlet |
| SEM | 2-trimethylsilylethoxymethyl |
| SEMCl | 2-trimethylsilylethoxymethyl chloride |
| SFC | supercritical fluid chromatography |
| SM | starting material |
| T | Triplet |
| T3P | 2,4,6-tripropyl-1,3,5,2,4,6-trioxatriphosphorinane-2,4,6-trioxide |
| TBAF | n-tetrabutylammonium fluoride |
| TBAI | n-tetrabutylammonium iodide |
| TBS | tert-butyldimethylsilyl |
| TBSCl | tert-butyldimethylsilyl chloride |
| TBDPS | tert-butyldiphenylsilyl |
| TBDPSCl | tert-butyldiphenylsilyl chloride |
| t-Bu | tert-butyl |
| TCCA | trichloroisocyanuric acid |
| TEA | Trimethylamine |
| TFA | trifluoroacetic acid |
| Tf | Trifluoromethanesulfonyl |
| TCFH | tetramethylchloroformamidinium hexafluorophosphate |
| THF | Tetrahydrofuran |
| TMG | Tetramethylguanidine |
| TMSD | Trimethylsilyldiazomethane |
| Trisyl | 2,4,6-triisopropylbenzenesulfonyl |
| V/V | volume to volume |
| X-Phos | 2-dicyclohexylphosphino-2',4',6'-triisopropylbiphenyl |

INTERMEDIATE 1

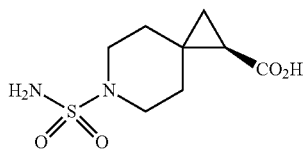

(1R)-6-Sulfamoyl-6-azaspiro[2.5]octane-1-carboxylic Acid

Step A: Ethyl (1R)-6-azaspiro[2.5]octane-1-carboxylate

To a solution of 6-benzyl 1-ethyl (1R)-6-azaspiro[2.5]octane-1,6-dicarboxylate (44.6 g, 141 mmol) (Brown et al. J. Med. Chem. (2014) 57:733-758) in methanol (400 mL) was added palladium hydroxide (20% w/w, on activated carbon, 4.94 g, 7.03 mmol). The reaction vessel was evacuated and backfilled with hydrogen (ca. 1 atm) and the reaction mixture was allowed to stir at ambient temperature for 18 h. The reaction mixture was filtered through a pad of Celite®, washing with methanol, and the filtrate was concentrated under reduced pressure to afford the title compound in sufficient purity for use in the next step. MS: m/z=184.3 [M+H].

Step B: Ethyl (1R)-6-sulfamoyl-6-azaspiro[2.5]octane-1-carboxylate

To a solution of ethyl (1R)-6-azaspiro[2.5]octane-1-carboxylate (25.6 g, 140 mmol) in 1,4-dioxane (400 mL) was added sulfamide (40.7 g, 423 mmol) and the reaction mixture warmed to 95° C. and allowed to stir for 18 h. Sulfamide (9.00 g, 93.7 mmol) was added and the reaction mixture was warmed to 100° C. and allowed to stir for 6 h. The reaction mixture was allowed to cool to ambient temperature, poured into a saturated aqueous solution of sodium bicarbonate, and extracted with ethyl acetate (2×). The combined organic extracts were washed with a saturated aqueous solution of sodium chloride, dried (sodium sulfate) and filtered and the filtrate was concentrated under reduced pressure. The crude residue was purified by silica gel chromatography, eluting with a gradient of methanol:dichloromethane—0:100 to 5:95 to afford the title compound. MS: m/z=263.1 [M+H].

Step C: (1R)-6-Sulfamoyl-6-azaspiro[2.5]octane-1-carboxylic Acid

To a solution of ethyl (1R)-6-sulfamoyl-6-azaspiro[2.5]octane-1-carboxylate (50.0 g, 191 mmol) in tetrahydrofuran (270 mL) and methanol (135 mL) was added an aqueous solution of sodium hydroxide (2 M, 286 mL, 572 mmol) and the reaction mixture was allowed to stir for 2 days at ambient temperature. The reaction mixture was diluted with ice water (200 mL) and the resulting mixture slowly adjusted to pH=5 with an aqueous solution of hydrochloric acid (12 M) and extracted with ethyl acetate (3×). The combined organic extracts were washed with a saturated aqueous solution of sodium chloride, dried (sodium sulfate), and filtered and the filtrate was concentrated under reduced pressure to afford the title compound in sufficient purity for use in the next step. MS: m/z=235.1 [M+H].

INTERMEDIATE 2

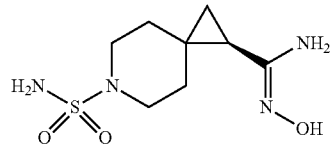

(1R)—N-Hydroxy-6-sulfamoyl-6-azaspiro[2.5]octane-1-carboximidamide

Step A: (1R)-6-Sulfamoyl-6-azaspiro[2.5]octane-1-carboxamide

To a solution of (1R)-6-sulfamoyl-6-azaspiro[2.5]octane-1-carboxylic acid (Intermediate 1) (1.20 g, 2.93 mmol) in dichloromethane (14 mL) were added HATU (1.15 g, 3.02 mmol), ammonium chloride (0.392 g, 7.32 mmol), and N-methylmorpholine (1.13 mL, 10.3 mmol) and the reaction mixture was allowed to stir for 18 h at ambient temperature. The reaction mixture was filtered, washing with dichloromethane, and the filtrate was concentrated under reduced pressure to afford the title compound in sufficient purity for use in the next step. MS: m/z=234.0 [M+H].

Step B: (1R)-1-Cyano-6-azaspiro[2.5]octane-6-sulfonamide

To a solution of (1R)-6-sulfamoyl-6-azaspiro[2.5]octane-1-carboxamide (1.84 g, 7.89 mmol) in acetonitrile (39 mL) was added phosphorus oxychloride (1.47 mL, 15.8 mmol) and the reaction mixture warmed to 80° C. and allowed to stir for 2 h. The reaction mixture was cooled to ambient temperature, water was added, and the resulting mixture extracted with ethyl acetate (2×). The combined organic extracts were concentrated under reduced pressure to afford the title compound in sufficient purity for use in the next step. MS: m/z=216.1 [M+H].

Step C: (1R)—N'-Hydroxy-6-sulfamoyl-6-azaspiro[2.5]octane-1-carboximidamide

To a solution of (1R)-1-cyano-6-azaspiro[2.5]octane-6-sulfonamide (1.30 g, 6.04 mmol) in methanol (14 mL) was added an aqueous solution of hydroxylamine (50% w/w, 3.50 mL, 57.1 mmol) and the reaction mixture warmed to 60° C. and allowed to stir for 1 h. The reaction mixture was cooled to ambient temperature and diluted with a saturated aqueous solution of sodium chloride and the resulting mixture extracted with ethyl acetate (3×). The combined organic extracts were concentrated under reduced pressure to afford the title compound in sufficient purity for use in the next step. MS: m/z=249.1 [M+H].

raphy, eluting with petroleum ether:ethyl acetate—95:5, to afford the title compound. MS: m/z=264.0 [M-tBu+H].

Step C: 6-(tert-Butoxycarbonyl)-2,2-difluoro-1-methyl-6-azaspiro[2.5]octane-1-carboxylic Acid To a solution of 6-tert-butyl 1-methyl 2,2-difluoro-1-methyl-6-azaspiro[2.5]octane-1,6-dicarboxylate (130 mg, 0.41 mmol) in methanol (3 mL), tetrahydrofuran (3 mL), and water (1.5 mL) was added sodium hydroxide (163 mg, 4.07 mmol) and the reaction mixture allowed to stir for 3 h. The reaction mixture was concentrated under reduced pressure and water (5 mL) was added and the resulting mixture extracted with ethyl acetate (5 mL). The aqueous phase was adjusted to pH=3 with an aqueous solution of hydrogen chloride (2 M) and extracted with ethyl acetate (3×10 mL). The combined organic extracts were washed with a saturated aqueous solution of sodium chloride (10 mL), dried (sodium sulfate), and filtered and the filtrate was concentrated under reduced pressure to afford the title compound in sufficient purity for use in the next step.

INTERMEDIATE 3

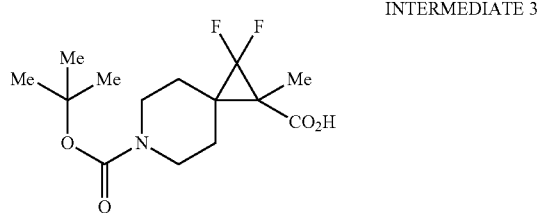 [SMILES: CC(C)(C)OC(=O)N1CCC2(CC1)C(F)(F)C2(C)C(=O)O]

6-(tert-Butoxycarbonyl)-2,2-difluoro-1-methyl-6-azaspiro[2.5]octane-1-carboxylic Acid Step A: 6-tert-Butyl 1-methyl 2,2-difluoro-6-azaspiro[2.5]octane-1,6-dicarboxylate To a solution of 6-(tert-butoxycarbonyl)-2,2-difluoro-6-azaspiro[2.5]octane-1-carboxylic acid (described in Intermediate 10) (1.0 g, 3.43 mmol) in methanol (4 mL) and dichloromethane (20 mL) was added a solution of (trimethylsilyl)diazomethane in hexane (2 M, 9.44 mL, 18.9 mmol) and the reaction mixture allowed to stir for 15 min. Methanol (15 mL) was added and the reaction mixture concentrated under reduced pressure. The residue was purified by silica gel chromatography, eluting with petroleum ether:ethyl acetate—95:5, to afford the title compound. MS: m/z=250.0 [M-tBu+H].

Step B: 6-tert-Butyl 1-methyl 2,2-difluoro-1-methyl-6-azaspiro[2.5]octane-1,6-dicarboxylate To a solution of 6-tert-butyl 1-methyl 2,2-difluoro-6-azaspiro[2.5]octane-1,6-dicarboxylate (200 mg, 0.66 mmol) and iodomethane (0.85 mL, 13.6 mmol) in tetrahydrofuran (5 mL) at −78° C. was added a solution of lithium diisopropylamide in tetrahydrofuran and hexanes (2 M 0.98 mL, 1.97 mmol) and the mixture was allowed to stir at −78° C. for 15 min then warmed to ambient temperature and allowed to stir for 30 min. A saturated aqueous solution of ammonium chloride (3 mL) and water (5 mL) were added and the aqueous layer extracted with ethyl acetate (3×5 mL). The combined organic extracts were dried (sodium sulfate) and filtered and the filtrate was concentrated under reduced pressure. The residue was purified by silica gel chromatog-

INTERMEDIATE 4

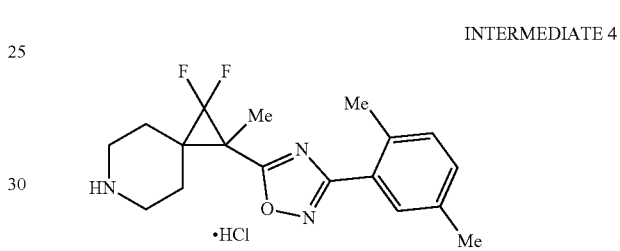

1-[3-(2,5-Dimethylphenyl)-1,2,4-oxadiazol-5-yl]-2,2-difluoro-1-methyl-6-azaspiro[2.5]octane Hydrochloride Essentially following the procedures described in Intermediate 17, but using 6-(tert-butoxycarbonyl)-2,2-difluoro-1-methyl-6-azaspiro[2.5]octane-1-carboxylic acid (Intermediate 3) in place of tert-butyl 2-{3-[2-(difluoromethoxy)pyridin-4-yl]-1,2,4-oxadiazol-5-yl}-1,1-difluoro-6-azaspiro[2.5]octane-6-carboxylate and N-hydroxy-2,5-dimethylbenzimidamide in place of 2-(difluoromethoxy)-N-hydroxypyridine-4-carboximidamide, the title compound was obtained. MS: m/z=334.0 [M+H].

INTERMEDIATE 5

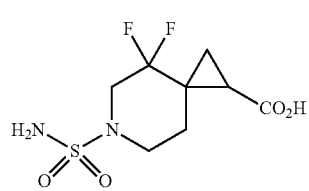

4,4-Difluoro-6-sulfamoyl-6-azaspiro[2.5]octane-1-carboxylic Acid

Step A: tert-Butyl 4-[2-(benzyloxy)-2-oxoethylidene]-3,3-difluoropiperidine-1-carboxylate To a solution of tert-butyl 3,3-difluoro-4-oxopiperidine-1-carboxylate (1.0 g, 4.3 mmol) in toluene (20 mL) was added benzyl 2-(triphenylphosphoranylidene)acetate (2.62 g, 6.38 mmol) and the reaction mixture warmed to 110° C. and allowed to stir for 4 h. The reaction mixture was cooled to ambient temperature and diluted with ethyl acetate. The organic layer was washed with water and a saturated aqueous solution of sodium chloride, dried (magnesium sulfate), and filtered and the filtrate was concentrated under reduced pressure. The residue was purified by silica gel chromatography, eluting with a gradient of hexanes:ethyl acetate— 100:0 to 75:25 to afford the title compound. MS: m/z=312.1 [M-tBu+H].

Step B: 1-Benzyl 6-tert-butyl 4,4-difluoro-6-azaspiro[2.5]octane-1,6-dicarboxylate To a mixture of sodium hydride (60% dispersion in mineral oil, 0.196 g, 4.90 mmol) and dimethylsulfoxide (15 mL) at 10° C. was added a solution of trimethylsulfoxonium iodide in dimethylsulfoxide (5.2 M, 10 mL) and the reaction mixture was allowed to stir at 10° C. for 2 h. A solution of tert-butyl 4-[2-(benzyloxy)-2-oxoethylidene]-3,3-difluoropiperidine-1-carboxylate in dimethylsulfoxide (6.6 M, 5 mL) was added and the reaction mixture was allowed to warm to ambient temperature and stir for 18 h. The reaction mixture was diluted with water and the resulting mixture extracted with ethyl acetate (2×). The combined organic extracts were washed with a saturated aqueous solution of sodium chloride, dried (magnesium sulfate), and filtered and the filtrate was concentrated under reduced pressure. The residue was purified by silica gel chromatography, eluting with a gradient of hexanes:ethyl acetate—100:0 to 80:20 to afford the title compound. MS: m/z=326.2 [M-tBu+H].

Step C: Benzyl 4,4-difluoro-6-azaspiro[2.5]octane-1-carboxylate Hydrochloride To a solution of 1-benzyl 6-tert-butyl 4,4-difluoro-6-azaspiro[2.5]octane-1,6-dicarboxylate (312 mg, 0.818 mmol) in ethyl acetate (2 mL) was added a solution of HCl in 1,4-dioxane (4 M, 1.0 mL, 4.0 mmol) and the reaction mixture allowed to stir for 18 h at ambient temperature. The reaction mixture was concentrated under reduced pressure to afford the title compound in sufficient purity for use in the next step. MS: m/z=282.2 [M+H].

Step D: Benzyl 4,4-difluoro-6-sulfamoyl-6-azaspiro [2.5]octane-1-carboxylate To a solution of benzyl 4,4-difluoro-6-azaspiro[2.5]octane-1-carboxylate hydrochloride (255 mg, 0.802 mmol) in 1,4-dioxane (4 mL) were added sulfamide (231 mg, 2.41 mmol) and triethylamine (0.168 mL, 1.20 mmol) and the reaction mixture was warmed to 90° C. and allowed to stir for 18 h. The reaction mixture was cooled to ambient temperature and concentrated under reduced pressure. The residue was purified by silica gel chromatography, eluting with a gradient of hexanes:ethyl acetate:ethanol—95:4:1 to 50:38:12 to afford the title compound. MS: m/z=361.2 [M+H].

Step E: 4,4-Difluoro-6-sulfamoyl-6-azaspiro[2.5]octane-1-carboxylic Acid

To a vessel containing benzyl 4,4-difluoro-6-sulfamoyl-6-azaspiro[2.5]octane-1-carboxylate (250 mg, 0.694 mmol) under an inert atmosphere were added palladium on activated carbon (10% w/w, 74 mg, 0.069 mmol) and methanol (3.5 mL) sequentially. The reaction mixture was placed under an atmosphere of hydrogen (ca. 1 atm) and allowed to stir for 3 h at ambient temperature. The reaction mixture was filtered over a pad of Celite®, washing with methanol, and the filtrate was concentrated under reduced pressure. MS: m/z=271.1 [M+H].

INTERMEDIATE 6

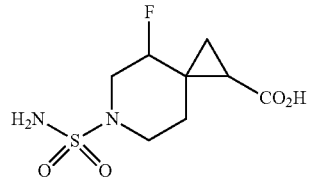

6-(tert-Butoxycarbonyl)-4-fluoro-6-azaspiro[2.5] octane-1-carboxylic Acid

Step A: tert-Butyl 3-fluoro-4-(2-methoxy-2-oxoethylidene)piperidine-1-carboxylate To a solution of tert-butyl 3-fluoro-4-oxopiperidine-1-carboxylate (10.0 g, 46.0 mmol) in toluene (115 mL) in a sealable vessel was added methyl 2-(triphenylphosphoranylidene)acetate (26.2 g, 78 mmol) and the vessel was sealed. The reaction mixture was warmed to 140° C. and allowed to stir for 5 h. The reaction mixture was concentrated under reduced pressure and hexanes were added to the residue. The resulting mixture was filtered, washing with hexanes, and the filtrate was concentrated under reduced pressure. The residue was purified by silica gel chromatography, eluting with a gradient of hexanes:ethyl acetate— 100:0 to 75:25 to afford the title compound. MS: m/z=218.1 [M-tBu+H].

Step B: 6-tert-Butyl 1-methyl 4-fluoro-6-azaspiro [2.5]octane-1,6-dicarboxylate To a vessel containing sodium hydride (60% dispersion in mineral oil, 2.51 g, 62.7 mmol) and dimethylsulfoxide (200 mL) at 0° C. was added trimethylsulfoxonium iodide (14.26 g, 64.8 mmol) portionwise over the course of 1.5 h. The reaction mixture was allowed to warm to ambient temperature and stir for 3 h. A solution of tert-butyl 3-fluoro-4-(2-methoxy-2-oxoethylidene)piperidine-1-carboxylate (6.03 g, 22.1 mmol) in dimethylsulfoxide (50 mL) was added dropwise and the reaction mixture allowed to stir for 18 h. The reaction mixture was added slowly to a mixture of ice and saturated aqueous solution of ammonium chloride (225 mL) and the resulting mixture extracted with ethyl acetate (3×200 mL). The combined organic extracts were washed with a saturated aqueous solution of ammonium chloride (2×100 mL) and a saturated aqueous solution of sodium chloride (1×100 mL), dried (magnesium sulfate), and filtered and the filtrate was concentrated under reduced pressure. The residue was purified by silica gel chromatography, eluting with a gradient of hexanes:ethyl acetate—100:0 to 60:40 to afford the title compound. MS: m/z=232.1 [M-tBu+H].

Step C: 6-(tert-Butoxycarbonyl)-4-fluoro-6-azaspiro [2.5]octane-1-carboxylic Acid To a solution of 6-tert-butyl 1-methyl 4-fluoro-6-azaspiro [2.5]octane-1,6-dicarboxylate (4.86 g, 16.9 mmol) in tetrahydrofuran (64 mL) and methanol (20 mL) was added an aqueous solution of sodium hydroxide (1 M, 34 mL, 34 mmol) and the reaction mixture was warmed to 55° C. and allowed to stir for 15 min. The reaction mixture was cooled to ambient temperature and an aqueous solution of HCl (12.1 M, 2.79 mL, 34.0 mmol) was added. The mixture was concentrated under reduced pressure and the residue co-evaporated with acetonitrile (2×). The residue was dissolved in ethyl acetate (100 mL), washed with water (15 mL), dried (magnesium sulfate), and filtered and the filtrate was concentrated under reduced pressure to afford the title compound in sufficient purity for use in the next step. MS: m/z=218.1 [M-tBu+H].

INTERMEDIATE 7

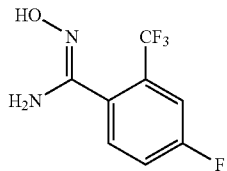

4-Fluoro-N-hydroxy-2-(trifluoromethyl)benzenecarboximidamide

To a solution of 4-fluoro-2-(trifluoromethyl)benzonitrile (15.0 g, 79.3 mmol) in methanol (190 mL) was added an aqueous solution of hydroxylamine (50% w/w, 48 mL, 783 mmol) and the reaction mixture was warmed to 60° C. and allowed to stir for 21 h. The reaction mixture was cooled and concentrated under reduced pressure. The residue was purified by silica gel chromatography, eluting with a gradient of hexanes:ethyl acetate—100:0 to 70:30 to afford the title compound. MS: m/z=223.3 [M+H].

INTERMEDIATE 8

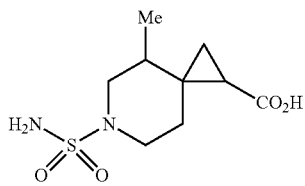

4-Methyl-6-sulfamoyl-6-azaspiro[2.5]octane-1-carboxylic Acid

Step A: tert-Butyl 3-methyl-4-methylidenepiperidine-1-carboxylate

To a solution of tert-butyl 3-methyl-4-oxopiperidine-1-carboxylate (2.95 g, 13.9 mmol) in dimethylsulfoxide (45 mL) were added methyltriphenylphosphonium bromide (7.42 g, 20.8 mmol) and potassium tert-butoxide (2.33 g, 20.8 mmol) sequentially and the reaction mixture was allowed to stir for 16 h at ambient temperature. The reaction mixture was poured into water (200 mL) and the resulting mixture extracted with ethyl acetate (2×300 mL). The combined organic extracts were washed with a saturated aqueous solution of sodium chloride (150 mL), dried (sodium sulfate), and concentrated under reduced pressure. The residue was purified by silica gel chromatography, eluting with a gradient of hexanes:ethyl acetate—100:0 to 70:30 to afford the title compound. MS: m/z=212.2 [M+H].

Step B: 6-tert-Butyl 1-ethyl 4-methyl-6-azaspiro [2.5]octane-1,6-dicarboxylate

To a solution of tert-butyl 3-methyl-4-methylidenepiperidine-1-carboxylate (2.78 g, 13.2 mmol) in dichloromethane (42 mL) was added rhodium(II) acetate dimer (0.582 g, 1.32 mmol). A solution of ethyl diazoacetate in dichloromethane (2.19 M, 18.0 mL, 39.4 mmol) was added dropwise over the course of 75 min at ambient temperature. The reaction mixture was poured into water (100 mL) and the resulting mixture extracted with dichloromethane (2×100 mL). The combined organic extracts were washed with a saturated aqueous solution of sodium chloride (60 mL), dried (sodium sulfate), and filtered and the filtrate was concentrated under reduced pressure. The residue was purified by silica gel chromatography, eluting with a gradient of hexanes:ethyl acetate—100:0 to 60:40 to afford the title compound. MS: m/z=298.2 [M+H].

Step C: Ethyl 4-methyl-6-azaspiro[2.5]octane-1-carboxylate

To a solution of 6-tert-butyl 1-ethyl 4-methyl-6-azaspiro [2.5]octane-1,6-dicarboxylate in 1,4-dioxane (63 mL) was added a solution of HCl in 1,4-dioxane (4 M, 31.5 mL, 126 mmol) and the reaction mixture was allowed to stir for 3 h at ambient temperature. The reaction mixture was concentrated under reduced pressure to afford the title compound in sufficient purity for use in the next step.

Step D: Ethyl 4-methyl-6-sulfamoyl-6-azaspiro[2.5] octane-1-carboxylate

To a solution of ethyl 4-methyl-6-azaspiro[2.5]octane-1-carboxylate (3.07 g, 13.1 mmol) in 1,4-dioxane (50 mL) were added sulfamide (3.78 g, 39.3 mmol) and triethylamine (2.74 mL, 19.7 mmol) and the reaction mixture was warmed to 110° C. and allowed to stir for 18 h. The reaction mixture was cooled to ambient temperature and poured into water (100 mL) and the resulting mixture was extracted with ethyl acetate (3×150 mL). The combined organic extracts were washed with a saturated aqueous solution of sodium chloride (100 mL), dried (sodium sulfate), and filtered and the filtrate was concentrated under reduced pressure. The residue was purified by silica gel chromatography, eluting with a gradient of dichloromethane:methanol—100:0 to 95:5 to afford the title compound. MS: m/z=277.2 [M+H].

Step E: 4-Methyl-6-sulfamoyl-6-azaspiro[2.5]octane-1-carboxylic Acid

To a solution of ethyl 4-methyl-6-sulfamoyl-6-azaspiro [2.5]octane-1-carboxylate (5.63 g, 21.5 mmol) in tetrahydrofuran (36 mL) and methanol (18 mL) was added an aqueous solution of sodium hydroxide (2 M, 37.0 mL, 74.0 mmol) and the reaction mixture was allowed to stir for 12 h. The reaction mixture was poured into water (70 mL) and the resulting mixture washed with diethyl ether (50 mL). The aqueous layer was adjusted to pH=5 with an aqueous solution of hydrochloric acid (12 M) and extracted with ethyl acetate (2×200 mL). The combined organic extracts were washed with a saturated aqueous solution of sodium chloride (50 mL), dried (sodium sulfate), and filtered and the filtrate was concentrated under reduced pressure to afford the title compound in sufficient purity for use in the next step. MS: m/z=249.1 [M+H].

INTERMEDIATE 9

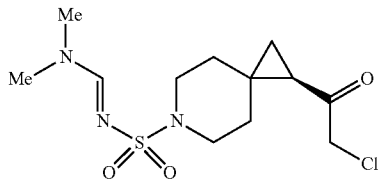

(1R)-1-(Chloroacetyl)-N-[(dimethylamino)methylidene]-6-azaspiro[2.5]octane-6-sulfonamide To a solution of (1R)-6-sulfamoyl-6-azaspiro[2.5]octane-1-carboxylic acid (Intermediate 1) (500 mg, 2.13 mmol) in dichloromethane (5 mL) and N,N-dimethylformamidine (0.1 mL) at 0° C. was added oxalyl chloride (0.558 mL, 6.51 mmol). The reaction mixture was allowed to warm to ambient temperature and stir for 10 min. The reaction mixture was concentrated under reduced pressure. The residue was dissolved in acetonitrile (6 mL), cooled to 0° C., and a solution of (trimethylsilyl)diazomethane (2 M, 3.90 mL, 7.80 mmol) was added. The reaction mixture was allowed to warm to ambient temperature and stir for 1 h. The reaction mixture was cooled to 0° C. and a solution of hydrogen chloride in 1,4-dioxane (4 M, 2.92 mL, 11.7 mmol) was added. The reaction mixture was allowed to warm to ambient temperature and stir for 1 h. A solution of saturated aqueous sodium bicarbonate was added and the aqueous layer was extracted with ethyl acetate (3×10 mL). The combined organic extracts were dried (sodium sulfate) and filtered and the filtrate was concentrated under reduced pressure to afford the title compound in sufficient purity for use in the next step. MS: m/z=322.0 [M+H].

INTERMEDIATE 10

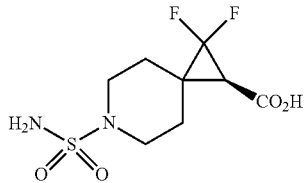

(1R)-2,2-Difluoro-6-sulfamoyl-6-azaspiro[2.5]octane-1-carboxylic Acid

Step A: tert-Butyl 4-(2-methoxy-2-oxoethylidene)piperidine-1-carboxylate

To a solution of tert-butyl 4-oxopiperidine-1-carboxylate (8.40 g, 42.2 mmol) in toluene (100 mL) was added methyl 2-(triphenylphosphoranylidene)acetate (17.6 g, 52.7 mmol) and the reaction mixture was warmed to 110° C. and allowed to stir for 4 h. The reaction mixture was cooled to ambient temperature and concentrated under reduced pressure. Hexanes were added to the residue and the resulting mixture filtered, washing with hexanes, and the filtrate was concentrated under reduced pressure. The residue was purified by silica gel chromatography, eluting with a gradient of hexanes:ethyl acetate—100:0 to 50:50 to afford the title compound. MS: m/z=200.1 [M-tBu+H].

Step B: tert-Butyl 4-(2-hydroxyethylidene)piperidine-1-carboxylate

To a solution of tert-butyl 4-(2-methoxy-2-oxoethylidene)piperidine-1-carboxylate (7.54 g, 29.5 mmol) in tetrahydrofuran (60 mL) at −78° C. was added a solution of diisobutylammonium hydride in tetrahydrofuran (1 M, 60.0 mL, 60.0 mmol) dropwise and the reaction mixture was allowed to stir for 1 h at −78° C. The reaction mixture was allowed to warm to 0° C. and stir for 1 h. A solution of diisobutylammonium hydride in tetrahydrofuran (1 M, 40.0 mL, 40.0 mmol) was added dropwise and the reaction mixture was allowed to stand at 0° C. for 18 h. An aqueous solution of Rochelle's salt (0.5 M) was added slowly and the resulting mixture was diluted with water and extracted with ethyl acetate (2×). The combined organic extracts were washed with a saturated aqueous solution of sodium chloride, dried (magnesium sulfate) and filtered and the filtrate was concentrated under reduced pressure to afford the title compound in sufficient purity for use in the next step. MS: m/z=195.2 [M+Na-tBu].

Step C: Tert-Butyl 4-(2-acetoxyethylidene)piperidine-1-carboxylate

To a solution of tert-butyl 4-(2-hydroxyethylidene)piperidine-1-carboxylate (5.80 g, 25.5 mmol) in dichloromethane (100 mL) were added pyridine (4.13 mL, 51.0 mmol), 4-dimethylaminopyridine (0.312 g, 2.55 mmol), and acetic anhydride (4.82 mL, 51.0 mmol) sequentially and the reaction mixture was allowed to stir for 2 h at ambient temperature. The reaction mixture was concentrated under reduced pressure and the residue was purified by silica gel chromatography, eluting with a gradient of hexanes:ethyl acetate—100:0 to 25:75 to afford the title compound. MS: m/z=292.2 [M+Na].

Step D: Tert-Butyl 2-(acetoxymethyl)-1,1-difluoro-6-azaspiro[2.5]octane-6-carboxylate To a solution of tert-butyl 4-(2-acetoxyethylidene)piperidine-1-carboxylate (3.23 g, 12.0 mmol) in tetrahydrofuran (30 mL) in a sealable vessel under an atmosphere of nitrogen were added sodium iodide (0.899 g, 6.00 mmol) and trimethyl(trifluoromethyl)silane (4.43 mL, 30.0 mmol) sequentially. The vessel was sealed and the reaction mixture was warmed to 90° C. and allowed to stir for 2 h. The reaction mixture was cooled to ambient temperature, sodium iodide (0.899 g, 6.00 mmol) and trimethyl(trifluoromethyl)silane (4.43 mL, 30.0 mmol) were added, and the reaction mixture was warmed to 90° C. and allowed to stir for 2 h. The reaction mixture was allowed to cool to ambient temperature, diluted with water, and the resulting mixture extracted with ethyl acetate. The organic layer was concentrated under reduced pressure and the residue was purified by silica gel chromatography, eluting with a gradient of hexanes:ethyl acetate—100:0 to 50:50 to afford the title compound. MS: m/z=264.1 [M-tBu+H].

Step E: Tert-Butyl 1,1-difluoro-2-(hydroxymethyl)-6-azaspiro[2.5]octane-6-carboxylate To a solution of tert-butyl 2-(acetoxymethyl)-1,1-difluoro-6-azaspiro[2.5]octane-6-carboxylate (5.68 g, 17.8 mmol) in methanol (50 mL) was added potassium carbonate (7.37 g, 53.4 mmol) and the reaction mixture was allowed to stir for 2 h at ambient temperature. The reaction mixture was filtered, washing with methanol, and the filtrate was concentrated under reduced pressure. Ethyl acetate and water were added, the layers separated, and the aqueous layer was adjusted to pH=5 and extracted with ethyl acetate. The organic extract was dried (magnesium sulfate) and filtered and the filtrate was concentrated under reduced pressure to afford the title compound in sufficient purity for use in the next step. MS: m/z=222.1 [M-tBu+H].

Step F: 6-(tert-Butoxycarbonyl)-2,2-difluoro-6-azaspiro[2.5]octane-1-carboxylic Acid To a solution of tert-butyl 1,1-difluoro-2-(hydroxymethyl)-6-azaspiro[2.5]octane-6-carboxylate (4.93 g, 17.9 mmol) in acetonitrile (100 mL) were added 4-methylmorpholine-4-oxide hydrate (24.0 g, 178 mmol) and tetrapropylammonium perruthenate (0.625 g, 1.78 mmol) sequentially and the reaction mixture was allowed to stir for 2 h at ambient temperature. The reaction mixture was diluted with an aqueous solution of hydrochloric acid (1 M) and extracted with ethyl acetate. The aqueous layer was diluted with water and a saturated aqueous solution of sodium chloride, extracted with ethyl acetate, and the combined organic extracts filtered over a pad of Celite® and concentrated under reduced pressure to afford the title compound in sufficient purity for use in the next step. MS: m/z=236.1 [M-tBu+H].

Step G: 1-Benzyl 6-tert-butyl 2,2-difluoro-6-azaspiro[2.5]octane-1,6-dicarboxylate To a solution of 6-(tert-butoxycarbonyl)-2,2-difluoro-6-azaspiro[2.5]octane-1-carboxylic acid (5.18 g, 17.9 mmol) in N,N-dimethylformamide (100 mL) were added HATU (10.1 g, 26.7 mmol), benzyl alcohol (2.77 mL, 26.7 mmol), and diisopropylethylamine (9.32 mL, 53.3 mmol) sequentially and the reaction mixture was allowed to stir for 1 h at ambient temperature. The reaction mixture was diluted with water and extracted with ethyl acetate (2×) The combined organic extracts were dried (magnesium sulfate) and filtered and the filtrate was concentrated under reduced pressure. The residue was purified by silica gel chromatography, eluting with a gradient of hexanes:ethyl acetate—100:0 to 50:50 to afford the title compound. MS: m/z=326.2 [M-tBu+H].

Step H: Benzyl 2,2-difluoro-6-azaspiro[2.5]octane-1-carboxylate Hydrochloride To a solution of 1-benzyl 6-tert-butyl 2,2-difluoro-6-azaspiro[2.5]octane-1,6-dicarboxylate (4.70 g, 12.3 mmol) in ethyl acetate (25 mL) was added a solution of hydrogen chloride in 1,4-dioxane (4 M, 12.3 mL, 49.3 mmol) and the reaction mixture was allowed to stir for 18 h at ambient temperature. The reaction mixture was concentrated under reduced pressure to afford the title compound in sufficient purity for use in the next step. MS: m/z=282.2 [M+H].

Step I: (1R)-Benzyl 2,2-difluoro-6-sulfamoyl-6-azaspiro[2.5]octane-1-carboxylate To a solution of benzyl 2,2-difluoro-6-azaspiro[2.5]octane-1-carboxylate hydrochloride (3.92 g, 12.3 mmol) in 1,4-dioxane (60 mL) were added triethylamine (2.58 mL, 18.5 mmol) and sulfamide (3.56 g, 37.0 mmol) and the reaction mixture was warmed to 90° C. and allowed to stir for 4 h. The reaction mixture was cooled to ambient temperature and sulfamide (3.56 g, 37.0 mmol) was added. The reaction mixture was warmed to 90° C. and allowed to stir for 4 h. The reaction mixture was concentrated under reduced pressure and ethyl acetate and water were added to the residue. The aqueous layer was extracted with ethyl acetate and the combined organic extracts were dried (magnesium sulfate) and filtered and the filtrate was concentrated under reduced pressure. The residue was purified by silica gel chromatography, eluting with a gradient of hexanes:ethyl acetate:ethanol—100:0:0 to 52:36:12 to afford the racemic title compound. The racemate was resolved by SFC, utilizing a ChiralPak AD-H column and eluting with methanol:carbon dioxide—40:60. The first major peak to elute was (1R)-benzyl 2,2-difluoro-6-sulfamoyl-6-azaspiro[2.5]octane-1-carboxylate, the title compound, and the second major peak to elute was (1S)-benzyl 2,2-difluoro-6-sulfamoyl-6-azaspiro[2.5]octane-1-carboxylate. MS: m/z=361.2 [M+H].

Step J: (1R)-2,2-Difluoro-6-sulfamoyl-6-azaspiro[2.5]octane-1-carboxylic Acid To a vessel containing (1R)-benzyl 2,2-difluoro-6-sulfamoyl-6-azaspiro[2.5]octane-1-carboxylate (1.20 g, 3.33 mmol) was added palladium on activated carbon (10% w/w, 0.354 g, 0.333 mmol) under an inert atmosphere. Methanol (17 mL) was added and the reaction mixture was placed under an atmosphere of hydrogen (ca. 1 atm) and allowed to stir for 3 h at ambient temperature. The reaction mixture was filtered over a pad of Celite®, washing with methanol, and the filtrate was concentrated under reduced pressure to afford the title compound in sufficient purity for use in the next step. MS: m/z=271.1 [M+H].

INTERMEDIATE 11

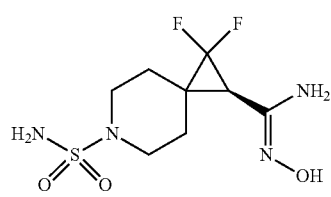

(1R)-2,2-Difluoro-N-hydroxy-6-sulfamoyl-6-azaspiro[2.5]octane-1-carboximidamide

Step A: (1R)-2,2-Difluoro-6-sulfamoyl-6-azaspiro[2.5]octane-1-carboxamide

To a solution of (1R)-2,2-difluoro-6-sulfamoyl-6-azaspiro[2.5]octane-1-carboxylic acid (Intermediate 10) (10.8 g, 40.0 mmol) in dichloromethane (200 mL) and dimethylsulfoxide (11 mL) were added ammonium chloride (6.5 g, 122 mmol), HATU (18.3 g, 48.0 mmol), and N-methylmorpholine (20 mL, 182 mmol) sequentially and the reaction mixture was allowed to stir for 18 h at ambient temperature. The reaction mixture was diluted with water and filtered and the precipitate dried under reduced pressure to afford the title compound in sufficient purity for use in the next step. MS: m/z=270.1 [M+H].

Step B: (2R)-2-Cyano-1,1-difluoro-6-azaspiro[2.5]octane-6-sulfonamide

To a solution of (1R)-2,2-difluoro-6-sulfamoyl-6-azaspiro[2.5]octane-1-carboxamide (6.16 g, 22.9 mmol) in acetonitrile (100 mL) was added phosphorous oxychloride (4.26 mL, 45.8 mmol) dropwise and the reaction mixture was warmed to 80° C. and allowed to stir for 3 h. The reaction mixture was cooled to ambient temperature and a saturated aqueous solution of sodium bicarbonate was added slowly. The resulting mixture was extracted with 15 ethyl acetate (2×). The combined organic extracts were dried (sodium sulfate) and filtered and the filtrate was concentrated under reduced pressure to afford the title compound in sufficient purity for use in the next step. MS: m/z=293.1 [M+CH$_3$CN+H].

Step C: (1R)-2,2-Difluoro-N'-hydroxy-6-sulfamoyl-6-azaspiro[2.5]octane-1-caboximidamide To a solution of (2R)-2-cyano-1,1-difluoro-6-azaspiro[2.5]octane-6-sulfonamide (320 mg, 1.27 mmol) in methanol (4 mL) was added an aqueous solution of hydroxylamine (50% w/w, 1.00 mL, 16.3 mmol) and the reaction mixture was allowed to stir for 2 days at ambient temperature. The reaction mixture was concentrated under reduced pressure to afford the title compound in sufficient purity for use in the next step. MS: m/z=285.2 [M+H].

INTERMEDIATE 12

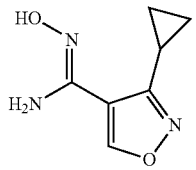

3-Cyclopropyl-N-hydroxyisoxazole-4-carboximidamide

Step A: 3-Cyclopropylisoxazole-4-carboxamide

To a solution of 3-cyclopropylisoxazole-4-carboxylic acid (0.758 g, 4.95 mmol) in dichloromethane (22 mL) and dimethylsulfoxide (2.2 mL) were added HATU (2.06 g, 5.42 mmol), ammonium chloride (0.545 g, 10.2 mmol), and N-methylmorpholine (1.60 mL, 14.6 mmol) and the reaction mixture was allowed to stir for 18 h at ambient temperature. The reaction mixture was washed with a saturated aqueous solution of ammonium chloride (4×20 mL) and a saturated aqueous solution of sodium chloride (1×20 mL), dried (magnesium sulfate), and filtered and the filtrate was concentrated under reduced pressure. The residue was purified by silica gel chromatography, eluting with a gradient of hexanes:ethyl acetate:ethanol—100:0:0 to 60:30:10 to afford the title compound. MS: m/z=153.2 [M+H].

Step B: 3-Cyclopropylisoxazole-4-carbonitrile

To a solution of 3-cyclopropylisoxazole-4-carboxamide (330 mg, 2.17 mmol) in acetonitrile (11 mL) was added phosphorus oxychloride (0.404 mL, 4.34 mmol) and the reaction mixture was warmed to 80° C. and allowed to stir for 1.3 h. The reaction mixture was cooled to ambient temperature and added slowly to a cold, saturated aqueous solution of sodium bicarbonate (30 mL) and the resulting mixture extracted with ethyl acetate (3×30 mL). The combined organic extracts were washed with a saturated aqueous solution of sodium chloride (1×15 mL), dried (magnesium sulfate), and filtered and the filtrate was concentrated under reduced pressure to afford the title compound in sufficient purity for use in the next step. $^1$H NMR (DMSO-d$_6$) δ 9.75 (s, 1H), 2.13-2.06 (m, 1H), 1.18-1.10 (m, 2H), 1.03-0.97 (m, 2H).

Step C: 3-Cyclopropyl-N-hydroxyisoxazole-4-carboximidamide

To a solution of 3-cyclopropylisoxazole-4-carbonitrile (230 mg, 1.72 mmol) in ethanol (5.80 mL) was added hydroxylamine (0.841 mL, 13.7 mmol) and the reaction mixture was warmed to 80° C. and allowed to stir for 3 h. The reaction mixture was cooled to ambient temperature and concentrated under reduced pressure. The residue was co-evaporated with ethanol (3×) and acetonitrile (2×) to afford the title compound in sufficient purity for use in the next step. MS: m/z=168.1 [M+H].

INTERMEDIATE 13

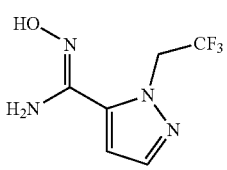

N-Hydroxy-1-(2,2,2-trifluoroethyl)-1H-pyrazole-5-carboximidamide

Step A: 1-(2,2,2-Trifluoroethyl)-1H-pyrazole-5-carboxamide

To a solution of 1-(2,2,2-trifluoroethyl)-1H-pyrazole-5-carboxylic acid (388 mg, 2.00 mmol) in dichloromethane (9.5 mL) and dimethylsulfoxide (0.50 mL) was added ammonium chloride (267 mg, 5.00 mmol), HATU (837 mg, 2.20 mmol), and N-methylmorpholine (0.660 mL, 6.00 mmol) sequentially and the reaction mixture was allowed to stir for 16 h at ambient temperature. The reaction mixture was diluted with water and the layers were separated. The aqueous layer was extracted with dichloromethane and the combined organic extracts were concentrated under reduced pressure. The residue was purified by silica gel chromatography, eluting with a gradient of hexanes:ethyl acetate:ethanol—96:3:1 to 52:36:12 to afford the title compound. MS: m/z=194.1 [M+H].

Step B: 5-Cyano-1-(2,2,2-trifluoroethyl)-1H-pyrazole

To a solution of 1-(2,2,2-trifluoroethyl)-1H-pyrazole-5-carboxamide (365 mg, 1.89 mmol) in acetonitrile (10 mL) was added phosphorous oxychloride (0.352 mL, 3.78 mmol) dropwise and the reaction mixture was warmed to 80° C. and allowed to stir for 2 h. The reaction mixture was cooled to ambient temperature, phosphorous oxychloride (0.352 mL, 3.78 mmol) was added dropwise, and the reaction mixture was warmed to 85° C. and allowed to stir for 1 h. The reaction mixture was allowed to cool to ambient temperature and a solution of saturated aqueous sodium bicarbonate was added slowly. The mixture was diluted with water and extracted with ethyl acetate (3×). The combined organic extracts were washed with a saturated aqueous solution of sodium chloride and concentrated under reduced pressure to give the title compound in sufficient purity for use in the next step.

Step C: (R)—N'-Hydroxy-1-(2,2,2-trifluoroethyl)-1H-pyrazole-5-carboximidamide

To a solution of 5-cyano-1-(2,2,2-trifluoroethyl)-1H-pyrazole (135 mg, 0.771 mmol) in methanol (1.6 mL) was added an aqueous solution of hydroxylamine (50% w/w, 0.400 mL, 6.53 mmol) and the reaction mixture was warmed to 65° C. and allowed to stir for 2 h. The reaction mixture was cooled to ambient temperature and the reaction mixture concentrated under reduced pressure to afford the title compound in sufficient purity for use in the next step. MS: m/z=209.1 [M+H].

INTERMEDIATE 14

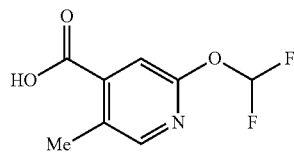

2-(Difluoromethoxy)-5-methylisonicotinic Acid

Step A: Methyl 5-bromo-2-(difluoromethoxy)isonicotinate

To a solution of methyl 5-bromo-2-hydroxyisonicotinate (2.00 g, 8.62 mmol) in acetonitrile (100 mL) was added sodium chlorodifluoroacetate (4.00 g, 26.2 mmol) and the reaction mixture was warmed to 90° C. and allowed to stir for 16 h. The reaction mixture was cooled to ambient temperature, filtered, and the filtrate was concentrated under reduced pressure. The residue was purified by silica gel chromatography, eluting with a gradient of ethyl acetate:hexanes—0:100 to 50:50 to afford the title compound. MS: m/z=284.0 [M+H].

Step B: Methyl 2-(difluoromethoxy)-5-methylisonicotinate

To a solution of 5-bromo-2-(difluoromethoxy)isonicotinate (282 mg, 1.00 mmol) and potassium phosphate (424 mg, 2.00 mmol) in 1,4-dioxane (4.50 mL) and water (0.50 mL) were added 1,1'-bis(di-tert-butylphosphino)ferrocene palladium dichloride (65.2 mg, 0.100 mmol) and 2,4,6-trimethyl-1,3,5,2,4,6-trioxatriborinane (251 mg, 2.00 mmol). The reaction mixture was warmed to 100° C. and allowed to stir for 16 h. The reaction mixture was cooled to ambient temperature, filtered through a pad of Celite©, washing with 1,4-dioxane, and the filtrate was concentrated under reduced pressure. The residue was purified by silica gel chromatography, eluting with a gradient of ethyl acetate:hexanes—0:100 to 50:50 to afford the title compound. MS: m/z=218.1 [M+H].

Step C: 2-(Difluoromethoxy)-5-methylisonicotinic Acid

To a solution of methyl 2-(difluoromethoxy)-5-methylisonicotinate (110 mg, 0.507 mmol) in tetrahydrofuran (1.5 mL) was added an aqueous solution of sodium hydroxide (1 M, 1.52 mL, 1.52 mmol) and the reaction mixture was warmed to 40° C. and allowed to stir for 1 h. The reaction mixture was cooled to ambient temperature and adjusted to pH=1 with an aqueous solution of hydrochloric acid (1 M) and the resulting mixture extracted with ethyl acetate. The combined organic extracts were dried (sodium sulfate) and filtered and the filtrate was concentrated under reduced pressure to afford the title compound in sufficient purity for use in the next step. MS: m/z=204.1 [M+H].

INTERMEDIATE 15

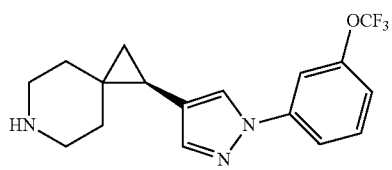

(1R)-1-{1-[3-(Trifluoromethoxy)phenyl]-1H-pyrazol-4-yl}-6-azaspiro[2.5]octane

Step A: (1R)-6-[(Benzyloxy)carbonyl]-6-azaspiro[2.5]octane-1-carboxylic Acid

To a stirred solution of 6-benzyl 1-ethyl (1R)-6-azaspiro[2.5]octane-1,6-dicarboxylate (Brown et al. *J. Med. Chem.* (2014) 57:733-758) (2.0 g, 6.3 mmol) in ethanol (30 mL) was added an aqueous solution of sodium hydroxide (1 M, 19 mL, 19 mmol) and the reaction mixture was warmed to 50° C. and allowed to stir for 2 h. The reaction mixture was cooled and concentrated under reduced pressure. Water (20 mL) was added and the resulting mixture adjusted to pH=4 by addition of an aqueous solution of hydrochloric acid (2 M). The aqueous layer was extracted with ethyl acetate (2×20 mL). The combined organic extracts were dried (sodium sulfate) and filtered and the filtrate was concentrated under reduced pressure to afford the title compound in sufficient purity for use in the next step. MS: m/z=290.0 [M+H].

Step B: Benzyl (1R)-1-(hydroxymethyl)-6-azaspiro[2.5]octane-6-carboxylate

To a solution of (1R)-6-((benzyloxy)carbonyl)-6-azaspiro[2.5]octane-1-carboxylic acid (100 mg, 0.35 mmol) in tetrahydrofuran (2 mL) at 0° C. was added borane dimethyl sulfide complex in tetrahydrofuran (10 M, 0.07 mL, 0.7 mmol) and the reaction mixture was allowed to stir for 0.5 h at 0° C. The reaction mixture was warmed to ambient temperature and allowed to stir for 1 h. Methanol was added slowly until gas evolution ceased and the resulting mixture concentrated under reduced pressure. The residue was purified by silica gel chromatography, eluting with petroleum ether:ethyl acetate—50:50 to afford the title compound. MS: m/z=276.1 [M+H].

Step C: Benzyl (1R)-1-formyl-6-azaspiro[2.5]octane-6-carboxylate

To a solution of benzyl (1R)-1-(hydroxymethyl)-6-azaspiro[2.5]octane-6-carboxylate (70 mg, 0.25 mmol) in dichloromethane (3 mL) was added Dess-Martin periodinane (162 mg, 0.382 mmol) and the reaction mixture was allowed to stir for 1 h at ambient temperature. Water (5 mL) was added and the aqueous layer extracted with dichloromethane (2×5 mL). The combined organic extracts were dried (sodium sulfate) and filtered and the filtrate was concentrated under reduced pressure. The residue was purified by silica gel chromatography, eluting with petroleum ether:ethyl acetate—75:25 to afford the title compound. MS: m/z=274.1 [M+H].

Step D: Benzyl (1S)-1-(2-methoxyvinyl)-6-azaspiro[2.5]octane-6-carboxylate

To a solution of (methoxymethyl)triphenylphosphonium chloride (188 mg, 0.55 mmol) in tetrahydrofuran (5 mL) at −78° C. was added a solution of lithium bis(trimethylsilyl) amide in tetrahydrofuran (1 M, 0.531 mL, 0.531 mmol) and the reaction mixture was allowed to stir for 0.5 h at −78° C. Benzyl (1R)-1-formyl-6-azaspiro[2.5]octane-6-carboxylate (50 mg, 0.18 mmol) was added and the reaction mixture was allowed to stir for 15 min. The reaction mixture was warmed to ambient temperature and allowed to stir for 1 h. Water (5 mL) was added and the resulting mixture extracted with ethyl acetate (2×5 mL). The combined organic extracts were dried (sodium sulfate), filtered, and the filtrate was concentrated under reduced pressure. The residue was purified by silica gel chromatography, eluting with petroleum ether:ethyl acetate—75:25 to afford the title compound. MS: m/z=302.1 [M+H].

Step E: N-[2-{(1R)-6-[(Benzyloxy)carbonyl]-6-azaspiro[2.5]oct-1-yl}-3-methoxyprop-2-en-1-ylidene]-N-methylmethanaminium Carbonate To a solution of N,N-dimethylformamide (0.032 mL, 0.42 mmol) in chloroform (1 mL) at 0° C. was added phosphorus oxychloride (0.039 mL, 0.42 mmol) and the reaction mixture was warmed to 40° C. and allowed to stir for 0.5 h. The reaction mixture was cooled to 0° C. and (1S)-benzyl 1-(2-methoxyvinyl)-6-azaspiro[2.5]octane-6-carboxylate (25 mg, 0.08 mmol) was added. The reaction mixture was warmed to 70° C. and allowed to stir for 1 h. The reaction mixture was cooled to 0° C. and an aqueous solution of potassium carbonate (0.83 M, 1 mL, 0.83 mmol) was added. The reaction mixture was diluted with water (3 mL) and the aqueous layer extracted with dichloromethane (2×5 mL). The combined organic extracts were dried (sodium sulfate) and filtered and the filtrate was concentrated under reduced pressure to afford the title compound in sufficient purity for use in the next step. MS: m/z=357.1 [M+H].

Step F: Benzyl (1R)-1-{1-[3-(trifluoromethoxy)phenyl]-1H-pyrazol-4-yl}-6-azaspiro[2.5]octane-6-carboxylate To a solution of (R)—N-(2-(6-((benzyloxy)carbonyl)-6-azaspiro[2.5]octan-1-yl)-3-methoxyallylidene)-N-methylmethanaminium carbonate (150 mg, 0.42 mmol) in methanol (4 mL) were added (3-(trifluoromethoxy)phenyl)hydrazine (806 mg, 4.20 mmol) and an aqueous solution of hydrochloric acid (2 M, 2.10 mL, 4.20 mmol) and the reaction mixture was warmed to 60° C. and allowed to stir for 1 h. The reaction mixture was adjusted to pH=10 with a saturated aqueous solution of sodium bicarbonate and the aqueous layer extracted with ethyl acetate (2×5 mL). The combined organic extracts were dried (sodium sulfate) and filtered and the filtrate was concentrated under reduced pressure. The residue was purified by silica gel chromatography, eluting with petroleum ether:ethyl acetate—75:25 to afford the title compound. MS: m/z=472.1 [M+H].

Step G: (1R)-1-{1-[3-(Trifluoromethoxy)phenyl]-1H-pyrazol-4-yl}-6-azaspiro[2.5]octane To a solution of benzyl (1R)-1-{1-[3-(trifluoromethoxy)phenyl]-1H-pyrazol-4-yl}-6-azaspiro[2.5]octane-6-carboxylate (150 mg, 0.32 mmol) in methanol (5 mL) and ethyl acetate (5 mL) was added palladium hydroxide on activated carbon (10% w/w, 22.3 mg, 0.032 mmol) and the reaction mixture was allowed to stir under an atmosphere of hydrogen (25 psi) for 1 h at ambient temperature. The reaction mixture was filtered through Celite® and the filtrate was concentrated under reduced pressure to afford the title compound. MS: m/z=338.1 [M+H].

INTERMEDIATE 16

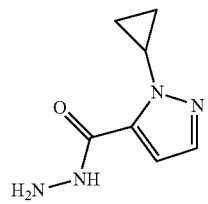

1-Cyclopropyl-1H-pyrazole-5-carbohydrazide

To a solution of 1-cyclopropyl-1H-pyrazole-5-carboxylic acid (300 mg, 1.97 mmol) in dichloromethane (4.0 mL) was added a solution of oxalyl chloride in dichloromethane (2 M, 2.96 mL, 5.92 mmol) and the reaction mixture was allowed to stir for 0.5 h at ambient temperature. The reaction mixture was concentrated under reduced pressure. Dichloromethane 5 (4.0 mL) and methanol (0.16 mL, 3.94 mmol) were added sequentially and the reaction mixture was allowed to stir for 2 h at ambient temperature. The reaction mixture was concentrated under reduced pressure. The residue was dissolved in ethanol (2.0 mL) and hydrazine (0.60 mL, 19 mmol) was added and the reaction mixture was allowed to stir for 18 h at ambient temperature. The reaction mixture was concentrated under reduced pressure. The residue was purified by 10 silica gel chromatography, eluting with a gradient of dichloromethane:methanol—100:0 to 95:5 to afford the title compound. MS: m/z=167.0 [M+H].

INTERMEDIATE 17

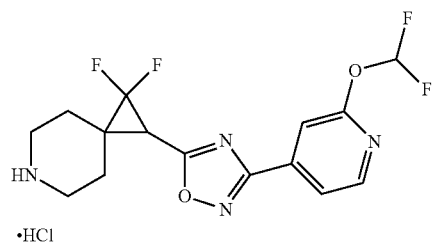

·HCl

2-{3-[2-(Difluoromethoxy)pyridin-4-yl]-1,2,4-oxadiazol-5-yl}-1,1-difluoro-6-azaspiro[2.5]octane Hydrochloride

Step A: 6-(tert-Butoxycarbonyl)-2,2-difluoro-6-azaspiro[2.5]octane-1-carboxylic Acid To a solution of 1-benzyl 6-tert-butyl 2,2-difluoro-6-azaspiro[2.5]octane-1,6-dicarboxylate (described in Intermediate 10) (500 mg, 1.31 mmol) in methanol (26 mL) was added palladium on carbon (10% w/w, 42 mg, 0.039 mmol) and the reaction mixture was allowed to stir under an atmosphere of hydrogen for 1.5 h at ambient temperature. The reaction mixture was filtered through Celite®, washing with methanol, and the filtrate was concentrated under reduced pressure to afford the title compound in sufficient purity for use in the next step. MS: m/z=236.1 [M-tBu+H].

Step B: tert-Butyl 2-{3-[2-(difluoromethoxy)pyridin-4-yl]-1,2,4-oxadiazol-5-yl}-1,1-difluoro-6-azaspiro[2.5]octane-6-carboxylate To a solution of 6-(tert-butoxycarbonyl)-2,2-difluoro-6-azaspiro[2.5]octane-1-carboxylic acid (386 mg, 1.325 mmol) in 1,2-dichloroethane (12 mL) and dimethylsulfoxide (1.2 mL) were added 1-(3-dimethylaminopropyl)-3-ethylcarbodiimide hydrochloride (330 mg, 1.72 mmol), 1-hydroxy-7-azabenzotriazole (126 mg, 0.928 mmol), and 2-(difluoromethoxy)-N-hydroxypyridine-4-carboximidamide (Intermediate A7) (350 mg, 1.72 mmol) and the reaction mixture was allowed to stir for 0.5 h at ambient temperature. The reaction mixture was warmed to 100° C. and allowed to stir for 4.5 h. The reaction mixture was cooled to ambient temperature and poured into a saturated aqueous solution of ammonium chloride (20 mL) and the resulting mixture extracted with dichloromethane (3×25 mL). The combined organic extracts were washed with a saturated aqueous solution of ammonium chloride (2×20 mL) and a saturated aqueous solution of sodium chloride (1×20 mL), dried (magnesium sulfate), and filtered and the filtrate was concentrated under reduced pressure. The residue was purified by silica gel chromatography, eluting with a gradient of hexanes:ethyl acetate—100:0 to 61:39 to afford the title compound. MS: m/z=403.2 [M-tBu+H].

Step C: 2-{3-[2-(Difluoromethoxy)pyridin-4-yl]-1,2,4-oxadiazol-5-yl}-1,1-difluoro-6-azaspiro[2.5]octane Hydrochloride To a solution of tert-butyl 2-{3-[2-(difluoromethoxy)pyridin-4-yl]-1,2,4-oxadiazol-5-yl}-1,1-difluoro-6-azaspiro[2.5]octane-6-carboxylate (393 mg, 0.858 mmol) in 1,4-dioxane (4.3 mL) was added a solution of HCl in 1,4-dioxane (4 M, 4.30 mL, 17.2 mmol) and the reaction mixture was allowed to stir for 2 h at ambient temperature. The reaction mixture was concentrated under a stream of nitrogen to afford the title compound in sufficient purity for use in the next step. MS: m/z=359.2 [M+H].

(1R)-1-[4-(3-Cyclopropylisoxazol-4-yl)-1,3-oxazol-2-yl]-6-azaspiro[2.5]octane

Step A: Benzyl (1R)-1-carbamoyl-6-azaspiro[2.5]octane-6-carboxylate

To a solution of (1R)-6-[(benzyloxy)carbonyl]-6-azaspiro[2.5]octane-1-carboxylic acid (described in Intermediate 15) (1.95 g, 6.74 mmol) in dichloromethane (60 mL) and dimethylsulfoxide (3.0 mL) were added HATU (2.69 g, 7.07 mmol), N-methylmorpholine (2.97 mL, 27.0 mmol), and ammonium chloride (1.44 g, 26.9 mmol) sequentially and the reaction mixture was allowed to stir for 18 h at ambient temperature. The reaction mixture was poured into a saturated aqueous solution of ammonium chloride (70 mL) and the resulting mixture extracted with dichloromethane (3×75 mL). The combined organic extracts were washed with a saturated aqueous solution of ammonium chloride (3×75 mL) and a saturated aqueous solution of sodium chloride (1×75 mL), dried (magnesium sulfate), and filtered and the filtrate was concentrated under reduced pressure. The residue was purified by silica gel chromatography, eluting with a gradient of hexanes:ethyl acetate:ethanol—100:0:0 to 40:45:15 to afford the title compound. MS: m/z=289.2 [M+H].

Step B: Benzyl (1R)-1-[4-(3-cyclopropylisoxazol-4-yl)-1,3-oxazol-2-yl]-6-azaspiro[2.5]octane-6-carboxylate To a solution of benzyl (1R)-1-carbamoyl-6-azaspiro[2.5]octane-6-carboxylate (106 mg, 0.369 mmol) in ethyl acetate (2.0 mL) were added 2-bromo-1-(3-cyclopropylisoxazol-4-yl)ethanone (Intermediate E1) (76.2 mg, 0.330 mmol) and silver trifluoromethanesulfonate (100 mg, 0.390 mmol) sequentially and the reaction mixture was warmed to 75° C. and allowed to stir for 3.5 h. The reaction mixture was filtered and the filtrate was concentrated under reduced pressure. The residue was purified by silica gel chromatography, eluting with a gradient of hexanes:ethyl acetate—100:0 to 70:30 to afford the title compound. MS: m/z=389.3 [M+H].

Step C: (1R)-1-[4-(3-Cyclopropylisoxazol-4-yl)-1,3-oxazol-2-yl]-6-azaspiro[2.5]octane To a solution of benzyl (1R)-1-[4-(3-cyclopropylisoxazol-4-yl)-1,3-oxazol-2-yl]-6-azaspiro[2.5]octane-6-carboxylate (22 mg, 0.057 mmol) in ethyl acetate (1.5 mL) and methanol (2 mL) was added palladium hydroxide on carbon (20% w/w, 4.0 mg, 5.7 μmol). The reaction mixture was placed under an atmosphere of hydrogen and allowed to stir for 5 h at ambient temperature. The reaction mixture was filtered and the filtrate was concentrated under reduced pressure to afford the title compound in sufficient purity for use in the next step. MS: m/z=255.1 [M+H].

INTERMEDIATE 18

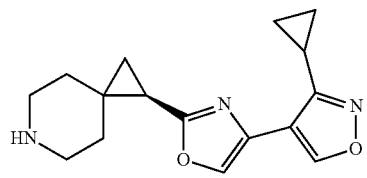

INTERMEDIATE 19

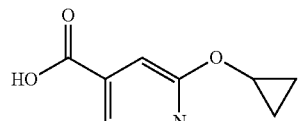

2-Cyclopropoxyisonicotinic Acid

To a mixture of sodium hydride (60% dispersion in mineral oil, 64.5 mg, 1.61 mmol) in tetrahydrofuran (8 mL) at ambient temperature was added cyclopropanol (94.0 mg, 1.61 mmol) dropwise and the reaction mixture was allowed to stir for 15 min after cessation of gas evolution. Methyl 2-fluoroisonicotinate (250 mg, 1.61 mmol) was added dropwise and the reaction mixture was allowed to stir for 16 h at ambient temperature. The reaction mixture was diluted with ethyl acetate and water and the layers separated and the aqueous layer adjusted to pH=1 with an aqueous solution of hydrochloric acid (1 M). The layers were separated and the organic layer concentrated under reduced pressure. The residue was purified by preparative HPLC, eluting with acetonitrile:water—0:100 to 95:5 to afford the title compound. MS: m/z=180.0 [M+H].

INTERMEDIATE 20

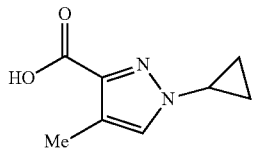

1-Cyclopropyl-4-methyl-1H-pyrazole-3-carboxylic Acid

Step A: Ethyl 1-cyclopropyl-4-methyl-1H-pyrazole-5-carboxylate

To a solution of ethyl 4-methyl-1H-pyrazole-5-carboxylate (1.00 g, 6.49 mmol) in 1,2-dichloroethane (50 mL) under an atmosphere of air were added cyclopropylboronic acid (1.11 g, 13.0 mmol) and sodium carbonate (1.38 g, 13.0 mmol). The reaction mixture was warmed to 70° C. and 2,2'-bipyridine (1.01 g, 6.49 mmol) and copper(II) acetate (1.18 g, 6.49 mmol) were added. The reaction mixture was allowed to stir for 18 h. The reaction mixture was cooled to ambient temperature and diluted with a saturated aqueous solution of sodium bicarbonate and the resulting mixture extracted with ethyl acetate (2×). The combined organic extracts were washed with a saturated aqueous solution of sodium chloride, dried (sodium sulfate), and filtered and the filtrate was concentrated under reduced pressure. The residue was purified by silica gel chromatography, eluting with a gradient of hexanes:ethyl acetate—100:0 to 50:50 to afford the title compound. MS: m/z=195.0 [M+H].

Step B: 1-Cyclopropyl-4-methyl-1H-pyrazole-5-carboxylic Acid

To a solution of ethyl 1-cyclopropyl-4-methyl-1H-pyrazole-5-carboxylate (425 mg, 2.19 mmol) in tetrahydrofuran (12 mL) was added an aqueous solution of sodium hydroxide (1 M, 9.00 mL, 9.00 mmol) and the reaction mixture was allowed to stir for 1.5 d at ambient temperature. The reaction mixture was adjusted to pH=1 with an aqueous solution of hydrochloric acid (1 M) and the mixture extracted with ethyl acetate (2×). The combined organic extracts were dried (sodium sulfate) and filtered and the filtrate was concentrated under reduced pressure to afford the title compound in sufficient purity for use in the next step. MS: m/z=189.1 [M+Na].

INTERMEDIATE 21

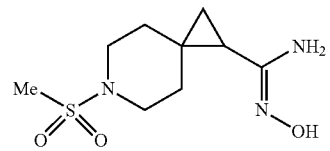

N'-Hydroxy-6-methylsulfonyl-6-azaspiro[2.5]octane-1-carboximidamide

Step A: Tert-Butyl 1-carbamoyl-6-azaspiro[2.5]octane-6-carboxylate

To a solution of 6-(tert-butoxycarbonyl)-6-azaspiro[2.5]octane-1-carboxylic acid (1.50 g, 5.88 mmol) in dichloromethane (28 mL) and dimethylsulfoxide (1.4 mL) was added HATU (2.30 g, 6.05 mmol), ammonium chloride (1.35 g, 25.2 mmol), and N-methylmorpholine (2.60 mL, 23.7 mmol) sequentially and the reaction mixture was allowed to stir for 18 h at ambient temperature. The reaction mixture was filtered and the precipitate washed with dichloromethane and water and dried under reduced pressure to afford the title compound in sufficient purity for use in the next step. MS: m/z=255.2 [M+H].

Step B: 6-Azaspiro[2.5]octane-1-carboxamide

To a solution of tert-butyl 1-carbamoyl-6-azaspiro[2.5]octane-6-carboxylate (703 mg, 2.76 mmol) in 1,4-dioxane (6.0 mL) and methanol (3.0 mL) was added HCl in dioxane (6.91 mL, 27.6 mmol) and the reaction mixture was allowed to stir for 0.5 h at ambient temperature. The reaction mixture was concentrated under reduced pressure to afford the title compound in sufficient purity for use in the next step. MS: m/z=155.1 [M+H].

Step C: 6-(Methylsulfonyl)-6-azaspiro[2.5]octane-1-carboxamide

To a solution of 6-azaspiro[2.5]octane-1-carboxamide hydrochloride (625 mg, 2.76 mmol) in dichloromethane (20 mL) were added triethylamine (2.30 mL, 16.5 mmol) and methanesulfonyl chloride (0.344 mL, 4.41 mmol) sequentially and the reaction mixture was allowed to stir for 2.5 h at ambient temperature. The reaction mixture was concentrated under reduced pressure and ethyl acetate (75 mL) added to the resulting residue. The mixture was filtered, washing with ethyl acetate, and the filtrate was concentrated under reduced pressure to afford the title compound in sufficient purity for use in the next step. MS: m/z=233.2 [M+H].

Step D: 6-(Methylsulfonyl)-6-azaspiro[2.5]octane-1-carbonitrile

To a solution of 6-(methylsulfonyl)-6-azaspiro[2.5]octane-1-carboxamide (702 mg, 2.75 mmol) in acetonitrile (25 mL) was added phosphorus oxychloride (0.940 mL, 10.1 mmol) and the reaction mixture was warmed to 60° C. and allowed to stir for 2 h. The reaction mixture was cooled to ambient temperature and slowly poured into a mixture of ice and a saturated aqueous solution of sodium bicarbonate (25 mL). The resulting mixture was extracted with ethyl acetate (3×35 mL). The combined organic phases were washed with a saturated aqueous solution of sodium chloride (1×15 mL), dried (sodium sulfate), and filtered and the filtrate was concentrated under reduced pressure. The residue was purified by silica gel chromatography, eluting with a gradient of hexanes:ethyl acetate:ethanol—100:0:0 to 35:49:16 to afford the title compound. MS: m/z=215.3 [M+H].

Step E: N-Hydroxy-6-methylsulfonyl-6-azaspiro [2.5]octane-1-carboximidamide

To a solution of 6-(methylsulfonyl)-6-azaspiro[2.5]octane-1-carbonitrile (370 mg, 1.73 mmol) in ethanol (8.60 mL) was added an aqueous solution of hydroxylamine (50% w/w, 0.969 mL, 17.2 mmol). The reaction mixture was warmed to 80° C. and allowed to stir for 3 h. The reaction mixture was cooled to ambient temperature and concentrated under a stream of nitrogen to afford the title compound in sufficient purity for use in the next step. MS: m/z=248.2 [M+H].

INTERMEDIATE 22

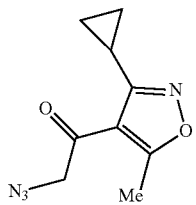

2-Azido-1-(3-cyclopropyl-5-methylisoxazol-4-yl) ethanone

Step A: 3-Cyclopropyl-N-methoxy-N,5-dimethyl-isoxazole-4-carboxamide

To a solution of 3-cyclopropyl-5-methylisoxazole-4-carboxylic acid (995 mg, 5.95 mmol) in dichloromethane (20 mL) and dimethylsulfoxide (2.0 mL) were added HATU (2.49 g, 6.55 mmol), 4-methylmorpholine (1.96 mL, 17.8 mmol), and N,O-dimethylhydroxylamine hydrochloride (639 mg, 6.55 mmol) and the reaction mixture was allowed to stir for 18 h at ambient temperature. The reaction mixture was poured into water (40 mL) and the resulting mixture extracted with dichloromethane (150 mL). The combined organic extracts were washed with a saturated aqueous solution of sodium chloride (50 mL), dried (sodium sulfate), and filtered and the filtrate was concentrated under reduced pressure. The residue was purified by silica gel chromatography, eluting with a gradient of dichloromethane:methanol—100:0 to 95:5 to afford the title compound. MS: m/z=211.1 [M+H].

Step B: 1-(3-Cyclopropyl-5-methylisoxazol-4-yl)ethanone

To a solution of 3-cyclopropyl-N-methoxy-N,5-dimethylisoxazole-4-carboxamide (1.04 g, 4.95 mmol) in tetrahydrofuran (15 mL) at 0° C. was added a solution of methylmagnesium bromide in toluene and tetrahydrofuran (1.4 M, 7.70 mL, 9.89 mmol) and the reaction mixture was allowed to stir for 1.5 h at 0° C. The reaction mixture was warmed to ambient temperature and poured into a saturated aqueous solution of ammonium chloride (30 mL) and the resulting mixture extracted with ethyl acetate (2×50 mL). The combined organic extracts were washed with a saturated aqueous solution of sodium chloride (50 mL), dried (sodium sulfate), and filtered and the filtrate was concentrated under reduced pressure. The residue was purified by silica gel chromatography, eluting with a gradient of hexanes:ethyl acetate—100:0 to 60:40 to afford the title compound. MS: m/z=166.0 [M+H].

Step C: 2-Bromo-1-(3-cyclopropyl-5-methylisoxazol-4-yl)ethanone

To a solution of 1-(3-cyclopropyl-5-methylisoxazol-4-yl) ethanone (682 mg, 4.13 mmol) in methanol (14 mL) at 0° C. was added bromine (0.25 mL, 4.85 mmol) dropwise and the reaction mixture was allowed to warm to ambient temperature and stir for 18 h. The reaction mixture was poured into water (40 mL) and the resulting mixture extracted with ethyl acetate (2×100 mL). The combined organic extracts were washed with a saturated aqueous solution of sodium chloride, dried (sodium sulfate), and filtered and the filtrate was concentrated under reduced pressure. The residue was purified by silica gel chromatography, eluting with a gradient of hexanes:ethyl acetate—100:0 to 50:50 to afford the title compound. MS: m/z=244.0 [M+H].

Step D: 2-Azido-1-(3-cyclopropyl-5-methylisoxazol-4-yl)ethanone

To a solution of 2-bromo-1-(3-cyclopropyl-5-methylisoxazol-4-yl)ethanone (856 mg, 3.51 mmol) in acetonitrile (11 mL) was added sodium azide (342 mg, 5.26 mmol) and the reaction mixture was allowed to stir for 18 h at ambient temperature. The reaction mixture was poured into water (40 mL) and the resulting mixture extracted with ethyl acetate (2×100 mL). The combined organic extracts were washed with a saturated aqueous solution of sodium chloride (30 mL), dried (sodium sulfate), and filtered and the filtrate was concentrated under reduced pressure to afford the title compound in sufficient purity for use in the next step. MS: m/z=207.1 [M+H].

INTERMEDIATE 23

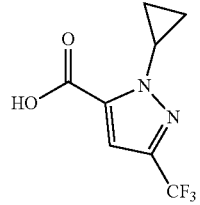

1-Cyclopropyl-3-(trifluoromethyl)-1H-pyrazole-5-carboxylic Acid

Step A: Ethyl 1-cyclopropyl-3-(trifluoromethyl)-1H-pyrazole-5-carboxylate

To a solution of ethyl 3-(trifluoromethyl)-1H-pyrazole-5-carboxylate (1.00 g, 4.80 mmol) in 1,2-dichloroethane (40 mL) were added cyclopropylboronic acid (0.825 g, 9.61 mmol) and sodium carbonate (1.02 g, 9.61 mmol). The reaction mixture was warmed to 70° C. and 2,2'-bipyridine (0.750 g, 4.80 mmol) and copper(II) acetate (0.873 g, 4.80 mmol) were added and the reaction mixture was allowed to stir for 18 h at 70° C. The reaction mixture was cooled to ambient temperature and diluted with a saturated aqueous solution of sodium bicarbonate and extracted with ethyl acetate (2×). The combined organic extracts were washed with a saturated aqueous solution of sodium chloride and concentrated under reduced pressure. The residue was purified by silica gel chromatography, eluting with a gradient of hexanes:ethyl acetate—95:5 to 50:50 to afford the title compound. MS: m/z=249.1 [M+H].

Step B: 1-Cyclopropyl-3-(trifluoromethyl)-1H-pyrazole-5-carboxylic Acid

To a solution of ethyl 1-cyclopropyl-3-(trifluoromethyl)-1H-pyrazole-5-carboxylate (368 mg, 1.48 mmol) in tetrahydrofuran (9 mL) was added aqueous sodium hydroxide (1 M, 4.5 mL, 4.50 mmol) and the reaction mixture was allowed to stir for 18 h at ambient temperature. The reaction mixture was acidified to pH=1 by addition of an aqueous solution of hydrochloric acid (1 M) and the resulting mixture extracted with ethyl acetate (2×). The combined organic extracts were dried (sodium sulfate) and filtered and the filtrate was concentrated under reduced pressure to afford the title compound in sufficient purity for use in the next step. MS: m/z=221.0 [M+H].

INTERMEDIATE 24

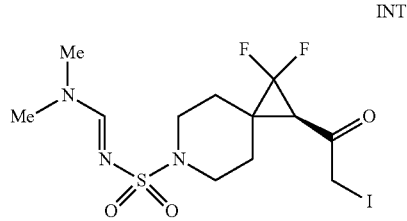

(2R)—N-[(Dimethylamino)methylidene]-1,1-difluoro-2-(iodoacetyl)-6-azaspiro[2.5]octane-6-sulfonamide Step A: (1R)-6-{[(Dimethylamino)methylidene]sulfamoyl}-2,2-difluoro-N-methoxy-N-methyl-6-azaspiro[2.5]octane-1-carboxamide To a solution of (1R)-2,2-difluoro-6-sulfamoyl-6-azaspiro[2.5]octane-1-carboxylic acid (Intermediate 10) (700 mg, 2.59 mmol) in N,N-dimethylformamide (13 mL) were added HATU (1083 mg, 2.85 mmol), 4-methylmorpholine (0.997 mL, 9.07 mmol), and N,O-dimethylhydroxylamine hydrochloride (303 mg, 3.11 mmol) sequentially and the reaction mixture was allowed to stir for 1 h at ambient temperature. Oxalyl chloride (3.11 mL, 6.22 mmol) was added and the reaction mixture was allowed to stir for 18 h at ambient temperature. Water was added and the resulting mixture concentrated under reduced pressure. The residue was diluted with ethyl acetate and washed with a saturated aqueous solution of sodium chloride (3×). The organic layer was dried (magnesium sulfate) and concentrated under reduced pressure. The residue was purified by silica gel chromatography, eluting with a gradient of hexanes:ethyl acetate:ethanol—100:0:0 to 40:45:15 to afford the title compound. MS: m/z=369.2 [M+H].

Step B: (2R)-2-(Chloroacetyl)-N-[(dimethylamino)methylidene]-1,1-difluoro-6-azaspiro[2.5]octane-6-sulfonamide To a solution of (1R)-6-{[(dimethylamino)methylidene]sulfamoyl}-2,2-difluoro-N-methoxy-N-methyl-6-azaspiro[2.5]octane-1-carboxamide (200 mg, 0.543 mmol) in tetrahydrofuran (5.4 mL) at −78° C. were added chloroiodomethane (0.162 mL, 2.17 mmol) and a solution of methyllithium lithium bromide complex in tetrahydrofuran (1.5 M, 1.09 mL, 1.63 mmol) dropwise and sequentially and the reaction mixture was allowed to stir for 2 h at −78° C. A saturated aqueous solution of ammonium chloride was added and the resulting mixture was warmed to ambient temperature and allowed to stir for 20 min. The mixture was diluted with ethyl acetate and the organic layer washed with a saturated aqueous solution of ammonium chloride (2×) and a saturated aqueous solution of sodium chloride, dried (magnesium sulfate), and filtered and the filtrate was concentrated under reduced pressure. The residue was purified by silica gel chromatography, eluting with a gradient of hexanes:ethyl acetate:ethanol—100:0:0 to 40:45:15 to afford the title compound. MS: m/z=358.1 [M+H].

Step C: (2R)—N-[(dimethylamino)methylidene]-1,1-difluoro-2-(iodoacetyl)-6-azaspiro[2.5]octane-6-sulfonamide To a solution of (2R)-2-(chloroacetyl)-N-[(dimethylamino)methylidene]-1,1-difluoro-6-azaspiro[2.5]octane-6-sulfonamide (65 mg, 0.18 mmol) in acetone (0.60 mL) was added sodium iodide (27.2 mg, 0.182 mmol) and the reaction mixture was allowed to stir for 0.5 h at ambient temperature. The reaction mixture was filtered, washing with acetone, and the filtrate was concentrated under reduced pressure. The residue was dissolved in dichloromethane and the organic layer washed with a saturated aqueous solution of sodium bicarbonate, dried (magnesium sulfate), and filtered and the filtrate was concentrated under reduced pressure to afford the title compound in sufficient purity for use in the next step. MS: m/z=450.1 [M+H].

INTERMEDIATE 25

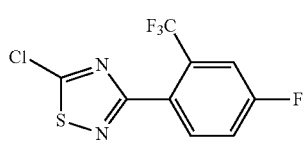

5-Chloro-3-[4-fluoro-2-(trifluoromethyl)phenyl]-1,2,4-thiadiazole

Step A: 3-[4-Fluoro-2-(trifluoromethyl)phenyl]-1,2,4-thiadiazol-5(4H)-one

To a solution of 4-fluoro-N-hydroxy-2-(trifluoromethyl)benzenecarboximidamide (500 mg, 2.25 mmol) in tetrahydrofuran (50 mL) at ambient temperature was added 1,1'-thiocarbonyldiimidazole (501 mg, 2.81 mmol) and the reaction mixture allowed to stir for 30 min. Water (50 mL) was added and the resulting mixture extracted with ethyl acetate (3×50 mL). The combined organic extracts were washed with a saturated aqueous solution of sodium chloride (100 mL), dried (sodium sulfate), and concentrated under reduced pressure. The residue was dissolved in tetrahydrofuran (15 mL), cooled to 0° C., and boron trifluoride diethyl etherate (1.43 mL, 11.3 mmol) was added and the reaction mixture allowed to stir for 10 min. Water (30 mL) was added and the resulting mixture extracted with ethyl acetate (3×30 mL). The combined organic extracts were washed with a saturated aqueous solution of sodium chloride (100 mL), dried (sodium sulfate), and filtered and the filtrate was concentrated under reduced pressure. The residue was purified by silica gel chromatography, eluting with a gradient of petroleum ether:ethyl acetate—100:0 to 72:28, to afford the title compound. $^1$H NMR (400 MHz, CDCl$_3$): δ 10.83 (m, 1H), 7.70 (m, 1H), 7.54 (m, 1H), 7.41 (m, 1H).

Step B: 5-Chloro-3-[4-fluoro-2-(trifluoromethyl)phenyl]-1,2,4-thiadiazole

To a flask containing 3-[4-fluoro-2-(trifluoromethyl)phenyl]-1,2,4-thiadiazol-5(4H)-one (180 mg, 0.68 mmol) was added phosphorous oxychloride (3.0 mL, 32 mmol) and the reaction mixture warmed to 120° C. and allowed to stir for 16 h. The reaction mixture was concentrated under reduced pressure and the residue re-dissolved in dichloromethane (50 mL). Water (cold, 50 mL) was added and the resulting mixture extracted with dichloromethane (2×50 mL). The combined organic extracts were washed with a saturated aqueous solution of sodium chloride (50 mL), dried (sodium sulfate), and filtered and the filtrate was concentrated under reduced pressure. The residue was purified by silica gel chromatography, eluting with a gradient of petroleum ether:ethyl acetate—100:0 to 90:10, to afford the title compound. $^1$H NMR (400 MHz, CDCl$_3$): δ 7.90 (m, 1H), 7.54 (m, 1H), 7.36 (m, 1H).

INTERMEDIATE 26

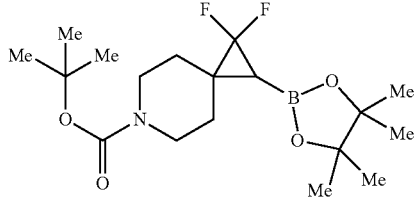

Tert-Butyl 1,1-difluoro-2-(4,4,5,5-tetramethyl-1,3,2-dioxaborolan-2-yl)-6-azaspiro[2.5]octane-6-carboxylate Step A: Tert-Butyl 4-[(4,4,5,5-tetramethyl-1,3,2-dioxaborolan-2-yl)methylidene]piperidine-1-carboxylate To a solution of 4,4,5,5-tetramethyl-2-vinyl-1,3,2-dioxaborolane (7.03 g, 45.6 mmol) in toluene (60 mL) were added tert-butyl 4-methylenepiperidine-1-carboxylate (3.0 g, 15.2 mmol) and dichloro[1,3-bis(2,4,6-trimethylphenyl)-2-imidazolidinylidene][[5-[(dimethylamino)sulfonyl]-2-(1-methylethoxy-O)phenyl]methylene-C]ruthenium(II) (0.56 g, 0.76 mmol) and the reaction mixture was warmed to 90° C. and allowed to stir for 3 h. The reaction mixture was cooled to ambient temperature and water (20 mL) added and the resulting mixture extracted with ethyl acetate (3×30 mL). The combined organic extracts were washed with a saturated aqueous solution of sodium chloride (20 mL), dried (sodium sulfate), and filtered and the filtrate was concentrated under reduced pressure. The residue was purified by silica gel chromatography, eluting with a gradient of petroleum ether: ethyl acetate—95:5 to 90:10 to afford the title compound. MS: m/z=224.1 [M-100+H].

Step B: Tert-Butyl 1,1-difluoro-2-(4,4,5,5-tetramethyl-1,3,2-dioxaborolan-2-yl)-6-azaspiro[2.5]octane-6-carboxylate To a solution of tert-butyl 4-((4,4,5,5-tetramethyl-1,3,2-dioxaborolan-2-yl)methylene)piperidine-1-carboxylate (1.00 g, 3.09 mmol) in tetrahydrofuran (10 mL) were added trimethyl(trifluoromethyl)silane (4.40 g, 30.9 mmol) and sodium iodide (0.23 g, 1.6 mmol) and the reaction mixture was warmed to 120° C. and allowed to stir for 12 h. The reaction mixture was allowed to cool to ambient temperature, water (15 mL) was added and the resulting mixture extracted with ethyl acetate (3×15 mL). The combined organic extracts were washed with a saturated aqueous solution of sodium chloride (20 mL), dried (sodium sulfate), and filtered and the filtrate was concentrated under reduced pressure. The residue was purified by silica gel chromatography, eluting with a gradient of petroleum ether:ethyl acetate—100:0 to 80:20 to afford the title compound. MS: m/z=359.2 [M-tBu+CH$_3$CN+H].

INTERMEDIATE 27

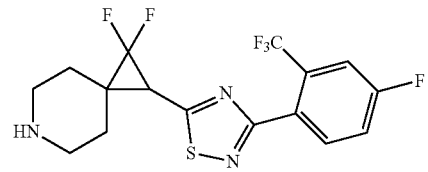

1,1-Difluoro-2-{3-[4-fluoro-2-(trifluoromethyl)phenyl]-1,2,4-thiadiazol-5-yl}-6-azaspiro[2.5]octane Essentially following the procedures described in Intermediate 35, but using 5-chloro-3-[4-fluoro-2-(trifluoromethyl)phenyl]-1,2,4-thiadiazole (Intermediate 25) in place of 3-bromo-5-[4-fluoro-2-(trifluoromethyl)phenyl]-1,2,4-thiadiazole, the title compound was obtained. MS: m/z=394.1 [M+H].

INTERMEDIATE 28

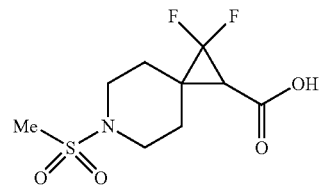

2,2-Difluoro-6-(methylsulfonyl)-6-azaspiro[2.5]octane-1-carboxylic Acid

Step A: Benzyl 2,2-difluoro-6-(methylsulfonyl)-6-azaspiro[2.5]octane-1-carboxylate To a solution of benzyl 2,2-difluoro-6-azaspiro[2.5]octane-1-carboxylate (described in Intermediate 10) (2.58 g, 9.17 mmol) in dichloromethane (30 mL) were added triethylamine (3.84 mL, 27.5 mmol) and methanesulfonyl chloride (1.07 mL, 13.8 mmol) sequentially and the reaction mixture was allowed to stir for 1 h at ambient temperature. Water (30 mL) was added and the resulting mixture extracted with dichloromethane (3×30 mL). The combined organic extracts were dried (sodium sulfate) and filtered and the filtrate was concentrated under reduced pressure. The residue was purified by silica gel chromatography, eluting with a gradient of dichloromethane:ethyl acetate—100:0 to 90:10 to afford the title compound. MS: m/z=382.1 [M+Na].

Step B: 2,2-Difluoro-6-(methylsulfonyl)-6-azaspiro[2.5]octane-1-carboxylic Acid

To a solution of benzyl 2,2-difluoro-6-(methylsulfonyl)-6-azaspiro[2.5]octane-1-carboxylate (2.9 g, 8.1 mmol) in methanol (50 mL) and dichloromethane (20 mL) was added palladium on activated carbon (wet, 10% w/w, 0.86 g, 0.81 mmol). The reaction mixture was placed under an atmosphere of hydrogen (30 psi) and allowed to stir for 3 h at ambient temperature. The reaction mixture was filtered and the filtrate was concentrated under reduce pressure to afford the title compound in sufficient purity for use in the next step. MS: m/z=270.0 [M+H].

INTERMEDIATE 29

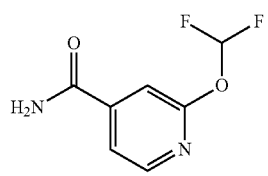

2-(Difluoromethoxy)pyridine-4-carboxamide

To a solution of 2-(difluoromethoxy)isonicotinic acid (5.0 g, 26 mmol) in dichloromethane (48 mL) and dimethylsulfoxide (4.80 mL) were added HATU (10.1 g, 50.4 mmol), ammonium chloride (5.66 g, 105 mmol), and N-methylmorpholine (12.2 mL, 58.2 mmol). The reaction mixture was allowed to stir for 18 h. A saturated aqueous solution of ammonium chloride (75 mL) was added and the resulting mixture extracted with dichloromethane (3×100 mL). The combined organic phases were washed with a saturated aqueous solution of ammonium chloride (2×30 mL) and a saturated aqueous solution of sodium chloride (1×30 mL), dried (magnesium sulfate), filtered, and the filtrate was concentrated under reduced pressure. The residue was purified by silica gel chromatography, eluting with a gradient of hexanes:ethyl acetate—80:20 to 15:85 to afford the title compound. MS: m/z=189.1 [M+H].

Tert-Butyl 1,1-difluoro-2-(1H-pyrazol-3-yl)-6-azaspiro[2.5]octane-6-carboxylate

Step A: Tert-Butyl 1,1-difluoro-2-[methoxy(methyl)carbamoyl]-6-azaspiro[2.5]octane-6-carboxylate To a solution of 6-(tert-butoxycarbonyl)-2,2-difluoro-6-azaspiro[2.5]octane-1-carboxylic acid (described in Intermediate 10) (4.0 g, 13.7 mmol) in dichloromethane (50 mL) were added triethylamine (5.74 mL, 41.2 mmol), 1,1'-carbonyldiimidazole (4.45 g, 27.5 mmol) and N,O-dimethylhydroxylamine hydrochloride (2.01 g, 20.6 mmol) and the reaction mixture was allowed to stir for 1 h at ambient temperature. Water (50 mL) was added and the resulting mixture was extracted with ethyl acetate (2×50 mL). The combined organic layers were dried (sodium sulfate) and filtered and the filtrate was concentrated under reduced pressure. The residue was purified by silica gel chromatography, eluting with a gradient of petroleum ether:ethyl acetate—90:10 to 75:25 to afford the title compound. MS: m/z=335.1 [M+H].

Step B: Tert-Butyl 1,1-difluoro-2-propioloyl-6-azaspiro[2.5]octane-6-carboxylate To a solution of tert-butyl 1,1-difluoro-2-[methoxy(methyl)carbamoyl]-6-azaspiro[2.5]octane-6-carboxylate (2.0 g, 5.98 mmol) in tetrahydrofuran (5 mL) at 0° C. was added a solution of ethynylmagnesium bromide in tetrahydrofuran (0.5 M, 120 mL, 59.8 mmol) and the reaction mixture was allowed to stir for 1 h at 0° C. Water (150 mL) was added and the resulting mixture extracted with ethyl acetate (2×100 mL). The combined organic extracts were dried (sodium sulfate) and filtered and the filtrate was concentrated under reduced pressure. The residue was purified by silica gel chromatography, eluting with a gradient of petroleum ether:ethyl acetate—95:5 to 75:25 to afford the title compound. $^1$H NMR (400 MHz, CDCl$_3$): δ 3.48-3.58 (m, 4H), 3.37 (s, 1H), 2.55-2.65 (m, 1H), 1.51-1.89 (m, 4H), 1.44 (s, 9H).

Step C: Tert-Butyl 1,1-difluoro-2-(1H-pyrazol-3-yl)-6-azaspiro[2.5]octane-6-carboxylate To a solution of tert-butyl 1,1-difluoro-2-propioloyl-6-azaspiro[2.5]octane-6-carboxylate (700 mg, 2.34 mmol) in ethanol (10 mL) was added hydrazine (85% w/w, 353 mg, 9.35 mmol) and the reaction mixture was allowed to stir for 6 h at ambient temperature. The reaction mixture was concentrated under reduced pressure and the residue was purified by silica gel chromatography, eluting with a gradient of petroleum ether:ethyl acetate—90:10 to 75:25 to afford the title compound. MS: m/z=314.0 [M+H].

INTERMEDIATE 30

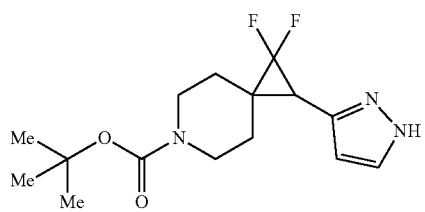

INTERMEDIATE 31

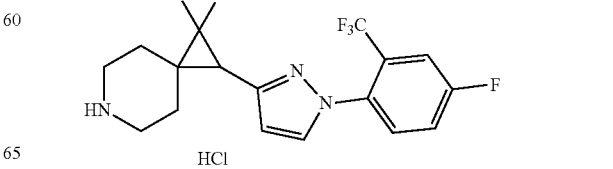

HCl

1,1-Difluoro-2-{1-[4-fluoro-2-(trifluoromethyl)phenyl]-1H-pyrazol-3-yl}-6-azaspiro[2.5]octane Hydrochloride

Step A: Tert-Butyl 1,1-difluoro-2-{1-[4-fluoro-2-(trifluoromethyl)phenyl]-1H-pyrazol-3-yl}-6-azaspiro[2.5]octane-6-carboxylate To a solution of tert-butyl 1,1-difluoro-2-(1H-pyrazol-3-yl)-6-azaspiro[2.5]octane-6-carboxylate (Intermediate 30) (200 mg, 0.64 mmol) in 1,4-dioxane (1 mL) were added [4-fluoro-2-(trifluoromethyl)phenyl]boronic acid (265 mg, 1.28 mmol), cesium carbonate (416 mg, 1.28 mmol), 4-(dimethylamino)pyridine (312 mg, 2.55 mmol), and copper(II) acetate (116 mg, 0.64 mmol) and the resulting mixture was placed under an atmosphere of oxygen (15 psi). The reaction mixture was warmed to 50° C. and allowed to stir for 15 h. The reaction mixture was cooled and filtered and the filtrate was concentrated under reduced pressure. The residue was purified by silica gel chromatography, eluting with petroleum ether:ethyl acetate—75:25 to afford the title compound. MS: m/z=476.0 [M+H].

Step B: 1,1-Difluoro-2-{1-[4-fluoro-2-(trifluoromethyl)phenyl]-1H-pyrazol-3-yl}-6-azaspiro[2.5]octane Hydrochloride To a flask containing tert-butyl 1,1-difluoro-2-{1-[4-fluoro-2-(trifluoromethyl)phenyl]-1H-pyrazol-3-yl}-6-azaspiro[2.5]octane-6-carboxylate (30 mg, 0.06 mmol) was added hydrogen chloride in 1,4-dioxane (4 M, 2.0 mL, 8.0 mmol) and the reaction mixture was allowed to stir for 30 min at ambient temperature. The reaction mixture was concentrated under reduced pressure to afford the title compound in sufficient purity for use in the next step. MS: m/z=376.0 [M+H].

INTERMEDIATE 32

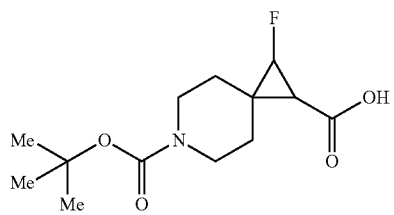

6-(tert-Butoxycarbonyl)-2-fluoro-6-azaspiro[2.5]octane-1-carboxylic Acid

Step A: Tert-Butyl 4-{2-[(tert-butyldimethylsilyl)oxy]ethylidene}piperidine-1-carboxylate To a solution of tert-butyl 4-(2-hydroxyethylidene)piperidine-1-carboxylate (750 mg, 3.30 mmol) in dichloromethane (10 mL) at ambient temperature was added imidazole (337 mg, 4.95 mmol) and tert-butylchlorodimethylsilane (547 mg, 3.63 mmol) and the reaction mixture allowed to stir for 2 h. The reaction mixture was diluted with water (10 mL) and the resulting mixture extracted with dichloromethane (3×10 mL). The combined organic extracts were dried (sodium sulfate) and filtered and the filtrate was concentrated under reduced pressure. The residue was purified by silica gel chromatography, eluting with a gradient of petroleum ether:ethyl acetate—95:5 to 90:10, to afford the title compound. MS: m/z=342.1 [M+H].

Step B: Tert-Butyl 1-bromo-2-{[(tert-butyldimethylsilyl)oxy]methyl}-1-fluoro-6-azaspiro[2.5]octane-6-carboxylate To a solution of tert-butyl 4-{2-[(tert-butyldimethylsilyl)oxy]ethylidene}piperidine-1-carboxylate (100 mg, 0.29 mmol) in dichloromethane (1 mL) at ambient temperature was added bromodifluoromethane (192 mg, 1.46 mmol), tetrabutylammonium iodide (10.8 mg, 0.0292 mmol), and an aqueous solution of sodium hydroxide (50%, 1.0 mL, 0.29 mmol) and the reaction mixture warmed to 40° C. and allowed to stir for 12 h. Water (5 mL) was added and the resulting mixture extracted with ethyl acetate (3×5 mL). The combined organic extracts were dried (sodium sulfate) and filtered and the filtrate was concentrated under reduced pressure. The residue was purified by silica gel chromatography, eluting with petroleum ether:ethyl acetate—95:5, to afford the title compound. MS: m/z=351.9 [M-100+H].

Step C: Tert-Butyl 1-{[(tert-butyldimethylsilyl)oxy]methyl}-2-fluoro-6-azaspiro[2.5]octane-6-carboxylate To a solution of tert-butyl 1-bromo-2-{[(tert-butyldimethylsilyl)oxy]methyl}-1-fluoro-6-azaspiro[2.5]octane-6-carboxylate (50 mg, 0.11 mmol) in ethanol (1 mL) was added zinc (29 mg, 0.44 mmol) and ammonium chloride (36 mg, 0.66 mmol) and the reaction mixture warmed to 70° C. and allowed to stir for 5 h. The reaction mixture was filtered and the solvent evaporated under reduced pressure. The residue was purified by silica gel chromatography, eluting with petroleum ether:ethyl acetate—95:5, to afford the title compound. MS: m/z=318.0 [M-tBu+H].

Step D: Tert-Butyl 1-fluoro-2-(hydroxymethyl)-6-azaspiro[2.5]octane-6-carboxylate To a solution of tert-butyl 1-{[(tert-butyldimethylsilyl)oxy]methyl}-2-fluoro-6-azaspiro[2.5]octane-6-carboxylate (400 mg, 1.07 mmol) in tetrahydrofuran (5 mL) was added a solution of tetrabutylammonium fluoride in tetrahydrofuran (1 M, 5.35 mL, 5.35 mmol) at ambient temperature and the reaction mixture allowed to stir for 3 h. The reaction mixture was diluted with water (10 mL) and the resulting mixture extracted with ethyl acetate (3×10 mL). The combined organic extracts were dried (sodium sulfate) and filtered and the filtrate was concentrated under reduced pressure. The residue was purified by silica gel chromatography, eluting with a gradient of petroleum ether:ethyl acetate—90:10 to 80:20, to afford the title compound. MS: m/z=204.0 [M-tBu+H].

Step E: Tert-Butyl 1-fluoro-2-formyl-6-azaspiro[2.5]octane-6-carboxylate

To a solution of tert-butyl 1-fluoro-2-(hydroxymethyl)-6-azaspiro[2.5]octane-6-carboxylate (50 mg, 0.19 mmol) in dichloromethane (2 mL) at ambient temperature was added Dess-Martin periodinane (164 mg, 0.39 mmol) and the reaction mixture allowed to stir for 2 h. Water (5 mL) was added and the resulting mixture extracted with dichloromethane (3×5 mL). The combined organic extracts were dried (sodium sulfate) and filtered and the filtrate was concentrated under reduced pressure. The residue was purified by silica gel chromatography, eluting with petroleum ether: ethyl acetate—75:25, to afford the title compound. $^1$H NMR (400 MHz, CDCl$_3$): δ 9.75-9.81 (m, 1H); 3.37-3.58 (m, 3H); 3.22-3.34 (m, 1H); 2.31 (brd, J=18.0 Hz, 1H); 1.64-1.84 (m, 3H); 1.53-1.59 (m, 1H); 1.45 (s, 9H); 1.20-1.33 (m, 1H).

Step F: 6-(tert-Butoxycarbonyl)-2-fluoro-6-azaspiro [2.5]octane-1-carboxylic Acid To a solution of tert-butyl 1-fluoro-2-formyl-6-azaspiro [2.5]octane-6-carboxylate (15 mg, 0.06 mmol) in t-BuOH (0.5 mL) at ambient temperature was added 2-methylbut-2-ene (20 mg, 0.29 mmol) and a solution of sodium chlorite (16 mg, 0.17 mmol) and sodium dihydrogenphosphate (28 mg, 0.23 mmol) in water (0.5 mL) and the reaction mixture allowed to stir for 12 h. The reaction mixture was diluted with water (5 mL) and the resulting mixture extracted with ethyl acetate (3×5 mL). The combined organic extracts were dried (sodium sulfate) and filtered and the filtrate was concentrated under reduced pressure to afford the title compound in sufficient purity for use in the next step. $^1$H NMR (400 MHz, CD$_3$OD): δ 3.39-3.57 (m, 3H); 1.96 (dd, J$_1$=18.4 Hz, J$_2$=2.6 Hz, 1H); 1.55-1.80 (m, 5H); 1.46 (s, 10H).

INTERMEDIATE 33

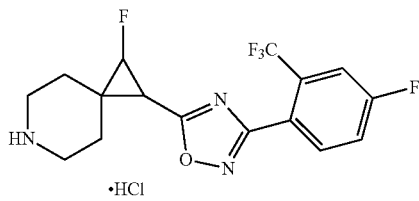

3-[4-Fluoro-2-(trifluoromethyl)phenyl]-5-(2-fluoro-6-azaspiro[2.5]octan-1-yl)-1,2,4-oxadiazole Hydrochloride Essentially following the procedures described in Intermediate 17, but using 6-(tert-butoxycarbonyl)-2-fluoro-6-azaspiro[2.5]octane-1-carboxylic acid (Intermediate 32) in place of tert-butyl 2-{3-[2-(difluoromethoxy)pyridin-4-yl]-1,2,4-oxadiazol-5-yl}-1,1-difluoro-6-azaspiro[2.5]octane-6-carboxylate and 4-fluoro-N-hydroxy-2-(trifluoromethyl)benzenecarboximidamide in place of 2-(difluoromethoxy)-N-hydroxypyridine-4-carboximidamide, the title compound was obtained. MS: m/z=360.0 [M+H].

INTERMEDIATE 34

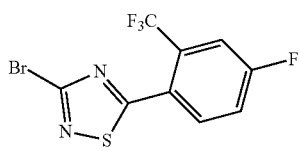

3-Bromo-5-[4-fluoro-2-(trifluoromethyl)phenyl]-1,2,4-thiadiazole

To a solution of 3-bromo-5-chloro-1,2,4-thiadiazole (60 mg, 0.30 mmol) in 1,4-dioxane (2 mL) and water (0.2 mL) were added [4-fluoro-2-(trifluoromethyl)phenyl]boronic acid (62.5 mg, 0.30 mmol), potassium carbonate (125 mg, 0.90 mmol), and [1,1'-bis(diphenylphosphino)ferrocene]palladium(II) dichloride (22.01 mg, 0.03 mmol). The reaction mixture was warmed to 100° C. and allowed to stir for 30 min. The mixture was cooled to ambient temperature and diluted with water (5 mL). The resulting mixture was extracted with ethyl acetate (3×5 mL), dried (sodium sulfate), and filtered and the filtrate was concentrated under reduced pressure. The residue was purified by silica gel chromatography, eluting with petroleum ether, to afford the title compound. MS: m/z=326.7, 328.7 [M+H].

INTERMEDIATE 35

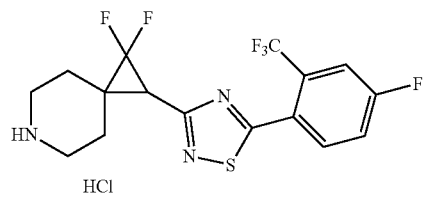

1,1-Difluoro-2-{5-[4-fluoro-2-(trifluoromethyl)phenyl]-1,2,4-thiadiazol-3-yl}-6-azaspiro[2.5]octane Hydrochloride Step A: tert-Butyl 1,1-difluoro-2-{5-[4-fluoro-2-(trifluoromethyl)phenyl]-1,2,4-thiadiazol-3-yl}-6-azaspiro[2.5]octane-6-carboxylate To a solution of 3-bromo-5-[4-fluoro-2-(trifluoromethyl)phenyl]-1,2,4-thiadiazole (Intermediate 34) (65 mg, 0.20 mmol) in tert-amyl alcohol (2 mL) were added cesium carbonate (0.40 mL, 0.60 mmol), tert-butyl 1,1-difluoro-2-(4,4,5,5-tetramethyl-1,3,2-dioxaborolan-2-yl)-6-azaspiro [2.5]octane-6-carboxylate (Intermediate 26) (89 mg, 0.24 mmol), and chloro{[di(1-adamantyl)-n-butylphosphine]-2-(2-aminobiphenyl)}palladium(II) (13.3 mg, 0.0199 mmol) sequentially. The reaction mixture was warmed to 100° C. and allowed to stir for 12 h. The reaction mixture was cooled to ambient temperature and diluted with water (5 mL). The resulting mixture was extracted with ethyl acetate (3×5 mL). The combined organic extracts were dried (sodium sulfate) and filtered and the filtrate was concentrated under reduced pressure.

The residue was purified by silica gel chromatography, eluting with petroleum ether:ethyl acetate—90:10, to afford the title compound. MS: m/z=438.1 [M-tBu+H].

Step B: 1,1-Difluoro-2-{5-[4-fluoro-2-(trifluoromethyl)phenyl]-1,2,4-thiadiazol-3-yl}-6-azaspiro[2.5]octane Hydrochloride To a flask containing tert-butyl 1,1-difluoro-2-{5-[4-fluoro-2-(trifluoromethyl)phenyl]-1,2,4-thiadiazol-3-yl}-6-azaspiro[2.5]octane-6-carboxylate (70 mg, 0.14 mmol) was added a solution of HCl in 1,4-dioxane (4 M, 10 mL, 40 mmol) and the reaction mixture allowed to stir for 1 h at ambient temperature. The reaction mixture was concentrated under reduced pressure to afford the title compound in sufficient purity for use in the next step. MS: m/z=394.1 [M+H].

INTERMEDIATE 36

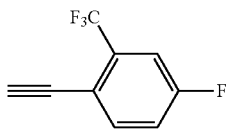

1-Ethynyl-4-fluoro-2-(trifluoromethyl)benzene

To a solution of 4-fluoro-2-(trifluoromethyl)benzaldehyde (1.0 g, 5.2 mmol) in methanol (15 mL) was added dimethyl (1-diazo-2-oxopropyl)phosphonate (1.20 g, 6.25 mmol) and potassium carbonate (2.16 g, 15.6 mmol) and the reaction mixture warmed to 50° C. and allowed to stir for 16 h. The reaction mixture was cooled to ambient temperature, water (15 mL) was added, and the resulting mixture extracted with dichloromethane (3×15 mL). The combined organic extracts were dried (sodium sulfate) and filtered and the filtrate was concentrated under reduced pressure to afford the title compound in sufficient purity for use in the next step. $^1$H NMR (400 MHz, CDCl$_3$): δ 7.63-7.65 (m, 1H); 7.47-7.40 (m, 1H); 7.22-7.27 (m, 1H); 3.35 (s, 1H).

INTERMEDIATE 37

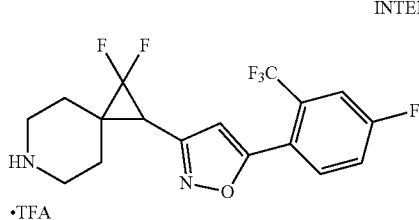

1,1-Difluoro-2-{5-[4-fluoro-2-(trifluoromethyl)phenyl]isoxazol-3-yl}-6-azaspiro[2.5]octane Trifluoroacetate Step A: tert-Butyl 1,1-difluoro-2-formyl-6-azaspiro[2.5]octane-6-carboxylate To a solution of tert-butyl 1,1-difluoro-2-(hydroxymethyl)-6-azaspiro[2.5]octane-6-carboxylate (described in Intermediate 10) (760 mg, 2.74 mmol) in dichloromethane (10 mL) at ambient temperature was added Dess-Martin periodinane (2.33 g, 5.48 mmol) and the reaction mixture allowed to stir for 2 h. A saturated aqueous solution of sodium bicarbonate (20 mL) was slowly added and the resulting mixture extracted with dichloromethane (3×10 mL). The combined organic extracts were dried (sodium sulfate) and filtered and the filtrate was concentrated under reduced pressure. The residue was purified by silica gel chromatography, eluting with a gradient of petroleum ether:ethyl acetate—95:5 to 90:10, to afford the title compound. MS: m/z=220.1 [M-tBu+H].

Step B: Tert-Butyl 1,1-difluoro-2-[(hydroxyimino)methyl]-6-azaspiro[2.5]octane-6-carboxylate To a solution of tert-butyl 1,1-difluoro-2-formyl-6-azaspiro[2.5]octane-6-carboxylate (1.0 g, 3.6 mmol) and sodium carbonate (0.78 g, 7.3 mmol) in ethanol (20 mL) at ambient temperature was added hydroxylamine hydrochloride (0.51 g, 7.3 mmol) and the reaction mixture allowed to stir for 1 h. The reaction mixture was filtered and the filtrate concentrated under reduced pressure. The residue was purified by silica gel chromatography, eluting with a gradient of petroleum ether:ethyl acetate—100:0 to 90:10, to afford the title compound.

Step C: Tert-Butyl 1,1-difluoro-2-{5-[4-fluoro-2-(trifluoromethyl)phenyl]isoxazol-3-yl}-6-azaspiro[2.5]octane-6-carboxylate To a solution of tert-butyl 1,1-difluoro-2-[(hydroxyimino)methyl]-6-azaspiro[2.5]octane-6-carboxylate (772 mg, 2.66 mmol) and 1-ethynyl-4-fluoro-2-(trifluoromethyl)benzene (Intermediate 36) (500 mg, 1.33 mmol) in methanol (10 mL) was added [bis(trifluoroacetoxy)iodo]benzene (1.71 g, 3.98 mmol) and the reaction mixture warmed to 50° C. and allowed to stir for 7 h. Water (15 mL) was added and the resulting mixture extracted with ethyl acetate (3×10 mL). The combined organic extracts were washed with a saturated aqueous solution of sodium chloride (15 mL), dried (sodium sulfate), and filtered and the filtrate was concentrated under reduced pressure. The residue was purified by silica gel chromatography, eluting with a gradient of petroleum ether:ethyl acetate—100:0 to 92:8, to afford the title compound. MS: m/z=421.1 [M-tBu+H].

1,1-Difluoro-2-{5-[4-fluoro-2-(trifluoromethyl)phenyl]isoxazol-3-yl}-6-azaspiro[2.5]octane Trifluoroacetate To a solution of tert-butyl 1,1-difluoro-2-{5-[4-fluoro-2-(trifluoromethyl)phenyl]isoxazol-3-yl}-6-azaspiro[2.5]octane-6-carboxylate (50 mg, 0.11 mmol) in dichloromethane (5 mL) at ambient temperature was added trifluoroacetic acid (2.0 mL, 26 mmol) and the reaction mixture allowed to stir for 1 h. The reaction mixture was concentrated under reduced pressure to afford the title compound in sufficient purity for use in the next step. MS: m/z=377.1 [M+H].

INTERMEDIATE 38

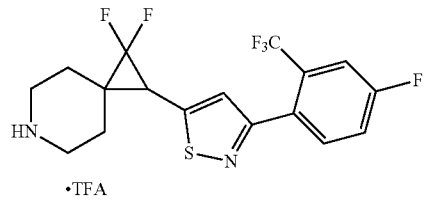

1,1-Difluoro-2-{3-[4-fluoro-2-(trifluoromethyl)phenyl]isothiazol-5-yl}-6-azaspiro[2.5]octane Trifluoroacetate Step A: Tert-Butyl 2-ethynyl-1,1-difluoro-6-azaspiro[2.5]octane-6-carboxylate To a solution of tert-butyl 1,1-difluoro-2-formyl-6-azaspiro[2.5]octane-6-carboxylate (described in Intermediate 37) (210 mg, 0.76 mmol) in methanol (10 mL) was added potassium carbonate (210 mg, 1.53 mmol) and dimethyl (1-diazo-2-oxopropyl)phosphonate (293 mg, 1.53 mmol) and the reaction mixture was allowed to stir for 16 h. Water (20 mL) was added and the resulting mixture extracted with ethyl acetate (2×30 mL). The combined organic extracts were washed with a saturated aqueous solution of sodium chloride (50 mL), dried (sodium sulfate), and filtered and the filtrate was concentrated under reduced pressure. The residue was purified by silica gel chromatography, eluting with a gradient of petroleum ether:ethyl acetate—100:0 to 85:15, to afford the title compound. MS: m/z=257.1 [M-tBu+CH₃CN+H].

Step B: Tert-Butyl 1,1-difluoro-2-{3-[3-fluoro-5-(trifluoromethyl)phenyl]isoxazol-5-yl}-6-azaspiro[2.5]octane-6-carboxylate To a solution of tert-butyl 2-ethynyl-1,1-difluoro-6-azaspiro[2.5]octane-6-carboxylate (500 mg, 1.84 mmol) and 3-fluoro-5-(trifluoromethyl)benzaldehyde oxime (916 mg, 4.42 mmol) in methanol (12 mL) at ambient temperature was added [bis(trifluoroacetoxy)iodo]benzene (2.38 g, 5.52 mmol) and the reaction mixture warmed to 60° C. and allowed to stir for 7 h. Water (15 mL) was added and the resulting mixture extracted with ethyl acetate (3×15 mL). The combined organic extracts were dried (sodium sulfate) and filtered and the filtrate was concentrated under reduced pressure. The residue was purified by silica gel chromatography, eluting with a gradient of petroleum ether:ethyl acetate—100:0 to 95:5, to afford the title compound. MS: m/z=421.2 [M-tBu+H].

Step C: Tert-Butyl 2-{3-amino-3-[4-fluoro-2-(trifluoromethyl)phenyl]acryloyl}-1,1-difluoro-6-azaspiro[2.5]octane-6-carboxylate To a solution of tert-butyl 1,1-difluoro-2-{3-[4-fluoro-2-(trifluoromethyl)phenyl]isoxazol-5-yl}-6-azaspiro[2.5]octane-6-carboxylate (400 mg, 0.84 mmol) in ethanol (25 mL) under Ar at ambient temperature was added Raney nickel (4.93 mg, 0.08 mmol). The reaction mixture was placed under an atmosphere of hydrogen (ca. 40 psi), warmed to 40° C. and allowed to stir for 8 h. The reaction mixture was cooled, purged with inert gas, and filtered through a pad of Celite®, washing with ethanol (100 mL). The filtrate was concentrated under reduced pressure to afford the title compound in sufficient purity for use in the next step. MS: m/z=479.1 [M+H].

Step D: Tert-Butyl 1,1-difluoro-2-{3-[4-fluoro-2-(trifluoromethyl)phenyl]isothiazol-5-yl}-6-azaspiro[2.5]octane-6-carboxylate To a solution of tert-butyl 2-{3-amino-3-[4-fluoro-2-(trifluoromethyl)phenyl]acryloyl}-1,1-difluoro-6-azaspiro[2.5]octane-6-carboxylate (380 mg, 0.79 mmol) in toluene (10 mL) at ambient temperature was added phosphorus pentasulfide (530 mg, 2.38 mmol) and chloranil (586 mg, 2.38 mmol) sequentially and the reaction mixture warmed to 115° C. and allowed to stir for 2 h. The reaction mixture was cooled to ambient temperature and water (5 mL), ethyl acetate (5 mL), sodium carbonate (421 mg, 3.97 mmol), and di-tert-butyl dicarbonate (1.84 mL, 7.94 mmol) were added. The reaction mixture was allowed to stir at ambient temperature for 1 h. Water (15 mL) was added and the resulting mixture extracted with ethyl acetate (3×10 mL). The combined organic extracts were washed with a saturated aqueous solution of sodium chloride (15 mL), dried (sodium sulfate), and filtered and the filtrate was concentrated under reduced pressure. The residue was purified by silica gel chromatography, eluting with a gradient of petroleum ether:ethyl acetate—100:0 to 90:10, to afford the title compound. MS: m/z=493.1 [M+H].

Step E: 1,1-Difluoro-2-{3-[4-fluoro-2-(trifluoromethyl)phenyl]isothiazol-5-yl}-6-azaspiro[2.5]octane Trifluoroacetate To a solution of tert-butyl 1,1-difluoro-2-{3-[4-fluoro-2-(trifluoromethyl)phenyl]isothiazol-5-yl}-6-azaspiro[2.5]octane-6-carboxylate (880 mg, 0.50 mmol) in dichloromethane (10 mL) was added trifluoroacetic acid (3 mL) and the reaction mixture allowed to stir for 1 h. The reaction mixture was concentrated under reduced pressure to afford the title compound in sufficient purity for use in the next step. MS: m/z=393.1 [M+H].

INTERMEDIATE 39

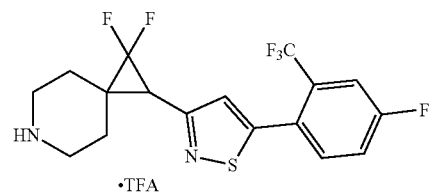

1,1-Difluoro-2-{5-[4-fluoro-2-(trifluoromethyl)phenyl]isothiazol-3-yl}-6-azaspiro[2.5]octane Trifluoroacetate Step A: Tert-Butyl 1,1-difluoro-2-{5-[4-fluoro-2-(trifluoromethyl)phenyl]isoxazol-3-yl}-6-azaspiro[2.5]octane-6-carboxylate To a solution of tert-butyl 1,1-difluoro-2-[(hydroxyimino)methyl]-6-azaspiro[2.5]octane-6-carboxylate (described in Intermediate 37) (772 mg, 2.66 mmol) and 1-ethynyl-4-fluoro-2-(trifluoromethyl)benzene (Intermediate 36) (500 mg, 1.33 mmol) in methanol (10 mL) was added [bis(trifluoroacetoxy)iodo]benzene (1.71 g, 3.98 mmol) and the mixture was stirred at 50° C. for 7 h. Water (15 mL) was added and the resulting mixture extracted with ethyl acetate (3×10 mL). The combined organic extracts were washed with a saturated aqueous solution of sodium chloride (15 mL), dried (sodium sulfate), and filtered and the filtrate was concentrated under reduced pressure. The residue was purified by silica gel chromatography, eluting with a gradient of petroleum ether:ethyl acetate—100:0 to 92:8, to afford the title compound. MS: m/z=421.1 [M-tBu+H].

Step B: Tert-Butyl 2-{1-amino-3-[4-fluoro-2-(trifluoromethyl)phenyl]-3-oxoprop-1-en-1-yl}-1,1-difluoro-6-azaspiro[2.5]octane-6-carboxylate To a solution of tert-butyl 1,1-difluoro-2-{5-[4-fluoro-2-(trifluoromethyl)phenyl]isoxazol-3-yl}-6-azaspiro[2.5]octane-6-carboxylate (100 mg, 0.21 mmol) in ethanol (10 mL) under Ar was added Raney nickel (1.2 mg, 0.021 mmol). The reaction mixture was placed under an atmosphere of hydrogen (ca. 40 psi), warmed to 35° C. and allowed to stir for 3 h. The reaction mixture was cooled, purged with inert gas, and filtered through a pad of Celite®, washing with ethanol (100 mL). The filtrate was concentrated under reduced pressure to afford the title compound in sufficient purity for use in the next step. MS: m/z=479.3 [M+H].

Step C: Tert-Butyl 1,1-difluoro-2-{5-[4-fluoro-2-(trifluoromethyl)phenyl]isothiazol-3-yl}-6-azaspiro[2.5]octane-6-carboxylate To a solution of tert-butyl 2-{1-amino-3-[4-fluoro-2-(trifluoromethyl)phenyl]-3-oxoprop-1-en-1-yl}-1,1-difluoro-6-azaspiro[2.5]octane-6-carboxylate (160 mg, 0.33 mmol) in toluene (8 mL) at ambient temperature was added phosphorus pentasulfide (223 mg, 1.00 mmol) and chloranil (247 mg, 1.00 mmol) sequentially and the reaction mixture warmed to 115° C. and allowed to stir for 1 h. The reaction mixture was cooled to ambient temperature and water (5 mL), ethyl acetate (5 mL), sodium carbonate (177 mg, 1.67 mmol), and di-tert-butyl dicarbonate (0.39 mL, 1.67 mmol) were added and the reaction mixture allowed to stir at ambient temperature for 1 h. Water (15 mL) was added and the resulting mixture extracted with ethyl acetate (3×10 mL). The combined organic extracts were washed with a saturated aqueous solution of sodium chloride (15 mL), dried (sodium sulfate), and filtered and the filtrate was concentrated under reduced pressure. The residue was purified by silica gel chromatography, eluting with a gradient of petroleum ether:ethyl acetate—100:0 to 92:8, to afford the title compound. MS: m/z=437.2 [M-tBu+H].

Step D: 1,1-Difluoro-2-{5-[4-fluoro-2-(trifluoromethyl)phenyl]isothiazol-3-yl}-6-azaspiro[2.5]octane Trifluoroacetate To a solution of tert-butyl 1,1-difluoro-2-{5-[4-fluoro-2-(trifluoromethyl)phenyl]isothiazol-3-yl}-6-azaspiro[2.5]octane-6-carboxylate (70 mg, 0.11 mmol) in dichloromethane (10 mL) at ambient temperature was added trifluoroacetic acid (3 mL, 38.9 mmol) and the reaction mixture allowed to stir for 1 h. The reaction mixture was concentrated under reduced pressure to afford the title compound in sufficient purity for use in the next step. MS: m/z=393.1 [M+H].

The intermediates appearing in the following tables were prepared by analogy to the above intermediates, as described or prepared as a result of similar transformations with modifications known to those skilled in the art. The requisite starting materials were described herein, commercially available, known in the literature, or readily synthesized by one skilled in the art. Straightforward protecting group strategies were applied in some routes.

TABLE INT-A

| Intermediate | R | MS [M + H] |
|---|---|---|
| A1 | 2-CF3, 5-F phenyl | 223.0 |
| A2 | 3-(OCHF2) phenyl | 203.1 |
| A3 | 4-(C(Me)2OH) phenyl | 195.1 |
| A4 | 3-cyclopropyl-5-methyl-isoxazol-4-yl | 182.1 |
| A5 | 2-methylpyridin-3-yl | 386.2 |
| A6 | 2-(CF3)pyridin-4-yl | 206.1 |
| A7 | 2-(OCHF2)pyridin-4-yl | 204.1 |
| A8 | 5-methyl-2-(OCHF2)pyridin-4-yl | 218.1 |
| A9 | imidazo[1,2-a]pyridin-7-yl | 177.0 |
| A10 | 3-(CF3)-5-cyclopropyl-isoxazol-4-yl | 236.1 |

TABLE INT-A-continued

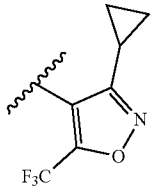 [SMILES: *c1c(C2CC2)noc1C(F)(F)F]

| Intermediate | R | MS [M + H] |
|---|---|---|
| A11 | (3-cyclopropyl-5-trifluoromethyl-isoxazol-4-yl) | 236.1 |
| A12 | (2-(2,2,2-trifluoroethoxy)pyridin-4-yl) | 236.3 |

TABLE INT-B

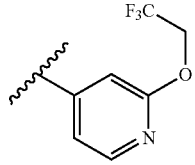 [SMILES: *c1ccnc(OCC(F)(F)F)c1]

| Intermediate | X¹ | X² | R | W | MS [M + H] |
|---|---|---|---|---|---|
| B1 | H | H | 5-(2-methoxy-5-chlorophenyl)-1,2,4-oxadiazol-3-yl | H | 320.2 |
| B2 | F | F | 5-(2-(difluoromethoxy)pyridin-4-yl)-1,2,4-oxadiazol-3-yl | H | 359.2 |
| B3 | H | H | —C(O)NHNH₂ | —SO₂NH₂ | 249.1 |
| B4 | Cl | Cl | 5-(2-trifluoromethyl-4-fluorophenyl)-1,2,4-oxadiazol-3-yl | H | 409.8 |
| B5 | Me | H | —CH(OH)— (carboxylic acid) | —SO₂NH₂ | 249.0 |
| B6 | Me | Me | —C(COOH)— | —SO₂NH₂ | 263.1 |

TABLE INT-C
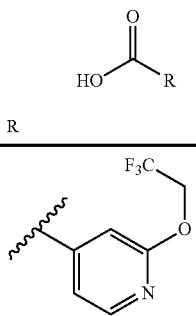
| Intermediate | R | MS [M + H] |
|---|---|---|
| C1 | 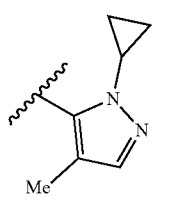 [SMILES: *c1c(C)cnn1C1CC1] | 222.1 |
| C2 | 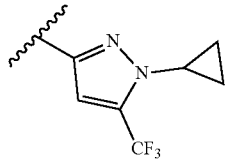 [SMILES: *c1cc(C(F)(F)F)n(C2CC2)n1] | 167.0 |
| C3 | 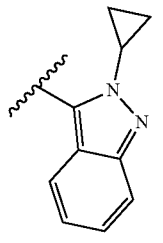 [SMILES: *c1c2ccccc2nn1C1CC1] | 221.1 |
| C4 | 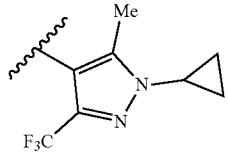 | 207.1 |
| C5 | 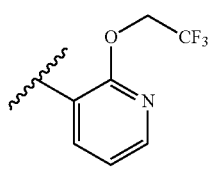 [SMILES: *c1cccnc1OCC(F)(F)F] | 235.1 |
| C6 | 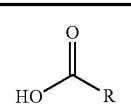 | 222.1 |
TABLE INT-C-continued
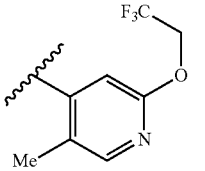 [SMILES: *c1cc(OCC(F)(F)F)ncc1C]
| Intermediate | R | MS [M + H] |
|---|---|---|
| C7 | 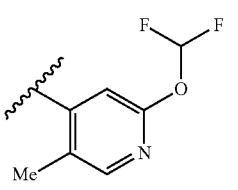 [SMILES: *c1cc(OC(F)F)ncc1C] | 236.1 |
| C8 |  | 204.1 |
| C9 | 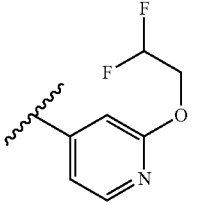 [SMILES: *c1ccnc(OCC(F)F)c1] | 236.1 |
| C10 | 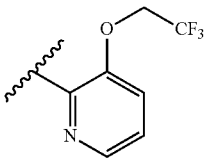 [SMILES: *c1ncccc1OCC(F)(F)F] | 204.1 |
| C11 |  | 222.1 |

TABLE INT-D

| Intermediate | Z | R | MS [M + H] |
|---|---|---|---|
| D1 | (Boc-azabicyclo structure) | C(=NOH)NH₂ amidoxime | 332.2 |
| D2 | (Boc-methylpiperidine structure) | C(=NOH)NH₂ amidoxime | 264.1 [M − tBu + H] |
| D3 | (azabicyclo HN structure) | 5-(2,5-dimethylphenyl)-1,2,4-oxadiazol-3-yl | 346.2 |
| D4 | (methylpiperidine HN structure) | 5-(2,5-dimethylphenyl)-1,2,4-oxadiazol-3-yl | 334.2 |

TABLE INT-E

| Intermediate | X | R | MS [M + H] |
|---|---|---|---|
| E1 | Br | 3-cyclopropylisoxazol-4-yl | 230.0, 232.0 |
| E2 | I | 3-cyclopropylisoxazol-4-yl | 278.03 |

Example 1

(1R)-1-{5-[2-Methyl-5-(trifluoromethyl)phenyl]-1,2,4-oxadiazol-3-yl}-6-azaspiro[2.5]octane-6-sulfonamide To a solution of 2-methyl-5-(trifluoromethyl)benzoic acid (40.4 mg, 0.198 mmol) in 1,4-dioxane (1 mL) was added 1,1'-carbonyldiimidazole (32.1 mg, 0.198 mmol) and the reaction mixture was warmed to 50° C. and allowed to stir for 2 h. (1R)—N-Hydroxy-6-sulfamoyl-6-azaspiro[2.5]octane-1-carboximidamide (Intermediate 2) (44.7 mg, 0.18 mmol) was added and the reaction mixture was warmed to 110° C. and allowed to stir for 16 h. The reaction mixture was cooled to ambient temperature and purified by silica gel chromatography, eluting with a gradient of hexanes:ethyl acetate:ethanol—96:3:1 to 24:57:19 to afford the title compound. MS: m/z=417.1 [M+H]. $^1$H NMR (DMSO-$d_6$) δ 8.26 (s, 1H), 7.94 (d, J=8.0 Hz, 1H), 7.73 (d, J=8.1 Hz, 1H), 6.71 (s, 2H), 3.17-3.09 (m, 1H), 3.08-2.95 (m, 2H), 2.85-2.75 (m, 1H), 2.70 (s, 3H), 2.28-2.17 (m, 1H), 1.81-1.59 (m, 4H), 1.28-1.17 (m, 2H).

Example 2

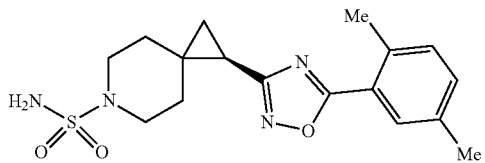 [SMILES: Cc1ccc(C)c(-c2nc([C@@H]3CC34CCN(S(N)(=O)=O)CC4)no2)c1]

(1R)-1-[5-(2,5-Dimethylphenyl)-1,2,4-oxadiazol-3-yl]-6-azaspiro[2.5]octane-6-sulfonamide To a solution of 2,5-dimethylbenzoic acid (30.0 mg, 0.200 mmol) in 1,4-dioxane (1 mL) was added 1,1'-carbonyldiimidazole (32.4 mg, 0.200 mmol) and the reaction mixture was warmed to 50° C. and allowed to stir for 2 h. (1R)—N-Hydroxy-6-sulfamoyl-6-azaspiro[2.5]octane-1-carboximidamide (Intermediate 2) (49.7 mg, 0.200 mmol) was added and the reaction mixture was warmed to 100° C. and allowed to stir for 16 h. The reaction mixture was cooled to ambient temperature and purified by silica gel chromatography, eluting with a gradient of hexanes:ethyl acetate:ethanol—96:3:1 to 52:36:12 to afford the title compound. MS: m/z=363.2 [M+H]. $^1$H NMR (DMSO-$d_6$) δ 7.82 (s, 1H), 7.37 (d, J=7.7 Hz, 1H), 7.34 (d, J=7.9 Hz, 1H), 6.72 (s, 2H), 3.12 (d, J=6.7 Hz, 1H), 3.02 (dt, J=15.1, 7.5 Hz, 2H), 2.78 (t, J=8.2 Hz, 1H), 2.56 (s, 3H), 2.36 (s, 3H), 2.18 (dd, J=7.8, 6.2 Hz, 1H), 1.83-1.56 (m, 4H), 1.19 (dd, J=7.5, 5.2 Hz, 2H).

Example 3

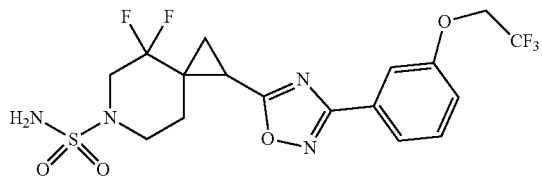 [SMILES: NS(=O)(=O)N1CCC2(CC2c2nc(-c3cccc(OCC(F)(F)F)c3)no2)C(F)(F)C1]

4,4-Difluoro-1-{3-[3-(2,2,2-trifluoroethoxy)phenyl]-1,2,4-oxadiazol-5-yl}-6-azaspiro[2.5]octane-6-sulfonamide, Diastereomer C To a solution of 4,4-difluoro-6-sulfamoyl-6-azaspiro[2.5]octane-1-carboxylic acid (Intermediate 5) (93.0 mg, 0.344 mmol) in 1,4-dioxane (2 mL) was added 1,1'-carbonyldiimidazole (61.4 mg, 0.379 mmol) and the reaction mixture was warmed to 50° C. and allowed to stir for 2 h. N-Hydroxy-3-(2,2,2-trifluoroethoxy)benzimidamide (81.0 mg, 0.344 mmol) was added and the reaction mixture was warmed to 90° C. and allowed to stir for 18 h. Sulfamide (50.0 mg, 0.52 mmol) was added and the reaction mixture was allowed to stir at 90° C. for 4 h. The reaction mixture was cooled to ambient temperature and concentrated under reduced pressure. The residue was purified by silica gel chromatography, eluting with a gradient of hexanes:ethyl acetate:ethanol—96:3:1 to 52:36:12 to afford a mixture of diastereomers. The mixture was resolved by SFC, utilizing a ChiralPak AD-H column, eluting with ethanol:carbon dioxide—20:80. The first major peak to elute was 4,4-difluoro-1-{3-[3-(2,2,2-trifluoroethoxy)phenyl]-1,2,4-oxadiazol-5-yl}-6-azaspiro[2.5]octane-6-sulfonamide, diastereomer A, the second major peak to elute was 4,4-difluoro-1-{3-[3-(2,2,2-trifluoroethoxy)phenyl]-1,2,4-oxadiazol-5-yl}-6-azaspiro[2.5]octane-6-sulfonamide, diastereomer B, the third major peak to elute was 4,4-difluoro-1-{3-[3-(2,2,2-trifluoroethoxy)phenyl]-1,2,4-oxadiazol-5-yl}-6-azaspiro[2.5]octane-6-sulfonamide, diastereomer C, the title compound, and the fourth major peak to elute was 4,4-difluoro-1-{3-[3-(2,2,2-trifluoroethoxy)phenyl]-1,2,4-oxadiazol-5-yl}-6-azaspiro[2.5]octane-6-sulfonamide, diastereomer D. Diastereomer C: MS: m/z=469.2 [M+H]. $^1$H NMR (DMSO-$d_6$) δ 7.69 (d, J=7.9 Hz, 1H), 7.60 (s, 1H), 7.55 (t, J=8.0 Hz, 1H), 7.31 (dd, J=8.3, 1.9 Hz, 1H), 7.08 (s, 2H), 4.89 (q, J=8.7 Hz, 2H), 3.53-3.41 (m, 1H), 3.38-3.23 (m, 1H), 3.14-2.98 (m, 2H), 2.92 (dd, J=9.1, 6.2 Hz, 1H), 1.99-1.83 (m, 2H), 1.75 (dd, J=8.9, 5.5 Hz, 1H), 1.63-1.54 (m, 1H).

Example 4

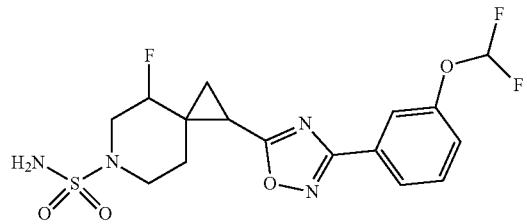 [SMILES: NS(=O)(=O)N1CCC2(CC2c2nc(-c3cccc(OC(F)F)c3)no2)C(F)C1]

1-{3-[3-(Difluoromethoxy)phenyl]-1,2,4-oxadiazol-5-yl}-4-fluoro-6-azaspiro[2.5]octane-6-sulfonamide, Diastereomer E Step A: Tert-Butyl 1-{3-[3-(difluoromethoxy)phenyl]-1,2,4-oxadiazol-5-yl}-4-fluoro-6-azaspiro[2.5]octane-6-carboxylate To a solution of 6-(tert-butoxycarbonyl)-4-fluoro-6-azaspiro[2.5]octane-1-carboxylic acid (Intermediate 6) (955.6 mg, 3.50 mmol) in 1,4-dioxane (18 mL) in a sealable vessel was added 1,1'-carbonyldiimidazole (854 mg, 5.27 mmol) and the vessel was sealed. The reaction mixture was warmed to 80° C. and allowed to stir for 1 h. The reaction mixture was cooled to ambient temperature and a solution of 3-(difluoromethoxy)-N'-hydroxybenzenecarboximidamide (843 mg, 4.17 mmol) in 1,4-dioxane (6 mL) was added. The reaction mixture was warmed to 120° C. and allowed to stir for 1.5 h. The reaction mixture was cooled to ambient temperature and concentrated under reduced pressure. The residue was purified by silica gel chromatography, eluting with a gradient of hexanes:ethyl acetate—100:0 to 70:30 to afford the title compound. MS: m/z=384.2 [M-tBu+H].

Step B: 1-{3-[3-(Difluoromethoxy)phenyl]-1,2,4-oxadiazol-5-yl}-4-fluoro-6-azaspiro[2.5]octane Hydrochloride To a vessel containing tert-butyl 1-{3-[3-(difluoromethoxy)phenyl]-1,2,4-oxadiazol-5-yl}-4-fluoro-6- azaspiro[2.5]octane-6-carboxylate (1.04 g, 2.32 mmol) was added a solution of HCl in 1,4-dioxane (4 M, 12 mL, 48.0 mmol) and the reaction mixture was allowed to stir for 18 h at ambient temperature. The reaction mixture was concentrated under reduced pressure to afford the title compound in sufficient purity for use in the next step. MS: m/z=340.2 [M+H].

Step C: 1-{3-[3-(Difluoromethoxy)phenyl]-1,2,4-oxadiazol-5-yl}-4-fluoro-6-azaspiro[2.5]octane-6-sulfonamide, Diastereomer E To a solution of 1-{3-[3-(difluoromethoxy)phenyl]-1,2,4-oxadiazol-5-yl}-4-fluoro-6-azaspiro[2.5]octane hydrochloride (913 mg, 2.31 mmol) in 1,4-dioxane (12 mL) were added sulfamide (571 mg, 5.94 mmol) and triethylamine (0.644 mL, 4.62 mmol) and the reaction mixture was warmed to 100° C. and allowed to stir for 2 h. The reaction mixture was cooled to ambient temperature and concentrated under reduced pressure. The residue was purified by silica gel chromatography, eluting with a gradient of hexanes:ethyl acetate—75:25 to 0:100 to afford a mixture of diastereomers. The mixture was resolved by SFC, utilizing a ChiralPak AD-H column, eluting with ethanol:carbon dioxide:ammonium hydroxide—30:70:0.2. The first major peak to elute was 1-{3-[3-(difluoromethoxy)phenyl]-1,2,4-oxadiazol-5-yl}-4-fluoro-6-azaspiro[2.5]octane-6-sulfonamide, diastereomer A, the second major peak to elute was 1-{3-[3-(difluoromethoxy)phenyl]-1,2,4-oxadiazol-5-yl}-4-fluoro-6-azaspiro[2.5]octane-6-sulfonamide, diastereomer B, the third major peak to elute was 1-{3-[3-(difluoromethoxy)phenyl]-1,2,4-oxadiazol-5-yl}-4-fluoro-6-azaspiro[2.5]octane-6-sulfonamide, diastereomer C, the fourth major peak to elute was 1-{3-[3-(difluoromethoxy)phenyl]-1,2,4-oxadiazol-5-yl}-4-fluoro-6-azaspiro[2.5]octane-6-sulfonamide, diastereomer D, the fifth major peak to elute was 1-{3-[3-(difluoromethoxy)phenyl]-1,2,4-oxadiazol-5-yl}-4-fluoro-6-azaspiro[2.5]octane-6-sulfonamide, diastereomer E, the title compound, and the sixth major peak to elute was 1-{3-[3-(difluoromethoxy)phenyl]-1,2,4-oxadiazol-5-yl}-4-fluoro-6-azaspiro[2.5]octane-6-sulfonamide, diastereomer F. Diastereomer E: MS: m/z=419.2 [M+H]. $^1$H NMR (CD$_3$OD) δ 7.91 (d, J=7.8 Hz, 1H), 7.78 (s, 1H), 7.55 (t, J=8.0 Hz, 1H), 7.33 (d, J=8.1 Hz, 1H), 6.91 (t, J=73.6 Hz, 1H), 4.39 (d, J=47.3 Hz, 1H), 3.64-3.55 (m, 1H), 3.30-3.24 (m, 1H), 2.75-2.66 (m, 1H), 2.63-2.56 (m, 1H), 2.32-2.24 (m, 1H), 1.78-1.71 (m, 1H), 1.71-1.65 (m, 1H), 1.55 (t, J=5.5 Hz, 1H).

Example 5

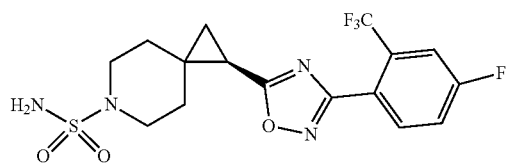 [SMILES: NS(=O)(=O)N1CCC2(CC1)C[C@H]2c1nc(-c2ccc(F)cc2C(F)(F)F)no1]

(1R)-1-{3-[4-Fluoro-2-(trifluoromethyl)phenyl]-1,2,4-oxadiazol-5-yl}-6-azaspiro[2.5]octane-6-sulfonamide To a solution of (1R)-6-sulfamoyl-6-azaspiro[2.5]octane-1-carboxylic acid (Intermediate 1) (5.00 g, 21.3 mmol) in 1,4-dioxane (80 mL) was added 1,1'-carbonyldiimidazole (5.19 g, 32.0 mmol) and the reaction mixture was warmed to 50° C. and allowed to stir for 3.5 h. The reaction mixture was cooled to ambient temperature and 4-fluoro-N'-hydroxy-2-(trifluoromethyl)benzenecarboximidamide (Intermediate 7) (4.98 g, 22.4 mmol) was added. The reaction mixture was warmed to 100° C. and allowed to stir for 2 days. The reaction mixture was cooled to ambient temperature and sulfamide (1.03 g, 10.7 mmol) was added. The reaction mixture was warmed to 100° C. and allowed to stir for 2 h. The reaction mixture was cooled to ambient temperature, a solution of saturated aqueous sodium bicarbonate (300 mL) was added, and the resulting mixture was extracted with ethyl acetate (2×700 mL). The combined organic extracts were washed with a saturated aqueous solution of sodium chloride (300 mL), dried (sodium sulfate), and concentrated under reduced pressure. The residue was purified by silica gel chromatography, eluting with a gradient of dichloromethane:methanol—100:0 to 96:4. The resulting solid was crystallized from hexanes:dichloromethane to afford the title compound. MS: m/z=421.1 [M+H]. $^1$H NMR (DMSO-d$_6$) δ 7.97-7.86 (m, 2H), 7.75 (td, J=8.3, 2.3 Hz, 1H), 6.77 (s, 2H), 3.22-3.12 (m, 1H), 3.10-3.01 (m, 1H), 3.02-2.92 (m, 1H), 2.69-2.58 (m, 1H), 2.53-2.45 (m, 1H), 1.84-1.78 (m, 1H), 1.78-1.72 (m, 1H), 1.72-1.66 (m, 1H), 1.65-1.59 (m, 1H), 1.43 (dd, J=8.3, 4.7 Hz, 1H), 1.34 (t, J=5.0 Hz, 1H).

Example 6

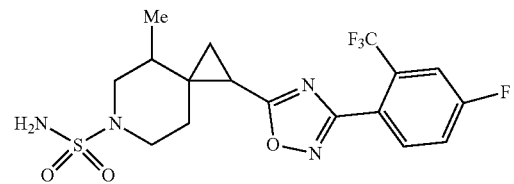 [SMILES: CC1CN(S(N)(=O)=O)CCC12CC2c1nc(-c2ccc(F)cc2C(F)(F)F)no1]

1-{3-[4-Fluoro-2-(trifluoromethyl)phenyl]-1,2,4-oxadiazol-5-yl}-4-methyl-6-azaspiro[2.5]octane-6-sulfonamide, Diastereomer D To a solution of 4-methyl-6-sulfamoyl-6-azaspiro[2.5]octane-1-carboxylic acid (Intermediate 8) (300 mg, 1.21 mmol) in 1,4-dioxane (5.0 mL) was added 1,1'-carbonyldiimidazole (206 mg, 1.27 mmol) and the reaction mixture was warmed to 50° C. and allowed to stir for 0.5 h. The reaction mixture was cooled to ambient temperature and 4-fluoro-N'-hydroxy-2-(trifluoromethyl)benzenecarboximidamide (Intermediate 7) (341 mg, 1.27 mmol) was added. The reaction mixture was warmed to 100° C. and allowed to stir for 2 days. The reaction mixture was cooled to ambient temperature and sulfamide (116 mg, 1.21 mmol) was added. The reaction mixture was warmed to 100° C. and allowed to stir for 18 h. The reaction mixture was cooled to ambient temperature and concentrated under reduced pressure. The residue was purified by silica gel chromatography, eluting with a gradient of hexanes:ethyl acetate—100:0 to 60:40 to afford three major eluting peaks, each a mixture of diastereomers of the title compound. The first major peak contained four isomers, the second major peak contained 2 isomers, and the third major peak contained two isomers. The first major peak to elute from silica gel chromatography was resolved by SFC, utilizing a ChiralPak AD-H column, eluting with methanol:carbon dioxide—12:88. The first major peak to elute was 1-{3-[4-fluoro-2-(trifluoromethyl)phenyl]-1,2,4-oxadiazol-5-yl}-4-methyl-6-azaspiro[2.5]octane-6-sulfonamide, diastereomer A, the second major peak to elute was 1-{3-[4-fluoro-2-(trifluoromethyl)phenyl]-1,2,4-oxadiazol-5-yl}-4-methyl-6-azaspiro[2.5]octane-6-sulfonamide, diastereomer B, the third major peak to elute was 1-{3-[4-fluoro-2-(trifluoromethyl)phenyl]-1,2,4-oxadiazol-5-yl}-4-methyl-6-azaspiro[2.5]octane-6-sulfonamide, diastereomer C, and the fourth major peak to elute was 1-{3-[4-fluoro-2-(trifluoromethyl)phenyl]-1,2,4-oxadiazol-5-yl}-4-methyl-6-azaspiro[2.5]octane-6-sulfonamide, diastereomer D, the title compound. Diastereomer D: MS: m/z=435.2 [M+H]. $^1$H NMR (DMSO-$d_6$) δ 7.96-7.87 (m, 2H), 7.75 (dt, J=8.4, 4.2 Hz, 1H), 6.72 (s, 2H), 3.21-3.13 (m, 1H), 3.13-3.05 (m, 1H), 2.92 (d, J=9.0 Hz, 1H), 2.55 (dd, J=8.3, 5.7 Hz, 1H), 2.35 (t, J=10.6 Hz, 1H), 1.97 (t, J=10.7 Hz, 1H), 1.64-1.58 (m, 1H), 1.55 (d, J=14.1 Hz, 1H), 1.43 (dd, J=8.3, 5.0 Hz, 1H), 1.26 (t, J=5.2 Hz, 1H), 1.04 (d, J=6.9 Hz, 3H).

Example 7

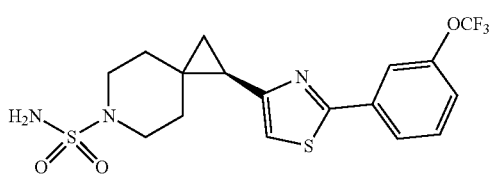 [SMILES: NS(=O)(=O)N1CCC2(CC1)C[C@H]2c1csc(-c2cccc(OC(F)(F)F)c2)n1]

(1R)-1-{2-[3-(Trifluoromethoxy)phenyl]-1,3-thiazol-4-yl}-6-azaspiro[2.5]octane-6-sulfonamide Step A: (1R)—N,N-Dimethyl-N'-{[1-(2-(3-(trifluoromethoxy)phenyl]thiazol-4-yl}-6-azaspiro[2.5]octan-6-yl)sulfonyl)formimidamide To a solution of (1R)—N-{[1-(2-chloroacetyl)-6-azaspiro[2.5]octan-6-yl]sulfonyl}-N,N-dimethylformimidamide (Intermediate 9) (100 mg, 0.31 mmol) in ethanol (1 mL) was added 3-(trifluoromethoxy)benzothioamide (68.7 mg, 0.31 mmol). The reaction mixture was warmed to 70° C. and allowed to stir for 2 h. The reaction mixture was cooled and concentrated under reduced pressure to afford the title compound in sufficient purity for use in the next step. MS: m/z=489.1 [M+H].

Step B: (1R)-1-{2-[3-(Trifluoromethoxy)phenyl]-1,3-thiazol-4-yl}-6-azaspiro[2.5]octane-6-sulfonamide To a solution of (1R)—N,N-dimethyl-N'-{[1-(2-(3-(trifluoromethoxy)phenyl]thiazol-4-yl}-6-azaspiro[2.5]octan-6-yl)sulfonyl)formimidamide (152 mg, 0.31 mmol) in ethanol (2 mL) was added hydrazine (0.5 mL, 0.31 mmol) and the reaction mixture was cooled to 10° C. and allowed to stir for 2 h. The reaction mixture was concentrated under reduced pressure and purified by preparative HPLC, eluting with a gradient of acetonitrile:water:ammonium hydroxide—48:52:0.05 to 78:22:0.05 to afford the title compound. MS: m/z=433.9 [M+H]. $^1$H NMR (400 MHz, CD$_3$OD): δ 7.90 (d, J=7.9 Hz, 1H), 7.83 (s, 1H), 7.57 (t, J=8.1 Hz, 1H), 7.36 (d, J=8.4 Hz, 1H), 7.23 (s, 1H), 3.25-3.27 (m, 1H), 3.02-3.08 (m, 1H), 2.95 (dd, $J_1$=7.9 Hz, $J_2$=3.5 Hz, 1H), 2.17 (dd, $J_1$=8.3 Hz, $J_2$=5.7 Hz, 1H), 1.66-1.75 (m, 2H), 1.52-1.66 (m, 3H), 1.21 (t, J=5.3 Hz, 1H), 1.03 (dd, $J_1$=8.6 Hz, $J_2$=5.0 Hz, 1H).

Example 8

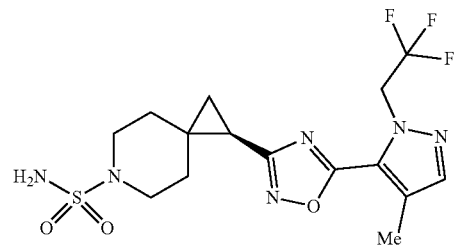 [SMILES: Cc1cnn(CC(F)(F)F)c1-c1nc([C@@H]2CC23CCN(S(N)(=O)=O)CC3)no1]

(1R)-1-{5-[4-Methyl-1-(2,2,2-trifluoroethyl)-1H-pyrazol-5-yl]-1,2,4-oxadiazol-3-yl}-6-azaspiro[2.5]octane-6-sulfonamide To a solution of 4-methyl-1-(2,2,2-trifluoroethyl)-1H-pyrazole-5-carboxylic acid (30 mg, 0.14 mmol) in 1,4-dioxane (2.4 mL) was added 1,1'-carbonyldiimidazole (30.4 mg, 0.19 mmol). The reaction mixture was warmed to 80° C. and allowed to stir for 1 h. The reaction mixture was cooled to 10° C. and (R)—N-hydroxy-6-sulfamoyl-6-azaspiro[2.5]octane-1-carboximidamide (Intermediate 2) (53.7 mg, 0.22 mmol) was added. The reaction mixture was warmed to 100° C. and allowed to stir for 12 h. The reaction mixture was filtered and the filtrate was concentrated under reduced pressure. The residue was purified by preparative HPLC, eluting with a gradient of acetonitrile:water:ammonium hydroxide—27:73:0.05 to 57:43:0.05 to afford the title compound. MS: m/z=421.0 [M+H]. $^1$H NMR (400 MHz, CD$_3$OD): δ 7.62 (s, 1H), 5.48-5.65 (m, 1H), 5.29-5.44 (m, 1H), 3.24-3.30 (m, 1H), 3.08-3.23 (m, 2H), 2.87-2.95 (m, 1H), 2.40 (s, 3H), 2.15-2.22 (m, 1H), 1.62-1.89 (m, 4H), 1.33 (t, J=5.3 Hz, 1H), 1.20-1.27 (m, 1H).

Example 9

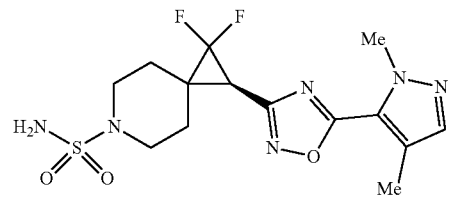 [SMILES: Cc1cnn(C)c1-c1nc([C@@H]2C(F)(F)C23CCN(S(N)(=O)=O)CC3)no1]

(2R)-2-[5-(1,4-Dimethyl-1H-pyrazol-5-yl)-1,2,4-oxadiazol-3-yl]-1,1-difluoro-6-azaspiro[2.5]octane-6-sulfonamide To a solution of 1,4-dimethyl-1H-pyrazole-5-carboxylic acid (28.1 mg, 0.201 mmol) in 1,4-dioxane (1 mL) was added 1,1'-carbonyldiimidazole (35.8 mg, 0.221 mmol) and the reaction mixture was warmed to 50° C. and allowed to stir for 2 h. The reaction mixture was cooled to ambient temperature, (1R)-2,2-difluoro-N-hydroxy-6-sulfamoyl-6-azaspiro[2.5]octane-1-carboximidamide (Intermediate 11)

(57.0 mg, 0.201 mmol) was added, and the reaction mixture was warmed to 85° C. and allowed to stir for 16 h. The reaction mixture was cooled to ambient temperature and concentrated under reduced pressure. The residue was purified by silica gel chromatography, eluting with a gradient of hexanes:ethyl acetate:ethanol—96:3:1 to 24:57:19 to afford the title compound. MS: m/z=389.3 [M+H]. $^1$H NMR (DMSO-d$_6$) δ 7.54 (s, 1H), 6.79 (s, 2H), 4.15 (s, 3H), 3.41-3.25 (m, 1H), 3.24-3.13 m, 1H), 3.13-2.98 (m, 2H), 2.94-2.81 (m, 1H), 2.31 (s, 3H), 2.02-1.83 (m, 4H)

Example 10

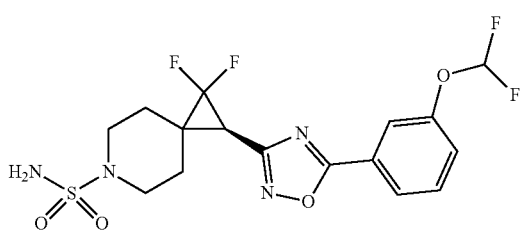 [SMILES: NS(=O)(=O)N1CCC2(CC1)[C@H](c1noc(-c3cccc(OC(F)F)c3)n1)C2(F)F]

(2R)-2-{5-[2-(Difluoromethoxy)pyridin-4-yl]-1,2,4-oxadiazol-3-yl}-1,1-difluoro-6-azaspiro[2.5]octane-6-sulfonamide To a solution of 2-difluoromethoxyisonicotinic acid (37.9 mg, 0.201 mmol) in 1,4-dioxane (1 mL) was added 1,1'-carbonyldiimidazole (35.8 mg, 0.221 mmol) and the reaction mixture was warmed to 50° C. and allowed to stir for 2 h. The reaction mixture was cooled to ambient temperature, (1R)-2,2-difluoro-N-hydroxy-6-sulfamoyl-6-azaspiro[2.5]octane-1-carboximidamide (Intermediate 11) (57.0 mg, 0.201 mmol) was added, and the reaction mixture was warmed to 85° C. and allowed to stir for 16 h. The reaction mixture was cooled to ambient temperature and concentrated under reduced pressure. The residue was purified by silica gel chromatography, eluting with a gradient of hexanes:ethyl acetate:ethanol—96:3:1 to 24:57:19 to afford the title compound. MS: m/z=438.2 [M+H]. $^1$H NMR (DMSO-d$_6$) δ 8.57 (d, J=5.2 Hz, 1H), 7.91 (d, J=5.1 Hz, 1H), 7.80 (t, J=72 Hz, 1H), 7.69 (s, 1H), 6.81 (s, 2H), 3.39 (d, J=12.0 Hz, 1H), 3.22-3.12 (m, 1H), 3.12-3.00 (m, 2H), 2.98-2.88 (m, 1H), 2.03-1.83 (m, 4H).

Example 11

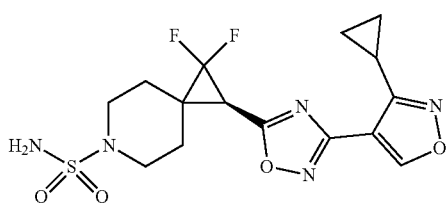 [SMILES: NS(=O)(=O)N1CCC2(CC1)[C@H](c1nc(-c3conc3C3CC3)no1)C2(F)F]

(2R)-2-[3-(3-Cyclopropylisoxazol-4-yl)-1,2,4-oxadiazol-5-yl]-1,1-difluoro-6-azaspiro[2.5]octane-6-sulfonamide To a solution of (2R)-2,2-difluoro-6-sulfamoyl-6-azaspiro[2.5]octane-1-carboxylic acid (Intermediate 10) (54.1 mg, 0.200 mmol) in 1,2-dichloroethane (0.90 mL) and dimethyl sulfoxide (0.10 mL) at ambient temperature were added 1-hydroxy-7-azabenzotriazole (13.6 mg, 0.100 mmol) and 1-(3-dimethylaminopropyl)-3-ethylcarbodiimide hydrochloride (57.5 mg, 0.300 mmol) sequentially and the reaction mixture was allowed to stir for 15 min. 3-Cyclopropyl-N-hydroxyisoxazole-4-carboximidamide (Intermediate 12) (36.8 mg, 0.220 mmol) was added and the reaction mixture was allowed to stir for 2 h. The reaction mixture was warmed to 90° C. and allowed to stir for 16 h. The reaction mixture was cooled to ambient temperature, diluted with water, the layers separated, and the organic layer purified by silica gel chromatography, eluting with a gradient of hexanes:ethyl acetate:ethanol—96:3:1 to 24:57:19 to afford the title compound. MS: m/z=402.2 [M+H]. $^1$H NMR (DMSO-d$_6$) δ 9.59 (s, 1H), 6.80 (s, 2H), 3.72 (d, J=11.1 Hz, 1H), 3.22-2.95 (m, 3H), 2.90-2.73 (m, 1H), 2.37 (ddd, J=13.3, 8.4, 5.1 Hz, 1H), 2.09-1.85 (m, 4H), 1.15-1.04 (m, 2H), 1.01-0.89 (m, 2H).

Example 12

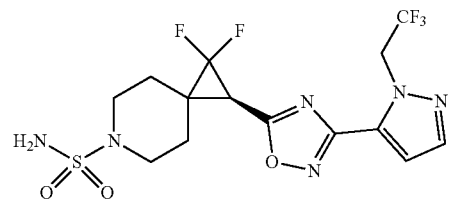 [SMILES: NS(=O)(=O)N1CCC2(CC1)[C@H](c1nc(-c3ccnn3CC(F)(F)F)no1)C2(F)F]

(2R)-1,1-Difluoro-2-{3-[1-(2,2,2-trifluoroethyl)-1H-pyrazol-5-yl]-1,2,4-oxadiazol-5-yl}-6-azaspiro[2.5]octane-6-sulfonamide To a solution of (2R)-2,2-difluoro-6-sulfamoyl-6-azaspiro[2.5]octane-1-carboxylic acid (Intermediate 10) (54.1 mg, 0.200 mmol) in 1,2-dichloroethane (0.90 mL) and dimethyl sulfoxide (0.10 mL) at ambient temperature were added 1-hydroxy-7-azabenzotriazole (13.6 mg, 0.100 mmol) and 1-(3-dimethylaminopropyl)-3-ethylcarbodiimide hydrochloride (57.5 mg, 0.300 mmol) sequentially and the reaction mixture was allowed to stir for 15 min. M-Hydroxy-1-(2,2,2-trifluoroethyl)-1H-pyrazole-5-carboximidamide (Intermediate 13) (45.8 mg, 0.220 mmol) was added and the reaction mixture allowed to stir for 1 h at ambient temperature. The reaction mixture was warmed to 90° C. and allowed to stir for 2 h. The reaction mixture was cooled to ambient temperature, diluted with water, the layers separated, and the organic layer purified by silica gel chromatography, eluting with a gradient of hexanes:ethyl acetate:ethanol—96:3:1 to 24:57:19 to afford the title compound. MS: m/z=443.2 [M+H]. $^1$H NMR (DMSO-d$_6$) δ 7.85 (d, J=1.9 Hz, 1H), 7.11 (d, J=1.9 Hz, 1H), 6.81 (s, 2H), 5.57-5.39 (m, 2H), 3.79 (d, J=11.5 Hz, 1H), 3.22-3.12 (m, 1H), 3.12-2.99 (m, 2H), 2.86-2.72 (m, 1H), 2.12-1.88 (m, 4H).

Example 13

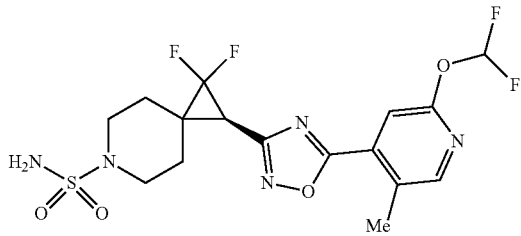 [SMILES: Cc1cnc(OC(F)F)cc1-c1nc([C@@H]2C(F)(F)C23CCN(S(N)(=O)=O)CC3)no1]

(2R)-2-{5-[2-(Difluoromethoxy)-5-methylpyridin-4-yl]-1,2,4-oxadiazol-3-yl}-1,1-difluoro-6-azaspiro[2.5]octane-6-sulfonamide To a solution of 2-(difluoromethoxy)-5-methylisonicotinic acid (Intermediate 14) (50.0 mg, 0.246 mmol) in 1,2-dichloroethane (1.10 mL) and dimethyl sulfoxide (0.12 mL) at ambient temperature were added 1-hydroxy-7-azabenzotriazole (33.5 mg, 0.246 mmol) and 1-(3-dimethylaminopropyl)-3-ethylcarbodiimide hydrochloride (70.8 mg, 0.369 mmol) and the reaction mixture was allowed to stir for 15 min. (1R)-2,2-Difluoro-N-hydroxy-6-sulfamoyl-6-azaspiro[2.5]octane-1-carboximidamide (Intermediate 11) (98.0 mg, 0.345 mmol) was added and the reaction mixture was allowed to stir for 1 h at ambient temperature. The reaction mixture was warmed to 90° C. and allowed to stir for 2 h. The reaction mixture was cooled to ambient temperature, diluted with water, the layers separated, and the organic layer purified by silica gel chromatography, eluting with a gradient of hexanes:ethyl acetate:ethanol—96:3:1 to 24:57:19 to afford the title compound. MS: m/z=452.1 [M+H]. $^1$H NMR (DMSO-d$_6$) δ 8.44 (s, 1H), 7.81 (t, J=72.7 Hz, 1H), 7.63 (s, 1H), 6.80 (s, 2H), 3.40 (d, J=12.0 Hz, 1H), 3.22-3.13 (m, 1H), 3.11-3.00 (m, 2H), 2.96-2.85 (m, 1H), 2.57 (s, 3H), 2.04-1.84 (m, 4H).

Example 14

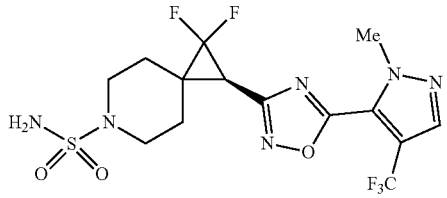 [SMILES: Cn1ncc(C(F)(F)F)c1-c1nc([C@@H]2C(F)(F)C23CCN(S(N)(=O)=O)CC3)no1]

(2R)-1,1-Difluoro-2-{5-[1-methyl-4-(trifluoromethyl)-1H-pyrazol-5-yl]-1,2,4-oxadiazol-3-yl}-6-azaspiro[2.5]octane-6-sulfonamide To a solution of 1-methyl-4-(trifluoromethyl)-1H-pyrazole-5-carboxylic acid (39.0 mg, 0.201 mmol) in 1,2-dichloroethane (0.90 mL) and dimethyl sulfoxide (0.10 mL) at ambient temperature were added 1-hydroxy-7-azabenzotriazole (27.3 mg, 0.201 mmol) and 1-(3-dimethylaminopropyl)-3-ethylcarbodiimide hydrochloride (57.8 mg, 0.301 mmol) and the reaction mixture allowed to stir for 15 min. (1R)-2,2-Difluoro-N-hydroxy-6-sulfamoyl-6-azaspiro[2.5]octane-1-carboximidamide (Intermediate 11) (80.0 mg, 0.281 mmol) was added and the reaction mixture allowed to stir for 1 h at ambient temperature. The reaction mixture was warmed to 90° C. and allowed to stir for 2 h. The reaction mixture was cooled to ambient temperature, diluted with water, the layers separated, and the organic layer purified by silica gel chromatography, eluting with a gradient of hexanes:ethyl acetate—95:5 to 25:75 to afford the title compound. MS: m/z=443.2 [M+H]. $^1$H NMR (DMSO-d$_6$) δ 8.21 (s, 1H), 6.80 (s, 2H), 4.24 (s, 3H), 3.44 (d, J=12.0 Hz, 1H), 3.25-3.12 (m, 1H), 3.12-2.99 (m, 2H), 2.96-2.83 (m, 1H), 2.04-1.86 (m, 4H).

Example 15

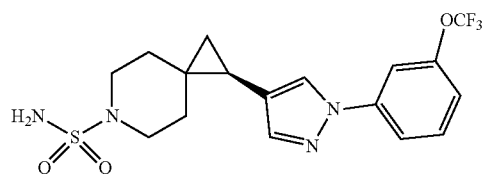 [SMILES: NS(=O)(=O)N1CCC2(CC1)C[C@H]2c1cnn(-c2cccc(OC(F)(F)F)c2)c1]

(1R)-1-{1-[3-(Trifluoromethoxy)phenyl]-1H-pyrazol-4-yl}-6-azaspiro[2.5]octane-6-sulfonamide To a solution of (1R)-1-{1-[3-(trifluoromethoxy)phenyl]-1H-pyrazol-4-yl}-6-azaspiro[2.5]octane (Intermediate 15) (100 mg, 0.30 mmol) in 1,4-dioxane (3 mL) were added triethylamine (0.062 mL, 0.45 mmol) and sulfamide (85 mg, 0.89 mmol) and the reaction mixture was warmed to 90° C. and allowed to stir for 10 h. The reaction mixture was concentrated under reduced pressure and the residue was purified by preparative HPLC, eluting with a gradient of acetonitrile:water:ammonium hydroxide—43:57:0.05 to 73:27:0.05, to afford the title compound. MS: m/z=417.1 [M+H]. $^1$H NMR (400 MHz, CDCl$_3$): δ 7.67 (s, 1H), 7.52-7.60 (m, 2H), 7.44-7.47 (m, 1H), 7.25 (s, 1H), 7.15-7.18 (s, 1H), 4.29-4.30 (m, 2H), 3.34-3.26 (m, 2H), 3.10-3.15 (m, 2H), 1.79-1.81 (m, 1H), 1.60-1.70 (m, 2H), 1.40-1.52 (m, 2H), 0.94-0.96 (m, 1H), 0.72-0.75 (m, 1H).

Example 16

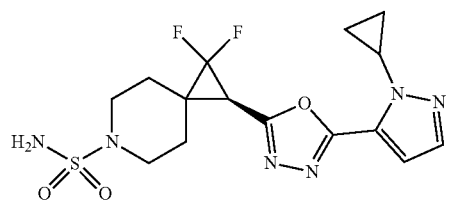 [SMILES: NS(=O)(=O)N1CCC2(CC1)[C@H](c1nnc(-c3ccnn3C3CC3)o1)C2(F)F]

(2R)-2-[5-(1-Cyclopropyl-1H-pyrazol-5-yl)-1,3,4-oxadiazol-2-yl]-1,1-difluoro-6-azaspiro[2.5]octane-6-sulfonamide Step A: (2R)-2-({2-[(1-Cyclopropyl-1H-pyrazol-5-yl)carbonyl]hydrazinyl}carbonyl)-1,1-difluoro-6-azaspiro[2.5]octane-6-sulfonamide To a solution of (1R)-2,2-difluoro-6-sulfamoyl-6-azaspiro[2.5]octane-1-carboxylic acid (Intermediate 10) (80 mg, 0.30 mmol) in dichloromethane (1.5 mL) and dimethylsulfoxide (0.20 mL) at ambient temperature were added 1-hydroxy-7-azabenzotriazole (24 mg, 0.18 mmol) and 1-(3-dimethylaminopropyl)-3-ethylcarbodiimide hydrochloride (91 mg, 0.48 mmol) and the reaction mixture was allowed to stir for 10 min. 1-Cyclopropyl-1H-pyrazole-5-carbohydrazide (Intermediate 16) (54 mg, 0.325 mmol) was added and the reaction mixture was allowed to stir for 18 h at ambient temperature. The reaction mixture was poured into water (30 mL) and the resulting mixture was extracted with ethyl acetate (2×80 mL). The combined organic extracts were washed with a saturated aqueous solution of sodium chloride (30 mL), dried (sodium sulfate), filtered and the filtrate was concentrated under reduced pressure. The residue was purified by silica gel chromatography, eluting with a gradient of dichloromethane:methanol—100:0 to 95:5 to afford the title compound. MS: m/z=419.2 [M+H].

Step B: (2R)-2-[5-(1-Cyclopropyl-1H-pyrazol-5-yl)-1,3,4-oxadiazol-2-yl]-1,1-difluoro-6-azaspiro[2.5]octane-6-sulfonamide To a solution of (2R)-2-({2-[(1-cyclopropyl-1H-pyrazol-5-yl)carbonyl]hydrazinyl}carbonyl)-1,1-difluoro-6-azaspiro[2.5]octane-6-sulfonamide (50 mg, 0.12 mmol) in acetonitrile (1.5 mL) was added phosphorous oxychloride (0.022 mL, 0.23 mmol) and the reaction mixture was warmed to 85° C. and allowed to stir for 10 h. The reaction mixture was cooled to ambient temperature and poured slowly into a saturated aqueous solution of sodium bicarbonate (30 mL) and the resulting mixture was extracted with ethyl acetate (2×70 mL). The combined organic extracts were dried (sodium sulfate), filtered, and the filtrate was concentrated under reduced pressure. The residue was purified by silica gel chromatography, eluting with a gradient of hexanes:ethyl acetate—100:0 to 50:50 to afford the title compound. MS: m/z=401.4 [M+H]. $^1$H NMR (DMSO-d$_6$) δ 7.62 (d, J=2.0 Hz, 1H), 6.99 (d, J=2.0 Hz, 1H), 6.82 (s, 2H), 4.25 (tt, J=7.4, 3.9 Hz, 1H), 3.58 (d, J=11.8 Hz, 1H), 3.20-3.12 (m, 1H), 3.12-3.03 (m, 2H), 2.98-2.86 (m, 1H), 2.03-1.87 (m, 4H), 1.22-1.04 (m, 4H).

Example 17

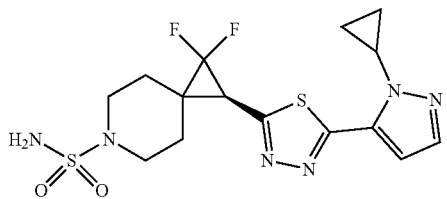 [SMILES: NS(=O)(=O)N1CCC2(CC1)[C@H](c1nnc(-c3ccnn3C3CC3)s1)C2(F)F]

(2S)-2-[5-(1-Cyclopropyl-1H-pyrazol-5-yl)-1,3,4-thiadiazol-2-yl]-1,1-difluoro-6-azaspiro[2.5]octane-6-sulfonamide To a solution of (2R)-2-({2-[(1-cyclopropyl-1H-pyrazol-5-yl)carbonyl]hydrazinyl}carbonyl)-1,1-difluoro-6-azaspiro[2.5]octane-6-sulfonamide (described in Example 16) (50 mg, 0.115 mmol) in tetrahydrofuran (1.50 mL) was added Lawesson's reagent (97 mg, 0.24 mmol) and the reaction mixture was warmed to 65° C. and allowed to stir for 3.5 h. The reaction mixture was concentrated under reduced pressure and the residue was purified by silica gel chromatography, eluting with a gradient of hexanes:ethyl acetate—100:0 to 50:50 to afford the title compound. MS: m/z=417.4 [M+H]. $^1$H NMR (DMSO-d$_6$) δ 7.57 (d, J=1.9 Hz, 1H), 6.98 (d, J=1.9 Hz, 1H), 6.81 (s, 2H), 4.18 (tt, J=7.4, 3.9 Hz, 1H), 3.77 (d, J=12.5 Hz, 1H), 3.20-3.07 (m, 2H), 3.07-2.96 (m, 1H), 2.96-2.85 (m, 1H), 2.03-1.80 (m, 4H), 1.22-1.06 (m, 4H).

Example 18

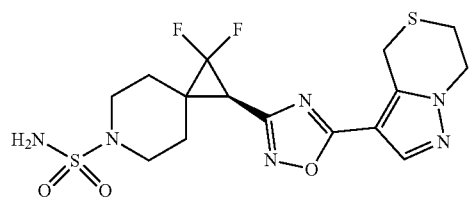 [SMILES: NS(=O)(=O)N1CCC2(CC1)[C@H](c1noc(-c3cnn4c3CSCC4)n1)C2(F)F]

(2R)-2-[5-(6,7-Dihydro-4H-pyrazolo[5,1-c][1,4]thiazin-3-yl)-1,2,4-oxadiazol-3-yl]-1,1-difluoro-6-azaspiro[2.5]octane-6-sulfonamide To a solution of 6,7-dihydro-4H-pyrazolo[5,1-c][1,4]thiazine-3-carboxylic acid (36.8 mg, 0.200 mmol) in 1,2-dichloroethane (0.90 mL) and dimethyl sulfoxide (0.10 mL) at ambient temperature were added 1-hydroxy-7-azabenzotriazole (27.2 mg, 0.200 mmol) and 1-(3-dimethylaminopropyl)-3-ethylcarbodiimide hydrochloride (57.5 mg, 0.300 mmol) sequentially and the reaction mixture was allowed to stir for 15 min. (1R)-2,2-Difluoro-N-hydroxy-6-sulfamoyl-6-azaspiro[2.5]octane-1-carboximidamide (Intermediate 11) (59.7 mg, 0.210 mmol) was added and the reaction mixture was allowed to stir for 2 h. The reaction mixture was warmed to 90° C. and allowed to stir for 4 h. The reaction mixture was cooled to ambient temperature, diluted with water, the layers separated, and the organic layer was purified by silica gel chromatography, eluting with a gradient of hexanes:ethyl acetate:ethanol—96:3:1 to 24:57:19 to afford the title compound. MS: m/z=433.2 [M+H]. $^1$H NMR (DMSO-d$_6$) δ 8.17 (s, 1H), 6.78 (s, 2H), 4.43-4.32 (m, 2H), 4.23 (s, 2H), 3.28-3.10 (m, 4H), 3.10-2.97 (m, 2H), 2.93-2.82 (m, 1H), 2.00-1.82 (m, 4H).

Example 19

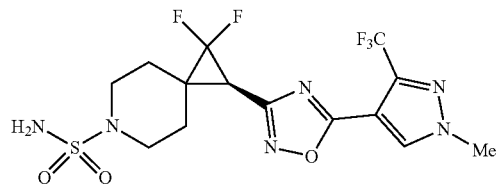 [SMILES: Cn1cc(-c2nc([C@@H]3C(F)(F)C34CCN(S(N)(=O)=O)CC4)no2)c(C(F)(F)F)n1]

(2R)-1,1-Difluoro-2-{5-[1-methyl-3-(trifluoromethyl)-1H-pyrazol-4-yl]-1,2,4-oxadiazol-3-yl}-6-azaspiro[2.5]octane-6-sulfonamide To a solution of 1-methyl-3-(trifluoromethyl)-1H-pyrazole-4-carboxylic acid (38.8 mg, 0.200 mmol) in 1,2-dichloroethane (0.90 mL) and dimethyl sulfoxide (0.10 mL) at ambient temperature were added 1-hydroxy-7-azabenzotriazole (27.2 mg, 0.200 mmol) and 1-(3-dimethylaminopropyl)-3-ethylcarbodiimide hydrochloride (57.5 mg, 0.300 mmol) sequentially and the reaction mixture was allowed to stir for 15 min. (1R)-2,2-Difluoro-N-hydroxy-6-sulfamoyl-6-azaspiro[2.5]octane-1-carboximidamide (Intermediate 11) (59.7 mg, 0.210 mmol) was added and the reaction mixture was allowed to stir for 2 h at ambient temperature. The reaction mixture was warmed to 90° C. and allowed to stir for 4 h. The reaction mixture was cooled to ambient temperature, diluted with water, the layers separated, and the organic layer purified by silica gel chromatography, eluting with a gradient of hexanes:ethyl acetate—95:5 to 25:75 to afford the title compound. MS: m/z=443.2 [M+H]. $^1$H NMR (DMSO-d$_6$) δ 8.91 (s, 1H), 6.78 (s, 2H), 4.03 (s, 3H), 3.37-3.24 (m, 1H), 3.22-3.09 (m, 1H), 3.10-2.97 (m, 2H), 2.95-2.79 (m, 1H), 2.04-1.83 (m, 4H).

Example 20

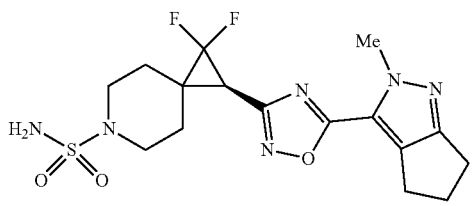 [SMILES: Cn1nc2c(c1-c1nc([C@@H]3C(F)(F)C34CCN(S(N)(=O)=O)CC4)no1)CCC2]

(2R)-1,1-Difluoro-2-[5-(2-methyl-2,4,5,6-tetrahydrocyclopenta[c]pyrazol-3-yl)-1,2,4-oxadiazol-3-yl]-6-azaspiro[2.5]octane-6-sulfonamide To a solution of 2-methyl-2,4,5,6-tetrahydrocyclopenta[c]pyrazole-3-carboxylic acid (33.2 mg, 0.200 mmol) in 1,2-dichloroethane (0.90 mL) and dimethyl sulfoxide (0.10 mL) at ambient temperature were added 1-hydroxy-7-azabenzotriazole (27.2 mg, 0.200 mmol) and 1-(3-dimethylaminopropyl)-3-ethylcarbodiimide hydrochloride (57.5 mg, 0.300 mmol) sequentially and the reaction mixture was allowed to stir for 15 min. (1R)-2,2-Difluoro-N-hydroxy-6-sulfamoyl-6-azaspiro[2.5]octane-1-carboximidamide (Intermediate 11) (68.2 mg, 0.240 mmol) was added and the reaction mixture was allowed to stir for 1 h at ambient temperature. The reaction mixture was warmed to 95° C. and allowed to stir for 3 h. The reaction mixture was cooled to ambient temperature, diluted with water, the layers separated, and the organic layer purified by silica gel chromatography, eluting with a gradient of hexanes:ethyl acetate—90:10 to 0:100 to afford the title compound. MS: m/z=415.2 [M+H]. $^1$H NMR (DMSO-d$_6$) δ 6.79 (s, 2H), 4.13 (s, 3H), 3.39-3.26 (m, 1H), 3.24-3.12 (m, 1H), 3.11-2.97 (m, 2H), 2.91-2.81 (m, 3H), 2.69 (t, J=7.3 Hz, 2H), 2.43 (p, J=7.4 Hz, 2H), 2.02-1.82 (m, 4H).

Example 21

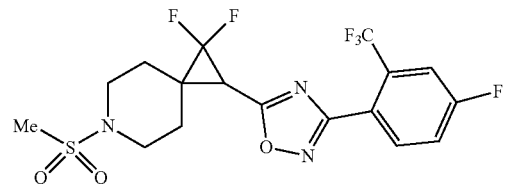 [SMILES: CS(=O)(=O)N1CCC2(CC1)C(c1nc(-c3ccc(F)cc3C(F)(F)F)no1)C2(F)F]

1,1-Difluoro-2-{3-[4-fluoro-2-(trifluoromethyl)phenyl]-1,2,4-oxadiazol-5-yl}-6-(methylsulfonyl)-6-azaspiro[2.5]octane To a solution of 2,2-difluoro-6-(methylsulfonyl)-6-azaspiro[2.5]octane-1-carboxylic acid (Intermediate 28) (135 mg, 0.501 mmol) in 1,2-dichloroethane (2.25 mL) and dimethylsulfoxide (0.25 mL) at ambient temperature was added 1-hydroxy-7-azabenzotriazole (77 mg, 0.50 mmol) followed by 1-(3-dimethylaminopropyl)-3-ethylcarbodiimide hydrochloride (115 mg, 0.600 mmol) and the reaction mixture was allowed to stir for 20 min. 4-Fluoro-N-hydroxy-2-(trifluoromethyl)benzimidamide (122 mg, 0.550 mmol) was added and the reaction mixture was allowed to stir for 18 h at ambient temperature. The reaction mixture was warmed to 95° C. and allowed to stir for 6 h. The reaction mixture was warmed to 105° C. and allowed to stir for 4 h. The reaction mixture was cooled to ambient temperature and diluted with water. The layers were separated and the organic layer purified by silica gel chromatography, eluting with a gradient of hexanes:ethyl acetate:ethanol—95:4:1 to 50:38:12. The product fractions were combined and concentrated under reduced pressure. The residue was purified by preparative HPLC, eluting with a gradient of acetonitrile:water:trifluoroacetic acid—10:90:0.1 to 95:5:0.1 to afford the title compound. MS: m/z=456.2 [M+H]. $^1$H NMR (DMSO-d$_6$) δ 8.00-7.91 (m, 2H), 7.77 (t, J=8.1 Hz, 1H), 3.77 (d, J=11.2 Hz, 1H), 3.37-3.29 (m, 1H), 3.28-3.18 (m, 2H), 3.03-2.94 (m, 1H), 2.90 (s, 3H), 2.06 (s, 2H), 2.02-1.90 (m, 2H).

Example 22

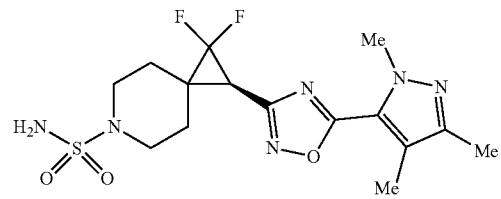 [SMILES: Cc1nn(C)c(-c2nc([C@@H]3C(F)(F)C34CCN(S(N)(=O)=O)CC4)no2)c1C]

(2R)-1,1-Difluoro-2-[5-(1,3,4-trimethyl-1H-pyrazol-5-yl)-1,2,4-oxadiazol-3-yl]-6-azaspiro[2.5]octane-6-sulfonamide To a solution of 1,3,4-trimethyl-1H-pyrazole-5-carboxylic acid (46.2 mg, 0.300 mmol) in 1,2-dichloroethane (1.4 mL) and dimethyl sulfoxide (0.15 mL) at ambient temperature were added 1-hydroxy-7-azabenzotriazole (40.8 mg, 0.300 mmol) and 1-(3-dimethylaminopropyl)-3-ethylcarbodiimide hydrochloride (86.0 mg, 0.450 mmol) and the reaction mixture was allowed to stir for 15 min. (1R)-2,2-Difluoro-N-hydroxy-6-sulfamoyl-6-azaspiro[2.5]octane-1-carboximidamide (Intermediate 11) (102 mg, 0.360 mmol) was added and the reaction mixture was stirred for 1 h at ambient temperature. The reaction mixture was warmed to 90° C. and allowed to stir for 2 h. The reaction mixture was cooled to ambient temperature, diluted with water, the layers separated, and the organic layer purified by silica gel chromatography, eluting with a gradient of hexanes:ethyl acetate:ethanol—96:3:1 to 52:36:12 to afford the title compound. MS: m/z=403.2 [M+H]. $^1$H NMR (DMSO-$d_6$) δ 6.79 (s, 2H), 4.07 (s, 3H), 3.34 (d, J=12.6 Hz, 1H), 3.23-3.13 (m, 1H), 3.12-2.98 (m, 2H), 2.95-2.81 (m, 1H), 2.24 (s, 3H), 2.17 (s, 3H), 2.02-1.85 (m, 4H).

Example 23

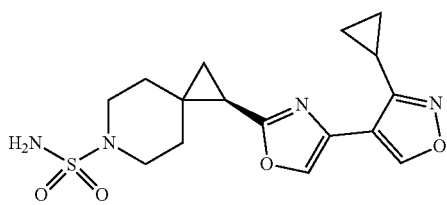 [SMILES: NS(=O)(=O)N1CCC2(CC1)C[C@H]2c1nc(-c2conc2C2CC2)co1]

(1R)-1-[4-(3-Cyclopropylisoxazol-4-yl)-1,3-oxazol-2-yl]-6-azaspiro[2.5]octane-6-sulfonamide To a solution of (1R)-1-[4-(3-cyclopropylisoxazol-4-yl)-1,3-oxazol-2-yl]-6-azaspiro[2.5]octane (Intermediate 18) (13.7 mg, 0.047 mmol) in 1,4-dioxane (0.50 mL) was added sulfamide (24 mg, 0.25 mmol) and the reaction mixture was warmed to 100° C. and allowed to stir for 2 h. The reaction mixture was cooled to ambient temperature and concentrated under reduced pressure. The residue was purified by silica gel chromatography, eluting with a gradient of hexanes:ethyl acetate—100:0 to 70:30 to afford the title compound. MS: m/z=365.1 [M+H]. $^1$H NMR (DMSO-$d_6$) δ 9.07 (s, 1H), 8.33 (s, 1H), 6.72 (s, 2H), 3.16-3.06 (m, 1H), 3.06-2.91 (m, 2H), 2.80-2.67 (m, 1H), 2.18 (dd, J=8.5, 5.7 Hz, 1H), 2.10 (ddd, J=13.4, 8.3, 5.0 Hz, 1H), 1.73-1.50 (m, 5H), 1.21-1.13 (m, 2H), 1.07-0.98 (m, 2H), 0.90-0.81 (m, 2H).

Example 24

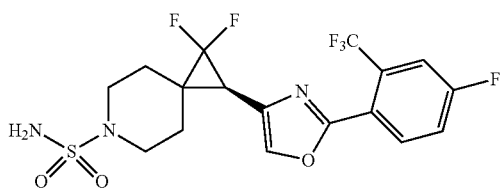 [SMILES: NS(=O)(=O)N1CCC2(CC1)[C@H](c1coc(-c3ccc(F)cc3C(F)(F)F)n1)C2(F)F]

(2R)-1,1-Difluoro-2-{2-[4-fluoro-2-(trifluoromethyl)phenyl]-1,3-oxazol-4-yl}-6-azaspiro[2.5]octane-6-sulfonamide Step A: (2R)—N-[(Dimethylamino)methylidene]-1,1-difluoro-2-{2-[4-fluoro-2-(trifluoromethyl)phenyl]-1,3-oxazol-4-yl}-6-azaspiro[2.5]octane-6-sulfonamide To a solution of (2R)—N-[(dimethylamino)methylidene]-1,1-difluoro-2-(iodoacetyl)-6-azaspiro[2.5]octane-6-sulfonamide (Intermediate 24) (133 mg, 0.296 mmol) in ethyl acetate (1.48 mL) were added 4-fluoro-2-(trifluoromethyl)benzamide (77 mg, 0.37 mmol) and silver trifluoromethanesulfonate (95 mg, 0.37 mmol) and the reaction mixture was warmed to 60° C. and allowed to stir for 3 h. The reaction mixture was cooled to ambient temperature and diluted with a saturated aqueous solution of sodium chloride (10 mL) and ethyl acetate (10 mL) and the resulting mixture was allowed to stir for 3.5 h. The mixture was filtered through Celite®, washing with ethyl acetate. The layers were separated and the aqueous layer was extracted with ethyl acetate (2×). The combined organic extracts were washed sequentially with a saturated aqueous solution of sodium bicarbonate, an aqueous solution of HCl (1 M), and a saturated aqueous solution of sodium chloride, dried (sodium sulfate), filtered, and the filtrate was concentrated under reduced pressure. The residue was purified by silica gel chromatography, eluting with a gradient of hexanes:ethyl acetate:ethanol—100:0:0 to 40:45:15 to afford the title compound. MS: m/z=511.2 [M+H].

Step B: (2R)-1,1-Difluoro-2-{2-[4-fluoro-2-(trifluoromethyl)phenyl]-1,3-oxazol-4-yl}-6-azaspiro[2.5]octane-6-sulfonamide To a solution of (2R)—N-[(dimethylamino)methylidene]-1,1-difluoro-2-{2-[4-fluoro-2-(trifluoromethyl)phenyl]-1,3-oxazol-4-yl}-6-azaspiro[2.5]octane-6-sulfonamide (72 mg, 0.14 mmol) in methanol (1.41 mL) was added hydrazine (0.0443 mL, 1.41 mmol) and the reaction mixture was warmed to 60° C. and allowed to stir for 4 h. The reaction mixture was concentrated under reduced pressure and the residue was purified by silica gel chromatography, eluting with a gradient of hexanes:ethyl acetate:ethanol—100:0:0 to 40:45:15 to afford the title compound. MS: m/z=456.2 [M+H]. $^1$H NMR (500 MHz, CDCl$_3$) δ 7.95 (dd, J=8.6, 5.4 Hz, 1H), 7.66 (s, 1H), 7.53 (dd, J=8.9, 2.5 Hz, 1H), 7.46-7.32 (m, 1H), 4.35 (s, 2H), 3.49-3.28 (m, 2H), 3.19 (m, 2H), 2.49 (d, J=13.7 Hz, 1H), 2.03 (m, 1H), 1.89 (m, 1H), 1.78 (m, 1H), 1.65 (m, 1H).

Example 25

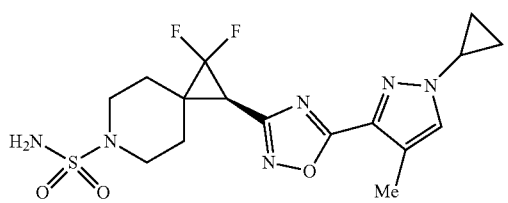 [SMILES: Cc1cn(C2CC2)nc1-c1nc([C@@H]2C(F)(F)C23CCN(S(N)(=O)=O)CC3)no1]

(2R)-2-[5-(1-Cyclopropyl-4-methyl-1H-pyrazol-3-yl)-1,2,4-oxadiazol-3-yl]-1,1-difluoro-6-azaspiro[2.5]octane-6-sulfonamide To a solution of 1-cyclopropyl-4-methyl-1H-pyrazole-3-carboxylic acid (Intermediate 20) (33.2 mg, 0.200 mmol) in 1,2-dichloroethane (0.90 mL) and dimethyl sulfoxide (0.10 mL) at ambient temperature were added 1-hydroxy-7-azabenzotriazole (30.8 mg, 0.200 mmol) and 1-(3-dimethylaminopropyl)-3-ethylcarbodiimide hydrochloride (49.8 mg, 0.260 mmol) and the reaction mixture was allowed to stir for 15 min. (1R)-2,2-Difluoro-N-hydroxy-6-sulfamoyl-6-azaspiro[2.5]octane-1-carboximidamide (Intermediate 11) (62.5 mg, 0.220 mmol) was added and the reaction mixture was allowed to stir for 16 h at ambient temperature. The reaction mixture was warmed to 90° C. and allowed to stir for 3 h. The reaction mixture was cooled to ambient temperature, diluted with water, the layers were separated, and the organic layer was purified by silica gel chromatography, eluting with a gradient of hexanes:ethyl acetate:ethanol—96:3:1 to 52:36:12 to afford the title compound. MS: m/z=415.3 [M+H]. $^1$H NMR (DMSO-$d_6$) δ 7.91 (s, 1H), 6.80 (s, 2H), 3.91-3.81 (m, 1H), 3.39-3.25 (m, 1H), 3.21-3.10 (m, 1H), 3.10-2.99 (m, 2H), 2.91-2.80 (m, 1H), 2.27 (s, 3H), 2.02-1.84 (m, 4H), 1.15-0.98 (m, 4H).

Example 26

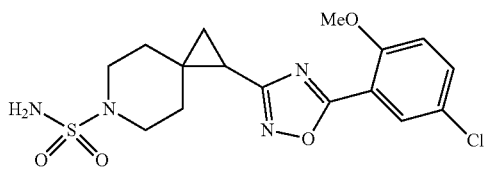 [SMILES: COc1ccc(Cl)cc1-c1nc(C2CC23CCN(S(N)(=O)=O)CC3)no1]

1-[5-(5-Chloro-2-methoxyphenyl)-1,2,4-oxadiazol-3-yl]-6-(methylsulfonyl)-6-azaspiro[2.5]octane, Enantiomer A To a solution of 5-chloro-5-methoxybenzoic acid (93.0 mg, 0.501 mmol) in 1,4-dioxane (2 mL) was added 1,1'-carbonyldiimidazole (89.0 mg, 0.550 mmol) and the reaction mixture was warmed to 50° C. and allowed to stir for 2 h. N-Hydroxy-6-methylsulfonyl-6-azaspiro[2.5]octane-1-carboximidamide (Intermediate 21) (124 mg, 0.498 mmol) was added and the reaction mixture was warmed to 120° C. and allowed to stir for 16 h. The reaction mixture was cooled to ambient temperature and concentrated under reduced pressure. The residue was purified by silica gel chromatography, eluting with a gradient of hexanes:ethyl acetate:ethanol—96:3:1 to 52:36:12 to afford the racemic title compound. The mixture was resolved by SFC, utilizing a ChiralPak AS-H column, and eluting with methanol:carbon dioxide—25:75. The first major peak to elute was 1-[5-(5-chloro-2-methoxyphenyl)-1,2,4-oxadiazol-3-yl]-6-(methylsulfonyl)-6-azaspiro[2.5]octane, enantiomer A, the title compound, and the second major peak to elute was 1-[5-(5-chloro-2-methoxyphenyl)-1,2,4-oxadiazol-3-yl]-6-(methylsulfonyl)-6-azaspiro[2.5]octane. MS: m/z=398.2 [M+H]. $^1$H NMR (DMSO-$d_6$) δ 7.94 (d, J=2.7 Hz, 1H), 7.71 (dd, J=9.0, 2.7 Hz, 1H), 7.33 (d, J=9.1 Hz, 1H), 3.93 (s, 3H), 3.36-3.27 (m, 1H), 3.21 (t, J=5.4 Hz, 2H), 3.11 (ddd, J=11.1, 7.3, 3.5 Hz, 1H), 2.98 (ddd, J=11.1, 7.0, 3.3 Hz, 1H), 2.87 (s, 3H), 2.19 (dd, J=7.9, 6.2 Hz, 1H), 1.77-1.56 (m, 3H), 1.26-1.13 (m, 2H).

Example 27

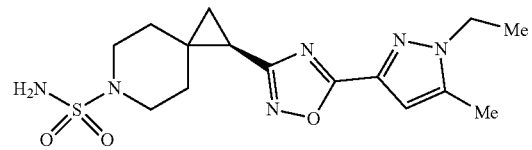 [SMILES: CCn1nc(-c2nc([C@@H]3CC34CCN(S(N)(=O)=O)CC4)no2)cc1C]

(1R)-1-[5-(1-Ethyl-5-methyl-TH-pyrazol-3-yl)-1,2,4-oxadiazol-3-yl]-6-azaspiro[2.5]octane-6-sulfonamide To a solution of 1-ethyl-5-methyl-H-pyrazole-3-carboxylic acid (31.0 mg, 0.201 mmol) in 1,4-dioxane (1 mL) was added 1,1'-carbonyldiimidazole (32.7 mg, 0.201 mmol) and the reaction mixture was warmed to 50° C. and allowed to stir for 2 h. (1R)—N-Hydroxy-6-sulfamoyl-6-azaspiro[2.5]octane-1-carboximidamide (Intermediate 2) (50.0 mg, 0.201 mmol) was added and the reaction mixture was warmed to 90° C. and allowed to stir for 16 h. The reaction mixture was cooled to ambient temperature and concentrated under reduced pressure. The residue was purified by HPLC, eluting with a gradient of acetonitrile:water:trifluoroacetic acid—5:95:0.1 to 95:5:0.1, to afford the title compound. MS: m/z=367.3 [M+H]. $^1$H NMR (DMSO-$d_6$) δ 6.74 (s, 1H), 6.72 (s, 2H), 4.18 (q, J=7.4 Hz, 2H), 3.13-3.07 (m, 1H), 3.06-2.93 (m, 2H), 2.79-2.72 (m, 1H), 2.35 (s, 3H), 2.17-2.10 (m, 1H), 1.73-1.55 (m, 4H), 1.35 (t, J=7.2 Hz, 3H), 1.21-1.12 (m, 2H).

Example 28

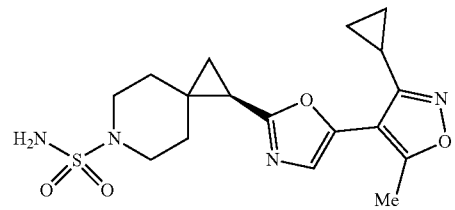 [SMILES: Cc1onc(C2CC2)c1-c1cnc([C@@H]2CC23CCN(S(N)(=O)=O)CC3)o1]

(1R)-1-[5-(3-Cyclopropyl-5-methylisoxazol-4-yl)-1,3-oxazol-2-yl]-6-azaspiro[2.5]octane-6-sulfonamide

Step A: (1R)—N-[2-(3-Cyclopropyl-5-methylisoxazol-4-yl)-2-oxoethyl]-6-sulfamoyl-6-azaspiro[2.5]octane-1-carboxamide To a solution of 2-azido-1-(3-cyclopropyl-5-methylisoxazol-4-yl)ethanone (Intermediate 22) (157 mg, 0.761 mmol) in tetrahydrofuran (3.0 mL) was added triphenylphosphine (200 mg, 0.761 mmol) and the reaction mixture was allowed to stir for 2 h at ambient temperature. Water (0.05 mL) was added and the reaction mixture was allowed to stir for 1 h at ambient temperature. 4 Å Molecular sieves were added and the reaction mixture was allowed to stir for 15 min at ambient temperature. (1R)-6-Sulfamoyl-6-azaspiro[2.5]octane-1-carboxylic acid (Intermediate 1) (0.196 g, 0.837 mmol), HATU (0.347 mg, 0.913 mmol), and 4-methylmorpholine (0.25 mL, 2.274 mmol) were added sequentially and the reaction mixture was allowed to stir for 18 h at ambient temperature. The reaction mixture was poured into water (50 mL) and the resulting mixture extracted with ethyl acetate (2×80 mL). The combined organic extracts were washed with a saturated aqueous solution of sodium chloride (50 mL), dried (sodium sulfate), filtered, and the filtrate was concentrated under reduced pressure. The residue was purified by silica gel chromatography, eluting with a gradient of dichloromethane:methanol—100:0 to 95:5 to afford the title compound. MS: m/z=397.2 [M+H].

Step B: (1R)-1-[5-(3-Cyclopropyl-5-methylisoxazol-4-yl)-1,3-oxazol-2-yl]-6-azaspiro[2.5]octane-6-sulfonamide To a solution of (1R)—N-[2-(3-cyclopropyl-5-methylisoxazol-4-yl)-2-oxoethyl]-6-sulfamoyl-6-azaspiro[2.5]octane-1-carboxamide (45 mg, 0.11 mmol) in acetonitrile (1 mL) was added phosphorous oxychloride (0.013 mL, 0.136 mmol) and the reaction mixture was warmed to 85° C. and allowed to stir for 2 h. The reaction mixture was cooled to ambient temperature and poured into a saturated aqueous solution of sodium bicarbonate (20 mL) and the resulting mixture was extracted with ethyl acetate (2×40 mL). The combined organic extracts were washed with a saturated aqueous solution of sodium chloride (20 mL), dried (sodium sulfate), filtered, and the filtrate was concentrated under reduced pressure. The residue was purified by silica gel chromatography, eluting with a gradient of hexanes:ethyl acetate—100:0 to 50:50 to afford the title compound. MS: m/z=379.1 [M+H]. $^1$H NMR (DMSO-d$_6$) δ 7.33 (s, 1H), 6.73 (s, 2H), 3.19-3.08 (m, 1H), 3.07-2.91 (m, 2H), 2.76-2.67 (m, 1H), 2.53 (s, 3H), 2.19 (dd, J=8.4, 5.6 Hz, 1H), 1.99 (ddd, J=13.3, 8.2, 5.0 Hz, 1H), 1.74-1.62 (m, 2H), 1.61-1.47 (m, 2H), 1.22-1.12 (m, 2H), 1.01 (dd, J=8.3, 2.5 Hz, 2H), 0.88-0.79 (m, 2H).

Example 29

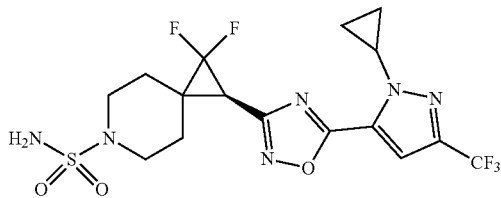 [SMILES: NS(=O)(=O)N1CCC2(CC1)[C@H](c1noc(-c3cc(C(F)(F)F)nn3C3CC3)n1)C2(F)F]

(2R)-2-{5-[1-Cyclopropyl-3-(trifluoromethyl)-1H-pyrazol-5-yl]-1,2,4-oxadiazol-3-yl}-1,1-difluoro-6-azaspiro[2.5]octane-6-sulfonamide To a solution of 1-cyclopropyl-3-(trifluoromethyl)-1H-pyrazole-5-carboxylic acid (Intermediate 23) (66.0 mg, 0.300 mmol) in 1,2-dichloroethane (1.4 mL) and dimethyl sulfoxide (0.15 mL) at ambient temperature were added 1-hydroxy-7-azabenzotriazole (40.8 mg, 0.300 mmol) and 1-(3-dimethylaminopropyl)-3-ethylcarbodiimide hydrochloride (86.0 mg, 0.450 mmol) and the reaction mixture allowed to stir for 15 min. (1R)-2,2-Difluoro-N-hydroxy-6-sulfamoyl-6-azaspiro[2.5]octane-1-carboximidamide (Intermediate 11) (102 mg, 0.360 mmol) was added and the reaction mixture was allowed to stir for 1 h at ambient temperature. The reaction mixture was warmed to 95° C. and allowed to stir for 2 h. The reaction mixture was cooled to ambient temperature, diluted with water, the layers separated, and the organic layer purified by silica gel chromatography, eluting with a gradient of hexanes:ethyl acetate:ethanol—96:3:1 to 52:36:12 to afford the title compound. MS: m/z=469.2 [M+H]. $^1$H NMR (DMSO-d$_6$) δ 7.74 (s, 1H), 6.80 (s, 2H), 4.31 (dt, J=7.1, 3.6 Hz, 1H), 3.39 (d, J=11.7 Hz, 1H), 3.23-3.13 (m, 1H), 3.11-3.00 (m, 2H), 2.95-2.85 (m, 1H), 2.02-1.87 (m, 4H), 1.30-1.22 (m, 2H), 1.22-1.13 (m, 2H).

Example 30

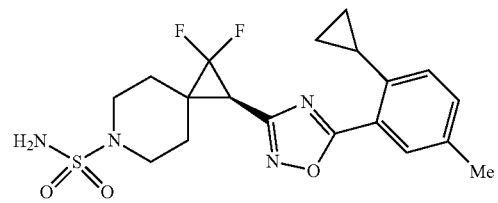 [SMILES: Cc1ccc(C2CC2)c(-c2nc([C@@H]3C(F)(F)C34CCN(S(N)(=O)=O)CC4)no2)c1]

(2R)-2-[5-(2-Cyclopropyl-5-methylphenyl)-1,2,4-oxadiazol-3-yl]-1,1-difluoro-6-azaspiro[2.5]octane-6-sulfonamide To a solution of 2-cyclopropyl-5-methylbenzoic acid (37.2 mg, 0.211 mmol) in 1,2-dichloroethane (1.6 mL) and dimethylsulfoxide (0.16 mL) were added 1-(3-dimethylaminopropyl)-3-ethylcarbodiimide hydrochloride (43.8 mg, 0.229 mmol), 1-hydroxy-7-azabenzotriazole (19.2 mg, 0.141 mmol), and (1R)-2,2-difluoro-N-hydroxy-6-sulfamoyl-6-azaspiro[2.5]octane-1-carboximidamide (Intermediate 11) (50 mg, 0.18 mmol) sequentially and the reaction mixture was allowed to stir for 1 h at ambient temperature. The reaction mixture was warmed to 110° C. and allowed to stir for 2.5 h. The reaction mixture was allowed to cool to ambient temperature and was filtered and the filtrate was concentrated under a stream of nitrogen. The residue was purified by HPLC, eluting with a gradient of acetonitrile:water—20:80 to 95:5 to afford the title compound. MS: m/z=425.2 [M+H]. $^1$H NMR (DMSO-d$_6$) δ 7.76 (s, 1H), 7.39 (d, J=8.0 Hz, 1H), 7.11 (d, J=8.0 Hz, 1H), 6.81 (s, 2H), 3.33 (s, 1H), 3.16 (s, 1H), 3.11-3.01 (m, 2H), 2.89 (d, J=6.6 Hz, 1H), 2.61-2.53 (m, 1H), 2.35 (s, 3H), 1.97 (d, J=6.9 Hz, 3H), 1.95-1.88 (m, 1H), 0.97 (d, J=8.5 Hz, 2H), 0.70 (q, J=5.8 Hz, 2H).

Example 31

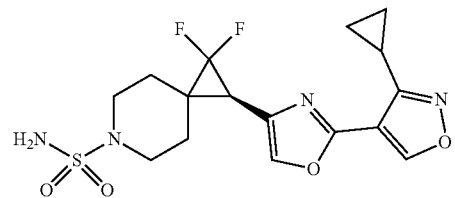 [SMILES: NS(=O)(=O)N1CCC2(CC1)[C@H](c1coc(-c3conc3C3CC3)n1)C2(F)F]

(2R)-2-[2-(3-Cyclopropylisoxazol-4-yl)-1,3-oxazol-4-yl]-1,1-difluoro-6-azaspiro[2.5]octane-6-sulfonamide Step A: (2R)-2-[2-(3-Cyclopropylisoxazol-4-yl)-1,3-oxazol-4-yl]-N-[(dimethylamino)methylidene]-1,1-difluoro-6-azaspiro[2.5]octane-6-sulfonamide To a solution of (2R)—N-[(dimethylamino)methylidene]-1,1-difluoro-2-(iodoacetyl)-6-azaspiro[2.5]octane-6-sulfonamide (Intermediate 24) (74.5 mg, 0.166 mmol) in ethyl acetate (0.83 mL) were added 3-cyclopropylisoxazole-4-carboxamide (31.5 mg, 0.207 mmol) and silver trifluoromethanesulfonate (53.3 mg, 0.207 mmol) and the reaction mixture was warmed to 60° C. and allowed to stir for 2 h. The mixture was diluted with a saturated aqueous solution of sodium chloride (10 mL) and ethyl acetate (10 mL) and the mixture allowed to stir for 4 h. The resulting mixture was filtered, washing with ethyl acetate, the layers of the filtrate were separated, and the aqueous layer was extracted with ethyl acetate (2×). The combined organic layers were washed with a saturated aqueous solution of sodium bicarbonate (2×), an aqueous solution of HCl (1 M), and a saturated aqueous solution of sodium chloride, dried (magnesium sulfate), filtered, and the filtrate was concentrated under reduced pressure. The residue was purified by silica gel chromatography, eluting with a gradient of hexanes:ethyl acetate:ethanol—100:0:0 to 60:30:10 to afford the title compound. MS: m/z=456.3 [M+H].

Step B: (2R)-2-[2-(3-Cyclopropylisoxazol-4-yl)-1,3-oxazol-4-yl]-1,1-difluoro-6-azaspiro[2.5]octane-6-sulfonamide To a solution of (2R)-2-[2-(3-cyclopropylisoxazol-4-yl)-1,3-oxazol-4-yl]-N-[(dimethylamino)methylidene]-1,1-difluoro-6-azaspiro[2.5]octane-6-sulfonamide (42 mg, 0.092 mmol) in methanol (0.92 mL) was added hydrazine (0.0289 mL, 0.922 mmol) and the reaction mixture was warmed to 50° C. and allowed to stir for 2 h. The reaction mixture was concentrated under reduced pressure and the residue was purified by silica gel chromatography, eluting with a gradient of hexanes:ethyl acetate:ethanol—100:0:0 to 70:23:7 to afford the title compound. MS: m/z=401.2 [M+H]. $^1$H NMR (500 MHz, CDCl$_3$) δ 8.82 (s, 1H), 7.54 (s, 1H), 4.34 (s, 2H), 3.45 (m, 1H), 3.33-3.24 (m, 2H), 3.11 (m, 1H), 2.55-2.52 (m, 1H), 2.49 (d, J=13.8 Hz, 1H), 1.97 (m, 2H), 1.79-1.70 (m, 1H), 1.71-1.63 (m, 1H), 1.17-1.07 (m, 4H).

Example 32

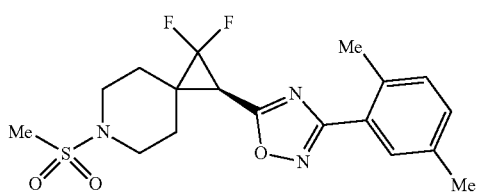 [SMILES: Cc1ccc(C)c(-c2noc([C@@H]3C(F)(F)C34CCN(S(C)(=O)=O)CC4)n2)c1]

2-[3-(2,5-Dimethylphenyl)-1,2,4-oxadiazol-5-yl]-1,1-difluoro-6-(methylsulfonyl)-6-azaspiro[2.5]octane Essentially following the procedures described in Example 21, but using N-hydroxy-2,5-dimethylbenzenecarboximidamide in place of 4-fluoro-N-hydroxy-2-(trifluoromethyl)benzimidamide, the title compound was obtained. MS: m/z=398.3 [M+H]. $^1$H NMR (DMSO-d$_6$) δ 7.70 (s, 1H), 7.29 (s, 2H), 3.69 (d, J=11.4 Hz, 1H), 3.31-3.20 (m, 3H), 3.10-3.03 (m, 1H), 2.90 (s, 3H), 2.48 (s, 3H), 2.35 (s, 3H), 2.14-2.03 (m, 2H), 2.02-1.91 (m, 2H).

Example 33

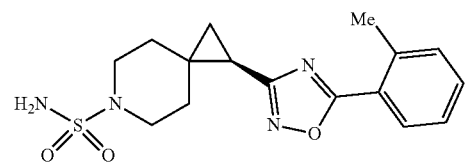 [SMILES: Cc1ccccc1-c1nc([C@@H]2CC23CCN(S(N)(=O)=O)CC3)no1]

(1R)-1-[5-(2-Methylphenyl)-1,2,4-oxadiazol-3-yl]-6-azaspiro[2.5]octane-6-sulfonamide Essentially following the procedures described in Example 1, but using 2-methylbenzoic acid in place of 2-methyl-5-(trifluoromethyl)benzoic acid, the title compound was obtained. MS: m/z=349.1 [M+H]. $^1$H NMR (DMSO-d$_6$) δ 8.00 (d, J=7.8 Hz, 1H), 7.56 (t, J=7.4 Hz, 1H), 7.46 (d, J=7.6 Hz, 1H), 7.42 (t, J=7.5 Hz, 1H), 6.71 (s, 2H), 3.17-3.10 (m, 1H), 3.07-2.98 (m, 2H), 2.62 (s, 3H), 2.19 (t, J=6.9 Hz, 1H), 1.80-1.73 (m, 1H), 1.72-1.59 (m, 3H), 1.20 (d, J=7.0 Hz, 2H).

Example 34

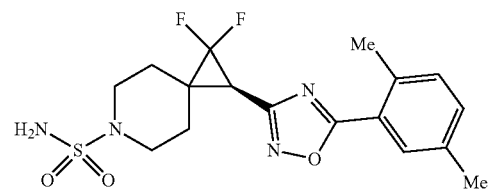 [SMILES: Cc1ccc(C)c(-c2nc([C@@H]3C(F)(F)C34CCN(S(N)(=O)=O)CC4)no2)c1]

(2R)-2-[5-(2,5-Dimethylphenyl)-1,2,4-oxadiazol-3-yl]-1,1-difluoro-6-azaspiro[2.5]octane-6-sulfonamide Essentially following the procedures described in Example 30, but using 2,5-dimethylbenzoic acid in place of 2-cyclopropyl-5-methylbenzoic acid, the title compound was obtained. MS: m/z=399.2 [M+H]. $^1$H NMR (DMSO-d$_6$) δ 7.85 (s, 1H), 7.42-7.35 (m, 2H), 6.79 (s, 2H), 3.32 (s, 1H), 3.20-3.14 (m, 1H), 3.10-3.01 (m, 2H), 2.92-2.85 (m, 1H), 2.58 (s, 3H), 2.37 (s, 3H), 2.03-1.88 (m, 4H).

Example 35

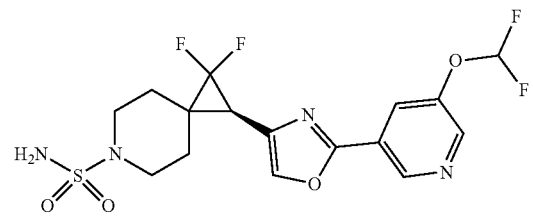 [SMILES: NS(=O)(=O)N1CCC2(CC1)[C@H](c1coc(-c3cncc(OC(F)F)c3)n1)C2(F)F]

(2R)-2-{2-[2-(Difluoromethoxy)pyridin-4-yl]-1,3-oxazol-4-yl}-1,1-difluoro-6-azaspiro[2.5]octane-6-sulfonamide Essentially following the procedures described in Example 24, but using 2-(difluoromethoxy)pyridine-4-carboxamide (Intermediate 29) in place of 4-fluoro-2-(trifluoromethyl)benzamide, the title compound was obtained. MS: m/z=437.2 [M+H]. $^1$H NMR (500 MHz, CDCl$_3$) δ 8.31 (d, J=5.2 Hz, 1H), 7.67 (d, J=5.3 Hz, 1H), 7.65 (s, 1H), 7.64-7.36 (t, J=74.5 Hz, 1H), 7.46 (s, 1H), 4.36 (s, 2H), 3.48-3.44 (m, 1H), 3.41-3.18 (m, 2H), 3.14-3.09 (m, 1H), 2.50 (d, J=13.6 Hz, 1H), 2.04-1.92 (m, 2H), 1.78-1.73 (m, 1H) 1.67-1.60 (m, 1H).

Example 36

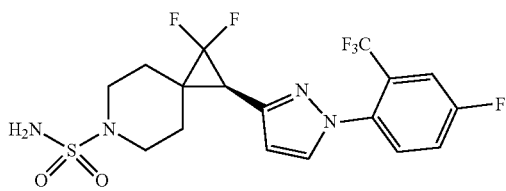 [SMILES: NS(=O)(=O)N1CCC2(CC1)[C@H](c1ccn(-c3ccc(F)cc3C(F)(F)F)n1)C2(F)F]

1,1-Difluoro-2-{1-[4-fluoro-2-(trifluoromethyl)phenyl]-1H-pyrazol-3-yl}-6-azaspiro[2.5]octane-6-sulfonamide To a solution of 1,1-difluoro-2-{1-[4-fluoro-2-(trifluoromethyl)phenyl]-1H-pyrazol-3-yl}-6-azaspiro[2.5]octane hydrochloride (Intermediate 31) (23.7 mg, 0.0576 mmol) in 1,4-dioxane (2 mL) were added sulfamide (24.3 mg, 0.253 mmol) and triethylamine (0.04 mL, 0.25 mmol) and the reaction mixture was warmed to 100° C. and allowed to stir for 12 h. The reaction mixture was cooled to ambient temperature and water (5 mL) was added. The resulting mixture was extracted with ethyl acetate (2×5 mL), dried (sodium sulfate), filtered, and the filtrate was concentrated under reduced pressure. The residue was purified by preparative HPLC, eluting with a gradient of acetonitrile:water:ammonium hydroxide—36:64:0.1 to 66:34:0.1, to afford the title compound. MS: m/z=454.9 [M+H]. $^1$H NMR (400 MHz, CD$_3$OD) δ 7.80 (s, 1H), 7.67-7.70 (m, 1H), 7.59-7.60 (m, 2H), 6.43 (s, 1H), 3.34-3.35 (m, 1H), 3.00-3.31 (m, 3H), 2.63-2.66 (m, 1H), 1.93-1.96 (m, 2H), 1.75-1.79 (m, 2H).

Example 37

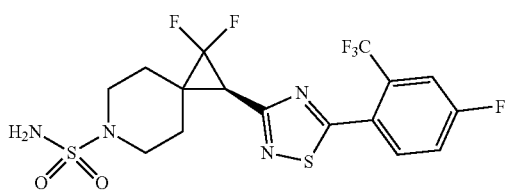 [SMILES: NS(=O)(=O)N1CCC2(CC1)[C@H](c1nsc(-c3ccc(F)cc3C(F)(F)F)n1)C2(F)F]

1,1-Difluoro-2-{5-[4-fluoro-2-(trifluoromethyl)phenyl]-1,2,4-thiadiazol-3-yl}-6-azaspiro[2.5]octane-6-sulfonamide To a solution of 1,1-difluoro-2-{5-[4-fluoro-2-(trifluoromethyl)phenyl]-1,2,4-thiadiazol-3-yl}-6-azaspiro[2.5]octane hydrochloride (Intermediate 35) (61 mg, 0.14 mmol) in 1,4-dioxane (2 mL) were added triethylamine (43.1 mg, 0.43 mmol) and sulfamide (68.2 mg, 0.71 mmol) and the reaction mixture was warmed to 95° C. and allowed to stir for 12 h. The reaction mixture was cooled to ambient temperature and diluted with water (5 mL). The resulting mixture was extracted with ethyl acetate (3×5 mL). The combined organic extracts were dried (sodium sulfate), filtered, and the filtrated was concentrated under reduced pressure. The residue was purified by silica gel chromatography, eluting with petroleum ether:ethyl acetate—50:50, to afford the title compound. MS: m/z=472.8 [M+H]. $^1$H NMR (400 MHz, CDCl$_3$): δ 7.71 (dd, J$_1$=8.4 Hz, J$_2$=5.6 Hz, 1H), 7.58 (dd, J$_1$=8.8 Hz, J$_2$=2.0 Hz, 1H), 7.40-7.57 (m, 1H), 4.43 (br, 2H), 3.39-3.42 (m, 1H), 3.29-3.31 (m, 1H), 3.15-3.18 (m, 2H), 2.99 (d, J=12.8 Hz, 1H), 2.13-2.19 (m, 2H), 1.99-2.01 (m, 2H).

The examples appearing in the following tables were prepared by analogy to the above examples, as described or prepared as a result of similar transformations with modifications known to those skilled in the art. The requisite starting materials were described herein, commercially available, known in the literature, or readily synthesized by one skilled in the art. Straightforward protecting group strategies were applied in some routes.

TABLE EX-A

| Example | X | R$^1$ | R$^2$ | R$^3$ | R$^4$ | R$^5$ | MS [M + H] |
|---|---|---|---|---|---|---|---|
| A1 | H | OMe | H | H | Cl | H | 399.1 |
| A2 | F | H | H | H | H | H | 371.1 |
| A3 | F | CF$_3$ | H | F | H | H | 457.1 |
| A4 | H | CF$_3$ | H | H | F | H | 421.1 |
| A5 | H | H | OCHF$_2$ | H | H | H | 401.2 |
| A6 | H | H | F | H | H | H | 389.2 |
| A7 | H | F | H | F | H | H | 407.2 |
| A8 | H | H | H | CMe$_2$OH | H | H | 429.2 |

TABLE EX-B

| Example | R | Stereochemistry Comment | MS [M + H] |
|---|---|---|---|
| B1 | (pyridin-2-ylmethylsulfonyl) | Racemic | 475.2 |

TABLE EX-B-continued

[Structure: piperidine-spiro-cyclopropane-oxadiazole-(2-methoxy-5-chlorophenyl) with R on N]

| Example | R | Stereochemistry Comment | MS [M + H] |
|---|---|---|---|
| B2 | thiophene-3-sulfonyl | Racemic | 466.2 |
| B3 | (tetrahydropyran-2-yl)methylsulfonyl | Mixture of isomers | 482.3 |
| B4 | 1-methylpyrazol-3-ylsulfonyl | Racemic | 464.2 |
| B5 | phenethylsulfonyl | Racemic | 488.3 |
| B6 | benzo[c][1,2,5]oxadiazol-4-ylsulfonyl | Racemic | 502.2 |
| B7 | benzothiazol-6-ylsulfonyl | Racemic | 517.2 |
| B8 | (3-hydroxy-2-methyl-furazan-2-ium-4-yl)sulfonyl, trifluoroacetate | Racemic | 482.2 [M] |
| B9 | tert-butylcarbamoyl | Racemic | 419.2 |
| B10 | cyclohexylcarbamoyl | Racemic | 445.3 |
| B11 | (pyridin-2-ylmethyl)sulfamoyl | Racemic | 490.2 |
| B12 | (isothiazol-5-ylmethyl)carbamoyl | Racemic | 460.2 |
| B13 | benzylcarbamoyl | Racemic | 453.3 |
| B14 | methylsulfonyl | Racemic | 398.2 |

TABLE EX-C

[Structure: H2N-SO2-piperidine-spiro-cyclopropane(X,X,Z)-oxadiazole-R]

| Example | X | Z | R | Stereochemistry Comment | MS [M + H] |
|---|---|---|---|---|---|
| C1 | H | H | 2-(methylamino)pyridin-3-yl | Racemic | 365.2 |
| C2 | H | H | 2-(pyrrolidin-1-yl)pyridin-4-yl | Racemic | 405.3 |

TABLE EX-C-continued

| Example | X | Z | R | Stereochemistry Comment | MS [M + H] |
|---|---|---|---|---|---|
| C3 | F | H | 3,5-dimethylisoxazol-4-yl | Racemic | 390.2 |
| C4 | H | H | 3-cyclopropylisoxazol-4-yl | R | 366.1 |
| C5 | F | H | 3-cyclopropyl-5-methylisoxazol-4-yl | R | 416.2 |
| C6 | F | H | cyclohexyl | R | 377.2 |
| C7 | F | H | 2-methylpyridin-3-yl | R | 386.2 |
| C8 | F | H | 2-(trifluoromethyl)pyridin-4-yl | R | 440.2 |
| C9 | F | H | 2-(difluoromethoxy)pyridin-4-yl | R | 438.1 |
| C10 | F | H | 4-methyl-1H-pyrazol-5-yl (1-cyclopropyl) | R | 415.2 |
| C11 | F | H | imidazo[1,2-a]pyridin-6-yl | R | 411.2 |
| C12 | H | H | 5-cyclopropyl-3-(trifluoromethyl)isoxazol-4-yl | R | 434.19 |
| C13 | H | H | 2-methoxy-5-chlorophenyl | Racemic | 399.1 |
| C14 | F | H | 1-cyclopropyl-1H-pyrazol-5-yl | R | 401.3 |
| C15 | F | H | 3-cyclopropyl-5-(trifluoromethyl)isoxazol-4-yl | R | 470.2 |
| C16 | F | H | 5-cyclopropyl-3-(trifluoromethyl)isoxazol-4-yl | R | 470.2 |

TABLE EX-C-continued

| Example | X | Z | R | Stereochemistry Comment | MS [M + H] |
|---|---|---|---|---|---|
| C17 | Cl | H | 2-CF₃-4-F-phenyl | Racemic | 488.8 |
| C18 | F | Me | 2,4-diMe-phenyl | Racemic | 413.0 |

TABLE EX-D

| Example | X | R$^1$ | R$^2$ | R$^3$ | R$^4$ | R$^5$ | MS [M + H] |
|---|---|---|---|---|---|---|---|
| D1 | H | H | H | CF₃ | H | H | 403.1 |
| D2 | H | OMe | H | H | Cl | H | 399.1 |
| D3 | H | H | CN | H | H | H | 360.1 |
| D4 | H | H | OCHF₂ | H | H | H | 401.1 |
| D5 | H | H | H | H | CF₃ | H | 403.1 |
| D6 | H | H | CF₃ | H | H | Br | H | 483.0 |
| D7 | H | H | CF₃ | H | Cl | H | 437.1 |
| D8 | H | H | H | H | H | H | 335.2 |
| D9 | H | H | OCHF₂ | H | CF₃ | H | 469.1 |
| D10 | H | H | OCHF₂ | H | Cl | H | 435.1 |
| D11 | H | H | H | OCHF₂ | H | H | 401.1 |
| D12 | H | H | F | H | H | H | CF₃ | 421.1 |
| D13 | H | H | H | H | OMe | H | 365.2 |
| D14 | H | H | H | H | OCHF₂ | H | 401.2 |
| D15 | H | H | F | H | F | H | 371.3 |
| D16 | H | H | CF₃ | H | F | H | 421.2 |
| D17 | H | H | CF₃ | H | H | H | 403.1 |
| D18 | H | H | OCH₂CF₃ | H | H | H | 433.1 |
| D19 | H | H | Me | H | Me | H | 363.2 |
| D20 | H | H | OCF₃ | H | H | H | 419.1 |
| D21 | H | H | OCF₃ | H | H | F | H | 437.1 |
| D22 | H | H | OCF₃ | H | H | Cl | H | 453.1 |
| D23 | H | H | H | H | CMe₂OH | H | 393.3 |
| D24 | H | H | OCHF₂ | H | F | H | 419.1 |
| D25 | H | H | Me | H | Me | Me | H | 377.2 |
| D26 | F | cPr | H | H | H | H | 411.3 |
| D27 | H | H | OMe | H | Cl | H | 383.2 |

TABLE EX-E

| Example | X | R | Stereochemistry Comment | MS [M + H] |
|---|---|---|---|---|
| E1 | H | 3-Me-1-cyclopropyl-indol-5-yl | R | 428.2 |
| E2 | H | 2-Me-pyridin-3-yl | R | 350.2 |

TABLE EX-E-continued
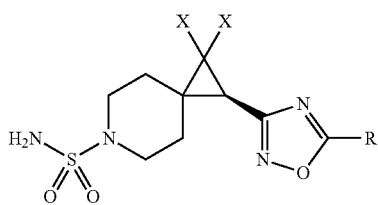
| Example | X | R | Stereochemistry Comment | MS [M + H] |
|---|---|---|---|---|
| E3 | H | (cyclobutyl-CH(Me)Me) | Mixture of isomers | 355.2 |
| E4 | H | (2-CF3, 6-F phenyl) | R | 435.1 |
| E5 | H | (2-F, 5-CF3 phenyl) | R | 435.2 |
| E6 | H | (2,6-diMe phenyl) | R | 377.2 |
| E7 | H | (3-Me cyclohexyl) | Mixture of isomers | 355.2 |
| E8 | H | (CH(Me)-2-Cl-phenyl) | Mixture of isomers | 397.1 |
| E9 | H | (2-CF3, 5-F phenyl) | R | 435.2 |

TABLE EX-E-continued

| Example | X | R | Stereochemistry Comment | MS [M + H] |
|---|---|---|---|---|
| E10 | H | (1-(2,5-difluorophenyl)cyclobutyl) | R | 425.2 |
| E11 | H | (spiro[2.5]oct-4-yl) | Mixture of isomers | 367.2 |
| E12 | H | (4-fluoro-2-(trifluoromethyl)benzyl) | R | 435.1 |
| E13 | H | (4-fluoro-2,3-dihydro-1H-inden-1-yl) | Mixture of isomers | 393.1 |
| E14 | H | (1-(3-(trifluoromethyl)phenyl)cyclopropyl) | R | 443.2 |
| E15 | H | (3-phenylcyclobutyl) | Mixture of isomers | 389.2 |
| E16 | H | (3,6-dimethylpyridin-2-yl) | R | 364.2 |
| E17 | H | (6-(trifluoromethyl)pyridin-2-yl) | R | 404.1 |

TABLE EX-E-continued
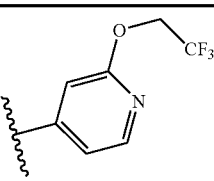
| Example | X | R | Stereochemistry | Comment | MS [M + H] |
|---|---|---|---|---|---|
| E18 | H | 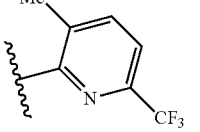 | R | | 434.2 |
| E19 | H | 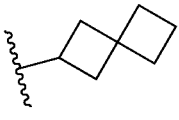 [SMILES: *C1CC2(CCC2)C1] | R | | 418.2 |
| E20 | H | 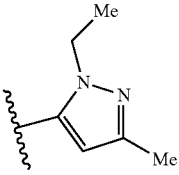 [SMILES: *c1cc(C)nn1CC] | R | | 353.2 |
| E21 | H | 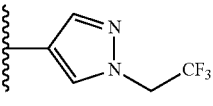 | R | | 367.3 |
| E22 | H | 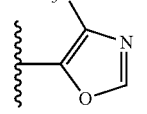 | R | | 407.2 |
| E23 | H | 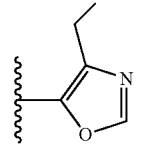 | R | | 394.1 |
| E24 | H | 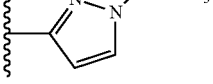 | R | | 354.2 |
| E25 | H | 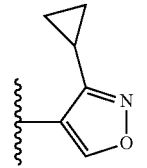 | R | | 407.2 |
| E26 | H |  | R | | 366.2 |

TABLE EX-E-continued
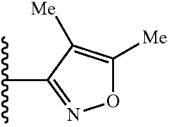 [SMILES: *c1noc(C)c1C]
| Example | X | R | Stereochemistry | Comment | MS [M + H] |
|---|---|---|---|---|---|
| E27 | H | 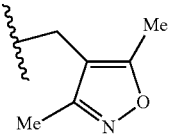 [SMILES: *Cc1c(C)noc1C] | R | | 354.2 |
| E28 | H | 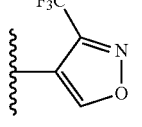 | R | | 368.2 |
| E29 | H | 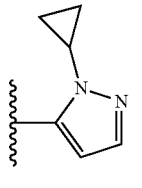 | R | | 394.1 |
| E30 | H | 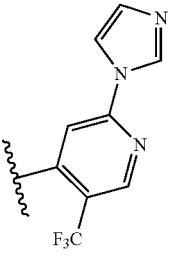 | R | | 365.2 |
| E31 | H | 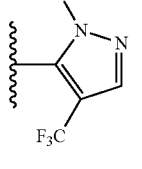 | R | | 470.2 |
| E32 | H | 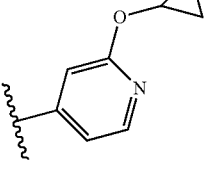 | R | | 407.2 |
| E33 | F |  | R | | 428.3 |

TABLE EX-E-continued
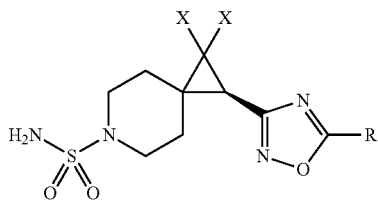
| Example | X | R | Stereochemistry | Comment | MS [M + H] |
|---|---|---|---|---|---|
| E34 | F | 1-cyclopropyl-pyrazol-5-yl | R | | 401.3 |
| E35 | F | 1-tert-butyl-pyrazol-5-yl | R | | 417.2 |
| E36 | F | 3-methyl-imidazo[1,2-a]pyridin-6-yl | R | | 425.2 |
| E37 | F | 3-cyclopropyl-1-ethyl-pyrazol-4-yl | R | | 429.2 |
| E38 | F | 1-methyl-5-(trifluoromethyl)-pyrazol-4-yl | R | | 443.2 |
| E39 | F | 1-tert-butyl-5-(trifluoromethyl)-pyrazol-4-yl | R | | 485.2 |
| E40 | F | 4,5,6,7-tetrahydropyrazolo[1,5-a]pyridin-3-yl | R | | 415.2 |

TABLE EX-E-continued
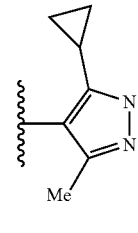
| Example | X | R | Stereochemistry | Comment | MS [M + H] |
|---|---|---|---|---|---|
| E41 | F | 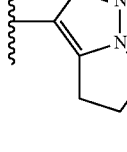 | R | | 415.2 |
| E42 | F | 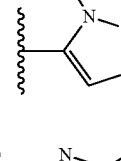 | R | | 401.3 |
| E43 | F | 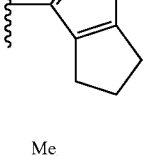 | R | | 375.2 |
| E44 | F | 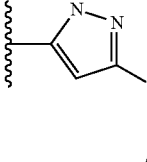 | R | | 415.3 |
| E45 | F | 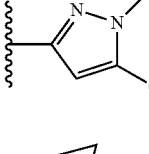 | R | | 443.2 |
| E46 | F | 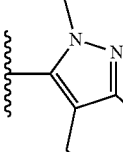 | R | | 469.2 |
| E47 | F | | R | | 455.2 |

TABLE EX-E-continued
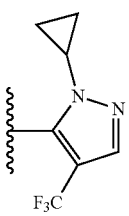
| Example | X | R | Stereochemistry Comment | MS [M + H] |
|---|---|---|---|---|
| E48 | F | 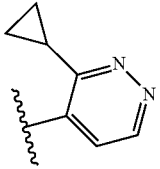 | R | 469.2 |
| E49 | F | 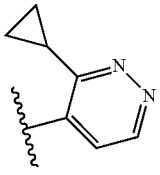 [SMILES: *c1ccnnc1C1CC1] | R | 413.2 |
| E50 | H | 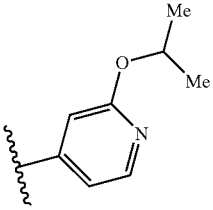 [SMILES: *c1ccnc(OC(C)C)c1] | R | 377.2 |
| E51 | F | 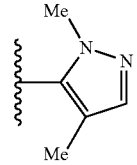 | R | 430.2 |
| E52 | H | 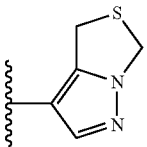 | R | 353.0 |
| E53 | F | 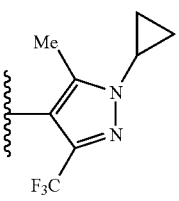 [SMILES: *c1c(C(F)(F)F)nn(C2CC2)c1C] | R | 419.1 |
| E54 | F |  | R | 483.2 |

TABLE EX-E-continued
| Example | X | R | Stereochemistry | Comment | MS [M + H] |
|---|---|---|---|---|---|
| E55 | F | 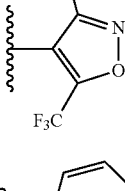 | R | | 470.2 |
| E56 | F | 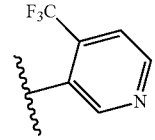 | R | | 372.2 |
| E57 | H | 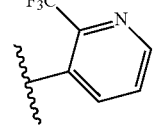 | R | | 404.1 |
| E58 | H | 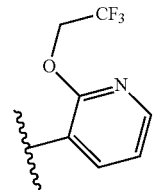 [SMILES: *c1cccnc1OCC(F)(F)F] | R | | 404.1 |
| E59 | H | 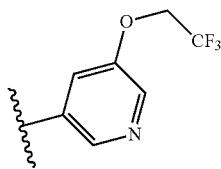 [SMILES: *c1cncc(OCC(F)(F)F)c1] | R | | 434.2 |
| E60 | H | 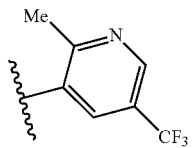 | R | | 434.2 |
| E61 | H | 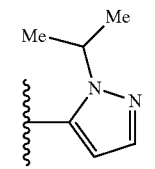 | R | | 418.2 |
| E62 | H |  | R | | 367.3 |

TABLE EX-E-continued
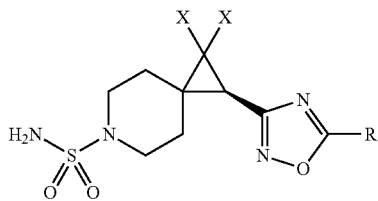
| Example | X | R | Stereochemistry Comment | MS [M + H] |
|---|---|---|---|---|
| E63 | H | 5-(2,2,2-trifluoroethoxy)pyridin-2-yl (F₃C-CH₂-O-pyridyl) | R | 434.2 |
| E64 | H | 1-cyclopropyl-4-methyl-1H-pyrazol-5-yl | R | 379.0 |
| E65 | H | 2-methyl-4,5,6,7-tetrahydro-2H-indazol-3-yl | R | 393.3 |
| E66 | F | 2-methyl-4,5,6,7-tetrahydro-2H-indazol-3-yl | R | 429.2 |
| E67 | F | pyridin-2-yl | R | 372.3 |
| E68 | F | 3-(trifluoromethyl)isoxazol-4-yl | R | 430.2 |
| E69 | H | 2,3-dihydro-1H-inden-4-yl | R | 375.2 |

TABLE EX-E-continued
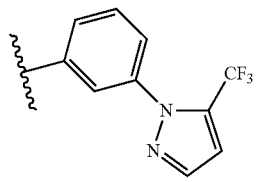 [SMILES: *c1cccc(-n2nccc2C(F)(F)F)c1]
| Example | X | R | Stereochemistry | Comment | MS [M + H] |
|---|---|---|---|---|---|
| E70 | H | 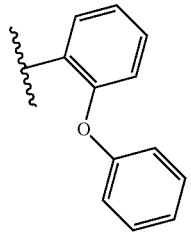 [SMILES: *c1ccccc1Oc1ccccc1] | R | | 469.1 |
| E71 | H | 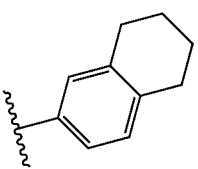 [SMILES: *c1ccc2c(c1)CCCC2] | R | | 427.1 |
| E72 | H | 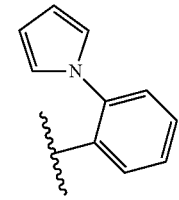 [SMILES: *c1ccccc1-n1cccc1] | R | | 389.2 |
| E73 | H | 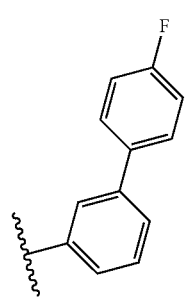 [SMILES: *c1cccc(-c2ccc(F)cc2)c1] | R | | 400.1 |
| E74 | H | 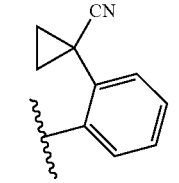 [SMILES: *c1ccccc1C1(C#N)CC1] | R | | 429.2 |
| E75 | H |  | R | | 400.1 |

TABLE EX-E-continued

| Example | X | R | Stereochemistry Comment | MS [M + H] |
|---|---|---|---|---|
| E76 | H | (2-pyrimidin-2-yl-phenyl) | R | 413.1 |
| E77 | H | (2-pyrazol-1-yl-phenyl) | R | 401.2 |
| E78 | H | (3-(2,2,2-trifluoroethoxy)pyridin-2-yl) | R | 434.2 |

TABLE EX-F

| Example | X | A | R | MS [M + H] |
|---|---|---|---|---|
| F1 | H | O | (2-CF3-4-F-phenyl) | 421.1 |
| F2 | H | O | (3-CF3-phenyl) | 403.1 |

TABLE EX-F-continued

| Example | X | A | R | MS [M + H] |
|---|---|---|---|---|
| F3 | H | O | (3-OCF3-phenyl) | 419.1 |
| F4 | H | S | (2,5-difluorophenyl) | 387.1 |

TABLE EX-F-continued

Structure: H₂N-S(O₂)-N-piperidine-spiro-cyclopropane(X,X)-A-heterocycle-R

| Example | X | A | R | MS [M + H] |
|---------|---|---|---|------------|
| F5 | H | O | 2-Me-5-F-phenyl | 367.1 |
| F6 | H | O | 2-(OCH₂CF₃)-phenyl | 433.2 |
| F7 | H | S | 2-(OCH₂CF₃)-phenyl | 449.1 |
| F8 | H | S | 2-Me-phenyl | 365.2 |
| F9 | H | S | 2-CF₃-4-F-phenyl | 437.2 |
| F10 | H | S | 3-(OCHF₂)-phenyl | 417.2 |
| F11 | H | O | 5-Me-3-cyclopropyl-isoxazol-4-yl | 380.2 |
| F12 | H | S | 5-Me-3-cyclopropyl-isoxazol-4-yl | 396.2 |
| F13 | F | O | 2-Me-phenyl | 385.1 |
| F14 | F | S | 2-Me-phenyl | 401.1 |

TABLE EX-G

Structure: H₂N-S(O₂)-N-piperidine-spiro-cyclopropane(X,X)-R

| Example | X | R | MS [M + H] |
|---------|---|---|------------|
| G1 | H | 4-phenyl-oxazol-2-yl | 334.2 |
| G2 | H | 3-cyclopropyl-isoxazol-4-yl-thiazol-4-yl | 381.0 |
| G3 | H | 1-(3,5-dimethyl-isoxazol-4-yl)-pyrazol-4-yl | 352 |

TABLE EX-G-continued
| Example | X | R | MS [M + H] |
|---|---|---|---|
| G4 | F | 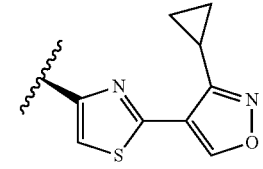 | 417.2 |
| G5 | F | 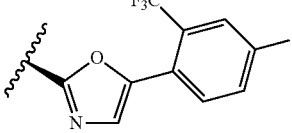 | 456.1 |
| G6 | F | 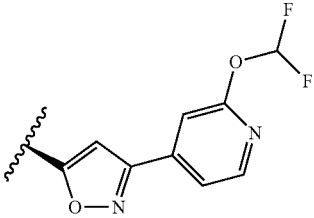 | 436.9 |
| G7 | F | 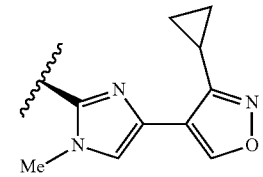 | 414.0 |
| G8 | F | 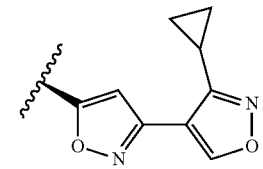 | 401.0 |
| G9 | F | 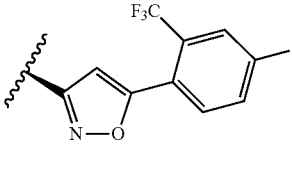 | 456.0 |
| G10 | F | 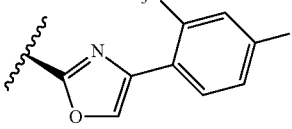 | 456.1 |
TABLE EX-G-continued
| Example | X | R | MS [M + H] |
|---|---|---|---|
| G11 | F | 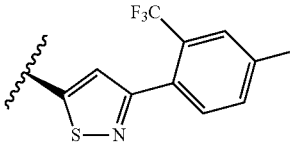 | 472.0 |
TABLE EX-H
| Example | X | R | MS [M + H] |
|---|---|---|---|
| H1 | H | 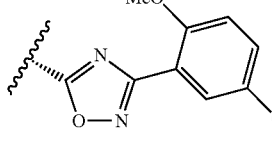 | 399.1 |
| H2 | F | 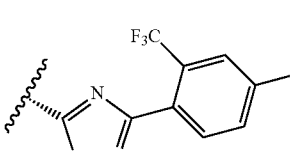 | 457.1 |
| H3 | F | 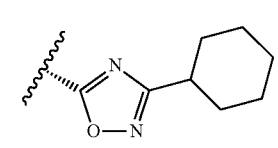 | 377.2 |
| H4 | F | 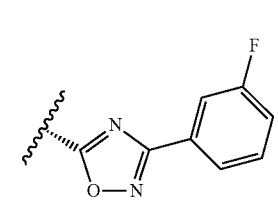 | 389.2 |

TABLE EX-H-continued

Structure: piperidine-sulfamoyl with gem-difluorocyclopropane spiro, substituent R

| Example | X | R | MS [M + H] |
|---|---|---|---|
| H5 | F | 5-(2-methylphenyl)-1,2,4-oxadiazol-3-yl (attached via oxadiazole) — Me on phenyl ortho | 385.1 |
| H6 | F | 5-(2-methylphenyl)-1,3,4-thiadiazol-2-yl | 401.1 |

TABLE EX-I

Structure: sulfamoyl piperidine spiro cyclopropane with X¹, X², Y¹, Y², R substituents

| Example | X¹ | X² | Y¹ | Y² | R | Stereochemistry Comment | MS [M + H] |
|---|---|---|---|---|---|---|---|
| I1 | H | H | F | H | 5-[3-(difluoromethoxy)phenyl]-1,2,4-oxadiazol-3-yl | Single isomer | 419.2 |
| I2 | H | H | F | H | 3-[3-(difluoromethoxy)phenyl]-1,2,4-oxadiazol-5-yl | Single isomer | 419.2 |
| I3 | H | H | F | F | 3-phenyl-1,2,4-oxadiazol-5-yl | Single isomer | 371.2 |
| I4 | H | H | F | F | 3-(2,5-dimethylphenyl)-1,2,4-oxadiazol-5-yl | Single isomer | 399.3 |

TABLE EX-I-continued

| Example | X¹ | X² | Y¹ | Y² | R | Stereochemistry Comment | MS [M + H] |
|---------|----|----|----|----|----|------------------------|-----------|
| I5 | H | H | Me | H | (F₃C-CH₂-O-pyridyl-oxadiazolyl) | Single isomer | 448.3 |
| I6 | H | H | F | H | (cyclopropyl-isoxazolyl-oxadiazolyl) | Single isomer | 384.2 |
| I7 | H | H | F | H | (cyclopropyl-isoxazolyl-oxadiazolyl) | Single isomer | 384.1 |
| I8 | H | H | F | H | (cyclopropyl-isoxazolyl-oxadiazolyl) | Single isomer | 384.1 |
| I9 | H | H | F | H | (cyclopropyl-isoxazolyl-oxadiazolyl) | Single isomer | 384.2 |
| I10 | H | H | F | H | (cyclopropyl-isoxazolyl-oxadiazolyl) | Single isomer | 384.2 |
| I11 | F | F | F | H | (cyclopropyl-isoxazolyl-oxadiazolyl) | Mixture of isomers | 420.2 |

TABLE EX-I-continued
| Example | X¹ | X² | Y¹ | Y² | R | Stereochemistry Comment | MS [M + H] |
|---|---|---|---|---|---|---|---|
| 112 | F | F | F | H | 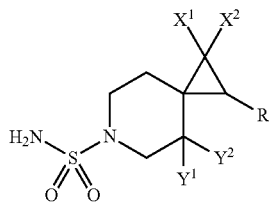 | Mixture of isomers | 420.2 |
| I13 | F | F | F | H | 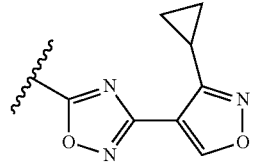 [SMILES: *c1nc(-c2conc2C2CC2)no1] | Single isomer | 420.2 |
| I14 | F | F | F | H | 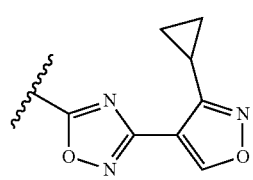 [SMILES: *c1nc(-c2conc2C2CC2)no1] | Single isomer | 420.1 |
| I15 | F | F | F | H | 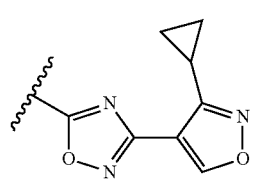 [SMILES: *c1nc(-c2conc2C2CC2)no1] | Mixture of isomers | 475.3 |
| I16 | F | F | F | H | 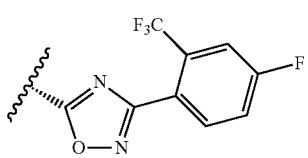 | Mixture of isomers | 475.2 |
| I17 | F | F | F | H | 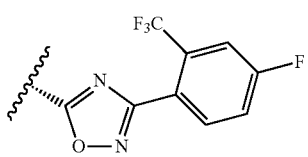 | Mixture of isomers | 475.2 |
| I18 | F | F | F | H | 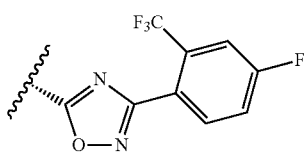 | Mixture of isomers | 475.2 |

TABLE EX-I-continued

| Example | X¹ | X² | Y¹ | Y² | R | Stereochemistry Comment | MS [M + H] |
|---|---|---|---|---|---|---|---|
| I19 | F | H | H | H | (3-(2-(trifluoromethyl)-4-fluorophenyl)-1,2,4-oxadiazol-5-yl) | Racemic | 473.0 |
| I20 | Me | H | H | H | (3-(2-(trifluoromethyl)-4-fluorophenyl)-1,2,4-oxadiazol-5-yl) | Mixture of isomers | 439.0 |
| I21 | Me | Me | H | H | (3-(2-(trifluoromethyl)-4-fluorophenyl)-1,2,4-oxadiazol-5-yl) | Single isomer | 435.0 |
| I22 | F | F | H | H | (3-(2-(trifluoromethyl)-4-fluorophenyl)-1,2,4-oxadiazol-5-yl) | Racemic | 449.2 |

TABLE EX-J

| Example | X¹ | X² | W | R | Stereochemistry Comment | MS [M + H] |
|---|---|---|---|---|---|---|
| J1 | H | H | Me-S(O)₂- | (3-(2-methoxy-5-chlorophenyl)-1,2,4-oxadiazol-5-yl) | Racemic | 398.1 |
| J2 | F | F | H₂N-S(O)₂- | (5-(piperidin-1-yl)-1,2,4-thiadiazol-3-yl) | Racemic | 394.0 |

TABLE EX-K

| Example | R | Stereochemistry Comment | MS [M + H] |
|---|---|---|---|
| K1 | (structure with H₂N-S(O)₂-N-bicyclic amine, cyclopropyl with two F) | Single isomer | 425.2 |
| K2 | (structure with Me, H₂N-S(O)₂-N-piperidine, cyclopropyl with two F) | Mixture of isomers | 413.0 |

The utility of the compounds in accordance with the present invention as positive allosteric modulators of α7 nicotinic acetylcholine receptor activity may be demonstrated by methodology known in the art. Direct activation of α7 (agonism), and potentiation of acetylcholine-evoked 7 currents was determined as follows:

Automated Patch-Clamp Electrophysiology Functional Assay (Assay A)

Automated patch-clamp electrophysiology was performed using the IonFlux HT (Fluxion Biosciences Inc., San Francisco, Calif.) in the whole-cell, population patch configuration. Test compounds were assessed for their ability to modulate the function of the α7 nicotinic acetylcholine receptor both in the presence, and in the absence of the natural α7 agonist acetylcholine. A HEK cell line stably expressing both human RIC-3 and human α7 (PrecisION hnAChR α7/RIC-3, Eurofins Pharma, St. Charles, Mo.) was cultured in 175 cm² triple-layer tissue culture flasks to no more than 90% confluency in DMEM/F-12 growth media supplemented with 10% heat-inactivated fetal bovine serum, 1% non-essential amino acids, 0.625 µg/mL Puromycin, and 400 µg/mL Geneticin. Immediately prior to assay, cells were detached by first aspirating growth media, rinsing with Dulbecco's phosphate buffered saline, and then adding 10 mL of Accutase (Innovative Cell Technologies, San Diego, Calif.) to the flask and then incubating at 37° C. for 5 minutes. Detached cells were then recovered by the addition of 40 mL of CHO-serum-free media supplemented with 25 mM HEPES, and rocked gently in a 50 mL conical tube for 20 minutes prior to patch-clamp assay. After recovery, cells were pelleted by centrifugation at 1,000 RPM for 1 minute in a compact bench top centrifuge; recovery media was aspirated and cells were resuspended in external recording solution (150 mM NaCl, 5 mM KCl, 2 mM $CaCl_2$), 1 mM $MgCl_2$, 10 mM HEPES, 12 mM dextrose) to a density of $5.0×10^6$ cells/mL. The cell suspension was added to the cell inlet wells on an IonFlux HT population patch plate which had previously been rinsed and primed with deionized $H_2O$. Test compounds were serially diluted in DMSO and then resuspended to the final test concentration in external recording solution, with, or without 40 µM acetylcholine added to the external recording solution; test compounds were then transferred to the IonFlux HT population patch plate. Internal recording solution (110 mM $TrisPO_4$, 28 mM TrisBase, 0.1 mM $CaCl_2$, 2 mM $MgCl_2$, 11 mM EGTA, 4 mM MgATP) was added to the internal recording solution inlet wells on the IonFlux HT patch plate previously loaded with cells and test compounds, and the plate loaded into the IonFlux HT instrument. A protocol was executed on the IonFlux HT to trap the cells, break into the cells, and establish the whole-cell recording configuration; cells were voltage-clamped at a holding potential of −60 mV for the duration of the experiment, all experiments were conducted at room temperature, and the IonFlux HT injection pressure was 8 psi for solution applications. Upon establishing the whole-cell configuration, external recording solution was perfused into the recording chambers for 120 seconds and then 40 µM acetylcholine was applied for 1 second and immediately washed off with external recording solution for 60 seconds. The 40 µM acetylcholine-evoked α7 current served as the current response to which subsequent test compound effects, in the presence, or in the absence of 40 µM acetylcholine would be quantified relative to. Next, test compounds were evaluated at multiple concentrations for their ability to induce, or modulate 7 current responses; three concentrations of test compound were evaluated in ascending dose fashion per recording. To assess test compound agonist activity, test compound diluted in external recording solution was applied starting from the lowest concentration of test compound being tested in the concentration series, for 58 seconds; the first 20 seconds of the 58 second compound application period coincided with a data collection sweep which was 20 seconds in duration, and collected at a rate of 5,000 samples/second. To assess test compound positive allosteric modulator activity, immediately following the 58 second test compound only application period, the same concentration of test compound, diluted in external recording solution containing 40 µM acetylcholine was applied for 1 second; in this way, the test compound and the natural receptor agonist acetylcholine were co-applied, and potentiating effects of test compound observed. The 1 second application of test compound diluted in external solution containing 40 µM acetylcholine coincided with a data collection sweep which was 20 seconds in duration, and collected at a rate of 5,000 samples/second, after which, external recording solution only was applied for 42 seconds. Following this 42 second wash with external recording solution only, the next highest concentration of the test compound in the concentration series was applied in the absence and then in the presence of acetylcholine as previously described, and data collected as previously described. After test compound agonist, and positive allosteric modulator activity were assessed at three ascending concentrations, the experiment was terminated and leak subtraction performed using the IonFlux HT data analysis software. Peak current amplitudes and the area under the curve (AUC) were both quantified for each current sweep using proprietary software and test compound effects where quantified as follows.

Test compound agonist activity was calculated as:

% Agonism=$(Y/X)×100$

Test compound potentiator activity was calculated as:

% Potentiation=$[(Z/X)×100]-100$

X=Peak current amplitude (or AUC) evoked by 40 μM acetylcholine
Y=Peak current amplitude (or AUC) evoked by test compound diluted in external recording solution
Z=Peak current amplitude (or AUC) evoked by test compound diluted in external recording solution containing 40 μM acetylcholine As such, test compounds which evoked the same current amplitude as 40 μM acetylcholine alone would exhibit a calculated % Agonism of 100%. Test compounds co-applied with 40 μM acetylcholine which evoked a current amplitude 2× the current evoked from 40 μM acetylcholine alone would exhibit a calculated % Potentiation of 100%, whereas test compounds co-applied with 40 μM acetylcholine which evoked the same current amplitude as 40 μM acetylcholine alone would be characterized as exhibiting no potentiation.

Agonist and potentiation data, derived by peak current amplitude or area under the curve (AUC) were graphed and fit using a 4-parameter logistic fit based on the Levenberg-Marquardt algorithm where $y=A+((B-A)/(1+((C/x)^D)))$ where:
A=Minimum
B=Maximum
C=$EC_{50}$
D=Slope
x=test compound concentration
y=% Agonism or % Potentiation Potency data for selected compounds of the present invention in the automated patch-clamp electrophysiology functional assay (Assay A) are represented in the table below:

| Example | α7 nAChR Potency |
|---|---|
| 1 | A |
| 2 | A |
| 3 | C |
| 4 | B |
| 5 | C |
| 6 | B |
| 7 | C |
| 8 | B |
| 9 | A |
| 10 | B |
| 11 | A |
| 12 | B |
| 13 | A |
| 14 | A |
| 15 | B |
| 16 | B |
| 17 | C |
| 18 | C |
| 19 | B |
| 20 | A |
| 21 | C |
| 22 | A |
| 23 | C |
| 24 | A |
| 25 | B |
| 26 | B |
| 27 | C |
| 28 | B |
| 29 | B |
| 30 | A |
| 31 | B |
| 32 | C |
| 33 | B |
| 34 | A |
| 35 | B |
| 36 | C |
| 37 | C |
| A1 | B |
| A2 | B |
| A3 | B |
| A4 | C |
| A5 | C |
| A6 | B |
| A7 | B |
| A8 | C |
| B1 | C |
| B2 | C |
| B3 | C |
| B4 | C |
| B5 | C |
| B6 | C |
| B7 | C |
| B8 | C |
| B9 | D |
| B10 | C |
| B11 | C |
| B12 | C |
| B13 | D |
| B14 | C |
| C1 | C |
| C2 | C |
| C3 | B |
| C4 | C |
| C5 | A |
| C6 | B |
| C7 | C |
| C8 | C |
| C9 | B |
| C10 | A |
| C11 | C |
| C12 | B |
| C13 | C |
| C14 | B |
| C15 | A |
| C16 | A |
| C17 | C |
| C18 | C |
| D1 | C |
| D2 | A |
| D3 | D |
| D4 | B |
| D5 | C |
| D6 | B |
| D7 | C |
| D8 | C |
| D9 | C |
| D10 | A |
| D11 | C |
| D12 | C |
| D13 | C |
| D14 | C |
| D15 | C |
| D16 | B |
| D17 | C |
| D18 | B |
| D19 | B |
| D20 | B |
| D21 | B |
| D22 | B |
| D23 | C |
| D24 | B |
| D25 | B |
| D26 | A |
| D27 | C |
| E1 | B |
| E2 | C |
| E3 | C |
| E4 | D |
| E5 | C |
| E6 | C |
| E7 | C |
| E8 | C |
| E9 | C |
| E10 | C |
| E11 | C |
| E12 | C |
| E13 | C |

| Example | α7 nAChR Potency |
| --- | --- |
| E14 | C |
| E15 | C |
| E16 | C |
| E17 | C |
| E18 | C |
| E19 | B |
| E20 | C |
| E21 | B |
| E22 | C |
| E23 | C |
| E24 | C |
| E25 | C |
| E26 | C |
| E27 | C |
| E28 | C |
| E29 | C |
| E30 | C |
| E31 | C |
| E32 | B |
| E33 | B |
| E34 | B |
| E35 | B |
| E36 | C |
| E37 | A |
| E38 | B |
| E39 | B |
| E40 | C |
| E41 | A |
| E42 | C |
| E43 | B |
| E44 | B |
| E45 | C |
| E46 | C |
| E47 | B |
| E48 | A |
| E49 | B |
| E50 | C |
| E51 | C |
| E52 | C |
| E53 | C |
| E54 | B |
| E55 | A |
| E56 | C |
| E57 | C |
| E58 | C |
| E59 | B |
| E60 | C |
| E61 | C |
| E62 | C |
| E63 | C |
| E64 | C |
| E65 | B |
| E66 | B |
| E67 | C |
| E68 | C |
| E69 | A |
| E70 | C |
| E71 | B |
| E72 | B |
| E73 | C |
| E74 | B |
| E75 | D |
| E76 | C |
| E77 | C |
| E78 | C |
| F1 | C |
| F2 | C |
| F3 | C |
| F4 | C |
| F5 | B |
| F6 | C |
| F7 | B |
| F8 | C |
| F9 | C |
| F10 | B |
| F11 | B |
| F12 | C |
| F13 | B |
| F14 | B |
| G1 | C |
| G2 | C |
| G3 | C |
| G4 | B |
| G5 | A |
| G6 | A |
| G7 | C |
| G8 | A |
| G9 | A |
| G10 | A |
| G11 | B |
| H1 | D |
| H2 | C |
| H3 | C |
| H4 | C |
| H5 | C |
| H6 | C |
| I1 | C |
| I2 | C |
| I3 | C |
| I4 | C |
| I5 | C |
| I6 | C |
| I7 | C |
| I8 | D |
| I9 | C |
| I10 | C |
| I11 | C |
| I12 | B |
| I13 | C |
| I14 | B |
| I15 | C |
| I16 | C |
| I17 | C |
| I18 | B |
| I19 | C |
| I20 | C |
| I21 | C |
| I22 | C |
| J1 | C |
| J2 | C |
| K1 | A |
| K2 | B |

*Potency defined as A ($EC_{50} \leq 0.1$ μM); B ($0.1$ μM $< EC_{50} \leq 0.5$ μM); C ($0.5$ μM $< EC_{50} \leq 5$ μM); D ($5$ μM $< EC_{50} \leq 50$ μM)

Electrophysiology $EC_{50}$ values for selected compounds of the present invention in the automated patch-clamp electrophysiology functional assay (Assay A) are provided in the table below:

| Example | α7 nAChR $EC_{50}$ (nM) |
| --- | --- |
| 1 | 98 |
| 2 | 82 |
| 3 | 1300 |
| 4 | 350 |
| 5 | 1200 |
| 6 | 280 |
| 7 | 1100 |
| 8 | 230 |
| 9 | 75 |
| 10 | 220 |
| 11 | 58 |
| 12 | 220 |
| 13 | 73 |
| 14 | 49 |
| 15 | 330 |
| 16 | 450 |
| 17 | 550 |
| 18 | 800 |
| 19 | 240 |
| 20 | 98 |

| Example | α7 nAChR EC$_{50}$ (nM) |
|---|---|
| 21 | 670 |
| 22 | 99 |
| 23 | 1400 |
| 24 | 90 |
| 25 | 210 |
| 26 | 480 |
| 27 | 4000 |
| 28 | 120 |
| 29 | 170 |
| 30 | 2.4 |
| 31 | 130 |
| 32 | 910 |
| 33 | 390 |
| 34 | 4.5 |
| 35 | 150 |
| 36 | 890 |
| 37 | 1200 |
| A1 | 490 |
| A2 | 320 |
| A3 | 190 |
| A4 | 850 |
| A5 | 760 |
| A6 | 140 |
| A7 | 170 |
| A8 | 1200 |
| B1 | 2300 |
| B3 | 1300 |
| B4 | 3200 |
| B5 | 3000 |
| B7 | 3300 |
| B9 | 5400 |
| B11 | 3500 |
| B12 | 3400 |
| B13 | 5100 |
| B14 | 1100 |
| C1 | 3600 |
| C3 | 400 |
| C4 | 1100 |
| C5 | 11 |
| C6 | 420 |
| C7 | 1100 |
| C8 | 1300 |
| C9 | 310 |
| C10 | 82 |
| C11 | 2500 |
| C12 | 170 |
| C14 | 150 |
| C16 | 37 |
| C17 | 2700 |
| C18 | 1600 |
| D1 | 520 |
| D2 | 59 |
| D3 | 5300 |
| D4 | 190 |
| D5 | 960 |
| D7 | 590 |
| D8 | 1300 |
| D9 | 820 |
| D10 | 88 |
| D11 | 510 |
| D12 | 1200 |
| D13 | 700 |
| D15 | 1200 |
| D16 | 160 |
| D17 | 630 |
| D18 | 160 |
| D20 | 200 |
| D21 | 240 |
| D22 | 410 |
| D23 | 1400 |
| D24 | 240 |
| D25 | 130 |
| D26 | 13 |
| E1 | 310 |
| E2 | 1100 |
| E3 | 1900 |
| E4 | 7200 |
| E6 | 930 |
| E7 | 3400 |
| E8 | 3900 |
| E10 | 3400 |
| E11 | 4300 |
| E12 | 3700 |
| E13 | 1300 |
| E14 | 2000 |
| E15 | 1500 |
| E16 | 1300 |
| E17 | 1400 |
| E18 | 1100 |
| E19 | 290 |
| E20 | 2700 |
| E21 | 400 |
| E22 | 3000 |
| E23 | 4500 |
| E24 | 3600 |
| E25 | 2200 |
| E26 | 570 |
| E27 | 1300 |
| E29 | 1600 |
| E30 | 780 |
| E31 | 4300 |
| E32 | 330 |
| E33 | 470 |
| E34 | 130 |
| E35 | 250 |
| E36 | 1100 |
| E37 | 78 |
| E38 | 270 |
| E39 | 150 |
| E40 | 840 |
| E41 | 15 |
| E42 | 1100 |
| E43 | 500 |
| E45 | 550 |
| E46 | 510 |
| E48 | 60 |
| E49 | 270 |
| E50 | 1400 |
| E51 | 530 |
| E52 | 1700 |
| E53 | 1200 |
| E54 | 500 |
| E55 | 30 |
| E56 | 2600 |
| E58 | 3400 |
| E59 | 220 |
| E60 | 2300 |
| E61 | 1500 |
| E62 | 1500 |
| E64 | 520 |
| E65 | 420 |
| E66 | 120 |
| E67 | 2100 |
| E68 | 680 |
| E70 | 2300 |
| E71 | 360 |
| E72 | 110 |
| E73 | 640 |
| E75 | 6300 |
| E76 | 3200 |
| E77 | 850 |
| E78 | 1200 |
| F1 | 1500 |
| F3 | 700 |
| F4 | 1100 |
| F5 | 420 |
| F6 | 590 |
| F7 | 480 |
| F8 | 750 |
| F9 | 750 |
| F10 | 450 |
| F11 | 410 |
| F12 | 850 |
| F13 | 400 |

-continued

| Example | α7 nAChR EC$_{50}$ (nM) |
|---|---|
| F14 | 290 |
| G1 | 4000 |
| G2 | 910 |
| G4 | 110 |
| G5 | 91 |
| G6 | 86 |
| G7 | 1600 |
| G8 | 16 |
| G9 | 78 |
| G10 | 28 |
| G11 | 120 |
| H2 | 2900 |
| H3 | 4500 |
| H4 | 1200 |
| H6 | 3400 |
| I1 | 750 |
| I2 | 1000 |
| I3 | 2300 |
| I4 | 1500 |
| I5 | 1200 |
| I6 | 840 |
| I7 | 1500 |
| I9 | 3300 |
| I10 | 3400 |
| I11 | 820 |
| I12 | 160 |
| I13 | 600 |
| I14 | 330 |
| I15 | 1400 |
| I16 | 2100 |
| I18 | 320 |
| I19 | 1100 |
| I20 | 720 |
| I21 | 1600 |
| I22 | 860 |
| J1 | 760 |
| J2 | 1000 |
| K1 | 87 |
| K2 | 430 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to been compassed by the following claims.

What is claimed is:

1. A compound having the formula I:

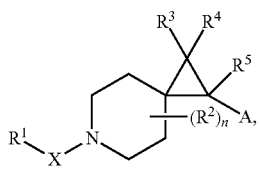

or a pharmaceutically acceptable salt thereof, wherein:
n is 0, 1 or 2;
X is S(O)$_2$;
R$^1$ is NR$^a$R$^b$;
R$^a$ is H;
R$^b$ is H;
A is a 5-membered heteroaryl ring which is substituted with 1 to 3 R groups each independently selected from OH, NR$^6$R$^7$, CN, alkoxy, halogen, aminoalkyl, hydroxyalkyl, alkyl, alkenyl, alkynyl, cycloalkyl, aryl, heteroaryl, and heterocyclyl, wherein said R groups selected from alkyl, alkenyl, alkynyl, cycloalkyl, aryl, heteroaryl, and heterocyclyl, are optionally substituted with one or more substituents independently selected from R$^{11}$;

R$^2$ is independently halogen, (C$_1$-C$_4$)alkyl, or O(C$_1$-C$_4$) alkyl, wherein said alkyl is optionally substituted with one or more halogen;

or, two R$^2$ when both are (C$_1$-C$_4$)alkyl and are attached to the same carbon atom, come together to form a cyclopropyl, cyclobutyl, or cyclopentyl ring or, two R$^2$ when both are (C$_1$-C$_4$)alkyl and are not attached to the same carbon atom, come together and form a bridged ring, wherein said cyclopropyl, cyclobutyl, cyclopentyl or bridged ring may be optionally substituted with one or more substituents independently selected from OH, halogen, or (C$_1$-C$_4$)alkyl;

R$^3$ is H, halogen or (C$_1$-C$_4$)alkyl, wherein said alkyl is optionally substituted with one or more halogen;

R$^4$ is H, halogen or (C$_1$-C$_4$)alkyl, wherein said alkyl is optionally substituted with one or more halogen;

or, R$^3$ and R$^4$ come together to form a cyclopropyl, cyclobutyl, cyclopentyl or cyclohexyl ring wherein said ring may be optionally substituted with one or more substituents independently selected from OH, halogen, or (C$_1$-C$_4$)alkyl;

R$^5$ is H or (C$_1$-C$_4$)alkyl;

R$^6$ is H or (C$_1$-C$_4$)alkyl;

R$^7$ is H or (C$_1$-C$_4$)alkyl;

R$^{11}$ is halogen, OH, oxo, CF$_3$, OCF$_3$, CN, (C$_1$-C$_6$)alkyl, O(C$_1$-C$_6$)alkyl, S(C$_1$-C$_4$)alkyl, C=O(C$_1$-C$_4$)alkyl, NR$^{12}$R$^{13}$, (C=O)NR$^6$R$^7$, (C=O)OR$^6$, (C$_2$-C$_4$)alkenyl, (C$_2$-C$_4$)alkynyl, (C$_3$-C$_6$)cycloalkyl, O(C$_3$-C$_6$)cycloalkyl, C=O(C$_3$-C$_6$)cycloalkyl, aryl, O-aryl, heteroaryl, or heterocyclyl, wherein said alkyl, cycloalkyl, aryl, heteroaryl, and heterocyclyl are optionally substituted with one or more halogen, (C$_1$-C$_4$)alkyl, (C$_3$-C$_6$)cycloalkyl, CF$_3$, OCF$_3$, OCH$_3$, CN, OH and oxo;

R$^{12}$ is (C$_1$-C$_4$)alkyl, heterocyclyl, cycloalkyl, heteroaryl, aryl, or (C=O)R$^6$, each optionally substituted with one or more substituents independently selected from halogen, (C$_1$-C$_4$)alkyl, and OH; and R$^{13}$ is (C$_1$-C$_4$)alkyl, heterocyclyl, cycloalkyl, heteroaryl, aryl, or (C=O)R$^6$, each optionally substituted with one or more substituents independently selected from halogen, (C$_1$-C$_4$)alkyl, and OH.

2. The compound according to claim 1, or a pharmaceutically acceptable salt thereof, wherein R$^2$ is independently methyl, ethyl or F.

3. The compound according to claim 2, or a pharmaceutically acceptable salt thereof, wherein A is a 5-membered heteroaryl ring which is substituted with 1 R group independently selected from OH, oxo, NR$^6$R$^7$, CN, alkoxy, halogen, aminoalkyl, hydroxyalkyl, alkyl, alkenyl, alkynyl, cycloalkyl, aryl, heteroaryl, and heterocyclyl, wherein said R group selected from alkyl, alkenyl, alkynyl, cycloalkyl, aryl, heteroaryl, and heterocyclyl, are further optionally substituted with one or more substituents independently selected from R$^{11}$.

4. The compound according to claim 3, or a pharmaceutically acceptable salt thereof, wherein R is alkyl, cycloalkyl, aryl, heteroaryl, or heterocyclyl, each optionally substituted with one or more substituents independently selected from R$^{11}$.

5. The compound according to claim 4, or a pharmaceutically acceptable salt thereof, wherein R is cyclohexyl, phenyl, pyrazolyl, pyridinyl or isoxazolyl, each optionally substituted with one or more substituents independently selected from R$^{11}$.

6. The compound according to claim 5, or a pharmaceutically acceptable salt thereof, wherein R³ and R⁴ are independently selected from H, F, and methyl.

7. The compound of claim 1, or a pharmaceutically acceptable salt thereof, having the formula (II):

(II)

wherein;
m is 0, 1, 2 or 3;
Z is independently selected from F, Cl, Br, methyl, methoxy, ethyl, ethoxy, propyl, —CH₂OH, —CH₂CH₂OH, —CF₃, —CH₂CF₃, —OCF₃, —OCHF₂, —OCH₂CF₃, and cyclopropyl;
Ring A is oxadiazolyl, oxazolyl, isoxazolyl, thiadiazolyl, isothiazolyl, thiazolyl, pyrazolyl or imidazolyl;
Ring B is cyclohexyl, phenyl, pyrazolyl, pyridinyl or isoxazolyl;
R³ is H, F or (C₁-C₄)alkyl, wherein said alkyl is optionally substituted with one or more halogen; and
R⁴ is H, F or (C₁-C₄)alkyl, wherein said alkyl is optionally substituted with one or more halogen.

8. The compound of claim 7, or a pharmaceutically acceptable salt thereof, having the formula (II) or a pharmaceutically acceptable salt thereof, wherein;
m is 0, 1 or 2;
Z is independently selected from F, Cl, Br, methyl, methoxy, ethyl, ethoxy, propyl, —CH₂OH, —CH₂CH₂OH, —CF₃, —CH₂CF₃, —OCF₃, —OCHF₂, —OCH₂CF₃, and cyclopropyl;
Ring A is oxadiazolyl, oxazolyl, isoxazolyl, or thiazolyl;
Ring B is phenyl, pyrazolyl, pyridinyl or isoxazolyl; and
R³ and R⁴ are both H, or R³ and R⁴ are both F.

9. The compound of claim 1 which is selected from the group consisting of
(1R)-1-{5-[2-Methyl-5-(trifluoromethyl)phenyl]-1,2,4-oxadiazol-3-yl}-6-azaspiro[2.5]octane-6-sulfonamide;
(1R)-1-[5-(2,5-Dimethylphenyl)-1,2,4-oxadiazol-3-yl]-6-azaspiro[2.5]octane-6-sulfonamide;
4,4-Difluoro-1-{3-[3-(2,2,2-trifluoroethoxy)phenyl]-1,2,4-oxadiazol-5-yl}-6-azaspiro[2.5]octane-6-sulfonamide, diastereomer C;
1-{3-[3-(Difluoromethoxy)phenyl]-1,2,4-oxadiazol-5-yl}-4-fluoro-6-azaspiro[2.5]octane-6-sulfonamide, diastereomer E;
(1R)-1-{3-[4-Fluoro-2-(trifluoromethyl)phenyl]-1,2,4-oxadiazol-5-yl}-6-azaspiro[2.5]octane-6-sulfonamide;
1-{3-[4-Fluoro-2-(trifluoromethyl)phenyl]-1,2,4-oxadiazol-5-yl}-4-methyl-6-azaspiro[2.5]octane-6-sulfonamide, diastereomer D;
(1R)-1-{2-[3-(Trifluoromethoxy)phenyl]-1,3-thiazol-4-yl}-6-azaspiro[2.5]octane-6-sulfonamide;
(1R)-1-{5-[4-Methyl-1-(2,2,2-trifluoroethyl)-1H-pyrazol-5-yl]-1,2,4-oxadiazol-3-yl}-6-azaspiro[2.5]octane-6-sulfonamide;
(2R)-2-[5-(1,4-Dimethyl-1H-pyrazol-5-yl)-1,2,4-oxadiazol-3-yl]-1,1-difluoro-6-azaspiro[2.5]octane-6-sulfonamide;
(2R)-2-{5-[2-(Difluoromethoxy)pyridin-4-yl]-1,2,4-oxadiazol-3-yl}-1,1-difluoro-6-azaspiro[2.5]octane-6-sulfonamide;
(2R)-2-[3-(3-Cyclopropylisoxazol-4-yl)-1,2,4-oxadiazol-5-yl]-1,1-difluoro-6-azaspiro[2.5]octane-6-sulfonamide;
(2R)-1,1-Difluoro-2-{3-[1-(2,2,2-trifluoroethyl)-1H-pyrazol-5-yl]-1,2,4-oxadiazol-5-yl}-6-azaspiro[2.5]octane-6-sulfonamide;
(2R)-2-{5-[2-(Difluoromethoxy)-5-methylpyridin-4-yl]-1,2,4-oxadiazol-3-yl}-1,1-difluoro-6-azaspiro[2.5]octane-6-sulfonamide;
(2R)-1,1-Difluoro-2-{5-[1-methyl-4-(trifluoromethyl)-1H-pyrazol-5-yl]-1,2,4-oxadiazol-3-yl}-6-azaspiro[2.5]octane-6-sulfonamide;
(1R)-1-{1-[3-(Trifluoromethoxy)phenyl]-1H-pyrazol-4-yl}-6-azaspiro[2.5]octane-6-sulfonamide;
(2R)-2-[5-(1-Cyclopropyl-1H-pyrazol-5-yl)-1,4-oxadiazol-2-yl]-1,1-difluoro-6-azaspiro[2.5]octane-6-sulfonamide;
(2S)-2-[5-(1-Cyclopropyl-1H-pyrazol-5-yl)-1,4-thiadiazol-2-yl]-1,1-difluoro-6-azaspiro[2.5]octane-6-sulfonamide;
(2R)-2-[5-(6,7-Dihydro-4H-pyrazolo[5,1-c][1,4]thiazin-3-yl)-1,2,4-oxadiazol-3-yl]-1,1-difluoro-6-azaspiro[2.5]octane-6-sulfonamide;
(2R)-1,1-Difluoro-2-{5-[1-methyl-3-(trifluoromethyl)-1H-pyrazol-4-yl]-1,2,4-oxadiazol-3-yl}-6-azaspiro[2.5]octane-6-sulfonamide;
(2R)-1,1-Difluoro-2-[5-(2-methyl-2,4,5,6-tetrahydrocyclopenta[c]pyrazol-3-yl)-1,2,4-oxadiazol-3-yl]-6-azaspiro[2.5]octane-6-sulfonamide;
(2R)-1,1-Difluoro-2-[5-(1,3,4-trimethyl-1H-pyrazol-5-yl)-1,2,4-oxadiazol-3-yl]-6-azaspiro[2.5]octane-6-sulfonamide;
(1R)-1-[4-(3-Cyclopropylisoxazol-4-yl)-1,3-oxazol-2-yl]-6-azaspiro[2.5]octane-6-sulfonamide;
(2R)-1,1-Difluoro-2-{2-[4-fluoro-2-(trifluoromethyl)phenyl]-1,3-oxazol-4-yl}-6-azaspiro[2.5]octane-6-sulfonamide;
(2R)-2-[5-(1-Cyclopropyl-4-methyl-1H-pyrazol-3-yl)-1,2,4-oxadiazol-3-yl]-1,1-difluoro-6-azaspiro[2.5]octane-6-sulfonamide;
(1R)-1-[5-(1-Ethyl-5-methyl-1H-pyrazol-3-yl)-1,2,4-oxadiazol-3-yl]-6-azaspiro[2.5]octane-6-sulfonamide;
(1R)-1-[5-(3-Cyclopropyl-5-methylisoxazol-4-yl)-1,3-oxazol-2-yl]-6-azaspiro[2.5]octane-6-sulfonamide;
(2R)-2-{5-[1-Cyclopropyl-3-(trifluoromethyl)-1H-pyrazol-5-yl]-1,2,4-oxadiazol-3-yl}-1,1-difluoro-6-azaspiro[2.5]octane-6-sulfonamide;
(2R)-2-[5-(2-Cyclopropyl-5-methylphenyl)-1,2,4-oxadiazol-3-yl]-1,1-difluoro-6-azaspiro[2.5]octane-6-sulfonamide;
(2R)-2-[2-(3-Cyclopropylisoxazol-4-yl)-1,3-oxazol-4-yl]-1,1-difluoro-6-azaspiro[2.5]octane-6-sulfonamide;
(1R)-1-[5-(2-Methylphenyl)-1,2,4-oxadiazol-3-yl]-6-azaspiro[2.5]octane-6-sulfonamide;
(2R)-2-[5-(2,5-Dimethylphenyl)-1,2,4-oxadiazol-3-yl]-1,1-difluoro-6-azaspiro[2.5]octane-6-sulfonamide;
(2R)-2-{2-[2-(Difluoromethoxy)pyridin-4-yl]-1,3-oxazol-4-yl}-1,1-difluoro-6-azaspiro[2.5]octane-6-sulfonamide;
1,1-Difluoro-2-{1-[4-fluoro-2-(trifluoromethyl)phenyl]-1H-pyrazol-3-yl}-6-azaspiro[2.5]octane-6-sulfonamide;

1,1-Difluoro-2-{5-[4-fluoro-2-(trifluoromethyl)phenyl]-1,2,4-thiadiazol-3-yl}-6-azaspiro[2.5]octane-6-sulfonamide;
(1R)-1-[3-(5-Chloro-2-methoxyphenyl)-1,2,4-oxadiazol-5-yl]-6-azaspiro[2.5]octane-6-sulfonamide;
(2R)-1,1-Difluoro-2-(3-phenyl-1,2,4-oxadiazol-5-yl)-6-azaspiro[2.5]octane-6-sulfonamide;
(2R)-1,1-Difluoro-2-{3-[4-fluoro-2-(trifluoromethyl)phenyl]-1,2,4-oxadiazol-5-yl}-6-azaspiro[2.5]octane-6-sulfonamide;
(1R)-1-{3-[5-Fluoro-2-(trifluoromethyl)phenyl]-1,2,4-oxadiazol-5-yl}-6-azaspiro[2.5]octane-6-sulfonamide;
(1R)-1-{3-[3-(Difluoromethoxy)phenyl]-1,2,4-oxadiazol-5-yl}-6-azaspiro[2.5]octane-6-sulfonamide;
(2R)-1,1-Difluoro-2-[3-(3-fluorophenyl)-1,2,4-oxadiazol-5-yl]-6-azaspiro[2.5]octane-6-sulfonamide;
(2R)-2-[3-(2,4-Difluorophenyl)-1,2,4-oxadiazol-5-yl]-1,1-difluoro-6-azaspiro[2.5]octane-6-sulfonamide;
(2R)-1,1-Difluoro-2-{3-[4-(2-hydroxypropan-2-yl)phenyl]-1,2,4-oxadiazol-5-yl}-6-azaspiro[2.5]octane-6-sulfonamide;
1-{3-[2-(Methylamino)pyridin-3-yl]-1,2,4-oxadiazol-5-yl}-6-azaspiro[2.5]octane-6-sulfonamide;
1-{3-[2-(Pyrrolidin-1-yl)pyridin-4-yl]-1,2,4-oxadiazol-5-yl}-6-azaspiro[2.5]octane-6-sulfonamide;
2-[3-(3,5-Dimethylisoxazol-4-yl)-1,2,4-oxadiazol-5-yl]-1,1-difluoro-6-azaspiro[2.5]octane-6-sulfonamide;
(1R)-1-[3-(3-Cyclopropylisoxazol-4-yl)-1,2,4-oxadiazol-5-yl]-6-azaspiro[2.5]octane-6-sulfonamide;
(2R)-2-[3-(3-Cyclopropyl-5-methylisoxazol-4-yl)-1,2,4-oxadiazol-5-yl]-1,1-difluoro-6-azaspiro[2.5]octane-6-sulfonamide;
(2R)-2-(3-Cyclohexyl-1,2,4-oxadiazol-5-yl)-1,1-difluoro-6-azaspiro[2.5]octane-6-sulfonamide;
(2R)-1,1-Difluoro-2-[3-(2-methylpyridin-3-yl)-1,2,4-oxadiazol-5-yl]-6-azaspiro[2.5]octane-6-sulfonamide;
(2R)-1,1-Difluoro-2-{3-[2-(trifluoromethyl)pyridin-4-yl]-1,2,4-oxadiazol-5-yl}-6-azaspiro[2.5]octane-6-sulfonamide;
(2R)-2-{3-[2-(Difluoromethoxy)pyridin-4-yl]-1,2,4-oxadiazol-5-yl}-1,1-difluoro-6-azaspiro[2.5]octane-6-sulfonamide;
(2R)-2-[3-(1-Cyclopropyl-4-methyl-1H-pyrazol-5-yl)-1,2,4-oxadiazol-5-yl]-1,1-difluoro-6-azaspiro[2.5]octane-6-sulfonamide;
(2R)-1,1-Difluoro-2-[3-(imidazo[1,2-a]pyridin-7-yl)-1,2,4-oxadiazol-5-yl]-6-azaspiro[2.5]octane-6-sulfonamide;
(1R)-1-{3-[5-Cyclopropyl-3-(trifluoromethyl)isoxazol-4-yl]-1,2,4-oxadiazol-5-yl}-6-azaspiro[2.5]octane-6-sulfonamide;
1-[3-(5-Chloro-2-methoxyphenyl)-1,2,4-oxadiazol-5-yl]-6-azaspiro[2.5]octane-6-sulfonamide;
(2R)-2-[3-(1-Cyclopropyl-1H-pyrazol-5-yl)-1,2,4-oxadiazol-5-yl]-1,1-difluoro-6-azaspiro[2.5]octane-6-sulfonamide;
(2R)-2-{3-[3-Cyclopropyl-5-(trifluoromethyl)isoxazol-4-yl]-1,2,4-oxadiazol-5-yl}-1,1-difluoro-6-azaspiro[2.5]octane-6-sulfonamide;
(2R)-2-{3-[5-Cyclopropyl-3-(trifluoromethyl)isoxazol-4-yl]-1,2,4-oxadiazol-5-yl}-1,1-difluoro-6-azaspiro[2.5]octane-6-sulfonamide;
1,1-Dichloro-2-{3-[4-fluoro-2-(trifluoromethyl)phenyl]-1,2,4-oxadiazol-5-yl}-6-azaspiro[2.5]octane-6-sulfonamide;
(1R)-1-{5-[3-(Trifluoromethyl)phenyl]-1,2,4-oxadiazol-3-yl}-6-azaspiro[2.5]octane-6-sulfonamide;
(1R)-1-[5-(5-Chloro-2-methoxyphenyl)-1,2,4-oxadiazol-3-yl]-6-azaspiro[2.5]octane-6-sulfonamide;
(1R)-1-[5-(2-Cyanophenyl)-1,2,4-oxadiazol-3-yl]-6-azaspiro[2.5]octane-6-sulfonamide;
(1R)-1-{5-[2-(Difluoromethoxy)phenyl]-1,2,4-oxadiazol-3-yl}-6-azaspiro[2.5]octane-6-sulfonamide;
(1R)-1-{5-[4-(Trifluoromethyl)phenyl]-1,2,4-oxadiazol-3-yl}-6-azaspiro[2.5]octane-6-sulfonamide;
(1R)-1-{5-[5-Bromo-2-(trifluoromethyl)phenyl]-1,2,4-oxadiazol-3-yl}-6-azaspiro[2.5]octane-6-sulfonamide;
(1R)-1-{5-[4-Chloro-2-(trifluoromethyl)phenyl]-1,2,4-oxadiazol-3-yl}-6-azaspiro[2.5]octane-6-sulfonamide;
(1R)-1-(5-Phenyl-1,2,4-oxadiazol-3-yl)-6-azaspiro[2.5]octane-6-sulfonamide;
(1R)-1-{5-[2-(Difluoromethoxy)-4-(trifluoromethyl)phenyl]-1,2,4-oxadiazol-3-yl}-6-azaspiro[2.5]octane-6-sulfonamide;
(1R)-1-{5-[4-Chloro-2-(difluoromethoxy)phenyl]-1,2,4-oxadiazol-3-yl}-6-azaspiro[2.5]octane-6-sulfonamide;
(1R)-1-{5-[3-(Difluoromethoxy)phenyl]-1,2,4-oxadiazol-3-yl}-6-azaspiro[2.5]octane-6-sulfonamide;
(1R)-1-{5-[2-Fluoro-6-(trifluoromethyl)phenyl]-1,2,4-oxadiazol-3-yl}-6-azaspiro[2.5]octane-6-sulfonamide;
(1R)-1-[5-(4-Methoxyphenyl)-1,2,4-oxadiazol-3-yl]-6-azaspiro[2.5]octane-6-sulfonamide;
(1R)-1-{5-[4-(Difluoromethoxy)phenyl]-1,2,4-oxadiazol-3-yl}-6-azaspiro[2.5]octane-6-sulfonamide;
(1R)-1-[5-(2,4-Difluorophenyl)-1,2,4-oxadiazol-3-yl]-6-azaspiro[2.5]octane-6-sulfonamide;
(1R)-1-{5-[4-Fluoro-2-(trifluoromethyl)phenyl]-1,2,4-oxadiazol-3-yl}-6-azaspiro[2.5]octane-6-sulfonamide;
(1R)-1-{5-[2-(Trifluoromethyl)phenyl]-1,2,4-oxadiazol-3-yl}-6-azaspiro[2.5]octane-6-sulfonamide;
(1R)-1-{5-[2-(2,2,2-Trifluoroethoxy)phenyl]-1,2,4-oxadiazol-3-yl}-6-azaspiro[2.5]octane-6-sulfonamide;
(1R)-1-[5-(2,4-Dimethylphenyl)-1,2,4-oxadiazol-3-yl]-6-azaspiro[2.5]octane-6-sulfonamide;
(1R)-1-{5-[2-(Trifluoromethoxy)phenyl]-1,2,4-oxadiazol-3-yl}-6-azaspiro[2.5]octane-6-sulfonamide;
(1R)-1-{5-[5-Fluoro-2-(trifluoromethoxy)phenyl]-1,2,4-oxadiazol-3-yl}-6-azaspiro[2.5]octane-6-sulfonamide;
(1R)-1-{5-[5-Chloro-2-(trifluoromethoxy)phenyl]-1,2,4-oxadiazol-3-yl}-6-azaspiro[2.5]octane-6-sulfonamide;
(1R)-1-{5-[4-(2-Hydroxypropan-2-yl)phenyl]-1,2,4-oxadiazol-3-yl}-6-azaspiro[2.5]octane-6-sulfonamide;
(1R)-1-{5-[2-(Difluoromethoxy)-4-fluorophenyl]-1,2,4-oxadiazol-3-yl}-6-azaspiro[2.5]octane-6-sulfonamide;
(1R)-1-[5-(2,4,5-Trimethylphenyl)-1,2,4-oxadiazol-3-yl]-6-azaspiro[2.5]octane-6-sulfonamide;
(2R)-2-[5-(2-Cyclopropylphenyl)-1,2,4-oxadiazol-3-yl]-1,1-difluoro-6-azaspiro[2.5]octane-6-sulfonamide;
(1R)-1-[5-(5-Fluoro-2-methoxyphenyl)-1,2,4-oxadiazol-3-yl]-6-azaspiro[2.5]octane-6-sulfonamide;
(1R)-1-[5-(1-Cyclopropyl-3-methyl-1H-indol-5-yl)-1,2,4-oxadiazol-3-yl]-6-azaspiro[2.5]octane-6-sulfonamide;
(1R)-1-[5-(2-Methylpyridin-3-yl)-1,2,4-oxadiazol-3-yl]-6-azaspiro[2.5]octane-6-sulfonamide;
(1R)-1-{5-[3-(Propan-2-yl)cyclobutyl]-1,2,4-oxadiazol-3-yl}-6-azaspiro[2.5]octane-6-sulfonamide;
(1R)-1-{5-[2-Fluoro-6-(trifluoromethyl)benzyl]-1,2,4-oxadiazol-3-yl}-6-azaspiro[2.5]octane-6-sulfonamide;
(1R)-1-{5-[2-Fluoro-5-(trifluoromethyl)benzyl]-1,2,4-oxadiazol-3-yl}-6-azaspiro[2.5]octane-6-sulfonamide;
(1R)-1-[5-(2,6-Dimethylbenzyl)-1,2,4-oxadiazol-3-yl]-6-azaspiro[2.5]octane-6-sulfonamide;

(1R)-1-[5-(3-Methylcyclohexyl)-1,2,4-oxadiazol-3-yl]-6-azaspiro[2.5]octane-6-sulfonamide;
(1R)-1-{5-[1-(2-Chlorophenyl)ethyl]-1,2,4-oxadiazol-3-yl}-6-azaspiro[2.5]octane-6-sulfonamide;
(1R)-1-{5-[5-Fluoro-2-(trifluoromethyl)benzyl]-1,2,4-oxadiazol-3-yl}-6-azaspiro[2.5]octane-6-sulfonamide;
(1R)-1-{5-[1-(2,5-Difluorophenyl)cyclobutyl]-1,2,4-oxadiazol-3-yl}-6-azaspiro[2.5]octane-6-sulfonamide;
(1R)-1-[5-(Spiro[2.5]oct-4-yl)-1,2,4-oxadiazol-3-yl]-6-azaspiro[2.5]octane-6-sulfonamide;
(1R)-1-{5-[4-Fluoro-2-(trifluoromethyl)benzyl]-1,2,4-oxadiazol-3-yl}-6-azaspiro[2.5]octane-6-sulfonamide;
(1R)-1-[5-(4-Fluoro-2,3-dihydro-1H-inden-1-yl)-1,2,4-oxadiazol-3-yl]-6-azaspiro[2.5]octane-6-sulfonamide;
(1R)-1-(5-{1-[3-(Trifluoromethyl)phenyl]cyclopropyl}-1,2,4-oxadiazol-3-yl)-6-azaspiro[2.5]octane-6-sulfonamide;
(1R)-1-[5-(3-Phenylcyclobutyl)-1,2,4-oxadiazol-3-yl]-6-azaspiro[2.5]octane-6-sulfonamide;
(1R)-1-[5-(3,6-Dimethylpyridin-2-yl)-1,2,4-oxadiazol-3-yl]-6-azaspiro[2.5]octane-6-sulfonamide;
(1R)-1-{5-[6-(Trifluoromethyl)pyridin-2-yl]-1,2,4-oxadiazol-3-yl}-6-azaspiro[2.5]octane-6-sulfonamide;
(1R)-1-{5-[2-(2,2,2-Trifluoroethoxy)pyridin-4-yl]-1,2,4-oxadiazol-3-yl}-6-azaspiro[2.5]octane-6-sulfonamide;
(1R)-1-{5-[3-Methyl-6-(trifluoromethyl)pyridin-2-yl]-1,2,4-oxadiazol-3-yl}-6-azaspiro[2.5]octane-6-sulfonamide;
(1R)-1-[5-(Spiro[3.3]hept-2-yl)-1,2,4-oxadiazol-3-yl]-6-azaspiro[2.5]octane-6-sulfonamide;
(1R)-1-[5-(1-Ethyl-3-methyl-1H-pyrazol-5-yl)-1,2,4-oxadiazol-3-yl]-6-azaspiro[2.5]octane-6-sulfonamide;
(1R)-1-{5-[1-(2,2,2-Trifluoroethyl)-1H-pyrazol-4-yl]-1,2,4-oxadiazol-3-yl}-6-azaspiro[2.5]octane-6-sulfonamide;
(1R)-1-{5-[4-(Trifluoromethyl)-1,3-oxazol-5-yl]-1,2,4-oxadiazol-3-yl}-6-azaspiro[2.5]octane-6-sulfonamide;
(1R)-1-[5-(4-Ethyl-1,3-oxazol-5-yl)-1,2,4-oxadiazol-3-yl]-6-azaspiro[2.5]octane-6-sulfonamide;
(1R)-1-{5-[1-(2,2,2-Trifluoroethyl)-1H-pyrazol-3-yl]-1,2,4-oxadiazol-3-yl}-6-azaspiro[2.5]octane-6-sulfonamide;
(1R)-1-[5-(3-Cyclopropylisoxazol-4-yl)-1,2,4-oxadiazol-3-yl]-6-azaspiro[2.5]octane-6-sulfonamide;
(1R)-1-[5-(4,5-Dimethylisoxazol-3-yl)-1,2,4-oxadiazol-3-yl]-6-azaspiro[2.5]octane-6-sulfonamide;
(1R)-1-{5-[(3,5-Dimethylisoxazol-4-yl)methyl]-1,2,4-oxadiazol-3-yl}-6-azaspiro[2.5]octane-6-sulfonamide;
(1R)-1-{5-[3-(Trifluoromethyl)isoxazol-4-yl]-1,2,4-oxadiazol-3-yl}-6-azaspiro[2.5]octane-6-sulfonamide;
(1R)-1-[5-(1-Cyclopropyl-1H-pyrazol-5-yl)-1,2,4-oxadiazol-3-yl]-6-azaspiro[2.5]octane-6-sulfonamide;
(1R)-1-{5-[2-(1H-Imidazol-1-yl)-5-(trifluoromethyl)pyridin-4-yl]-1,2,4-oxadiazol-3-yl}-6-azaspiro[2.5]octane-6-sulfonamide;
(1R)-1-{5-[1-Methyl-4-(trifluoromethyl)-1H-pyrazol-5-yl]-1,2,4-oxadiazol-3-yl}-6-azaspiro[2.5]octane-6-sulfonamide;
(2R)-2-{5-[2-(Cyclopropyloxy)pyridin-4-yl]-1,2,4-oxadiazol-3-yl}-1,1-difluoro-6-azaspiro[2.5]octane-6-sulfonamide;
(2R)-2-[5-(1-Cyclopropyl-1H-pyrazol-3-yl)-1,2,4-oxadiazol-3-yl]-1,1-difluoro-6-azaspiro[2.5]octane-6-sulfonamide;
(2R)-2-[5-(1-tert-Butyl-1H-pyrazol-5-yl)-1,2,4-oxadiazol-3-yl]-1,1-difluoro-6-azaspiro[2.5]octane-6-sulfonamide;
(2R)-1,1-Difluoro-2-[5-(3-methylimidazo[1,2-a]pyridin-7-yl)-1,2,4-oxadiazol-3-yl]-6-azaspiro[2.5]octane-6-sulfonamide;
(2R)-2-[5-(3-Cyclopropyl-1-ethyl-1H-pyrazol-4-yl)-1,2,4-oxadiazol-3-yl]-1,1-difluoro-6-azaspiro[2.5]octane-6-sulfonamide;
(2R)-1,1-Difluoro-2-{5-[1-methyl-5-(trifluoromethyl)-1H-pyrazol-4-yl]-1,2,4-oxadiazol-3-yl}-6-azaspiro[2.5]octane-6-sulfonamide;
(2R)-2-{5-[1-tert-Butyl-5-(trifluoromethyl)-1H-pyrazol-4-yl]-1,2,4-oxadiazol-3-yl}-1,1-difluoro-6-azaspiro[2.5]octane-6-sulfonamide;
(2R)-1,1-Difluoro-2-[5-(4,5,6,7-tetrahydropyrazolo[1,5-a]pyridin-3-yl)-1,2,4-oxadiazol-3-yl]-6-azaspiro[2.5]octane-6-sulfonamide;
(2R)-2-[5-(1-Cyclopropyl-4-methyl-1H-pyrazol-5-yl)-1,2,4-oxadiazol-3-yl]-1,1-difluoro-6-azaspiro[2.5]octane-6-sulfonamide;
(2R)-2-[5-(5,6-Dihydro-4H-pyrrolo[1,2-b]pyrazol-3-yl)-1,2,4-oxadiazol-3-yl]-1,1-difluoro-6-azaspiro[2.5]octane-6-sulfonamide;
(2R)-1,1-Difluoro-2-[5-(1-methyl-1H-pyrazol-5-yl)-1,2,4-oxadiazol-3-yl]-6-azaspiro[2.5]octane-6-sulfonamide;
(2R)-1,1-Difluoro-2-[5-(1-methyl-1,4,5,6-tetrahydrocyclopenta[c]pyrazol-3-yl)-1,2,4-oxadiazol-3-yl]-6-azaspiro[2.5]octane-6-sulfonamide;
(2R)-1,1-Difluoro-2-{5-[1-methyl-3-(trifluoromethyl)-1H-pyrazol-5-yl]-1,2,4-oxadiazol-3-yl}-6-azaspiro[2.5]octane-6-sulfonamide;
(2R)-2-{5-[1-Cyclopropyl-5-(trifluoromethyl)-1H-pyrazol-3-yl]-1,2,4-oxadiazol-3-yl}-1,1-difluoro-6-azaspiro[2.5]octane-6-sulfonamide;
(2R)-2-[5-(2-Cyclopropyl-4,5,6,7-tetrahydro-2H-indazol-3-yl)-1,2,4-oxadiazol-3-yl]-1,1-difluoro-6-azaspiro[2.5]octane-6-sulfonamide;
(2R)-2-{5-[1-Cyclopropyl-4-(trifluoromethyl)-1H-pyrazol-5-yl]-1,2,4-oxadiazol-3-yl}-1,1-difluoro-6-azaspiro[2.5]octane-6-sulfonamide;
(2R)-2-[5-(3-Cyclopropylpyridazin-4-yl)-1,2,4-oxadiazol-3-yl]-1,1-difluoro-6-azaspiro[2.5]octane-6-sulfonamide;
(1R)-1-[5-(3-Cyclopropylpyridazin-4-yl)-1,2,4-oxadiazol-3-yl]-6-azaspiro[2.5]octane-6-sulfonamide;
(2R)-1,1-Difluoro-2-{5-[2-(propan-2-yloxy)pyridin-4-yl]-1,2,4-oxadiazol-3-yl}-6-azaspiro[2.5]octane-6-sulfonamide;
(1R)-1-[5-(1,4-Dimethyl-1H-pyrazol-5-yl)-1,2,4-oxadiazol-3-yl]-6-azaspiro[2.5]octane-6-sulfonamide;
(2R)-1,1-Difluoro-2-[5-(4H-pyrazolo[1,5-c][1,3]thiazol-3-yl)-1,2,4-oxadiazol-3-yl]-6-azaspiro[2.5]octane-6-sulfonamide;
(2R)-2-{5-[1-Cyclopropyl-5-methyl-3-(trifluoromethyl)-1H-pyrazol-4-yl]-1,2,4-oxadiazol-3-yl}-1,1-difluoro-6-azaspiro[2.5]octane-6-sulfonamide;
(2R)-2-{5-[3-Cyclopropyl-5-(trifluoromethyl)isoxazol-4-yl]-1,2,4-oxadiazol-3-yl}-1,1-difluoro-6-azaspiro[2.5]octane-6-sulfonamide;
(2R)-1,1-Difluoro-2-[5-(pyridin-3-yl)-1,2,4-oxadiazol-3-yl]-6-azaspiro[2.5]octane-6-sulfonamide;
(1R)-1-{5-[4-(Trifluoromethyl)pyridin-3-yl]-1,2,4-oxadiazol-3-yl}-6-azaspiro[2.5]octane-6-sulfonamide;
(1R)-1-{5-[2-(Trifluoromethyl)pyridin-3-yl]-1,2,4-oxadiazol-3-yl}-6-azaspiro[2.5]octane-6-sulfonamide;
(1R)-1-{5-[2-(2,2,2-Trifluoroethoxy)pyridin-3-yl]-1,2,4-oxadiazol-3-yl}-6-azaspiro[2.5]octane-6-sulfonamide;

(1R)-1-{5-[5-(2,2,2-Trifluoroethoxy)pyridin-3-yl]-1,2,4-oxadiazol-3-yl}-6-azaspiro[2.5]octane-6-sulfonamide;
(1R)-1-{5-[2-Methyl-5-(trifluoromethyl)pyridin-3-yl]-1,2,4-oxadiazol-3-yl}-6-azaspiro[2.5]octane-6-sulfonamide;
(1R)-1-{5-[1-(Propan-2-yl)-1H-pyrazol-5-yl]-1,2,4-oxadiazol-3-yl}-6-azaspiro[2.5]octane-6-sulfonamide;
(1R)-1-{5-[6-(2,2,2-Trifluoroethoxy)pyridin-3-yl]-1,2,4-oxadiazol-3-yl}-6-azaspiro[2.5]octane-6-sulfonamide;
(1R)-1-[5-(1-Cyclopropyl-4-methyl-1H-pyrazol-5-yl)-1,2,4-oxadiazol-3-yl]-6-azaspiro[2.5]octane-6-sulfonamide;
(1R)-1-[5-(2-Methyl-4,5,6,7-tetrahydro-2H-indazol-3-yl)-1,2,4-oxadiazol-3-yl]-6-azaspiro[2.5]octane-6-sulfonamide;
(2R)-1,1-Difluoro-2-[5-(2-methyl-4,5,6,7-tetrahydro-2H-indazol-3-yl)-1,2,4-oxadiazol-3-yl]-6-azaspiro[2.5]octane-6-sulfonamide;
(2R)-1,1-Difluoro-2-[5-(pyridin-2-yl)-1,2,4-oxadiazol-3-yl]-6-azaspiro[2.5]octane-6-sulfonamide;
(2R)-1,1-Difluoro-2-{5-[3-(trifluoromethyl)isoxazol-4-yl]-1,2,4-oxadiazol-3-yl}-6-azaspiro[2.5]octane-6-sulfonamide;
(1R)-1-[5-(2,3-Dihydro-1H-inden-4-yl)-1,2,4-oxadiazol-3-yl]-6-azaspiro[2.5]octane-6-sulfonamide;
(1R)-1-(5-{3-[5-(Trifluoromethyl)-1H-pyrazol-1-yl]phenyl}-1,2,4-oxadiazol-3-yl)-6-azaspiro[2.5]octane-6-sulfonamide;
(1R)-1-[5-(2-Phenoxyphenyl)-1,2,4-oxadiazol-3-yl]-6-azaspiro[2.5]octane-6-sulfonamide;
(1R)-1-[5-(5,6,7,8-Tetrahydronaphthalen-2-yl)-1,2,4-oxadiazol-3-yl]-6-azaspiro[2.5]octane-6-sulfonamide;
(1R)-1-{5-[2-(1H-Pyrrol-1-yl)phenyl]-1,2,4-oxadiazol-3-yl}-6-azaspiro[2.5]octane-6-sulfonamide;
(1R)-1-[5-(4'-Fluorobiphenyl-3-yl)-1,2,4-oxadiazol-3-yl]-6-azaspiro[2.5]octane-6-sulfonamide;
(1R)-1-{5-[2-(1-Cyanocyclopropyl)phenyl]-1,2,4-oxadiazol-3-yl}-6-azaspiro[2.5]octane-6-sulfonamide;
(1R)-1-{5-[2-(Pyrimidin-2-yl)phenyl]-1,2,4-oxadiazol-3-yl}-6-azaspiro[2.5]octane-6-sulfonamide;
(1R)-1-{5-[2-(1H-Pyrazol-1-yl)phenyl]-1,2,4-oxadiazol-3-yl}-6-azaspiro[2.5]octane-6-sulfonamide;
(1R)-1-{5-[3-(2,2,2-Trifluoroethoxy)pyridin-2-yl]-1,2,4-oxadiazol-3-yl}-6-azaspiro[2.5]octane-6-sulfonamide;
(1R)-1-{5-[4-Fluoro-2-(trifluoromethyl)phenyl]-1,3,4-oxadiazol-2-yl}-6-azaspiro[2.5]octane-6-sulfonamide;
(1R)-1-{5-[3-(Trifluoromethyl)phenyl]-1,3,4-oxadiazol-2-yl}-6-azaspiro[2.5]octane-6-sulfonamide;
(1R)-1-{5-[3-(Trifluoromethoxy)phenyl]-1,3,4-oxadiazol-2-yl}-6-azaspiro[2.5]octane-6-sulfonamide;
(1R)-1-[5-(2,5-Difluorophenyl)-1,3,4-thiadiazol-2-yl]-6-azaspiro[2.5]octane-6-sulfonamide;
(1R)-1-[5-(5-Fluoro-2-methylphenyl)-1,3,4-oxadiazol-2-yl]-6-azaspiro[2.5]octane-6-sulfonamide;
(1R)-1-{5-[2-(2,2,2-Trifluoroethoxy)phenyl]-1,3,4-oxadiazol-2-yl}-6-azaspiro[2.5]octane-6-sulfonamide;
(1R)-1-{5-[2-(2,2,2-Trifluoroethoxy)phenyl]-1,3,4-thiadiazol-2-yl}-6-azaspiro[2.5]octane-6-sulfonamide;
(1R)-1-[5-(2-Methylphenyl)-1,3,4-thiadiazol-2-yl]-6-azaspiro[2.5]octane-6-sulfonamide;
(1R)-1-{5-[4-Fluoro-2-(trifluoromethyl)phenyl]-1,3,4-thiadiazol-2-yl}-6-azaspiro[2.5]octane-6-sulfonamide;
(1R)-1-{5-[3-(Difluoromethoxy)phenyl]-1,3,4-thiadiazol-2-yl}-6-azaspiro[2.5]octane-6-sulfonamide;
(1R)-1-[5-(3-Cyclopropyl-5-methylisoxazol-4-yl)-1,3,4-oxadiazol-2-yl]-6-azaspiro[2.5]octane-6-sulfonamide;
(1R)-1-[5-(3-Cyclopropyl-5-methylisoxazol-4-yl)-1,3,4-thiadiazol-2-yl]-6-azaspiro[2.5]octane-6-sulfonamide;
(2R)-1,1-Difluoro-2-[5-(2-methylphenyl)-1,3,4-oxadiazol-2-yl]-6-azaspiro[2.5]octane-6-sulfonamide;
(2R)-1,1-Difluoro-2-[5-(2-methylphenyl)-1,3,4-thiadiazol-2-yl]-6-azaspiro[2.5]octane-6-sulfonamide;
(1R)-1-(4-Phenyl-1,3-oxazol-2-yl)-6-azaspiro[2.5]octane-6-sulfonamide;
(1R)-1-[2-(3-Cyclopropylisoxazol-4-yl)-1,3-thiazol-4-yl]-6-azaspiro[2.5]octane-6-sulfonamide;
(1R)-1-[1-(3,5-Dimethylisoxazol-4-yl)-1H-pyrazol-4-yl]-6-azaspiro[2.5]octane-6-sulfonamide;
(2R)-2-[2-(3-Cyclopropylisoxazol-4-yl)-1,3-thiazol-4-yl]-1,1-difluoro-6-azaspiro[2.5]octane-6-sulfonamide;
(2R)-2-{3-[2-(Difluoromethoxy)pyridin-4-yl]isoxazol-5-yl}-1,1-difluoro-6-azaspiro[2.5]octane-6-sulfonamide;
(2R)-2-[4-(3-Cyclopropylisoxazol-4-yl)-1-methyl-1H-imidazol-2-yl]-1,1-difluoro-6-azaspiro[2.5]octane-6-sulfonamide;
(2R)-2-(3'-Cyclopropyl-3,4'-biisoxazol-5-yl)-1,1-difluoro-6-azaspiro[2.5]octane-6-sulfonamide;
(2R)-1,1-Difluoro-2-{4-[4-fluoro-2-(trifluoromethyl)phenyl]-1,3-oxazol-2-yl}-6-azaspiro[2.5]octane-6-sulfonamide;
(1S)-1-[3-(5-Chloro-2-methoxyphenyl)-1,2,4-oxadiazol-5-yl]-6-azaspiro[2.5]octane-6-sulfonamide;
(2S)-1,1-Difluoro-2-{3-[4-fluoro-2-(trifluoromethyl)phenyl]-1,2,4-oxadiazol-5-yl}-6-azaspiro[2.5]octane-6-sulfonamide;
(2S)-2-(3-Cyclohexyl-1,2,4-oxadiazol-5-yl)-1,1-difluoro-6-azaspiro[2.5]octane-6-sulfonamide;
(2S)-1,1-Difluoro-2-[3-(3-fluorophenyl)-1,2,4-oxadiazol-5-yl]-6-azaspiro[2.5]octane-6-sulfonamide;
(2S)-1,1-Difluoro-2-[5-(2-methylphenyl)-1,3,4-oxadiazol-2-yl]-6-azaspiro[2.5]octane-6-sulfonamide;
(2R)-1,1-Difluoro-2-[5-(2-methylphenyl)-1,3,4-thiadiazol-2-yl]-6-azaspiro[2.5]octane-6-sulfonamide;
1-{3-[3-(Difluoromethoxy)phenyl]-1,2,4-oxadiazol-5-yl}-4-fluoro-6-azaspiro[2.5]octane-6-sulfonamide;
1-{3-[3-(Difluoromethoxy)phenyl]-1,2,4-oxadiazol-5-yl}-4-fluoro-6-azaspiro[2.5]octane-6-sulfonamide;
4,4-Difluoro-1-(3-phenyl-1,2,4-oxadiazol-5-yl)-6-azaspiro[2.5]octane-6-sulfonamide;
1-[3-(2,5-Dimethylphenyl)-1,2,4-oxadiazol-5-yl]-4,4-difluoro-6-azaspiro[2.5]octane-6-sulfonamide;
4-Methyl-1-{3-[2-(2,2,2-trifluoroethoxy)pyridin-4-yl]-1,2,4-oxadiazol-5-yl}-6-azaspiro[2.5]octane-6-sulfonamide;
1-[3-(3-Cyclopropylisoxazol-4-yl)-1,2,4-oxadiazol-5-yl]-4-fluoro-6-azaspiro[2.5]octane-6-sulfonamide;
1-[3-(3-Cyclopropylisoxazol-4-yl)-1,2,4-oxadiazol-5-yl]-4-fluoro-6-azaspiro[2.5]octane-6-sulfonamide;
1-[3-(3-Cyclopropylisoxazol-4-yl)-1,2,4-oxadiazol-5-yl]-4-fluoro-6-azaspiro[2.5]octane-6-sulfonamide;
1-[3-(3-Cyclopropylisoxazol-4-yl)-1,2,4-oxadiazol-5-yl]-4-fluoro-6-azaspiro[2.5]octane-6-sulfonamide;
1-[3-(3-Cyclopropylisoxazol-4-yl)-1,2,4-oxadiazol-5-yl]-4-fluoro-6-azaspiro[2.5]octane-6-sulfonamide;
2-[3-(3-Cyclopropylisoxazol-4-yl)-1,2,4-oxadiazol-5-yl]-1,1,4-trifluoro-6-azaspiro[2.5]octane-6-sulfonamide;
2-[3-(3-Cyclopropylisoxazol-4-yl)-1,2,4-oxadiazol-5-yl]-1,1,4-trifluoro-6-azaspiro[2.5]octane-6-sulfonamide;
2-[3-(3-Cyclopropylisoxazol-4-yl)-1,2,4-oxadiazol-5-yl]-1,1,4-trifluoro-6-azaspiro[2.5]octane-6-sulfonamide;
2-[3-(3-Cyclopropylisoxazol-4-yl)-1,2,4-oxadiazol-5-yl]-1,1,4-trifluoro-6-azaspiro[2.5]octane-6-sulfonamide;

1,1,4-Trifluoro-2-{3-[4-fluoro-2-(trifluoromethyl)phenyl]-1,2,4-oxadiazol-5-yl}-6-azaspiro[2.5]octane-6-sulfonamide;

1,1,4-Trifluoro-2-{3-[4-fluoro-2-(trifluoromethyl)phenyl]-1,2,4-oxadiazol-5-yl}-6-azaspiro[2.5]octane-6-sulfonamide;

1,1,4-Trifluoro-2-{3-[4-fluoro-2-(trifluoromethyl)phenyl]-1,2,4-oxadiazol-5-yl}-6-azaspiro[2.5]octane-6-sulfonamide;

1,1-Difluoro-2-{3-[4-fluoro-2-(trifluoromethyl)phenyl]-1,2,4-thiadiazol-5-yl}-6-azaspiro[2.5]octane-6-sulfonamide;

1-Fluoro-2-{3-[4-fluoro-2-(trifluoromethyl)phenyl]-1,2,4-oxadiazol-5-yl}-6-azaspiro[2.5]octane-6-sulfonamide;

1-{3-[4-Fluoro-2-(trifluoromethyl)phenyl]-1,2,4-oxadiazol-5-yl}-2-methyl-6-azaspiro[2.5]octane-6-sulfonamide;

2-{3-[4-Fluoro-2-(trifluoromethyl)phenyl]-1,2,4-oxadiazol-5-yl}-1,1-dimethyl-6-azaspiro[2.5]octane-6-sulfonamide;

1,1-Difluoro-2-{5-[4-fluoro-2-(trifluoromethyl)phenyl]isothiazol-3-yl}-6-azaspiro[2.5]octane-6-sulfonamide;

1,1-Difluoro-2-[5-(piperidin-1-yl)-1,2,4-thiadiazol-3-yl]-6-azaspiro[2.5]octane-6-sulfonamide;

1,1-Difluoro-2-[5-(piperidin-1-yl)-1,2,4-thiadiazol-3-yl]-6-azaspiro[2.5]octane-6-sulfonamide;

3'-[5-(2,5-Dimethylphenyl)-1,2,4-oxadiazol-3-yl]-2',2'-difluoro-3-azaspiro[bicyclo[3.2.1]octane-8,1'-cyclopropane]-3-sulfonamide; and 2-[5-(2,5-Dimethylphenyl)-1,2,4-oxadiazol-3-yl]-1,1-difluoro-5-methyl-6-azaspiro[2.5]octane-6-sulfonamide; or a pharmaceutically acceptable salt thereof.

10. A pharmaceutical composition comprising (i) a pharmaceutically acceptable carrier and (ii) a compound of claim 1 or a pharmaceutically acceptable salt thereof.

11. The pharmaceutical composition of claim 10, further comprising a therapeutic agent selected from the group consisting of acetylcholinesterase inhibitors; NMDA receptor antagonists; antipsychotics; MAO-B inhibitors; and levodopa.

12. A method of treating a patient with cognitive impairments associated with Alzheimer's disease, Parkinson's disease, and schizophrenia, the method comprising administering to the patient the compound of claim 1 or a pharmaceutically acceptable salt thereof, in an amount effective to treat the patient.

13. A compound which is

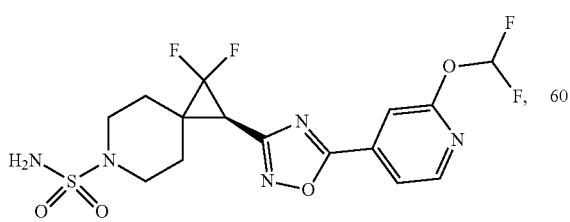

or a pharmaceutically acceptable salt thereof.

14. A compound according to claim 13 which is

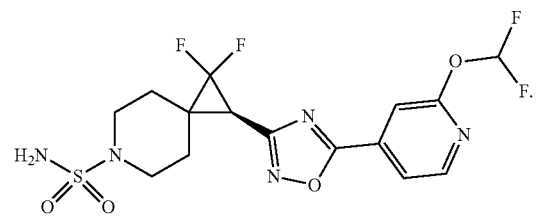 [SMILES: NS(=O)(=O)N1CCC2(CC1)[C@H](c1noc(-c3ccnc(OC(F)F)c3)n1)C2(F)F]

15. A compound according to claim 13 which is a pharmaceutically acceptable salt of

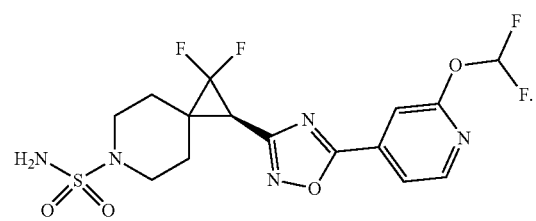 [SMILES: NS(=O)(=O)N1CCC2(CC1)[C@H](c1noc(-c3ccnc(OC(F)F)c3)n1)C2(F)F]

16. A pharmaceutical composition comprising (i) a pharmaceutically acceptable carrier and (ii) the compound of claim 14.

17. A pharmaceutical composition comprising (i) a pharmaceutically acceptable carrier and (ii) the compound of claim 15.

18. A method of treating a patient with mild to moderate dementia of the Alzheimer's type, the method comprising administering to the patient the compound of claim 14 in an amount effective to treat the patient.

19. A compound which is

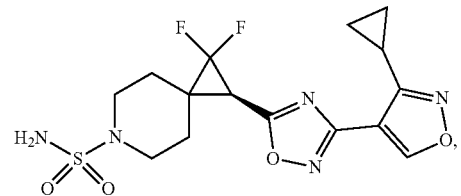 [SMILES: NS(=O)(=O)N1CCC2(CC1)[C@H](c1nc(-c3conc3C3CC3)no1)C2(F)F]

or a pharmaceutically acceptable salt thereof.

20. A compound according to claim 19 which is

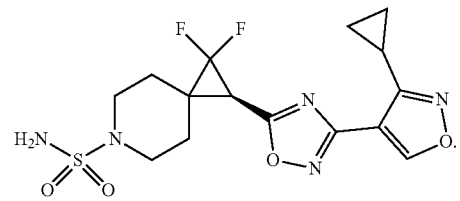

21. A compound according to claim 19 which is a pharmaceutically acceptable salt of

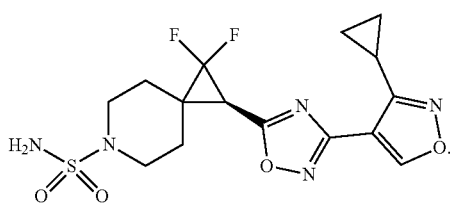 [SMILES: NS(=O)(=O)N1CCC2(CC1)[C@H](c1nc(-c3conc3C3CC3)no1)C2(F)F]

22. A pharmaceutical composition comprising (i) a pharmaceutically acceptable carrier and (ii) the compound of claim 20.

23. A pharmaceutical composition comprising (i) a pharmaceutically acceptable carrier and (ii) the compound of claim 21.

24. A method of treating a patient with mild to moderate dementia of the Alzheimer's type, the method comprising administering to the patient the compound of claim 20 in an amount effective to treat the patient.

25. A compound which is

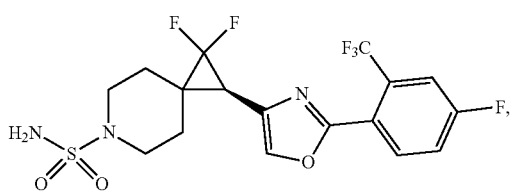 [SMILES: NS(=O)(=O)N1CCC2(CC1)[C@H](c1coc(-c3ccc(F)cc3C(F)(F)F)n1)C2(F)F]

or a pharmaceutically acceptable salt thereof.

26. A compound according to claim 25 which is

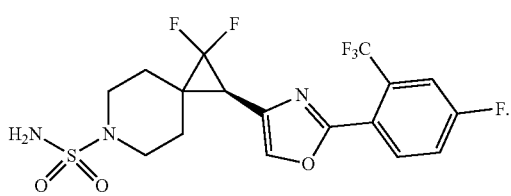 [SMILES: NS(=O)(=O)N1CCC2(CC1)[C@H](c1coc(-c3ccc(F)cc3C(F)(F)F)n1)C2(F)F]

27. A compound according to claim 25 which is a pharmaceutically acceptable salt of

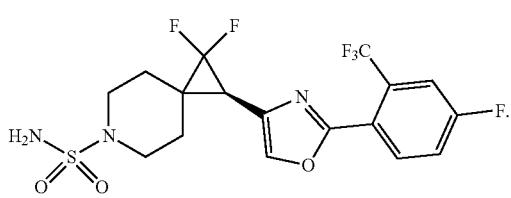 [SMILES: NS(=O)(=O)N1CCC2(CC1)[C@H](c1coc(-c3ccc(F)cc3C(F)(F)F)n1)C2(F)F]

28. A pharmaceutical composition comprising (i) a pharmaceutically acceptable carrier and (ii) the compound of claim 26.

29. A pharmaceutical composition comprising (i) a pharmaceutically acceptable carrier and (ii) the compound of claim 27.

30. A method of treating a patient with mild to moderate dementia of the Alzheimer's type, the method comprising administering to the patient the compound of claim 26 in an amount effective to treat the patient.

31. A compound which is

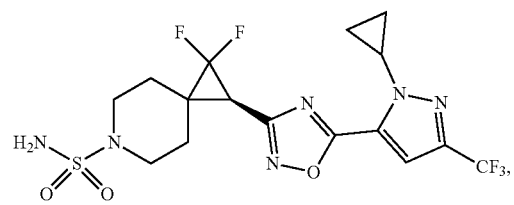 [SMILES: NS(=O)(=O)N1CCC2(CC1)[C@H](c1noc(-c3cc(C(F)(F)F)nn3C3CC3)n1)C2(F)F]

or a pharmaceutically acceptable salt thereof.

32. A compound according to claim 31 which is

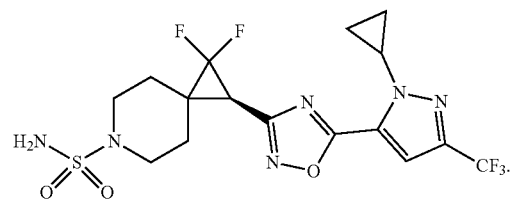 [SMILES: NS(=O)(=O)N1CCC2(CC1)[C@H](c1noc(-c3cc(C(F)(F)F)nn3C3CC3)n1)C2(F)F]

33. A compound according to claim 31 which is a pharmaceutically acceptable salt of

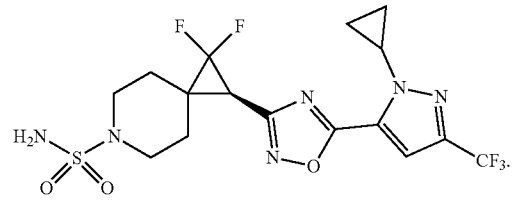 [SMILES: NS(=O)(=O)N1CCC2(CC1)[C@H](c1noc(-c3cc(C(F)(F)F)nn3C3CC3)n1)C2(F)F]

34. A pharmaceutical composition comprising (i) a pharmaceutically acceptable carrier and (ii) the compound of claim 32.

35. A pharmaceutical composition comprising (i) a pharmaceutically acceptable carrier and (ii) the compound of claim 33.

36. A method of treating a patient with mild to moderate dementia of the Alzheimer's type, the method comprising administering to the patient the compound of claim 31 in an amount effective to treat the patient.

37. A compound which is

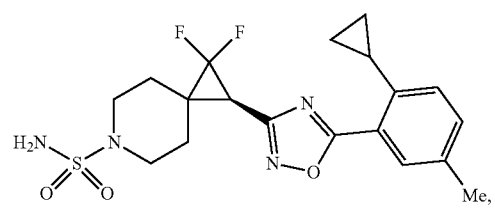 [SMILES: Cc1ccc(C2CC2)c(-c2nc([C@@H]3C(F)(F)C34CCN(S(N)(=O)=O)CC4)no2)c1]

or a pharmaceutically acceptable salt thereof.

38. A compound according to claim 37 which is

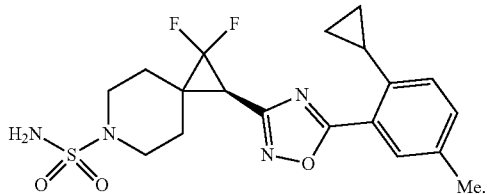 [SMILES: Cc1ccc(C2CC2)c(-c2nc([C@@H]3C(F)(F)C34CCN(S(N)(=O)=O)CC4)no2)c1]

39. A compound according to claim 37 which is a pharmaceutically acceptable salt of

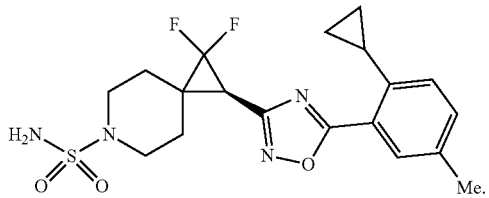 [SMILES: Cc1ccc(C2CC2)c(-c2nc([C@@H]3C(F)(F)C34CCN(S(N)(=O)=O)CC4)no2)c1]

40. A pharmaceutical composition comprising (i) a pharmaceutically acceptable carrier and (ii) the compound of claim 38.

41. A pharmaceutical composition comprising (i) a pharmaceutically acceptable carrier and (ii) the compound of claim 39.

42. A method of treating a patient with mild to moderate dementia of the Alzheimer's type, the method comprising administering to the patient the compound of claim 38 in an amount effective to treat the patient.

43. A compound which is

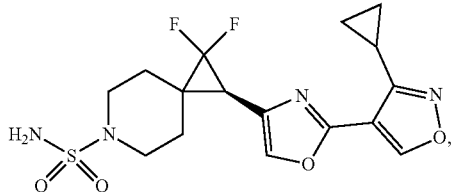 [SMILES: NS(=O)(=O)N1CCC2(CC1)[C@H](c1coc(-c3conc3C3CC3)n1)C2(F)F]

or a pharmaceutically acceptable salt thereof.

44. A compound according to claim 43 which is

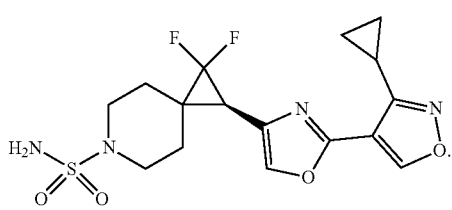 [SMILES: NS(=O)(=O)N1CCC2(CC1)[C@H](c1coc(-c3conc3C3CC3)n1)C2(F)F]

45. A compound according to claim 43 which is a pharmaceutically acceptable salt of

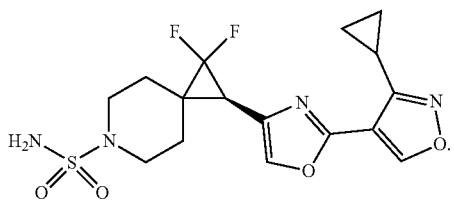 [SMILES: NS(=O)(=O)N1CCC2(CC1)[C@H](c1coc(-c3conc3C3CC3)n1)C2(F)F]

46. A pharmaceutical composition comprising (i) a pharmaceutically acceptable carrier and (ii) the compound of claim 44.

47. A pharmaceutical composition comprising (i) a pharmaceutically acceptable carrier and (ii) the compound of claim 45.

48. A method of treating a patient with mild to moderate dementia of the Alzheimer's type, the method comprising administering to the patient the compound of claim 44 in an amount effective to treat the patient.

49. A compound which is

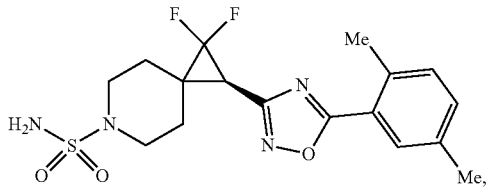 [SMILES: Cc1ccc(C)c(-c2nc([C@@H]3C(F)(F)C34CCN(S(N)(=O)=O)CC4)no2)c1]

or a pharmaceutically acceptable salt thereof.

50. A compound according to claim 49 which is

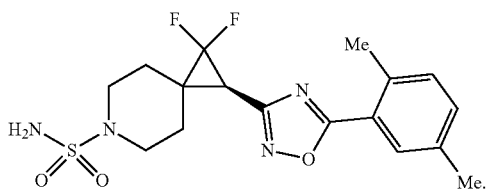 [SMILES: Cc1ccc(C)c(-c2nc([C@@H]3C(F)(F)C34CCN(S(N)(=O)=O)CC4)no2)c1]

51. A compound according to claim 49 which is a pharmaceutically acceptable salt of

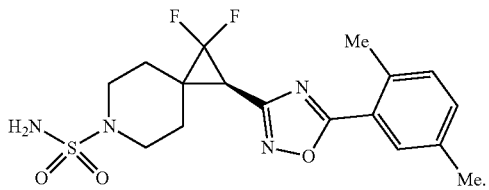 [SMILES: Cc1ccc(C)c(-c2nc([C@@H]3C(F)(F)C34CCN(S(N)(=O)=O)CC4)no2)c1]

52. A pharmaceutical composition comprising (i) a pharmaceutically acceptable carrier and (ii) the compound of claim 50.

53. A pharmaceutical composition comprising (i) a pharmaceutically acceptable carrier and (ii) the compound of claim 51.

54. A method of treating a patient with mild to moderate dementia of the Alzheimer's type, the method comprising administering to the patient the compound of claim 50 in an amount effective to treat the patient.

* * * * *

UNITED STATES PATENT AND TRADEMARK OFFICE
CERTIFICATE OF CORRECTION

| | | |
|---|---|---|
| PATENT NO. | : 11,332,463 B2 | Page 1 of 1 |
| APPLICATION NO. | : 17/049653 | |
| DATED | : May 17, 2022 | |
| INVENTOR(S) | : Crowley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 38 days.

Signed and Sealed this
Fifteenth Day of November, 2022

*Katherine Kelly Vidal*

Katherine Kelly Vidal
*Director of the United States Patent and Trademark Office*